US011771718B2

(12) United States Patent
Shah

(10) Patent No.: US 11,771,718 B2
(45) Date of Patent: Oct. 3, 2023

(54) POLYPEPTIDE COMPOSITIONS COMPRISING SPACERS

(71) Applicant: Intrexon Corporation, Blacksburg, VA (US)

(72) Inventor: Rutul R. Shah, Blacksburg, VA (US)

(73) Assignee: PRECIGEN, INC., Germantown, MD (US)

( * ) Notice: Subject to any disclaimer, the term of this patent is extended or adjusted under 35 U.S.C. 154(b) by 1322 days.

(21) Appl. No.: 16/163,233

(22) Filed: Oct. 17, 2018

(65) Prior Publication Data

US 2019/0111080 A1 Apr. 18, 2019

Related U.S. Application Data

(60) Provisional application No. 62/574,061, filed on Oct. 18, 2017.

(51) Int. Cl.

| | |
|---|---|
| ***A61K 35/17*** | (2015.01) |
| ***C07K 16/28*** | (2006.01) |
| ***C07K 14/705*** | (2006.01) |
| ***C07K 14/725*** | (2006.01) |
| ***C12N 15/62*** | (2006.01) |
| ***C12N 15/85*** | (2006.01) |
| ***A61P 37/06*** | (2006.01) |
| ***A61P 35/00*** | (2006.01) |
| ***C12N 15/113*** | (2010.01) |

(52) U.S. Cl.

CPC .............. *A61K 35/17* (2013.01); *A61P 35/00* (2018.01); *A61P 37/06* (2018.01); *C07K 14/705* (2013.01); *C07K 14/7051* (2013.01); *C07K 14/70517* (2013.01); *C07K 14/70521* (2013.01); *C07K 16/2803* (2013.01); *C07K 16/2815* (2013.01); *C07K 16/2818* (2013.01); *C07K 16/2863* (2013.01); *C07K 16/2878* (2013.01); *C07K 16/2896* (2013.01); *C12N 15/113* (2013.01); *C12N 15/62* (2013.01); *C12N 15/8509* (2013.01); *C07K 2317/622* (2013.01); *C07K 2319/03* (2013.01); *C07K 2319/33* (2013.01); *C12N 15/85* (2013.01)

(58) Field of Classification Search

None

See application file for complete search history.

(56) References Cited

U.S. PATENT DOCUMENTS

| | | | | |
|---|---|---|---|---|
| 9,629,877 | B2 | 4/2017 | Cooper et al. | |
| 11,118,168 | B2 * | 9/2021 | Shah | C07K 14/71 |
| 11,319,380 | B2 * | 5/2022 | Sabzevari | C07K 14/70578 |
| 2015/0306141 | A1 | 10/2015 | Jensen et al. | |
| 2016/0311907 | A1 | 10/2016 | Brogdon et al. | |
| 2016/0362467 | A1 * | 12/2016 | Pule | C12N 15/85 |
| 2017/0008951 | A1 | 1/2017 | Block et al. | |
| 2018/0002397 | A1 * | 1/2018 | Shah | C07K 14/7051 |
| 2018/0100026 | A1 | 4/2018 | Kim et al. | |
| 2018/0291384 | A1 * | 10/2018 | Shah | C12N 15/635 |
| 2020/0048351 | A1 * | 2/2020 | Sabzevari | A61K 35/17 |
| 2020/0283778 | A1 * | 9/2020 | Shah | C12N 15/1055 |
| 2021/0177902 | A1 * | 6/2021 | Shah | C12N 5/0636 |
| 2021/0324350 | A1 * | 10/2021 | Shah | C12N 9/12 |
| 2022/0023420 | A1 * | 1/2022 | Sabzevari | C07K 16/30 |
| 2022/0064609 | A1 * | 3/2022 | Shah | C12Y 207/10001 |
| 2022/0153866 | A1 * | 5/2022 | Sabzevari | A61K 9/0019 |
| 2022/0153867 | A1 * | 5/2022 | Sabzevari | C12N 7/00 |
| 2022/0220187 | A1 * | 7/2022 | Sabzevari | C07K 14/7051 |

FOREIGN PATENT DOCUMENTS

| | | | |
|---|---|---|---|
| WO | 2011/109789 | A2 | 9/2011 |
| WO | 2012/031744 | A1 | 3/2012 |
| WO | 2013/059593 | A1 | 4/2013 |
| WO | WO-2014186469 | A3 | 4/2015 |
| WO | WO-2015095895 | A1 | 6/2015 |
| WO | 2015/123642 | A1 | 8/2015 |
| WO | WO-2015157432 | A1 | 10/2015 |
| WO | WO-2016210447 | A1 | 2/2016 |
| WO | WO-2016042461 | A1 | 3/2016 |
| WO | 2016/055551 | A1 | 4/2016 |
| WO | WO-2016168766 | A1 | 10/2016 |
| WO | 2016/201304 | A1 | 12/2016 |
| WO | WO-2017027291 | A1 | 2/2017 |
| WO | WO-2017088012 | A1 | 6/2017 |
| WO | WO-2017214207 | A2 | 12/2017 |

OTHER PUBLICATIONS

Gacerez et al., Journal of Cellular Physiology, 231:2590-2598 (2016).

Guest, et al., "The Role of Extracellular Spacer Regions in the Optimal Design of Chimeric Immune Receptors Evaluation of Four Different scFvs and Antigens", J Immunother, vol. 28, No. 3, May/Jun. 2005.

Hudecek et al.,"Receptor affinity and extracellular domain modifications affect tumor recognition by ROR1-specific chimeric antigen receptor Tcells", Clin Cancer Res; 19(12); 3153-64.

Srivastava, et al. "Engineering CAR-T Cells: Design Concepts" Trends Immunol. Aug. 2015; 36(8): 492-502.

Hudecek et al.,"The nonsignaling Extracellular Spacer Domain of Chimeric Antigen Receptros is Decisive for In Vivo Antitumor Activity", Cancer Immunology Research (Sep. 11, 2014) pp. 125-136.

Hurton et al., Blood, 128:2807 (2016).

Gacerez et al., J. Cell Physiology, 231:2590-2598 (2016).

Zah et al., Cancer Immunol Res. (2016), 4:498-508.

* cited by examiner

*Primary Examiner* — Ilia I Ouspenski

(74) *Attorney, Agent, or Firm* — Gene J. Yao; Barnes & Thornburg LLP

(57) ABSTRACT

Disclosed herein are methods and compositions including antigen-binding polypeptides comprising a stalk region and a stalk extension region. In some cases, the antigen-binding compositions comprising the stalk extension region has increased expression on a cell surface and, in some cases, has increased antigen-binding efficiency. A subject antigen binding polypeptide can be a chimeric antigen receptor (CAR).

34 Claims, 19 Drawing Sheets

Specification includes a Sequence Listing.

SEQUENCE LISTING

```
<160> NUMBER OF SEQ ID NOS: 257

<210> SEQ ID NO 1
<211> LENGTH: 235
<212> TYPE: PRT
<213> ORGANISM: Homo sapiens

<400> SEQUENCE: 1

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140
```

-continued

```
Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235


<210> SEQ ID NO 2
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp
        35                  40                  45


<210> SEQ ID NO 3
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp
        35                  40                  45


<210> SEQ ID NO 4
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro Thr Thr Thr Pro Ala Pro Arg Pro Pro Thr Pro Ala Pro Thr Ile
```

```
    50                  55                  60

Ala Ser Gln Pro Leu Ser Leu Arg Pro Glu Ala Cys Arg Pro Ala Ala
65                  70                  75                  80

Gly Gly Ala Val His Thr Arg Gly Leu Asp Phe Ala Cys Asp
                85                  90
```

```
<210> SEQ ID NO 5
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro Thr Thr Thr Pro Ala Pro Arg Pro Pro Thr Pro Ala Pro Thr Ile
    50                  55                  60

Ala Ser Gln Pro Leu Ser Leu Arg Pro Glu Ala Ser Arg Pro Ala Ala
65                  70                  75                  80

Gly Gly Ala Val His Thr Arg Gly Leu Asp Phe Ala Ser Asp Lys Pro
                85                  90                  95

Thr Thr Thr Pro Ala Pro Arg Pro Pro Thr Pro Ala Pro Thr Ile Ala
            100                 105                 110

Ser Gln Pro Leu Ser Leu Arg Pro Glu Ala Cys Arg Pro Ala Ala Gly
        115                 120                 125

Gly Ala Val His Thr Arg Gly Leu Asp Phe Ala Cys Asp
    130                 135                 140
```

```
<210> SEQ ID NO 6
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Lys
        35                  40                  45

Pro Thr Thr Thr Pro Ala Pro Arg Pro Pro Thr Pro Ala Pro Thr Ile
    50                  55                  60

Ala Ser Gln Pro Leu Ser Leu Arg Pro Glu Ala Ser Arg Pro Ala Ala
65                  70                  75                  80

Gly Gly Ala Val His Thr Arg Gly Leu Asp Phe Ala Ser Asp Lys Pro
                85                  90                  95

Thr Thr Thr Pro Ala Pro Arg Pro Pro Thr Pro Ala Pro Thr Ile Ala
            100                 105                 110

Ser Gln Pro Leu Ser Leu Arg Pro Glu Ala Ser Arg Pro Ala Ala Gly
```

```
        115                 120                 125

Gly Ala Val His Thr Arg Gly Leu Asp Phe Ala Ser Asp
    130                 135                 140


<210> SEQ ID NO 7
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro Thr Thr Thr Pro Ala Pro Arg Pro Pro Thr Pro Ala Pro Thr Ile
    50                  55                  60

Ala Ser Gln Pro Leu Ser Leu Arg Pro Glu Ala Ser Arg Pro Ala Ala
65                  70                  75                  80

Gly Gly Ala Val His Thr Arg Gly Leu Asp Phe Ala Ser Asp Lys Pro
                85                  90                  95

Thr Thr Thr Pro Ala Pro Arg Pro Pro Thr Pro Ala Pro Thr Ile Ala
            100                 105                 110

Ser Gln Pro Leu Ser Leu Arg Pro Glu Ala Ser Arg Pro Ala Ala Gly
        115                 120                 125

Gly Ala Val His Thr Arg Gly Leu Asp Phe Ala Ser Asp Lys Pro Thr
    130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp
            180                 185


<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Thr Ser Gly Ser Gly Lys Pro Gly Ser Gly Glu Gly Ser Thr
1               5                   10                  15

Lys Gly


<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Gly Ser Gly
1


<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gly Ser Gly
1


<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser Gly Gly Gly Gly Ser
1               5                   10                  15


<210> SEQ ID NO 12
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Gly Gly Gly Ser Gly Gly Gly Gly Ser Gly Gly Gly Gly Ser Gly
1               5                   10                  15

Gly Gly Gly Ser Lys Pro Thr Thr Thr Pro Ala Pro Arg Pro Pro Thr
            20                  25                  30

Pro Ala Pro Thr Ile Ala Ser Gln Pro Leu Ser Leu Arg Pro Glu Ala
        35                  40                  45

Cys Arg Pro Ala Ala Gly Gly Ala Val His Thr Arg Gly Leu Asp Phe
    50                  55                  60

Ala Cys Asp
65


<210> SEQ ID NO 13
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Ser Thr Ser Gly Ser Gly Lys Pro Gly Ser Gly Glu Gly Ser Thr
1               5                   10                  15

Lys Gly Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60
```

Asp
65

<210> SEQ ID NO 14
<211> LENGTH: 83
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

Gly Ser Thr Ser Gly Ser Gly Lys Pro Gly Ser Gly Glu Gly Ser Thr
1 5 10 15

Lys Gly Gly Ser Thr Ser Gly Ser Gly Lys Pro Gly Ser Gly Glu Gly
20 25 30

Ser Thr Lys Gly Lys Pro Thr Thr Thr Pro Ala Pro Arg Pro Pro Thr
35 40 45

Pro Ala Pro Thr Ile Ala Ser Gln Pro Leu Ser Leu Arg Pro Glu Ala
50 55 60

Cys Arg Pro Ala Ala Gly Gly Ala Val His Thr Arg Gly Leu Asp Phe
65 70 75 80

Ala Cys Asp

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 15

Gly Ser Thr Ser Gly Ser Gly Lys Pro Gly Ser Gly Glu Gly Ser Thr
1 5 10 15

Lys Gly Lys Pro Thr Thr Thr Pro Ala Pro Arg Pro Pro Thr Pro Ala
20 25 30

Pro Thr Ile Ala Ser Gln Pro Leu Ser Leu Arg Pro Glu Ala Ser Arg
35 40 45

Pro Ala Ala Gly Gly Ala Val His Thr Arg Gly Leu Asp Phe Ala Ser
50 55 60

Asp Lys Pro Thr Thr Thr Pro Ala Pro Arg Pro Pro Thr Pro Ala Pro
65 70 75 80

Thr Ile Ala Ser Gln Pro Leu Ser Leu Arg Pro Glu Ala Cys Arg Pro
85 90 95

Ala Ala Gly Gly Ala Val His Thr Arg Gly Leu Asp Phe Ala Cys Asp
100 105 110

<210> SEQ ID NO 16
<211> LENGTH: 222
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

Lys Glu Ala Cys Pro Thr Gly Leu Tyr Thr His Ser Gly Glu Cys Cys
1 5 10 15

Lys Ala Cys Asn Leu Gly Glu Gly Val Ala Gln Pro Cys Gly Ala Asn

```
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205

Gly Ser Ser Gln Pro Val Val Thr Arg Gly Thr Thr Asp Asn
    210                 215                 220


<210> SEQ ID NO 17
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160
```

-continued

```
Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205

Gly Ser Ser Gln Pro Val Val Thr Arg Gly Thr Thr Asp Asn Lys Glu
    210                 215                 220

Ala Cys Pro Thr Gly Leu Tyr Thr His Ser Gly Glu Cys Cys Lys Ala
225                 230                 235                 240

Cys Asn Leu Gly Glu Gly Val Ala Gln Pro Cys Gly Ala Asn Gln Thr
                245                 250                 255

Val Cys Glu Pro Cys Leu Asp Ser Val Thr Phe Ser Asp Val Val Ser
            260                 265                 270

Ala Thr Glu Pro Cys Lys Pro Cys Thr Glu Cys Val Gly Leu Gln Ser
        275                 280                 285

Met Ser Ala Pro Cys Val Glu Ala Asp Asp Ala Val Cys Arg Cys Ala
    290                 295                 300

Tyr Gly Tyr Tyr Gln Asp Glu Thr Thr Gly Arg Cys Glu Ala Cys Arg
305                 310                 315                 320

Val Cys Glu Ala Gly Ser Gly Leu Val Phe Ser Cys Gln Asp Lys Gln
                325                 330                 335

Asn Thr Val Cys Glu Glu Cys Pro Asp Gly Thr Tyr Ser Asp Glu Ala
            340                 345                 350

Asn His Val Asp Pro Cys Leu Pro Cys Thr Val Cys Glu Asp Thr Glu
        355                 360                 365

Arg Gln Leu Arg Glu Cys Thr Arg Trp Ala Asp Ala Glu Cys Glu Glu
    370                 375                 380

Ile Pro Gly Arg Trp Ile Thr Arg Ser Thr Pro Pro Glu Gly Ser Asp
385                 390                 395                 400

Ser Thr Ala Pro Ser Thr Gln Glu Pro Glu Ala Pro Pro Glu Gln Asp
                405                 410                 415

Leu Ile Ala Ser Thr Val Ala Gly Val Val Thr Thr Val Met Gly Ser
            420                 425                 430

Ser Gln Pro Val Val Thr Arg Gly Thr Thr Asp Asn
        435                 440
```

```
<210> SEQ ID NO 18
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Pro Cys Leu Asp Ser Val Thr Phe Ser Asp Val Val Ser Ala Thr
1               5                   10                  15

Glu Pro Cys Lys Pro Cys Thr Glu Cys Val Gly Leu Gln Ser Met Ser
            20                  25                  30

Ala Pro Cys Val Glu Ala Asp Asp Ala Val Cys Arg Cys Ala Tyr Gly
        35                  40                  45

Tyr Tyr Gln Asp Glu Thr Thr Gly Arg Cys Glu Ala Cys Arg Val Cys
    50                  55                  60

Glu Ala Gly Ser Gly Leu Val Phe Ser Cys Gln Asp Lys Gln Asn Thr
65                  70                  75                  80
```

Val Cys Glu Glu Cys Pro Asp Gly Thr Tyr Ser Asp Glu Ala Asn His
85 90 95

Val Asp Pro Cys Leu Pro Cys Thr Val Cys Glu Asp Thr Glu Arg Gln
100 105 110

Leu Arg Glu Cys Thr Arg Trp Ala Asp Ala Glu Cys Glu Glu Ile Pro
115 120 125

Gly Arg Trp Ile Thr Arg Ser Thr Pro Pro Glu Gly Ser Asp Ser Thr
130 135 140

Ala Pro Ser Thr Gln Glu Pro Glu Ala Pro Pro Glu Gln Asp Leu Ile
145 150 155 160

Ala Ser Thr Val Ala Gly Val Val Thr Thr Val Met Gly Ser Ser Gln
165 170 175

Pro Val Val Thr Arg Gly Thr Thr Asp Asn
180 185

<210> SEQ ID NO 19
<211> LENGTH: 372
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Glu Pro Cys Leu Asp Ser Val Thr Phe Ser Asp Val Val Ser Ala Thr
1 5 10 15

Glu Pro Cys Lys Pro Cys Thr Glu Cys Val Gly Leu Gln Ser Met Ser
20 25 30

Ala Pro Cys Val Glu Ala Asp Asp Ala Val Cys Arg Cys Ala Tyr Gly
35 40 45

Tyr Tyr Gln Asp Glu Thr Thr Gly Arg Cys Glu Ala Cys Arg Val Cys
50 55 60

Glu Ala Gly Ser Gly Leu Val Phe Ser Cys Gln Asp Lys Gln Asn Thr
65 70 75 80

Val Cys Glu Glu Cys Pro Asp Gly Thr Tyr Ser Asp Glu Ala Asn His
85 90 95

Val Asp Pro Cys Leu Pro Cys Thr Val Cys Glu Asp Thr Glu Arg Gln
100 105 110

Leu Arg Glu Cys Thr Arg Trp Ala Asp Ala Glu Cys Glu Glu Ile Pro
115 120 125

Gly Arg Trp Ile Thr Arg Ser Thr Pro Pro Glu Gly Ser Asp Ser Thr
130 135 140

Ala Pro Ser Thr Gln Glu Pro Glu Ala Pro Pro Glu Gln Asp Leu Ile
145 150 155 160

Ala Ser Thr Val Ala Gly Val Val Thr Thr Val Met Gly Ser Ser Gln
165 170 175

Pro Val Val Thr Arg Gly Thr Thr Asp Asn Glu Pro Cys Leu Asp Ser
180 185 190

Val Thr Phe Ser Asp Val Val Ser Ala Thr Glu Pro Cys Lys Pro Cys
195 200 205

Thr Glu Cys Val Gly Leu Gln Ser Met Ser Ala Pro Cys Val Glu Ala
210 215 220

Asp Asp Ala Val Cys Arg Cys Ala Tyr Gly Tyr Tyr Gln Asp Glu Thr
225 230 235 240

Thr Gly Arg Cys Glu Ala Cys Arg Val Cys Glu Ala Gly Ser Gly Leu

```
                245                 250                 255

Val Phe Ser Cys Gln Asp Lys Gln Asn Thr Val Cys Glu Glu Cys Pro
            260                 265                 270

Asp Gly Thr Tyr Ser Asp Glu Ala Asn His Val Asp Pro Cys Leu Pro
        275                 280                 285

Cys Thr Val Cys Glu Asp Thr Glu Arg Gln Leu Arg Glu Cys Thr Arg
    290                 295                 300

Trp Ala Asp Ala Glu Cys Glu Glu Ile Pro Gly Arg Trp Ile Thr Arg
305                 310                 315                 320

Ser Thr Pro Pro Glu Gly Ser Asp Ser Thr Ala Pro Ser Thr Gln Glu
                325                 330                 335

Pro Glu Ala Pro Pro Glu Gln Asp Leu Ile Ala Ser Thr Val Ala Gly
            340                 345                 350

Val Val Thr Thr Val Met Gly Ser Ser Gln Pro Val Val Thr Arg Gly
        355                 360                 365

Thr Thr Asp Asn
    370


<210> SEQ ID NO 20
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
            20                  25                  30

Asp Lys Gln Asn Thr Val Cys Glu Glu Cys Pro Asp Gly Thr Tyr Ser
        35                  40                  45

Asp Glu Ala Asn His Val Asp Pro Cys Leu Pro Cys Thr Val Cys Glu
    50                  55                  60

Asp Thr Glu Arg Gln Leu Arg Glu Cys Thr Arg Trp Ala Asp Ala Glu
65                  70                  75                  80

Cys Glu Glu Ile Pro Gly Arg Trp Ile Thr Arg Ser Thr Pro Pro Glu
                85                  90                  95

Gly Ser Asp Ser Thr Ala Pro Ser Thr Gln Glu Pro Glu Ala Pro Pro
            100                 105                 110

Glu Gln Asp Leu Ile Ala Ser Thr Val Ala Gly Val Val Thr Thr Val
        115                 120                 125

Met Gly Ser Ser Gln Pro Val Val Thr Arg Gly Thr Thr Asp Asn
    130                 135                 140


<210> SEQ ID NO 21
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
```

```
            20                  25                  30

Asp Lys Gln Asn Thr Val Cys Glu Glu Cys Pro Asp Gly Thr Tyr Ser
        35                  40                  45

Asp Glu Ala Asn His Val Asp Pro Cys Leu Pro Cys Thr Val Cys Glu
    50                  55                  60

Asp Thr Glu Arg Gln Leu Arg Glu Cys Thr Arg Trp Ala Asp Ala Glu
65                  70                  75                  80

Cys Glu Glu Ile Pro Gly Arg Trp Ile Thr Arg Ser Thr Pro Pro Glu
                85                  90                  95

Gly Ser Asp Ser Thr Ala Pro Ser Thr Gln Glu Pro Glu Ala Pro Pro
            100                 105                 110

Glu Gln Asp Leu Ile Ala Ser Thr Val Ala Gly Val Val Thr Thr Val
        115                 120                 125

Met Gly Ser Ser Gln Pro Val Val Thr Arg Gly Thr Thr Asp Asn Arg
    130                 135                 140

Cys Ala Tyr Gly Tyr Tyr Gln Asp Glu Thr Thr Gly Arg Cys Glu Ala
145                 150                 155                 160

Cys Arg Val Cys Glu Ala Gly Ser Gly Leu Val Phe Ser Cys Gln Asp
                165                 170                 175

Lys Gln Asn Thr Val Cys Glu Glu Cys Pro Asp Gly Thr Tyr Ser Asp
            180                 185                 190

Glu Ala Asn His Val Asp Pro Cys Leu Pro Cys Thr Val Cys Glu Asp
        195                 200                 205

Thr Glu Arg Gln Leu Arg Glu Cys Thr Arg Trp Ala Asp Ala Glu Cys
    210                 215                 220

Glu Glu Ile Pro Gly Arg Trp Ile Thr Arg Ser Thr Pro Pro Glu Gly
225                 230                 235                 240

Ser Asp Ser Thr Ala Pro Ser Thr Gln Glu Pro Glu Ala Pro Pro Glu
                245                 250                 255

Gln Asp Leu Ile Ala Ser Thr Val Ala Gly Val Val Thr Thr Val Met
            260                 265                 270

Gly Ser Ser Gln Pro Val Val Thr Arg Gly Thr Thr Asp Asn
        275                 280                 285


<210> SEQ ID NO 22
<211> LENGTH: 429
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
            20                  25                  30

Asp Lys Gln Asn Thr Val Cys Glu Glu Cys Pro Asp Gly Thr Tyr Ser
        35                  40                  45

Asp Glu Ala Asn His Val Asp Pro Cys Leu Pro Cys Thr Val Cys Glu
    50                  55                  60

Asp Thr Glu Arg Gln Leu Arg Glu Cys Thr Arg Trp Ala Asp Ala Glu
65                  70                  75                  80

Cys Glu Glu Ile Pro Gly Arg Trp Ile Thr Arg Ser Thr Pro Pro Glu
                85                  90                  95
```

-continued

Gly Ser Asp Ser Thr Ala Pro Ser Thr Gln Glu Pro Glu Ala Pro Pro
100 105 110

Glu Gln Asp Leu Ile Ala Ser Thr Val Ala Gly Val Val Thr Thr Val
115 120 125

Met Gly Ser Ser Gln Pro Val Val Thr Arg Gly Thr Thr Asp Asn Arg
130 135 140

Cys Ala Tyr Gly Tyr Tyr Gln Asp Glu Thr Thr Gly Arg Cys Glu Ala
145 150 155 160

Cys Arg Val Cys Glu Ala Gly Ser Gly Leu Val Phe Ser Cys Gln Asp
165 170 175

Lys Gln Asn Thr Val Cys Glu Glu Cys Pro Asp Gly Thr Tyr Ser Asp
180 185 190

Glu Ala Asn His Val Asp Pro Cys Leu Pro Cys Thr Val Cys Glu Asp
195 200 205

Thr Glu Arg Gln Leu Arg Glu Cys Thr Arg Trp Ala Asp Ala Glu Cys
210 215 220

Glu Glu Ile Pro Gly Arg Trp Ile Thr Arg Ser Thr Pro Pro Glu Gly
225 230 235 240

Ser Asp Ser Thr Ala Pro Ser Thr Gln Glu Pro Glu Ala Pro Pro Glu
245 250 255

Gln Asp Leu Ile Ala Ser Thr Val Ala Gly Val Val Thr Thr Val Met
260 265 270

Gly Ser Ser Gln Pro Val Val Thr Arg Gly Thr Thr Asp Asn Arg Cys
275 280 285

Ala Tyr Gly Tyr Tyr Gln Asp Glu Thr Thr Gly Arg Cys Glu Ala Cys
290 295 300

Arg Val Cys Glu Ala Gly Ser Gly Leu Val Phe Ser Cys Gln Asp Lys
305 310 315 320

Gln Asn Thr Val Cys Glu Glu Cys Pro Asp Gly Thr Tyr Ser Asp Glu
325 330 335

Ala Asn His Val Asp Pro Cys Leu Pro Cys Thr Val Cys Glu Asp Thr
340 345 350

Glu Arg Gln Leu Arg Glu Cys Thr Arg Trp Ala Asp Ala Glu Cys Glu
355 360 365

Glu Ile Pro Gly Arg Trp Ile Thr Arg Ser Thr Pro Pro Glu Gly Ser
370 375 380

Asp Ser Thr Ala Pro Ser Thr Gln Glu Pro Glu Ala Pro Pro Glu Gln
385 390 395 400

Asp Leu Ile Ala Ser Thr Val Ala Gly Val Val Thr Thr Val Met Gly
405 410 415

Ser Ser Gln Pro Val Val Thr Arg Gly Thr Thr Asp Asn
420 425

<210> SEQ ID NO 23
<211> LENGTH: 572
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Arg Cys Ala Tyr Gly Tyr Tyr Gln Asp Glu Thr Thr Gly Arg Cys Glu
1 5 10 15

Ala Cys Arg Val Cys Glu Ala Gly Ser Gly Leu Val Phe Ser Cys Gln
20 25 30

-continued

```
Asp Lys Gln Asn Thr Val Cys Glu Glu Cys Pro Asp Gly Thr Tyr Ser
        35                  40                  45

Asp Glu Ala Asn His Val Asp Pro Cys Leu Pro Cys Thr Val Cys Glu
    50                  55                  60

Asp Thr Glu Arg Gln Leu Arg Glu Cys Thr Arg Trp Ala Asp Ala Glu
65                  70                  75                  80

Cys Glu Glu Ile Pro Gly Arg Trp Ile Thr Arg Ser Thr Pro Pro Glu
                85                  90                  95

Gly Ser Asp Ser Thr Ala Pro Ser Thr Gln Glu Pro Glu Ala Pro Pro
            100                 105                 110

Glu Gln Asp Leu Ile Ala Ser Thr Val Ala Gly Val Val Thr Thr Val
        115                 120                 125

Met Gly Ser Ser Gln Pro Val Val Thr Arg Gly Thr Thr Asp Asn Arg
    130                 135                 140

Cys Ala Tyr Gly Tyr Tyr Gln Asp Glu Thr Thr Gly Arg Cys Glu Ala
145                 150                 155                 160

Cys Arg Val Cys Glu Ala Gly Ser Gly Leu Val Phe Ser Cys Gln Asp
                165                 170                 175

Lys Gln Asn Thr Val Cys Glu Glu Cys Pro Asp Gly Thr Tyr Ser Asp
            180                 185                 190

Glu Ala Asn His Val Asp Pro Cys Leu Pro Cys Thr Val Cys Glu Asp
        195                 200                 205

Thr Glu Arg Gln Leu Arg Glu Cys Thr Arg Trp Ala Asp Ala Glu Cys
    210                 215                 220

Glu Glu Ile Pro Gly Arg Trp Ile Thr Arg Ser Thr Pro Pro Glu Gly
225                 230                 235                 240

Ser Asp Ser Thr Ala Pro Ser Thr Gln Glu Pro Glu Ala Pro Pro Glu
                245                 250                 255

Gln Asp Leu Ile Ala Ser Thr Val Ala Gly Val Val Thr Thr Val Met
            260                 265                 270

Gly Ser Ser Gln Pro Val Val Thr Arg Gly Thr Thr Asp Asn Arg Cys
        275                 280                 285

Ala Tyr Gly Tyr Tyr Gln Asp Glu Thr Thr Gly Arg Cys Glu Ala Cys
    290                 295                 300

Arg Val Cys Glu Ala Gly Ser Gly Leu Val Phe Ser Cys Gln Asp Lys
305                 310                 315                 320

Gln Asn Thr Val Cys Glu Glu Cys Pro Asp Gly Thr Tyr Ser Asp Glu
                325                 330                 335

Ala Asn His Val Asp Pro Cys Leu Pro Cys Thr Val Cys Glu Asp Thr
            340                 345                 350

Glu Arg Gln Leu Arg Glu Cys Thr Arg Trp Ala Asp Ala Glu Cys Glu
        355                 360                 365

Glu Ile Pro Gly Arg Trp Ile Thr Arg Ser Thr Pro Pro Glu Gly Ser
    370                 375                 380

Asp Ser Thr Ala Pro Ser Thr Gln Glu Pro Glu Ala Pro Pro Glu Gln
385                 390                 395                 400

Asp Leu Ile Ala Ser Thr Val Ala Gly Val Val Thr Thr Val Met Gly
                405                 410                 415

Ser Ser Gln Pro Val Val Thr Arg Gly Thr Thr Asp Asn Arg Cys Ala
            420                 425                 430

Tyr Gly Tyr Tyr Gln Asp Glu Thr Thr Gly Arg Cys Glu Ala Cys Arg
        435                 440                 445
```

-continued

```
Val Cys Glu Ala Gly Ser Gly Leu Val Phe Ser Cys Gln Asp Lys Gln
    450                 455                 460

Asn Thr Val Cys Glu Glu Cys Pro Asp Gly Thr Tyr Ser Asp Glu Ala
465                 470                 475                 480

Asn His Val Asp Pro Cys Leu Pro Cys Thr Val Cys Glu Asp Thr Glu
                485                 490                 495

Arg Gln Leu Arg Glu Cys Thr Arg Trp Ala Asp Ala Glu Cys Glu Glu
            500                 505                 510

Ile Pro Gly Arg Trp Ile Thr Arg Ser Thr Pro Pro Glu Gly Ser Asp
        515                 520                 525

Ser Thr Ala Pro Ser Thr Gln Glu Pro Glu Ala Pro Pro Glu Gln Asp
    530                 535                 540

Leu Ile Ala Ser Thr Val Ala Gly Val Val Thr Thr Val Met Gly Ser
545                 550                 555                 560

Ser Gln Pro Val Val Thr Arg Gly Thr Thr Asp Asn
                565                 570


<210> SEQ ID NO 24
<211> LENGTH: 28
<212> TYPE: PRT
<213> ORGANISM: Homo sapiens

<400> SEQUENCE: 24

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25


<210> SEQ ID NO 25
<211> LENGTH: 27
<212> TYPE: PRT
<213> ORGANISM: Homo sapiens

<400> SEQUENCE: 25

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 26
<211> LENGTH: 41
<212> TYPE: PRT
<213> ORGANISM: Unknown
<220> FEATURE:
<223> OTHER INFORMATION: Description of Unknown:
      CD28 co-stimulatory endodomain sequence

<400> SEQUENCE: 26

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 27
<211> LENGTH: 42
<212> TYPE: PRT
<213> ORGANISM: Unknown
<220> FEATURE:
<223> OTHER INFORMATION: Description of Unknown:
```

```
      4-1BB (CD137) co-stimulatory endodomain sequence

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 28
<211> LENGTH: 112
<212> TYPE: PRT
<213> ORGANISM: Unknown
<220> FEATURE:
<223> OTHER INFORMATION: Description of Unknown:
      CD3 zetaz stimulatory endodomain sequence

<400> SEQUENCE: 28

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 29
<211> LENGTH: 24
<212> TYPE: PRT
<213> ORGANISM: Unknown
<220> FEATURE:
<223> OTHER INFORMATION: Description of Unknown:
      DNAX-activation protein 10 (DAP 10) Signaling Domain sequence

<400> SEQUENCE: 29

Leu Cys Ala Arg Pro Arg Arg Ser Pro Ala Gln Glu Asp Gly Lys Val
1               5                   10                  15

Tyr Ile Asn Met Pro Gly Arg Gly
            20


<210> SEQ ID NO 30
<211> LENGTH: 52
<212> TYPE: PRT
<213> ORGANISM: Unknown
<220> FEATURE:
<223> OTHER INFORMATION: Description of Unknown:
      DNAX-activation protein 12 (DAP12) Signaling Domain sequence

<400> SEQUENCE: 30

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30
```

-continued

```
Leu Gln Gly Gln Arg Ser Asp Val Tyr Ser Asp Leu Asn Thr Gln Arg
        35                  40                  45

Pro Tyr Tyr Lys
    50


<210> SEQ ID NO 31
<211> LENGTH: 220
<212> TYPE: PRT
<213> ORGANISM: Homo sapiens

<400> SEQUENCE: 31

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220


<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35


<210> SEQ ID NO 33
<211> LENGTH: 78
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Ser Pro Ser Pro Leu
            20                  25                  30

Phe Pro Gly Pro Ser Lys Pro Ile Glu Val Met Tyr Pro Pro Pro Tyr
        35                  40                  45

Leu Asp Asn Glu Lys Ser Asn Gly Thr Ile Ile His Val Lys Gly Lys
    50                  55                  60

His Leu Cys Pro Ser Pro Leu Phe Pro Gly Pro Ser Lys Pro
65                  70                  75
```

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Ser Pro Ser Pro Leu
            20                  25                  30

Phe Pro Gly Pro Ser Lys Pro Ile Glu Val Met Tyr Pro Pro Pro Tyr
        35                  40                  45

Leu Asp Asn Glu Lys Ser Asn Gly Thr Ile Ile His Val Lys Gly Lys
    50                  55                  60

His Leu Ser Pro Ser Pro Leu Phe Pro Gly Pro Ser Lys Pro Ile Glu
65                  70                  75                  80

Val Met Tyr Pro Pro Pro Tyr Leu Asp Asn Glu Lys Ser Asn Gly Thr
                85                  90                  95

Ile Ile His Val Lys Gly Lys His Leu Cys Pro Ser Pro Leu Phe Pro
            100                 105                 110

Gly Pro Ser Lys Pro
        115
```

<210> SEQ ID NO 35
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Ser Pro Ser Pro Leu
            20                  25                  30

Phe Pro Gly Pro Ser Lys Pro Ile Glu Val Met Tyr Pro Pro Pro Tyr
        35                  40                  45

Leu Asp Asn Glu Lys Ser Asn Gly Thr Ile Ile His Val Lys Gly Lys
```

```
    50                  55                  60

His Leu Ser Pro Ser Pro Leu Phe Pro Gly Pro Ser Lys Pro Ile Glu
65                  70                  75                  80

Val Met Tyr Pro Pro Pro Tyr Leu Asp Asn Glu Lys Ser Asn Gly Thr
                85                  90                  95

Ile Ile His Val Lys Gly Lys His Leu Ser Pro Ser Pro Leu Phe Pro
            100                 105                 110

Gly Pro Ser Lys Pro Ile Glu Val Met Tyr Pro Pro Pro Tyr Leu Asp
        115                 120                 125

Asn Glu Lys Ser Asn Gly Thr Ile Ile His Val Lys Gly Lys His Leu
    130                 135                 140

Cys Pro Ser Pro Leu Phe Pro Gly Pro Ser Lys Pro
145                 150                 155


<210> SEQ ID NO 36
<211> LENGTH: 223
<212> TYPE: PRT
<213> ORGANISM: Homo sapiens

<400> SEQUENCE: 36

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 37
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 37

```
Val Glu Leu Met Tyr Pro Pro Pro Tyr Tyr Leu Gly Ile Gly Asn Gly
1               5                   10                  15

Thr Gln Ile Tyr Val Ile Asp Pro Glu Pro Cys Pro Asp Ser Asp
            20                  25                  30
```

<210> SEQ ID NO 38
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Val Glu Leu Met Tyr Pro Pro Pro Tyr Tyr Leu Gly Ile Gly Asn Gly
1               5                   10                  15

Thr Gln Ile Tyr Val Ile Asp Pro Glu Pro Ser Pro Asp Ser Asp Val
            20                  25                  30

Glu Leu Met Tyr Pro Pro Pro Tyr Tyr Leu Gly Ile Gly Asn Gly Thr
        35                  40                  45

Gln Ile Tyr Val Ile Asp Pro Glu Pro Cys Pro Asp Ser Asp
    50                  55                  60
```

<210> SEQ ID NO 39
<211> LENGTH: 93
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Val Glu Leu Met Tyr Pro Pro Pro Tyr Tyr Leu Gly Ile Gly Asn Gly
1               5                   10                  15

Thr Gln Ile Tyr Val Ile Asp Pro Glu Pro Ser Pro Asp Ser Asp Val
            20                  25                  30

Glu Leu Met Tyr Pro Pro Pro Tyr Tyr Leu Gly Ile Gly Asn Gly Thr
        35                  40                  45

Gln Ile Tyr Val Ile Asp Pro Glu Pro Ser Pro Asp Ser Asp Val Glu
    50                  55                  60

Leu Met Tyr Pro Pro Pro Tyr Tyr Leu Gly Ile Gly Asn Gly Thr Gln
65                  70                  75                  80

Ile Tyr Val Ile Asp Pro Glu Pro Cys Pro Asp Ser Asp
                85                  90
```

<210> SEQ ID NO 40
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Val Glu Leu Met Tyr Pro Pro Pro Tyr Tyr Leu Gly Ile Gly Asn Gly
1               5                   10                  15

Thr Gln Ile Tyr Val Ile Asp Pro Glu Pro Ser Pro Asp Ser Asp Val
            20                  25                  30

Glu Leu Met Tyr Pro Pro Pro Tyr Tyr Leu Gly Ile Gly Asn Gly Thr
        35                  40                  45
```

```
Gln Ile Tyr Val Ile Asp Pro Glu Pro Ser Pro Asp Ser Asp Val Glu
    50                  55                  60

Leu Met Tyr Pro Pro Pro Tyr Tyr Leu Gly Ile Gly Asn Gly Thr Gln
65                  70                  75                  80

Ile Tyr Val Ile Asp Pro Glu Pro Ser Pro Asp Ser Asp Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 41
<211> LENGTH: 62
<212> TYPE: PRT
<213> ORGANISM: Homo sapiens

<400> SEQUENCE: 41

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro
    50                  55                  60


<210> SEQ ID NO 42
<211> LENGTH: 13
<212> TYPE: PRT
<213> ORGANISM: Homo sapiens

<400> SEQUENCE: 42

Glu Ser Lys Tyr Gly Pro Pro Cys Pro Ser Pro Cys Pro
1               5                   10


<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Ser Lys Tyr Gly Pro Pro Cys Pro Pro Cys Pro
1               5                   10


<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Ser Lys Tyr Gly Pro Pro Cys Pro Pro Cys Pro Glu Ser Lys Tyr
1               5                   10                  15

Gly Pro Pro Ser Pro Pro Ser Pro
            20
```

-continued

<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Glu Ser Lys Tyr Gly Pro Pro Cys Pro Pro Cys Pro Glu Ser Lys Tyr
1               5                   10                  15

Gly Pro Pro Ser Pro Pro Ser Pro Glu Ser Lys Tyr Gly Pro Pro Ser
            20                  25                  30

Pro Pro Ser Pro
        35
```

<210> SEQ ID NO 46
<211> LENGTH: 48
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Glu Ser Lys Tyr Gly Pro Pro Cys Pro Pro Cys Pro Glu Ser Lys Tyr
1               5                   10                  15

Gly Pro Pro Ser Pro Pro Ser Pro Glu Ser Lys Tyr Gly Pro Pro Ser
            20                  25                  30

Pro Pro Ser Pro Glu Ser Lys Tyr Gly Pro Pro Ser Pro Pro Ser Pro
        35                  40                  45
```

<210> SEQ ID NO 47
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Glu Ser Lys Tyr Gly Pro Pro Cys Pro Pro Cys Pro Glu Ser Lys Tyr
1               5                   10                  15

Gly Pro Pro Ser Pro Pro Ser Pro Glu Ser Lys Tyr Gly Pro Pro Ser
            20                  25                  30

Pro Pro Ser Pro Glu Ser Lys Tyr Gly Pro Pro Ser Pro Pro Ser Pro
        35                  40                  45

Glu Ser Lys Tyr Gly Pro Pro Ser Pro Pro Ser Pro
    50                  55                  60
```

<210> SEQ ID NO 48
<211> LENGTH: 72
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Glu Ser Lys Tyr Gly Pro Pro Cys Pro Pro Cys Pro Glu Ser Lys Tyr
1               5                   10                  15

Gly Pro Pro Ser Pro Pro Ser Pro Glu Ser Lys Tyr Gly Pro Pro Ser
            20                  25                  30
```

```
Pro Pro Ser Pro Glu Ser Lys Tyr Gly Pro Pro Ser Pro Pro Ser Pro
        35                  40                  45

Glu Ser Lys Tyr Gly Pro Pro Ser Pro Pro Ser Pro Glu Ser Lys Tyr
    50                  55                  60

Gly Pro Pro Ser Pro Pro Ser Pro
65                  70


<210> SEQ ID NO 49
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ser Lys Tyr Gly Pro Pro Cys Pro Pro Cys Pro Gly Gln Pro Arg
1               5                   10                  15
```

```
Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115


<210> SEQ ID NO 51
<211> LENGTH: 556
<212> TYPE: PRT
<213> ORGANISM: Homo sapiens

<400> SEQUENCE: 51

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270
```

```
Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555


<210> SEQ ID NO 52
<211> LENGTH: 22
<212> TYPE: PRT
<213> ORGANISM: Unknown
<220> FEATURE:
<223> OTHER INFORMATION: Description of Unknown:
      Granulocyte macrophage colony-stimulating
      factor receptor alpha Signal Peptide sequence

<400> SEQUENCE: 52

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 53
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 53

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

<210> SEQ ID NO 54
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 55
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
```

```
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 56
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140
```

```
Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Lys Pro Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Asn His Arg Asn
305                 310                 315                 320

Arg Ser Lys Arg Ser Arg Gly Gly His Ser Asp Tyr Met Asn Met Thr
                325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470
```

<210> SEQ ID NO 57
<211> LENGTH: 520
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30
```

```
Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Lys Pro Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Ser Arg Pro Ala Ala Gly Gly Ala Val His Thr Arg Gly Leu Asp
        275                 280                 285

Phe Ala Ser Asp Lys Pro Thr Thr Thr Pro Ala Pro Arg Pro Pro Thr
    290                 295                 300

Pro Ala Pro Thr Ile Ala Ser Gln Pro Leu Ser Leu Arg Pro Glu Ala
305                 310                 315                 320

Cys Arg Pro Ala Ala Gly Gly Ala Val His Thr Arg Gly Leu Asp Phe
                325                 330                 335

Ala Cys Asp Ile Tyr Ile Trp Ala Pro Leu Ala Gly Thr Cys Gly Val
            340                 345                 350

Leu Leu Leu Ser Leu Val Ile Thr Leu Tyr Cys Asn His Arg Asn Arg
        355                 360                 365

Ser Lys Arg Ser Arg Gly Gly His Ser Asp Tyr Met Asn Met Thr Pro
    370                 375                 380

Arg Arg Pro Gly Pro Thr Arg Lys His Tyr Gln Pro Tyr Ala Pro Pro
385                 390                 395                 400

Arg Asp Phe Ala Ala Tyr Arg Ser Arg Val Lys Phe Ser Arg Ser Ala
                405                 410                 415

Asp Ala Pro Ala Tyr Gln Gln Gly Gln Asn Gln Leu Tyr Asn Glu Leu
            420                 425                 430

Asn Leu Gly Arg Arg Glu Glu Tyr Asp Val Leu Asp Lys Arg Arg Gly
        435                 440                 445
```

```
Arg Asp Pro Glu Met Gly Gly Lys Pro Arg Arg Lys Asn Pro Gln Glu
    450                 455                 460

Gly Leu Tyr Asn Glu Leu Gln Lys Asp Lys Met Ala Glu Ala Tyr Ser
465                 470                 475                 480

Glu Ile Gly Met Lys Gly Glu Arg Arg Arg Gly Lys Gly His Asp Gly
                485                 490                 495

Leu Tyr Gln Gly Leu Ser Thr Ala Thr Lys Asp Thr Tyr Asp Ala Leu
            500                 505                 510

His Met Gln Ala Leu Pro Pro Arg
        515                 520
```

<210> SEQ ID NO 58
<211> LENGTH: 567
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Lys Pro Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Ser Arg Pro Ala Ala Gly Gly Ala Val His Thr Arg Gly Leu Asp
        275                 280                 285
```

Phe Ala Ser Asp Lys Pro Thr Thr Thr Pro Ala Pro Arg Pro Pro Thr
    290                 295                 300

Pro Ala Pro Thr Ile Ala Ser Gln Pro Leu Ser Leu Arg Pro Glu Ala
305                 310                 315                 320

Ser Arg Pro Ala Ala Gly Gly Ala Val His Thr Arg Gly Leu Asp Phe
                325                 330                 335

Ala Ser Asp Lys Pro Thr Thr Thr Pro Ala Pro Arg Pro Pro Thr Pro
            340                 345                 350

Ala Pro Thr Ile Ala Ser Gln Pro Leu Ser Leu Arg Pro Glu Ala Cys
        355                 360                 365

Arg Pro Ala Ala Gly Gly Ala Val His Thr Arg Gly Leu Asp Phe Ala
    370                 375                 380

Cys Asp Ile Tyr Ile Trp Ala Pro Leu Ala Gly Thr Cys Gly Val Leu
385                 390                 395                 400

Leu Leu Ser Leu Val Ile Thr Leu Tyr Cys Asn His Arg Asn Arg Ser
                405                 410                 415

Lys Arg Ser Arg Gly Gly His Ser Asp Tyr Met Asn Met Thr Pro Arg
            420                 425                 430

Arg Pro Gly Pro Thr Arg Lys His Tyr Gln Pro Tyr Ala Pro Pro Arg
        435                 440                 445

Asp Phe Ala Ala Tyr Arg Ser Arg Val Lys Phe Ser Arg Ser Ala Asp
    450                 455                 460

Ala Pro Ala Tyr Gln Gln Gly Gln Asn Gln Leu Tyr Asn Glu Leu Asn
465                 470                 475                 480

Leu Gly Arg Arg Glu Glu Tyr Asp Val Leu Asp Lys Arg Arg Gly Arg
                485                 490                 495

Asp Pro Glu Met Gly Gly Lys Pro Arg Arg Lys Asn Pro Gln Glu Gly
            500                 505                 510

Leu Tyr Asn Glu Leu Gln Lys Asp Lys Met Ala Glu Ala Tyr Ser Glu
        515                 520                 525

Ile Gly Met Lys Gly Glu Arg Arg Arg Gly Lys Gly His Asp Gly Leu
    530                 535                 540

Tyr Gln Gly Leu Ser Thr Ala Thr Lys Asp Thr Tyr Asp Ala Leu His
545                 550                 555                 560

Met Gln Ala Leu Pro Pro Arg
                565

<210> SEQ ID NO 59
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln

-continued

```
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Lys Pro Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Lys Pro Thr Thr Thr Pro Ala Pro Arg Pro Pro Thr
    290                 295                 300

Pro Ala Pro Thr Ile Ala Ser Gln Pro Leu Ser Leu Arg Pro Glu Ala
305                 310                 315                 320

Ser Arg Pro Ala Ala Gly Gly Ala Val His Thr Arg Gly Leu Asp Phe
                325                 330                 335

Ala Ser Asp Lys Pro Thr Thr Thr Pro Ala Pro Arg Pro Pro Thr Pro
            340                 345                 350

Ala Pro Thr Ile Ala Ser Gln Pro Leu Ser Leu Arg Pro Glu Ala Ser
        355                 360                 365

Arg Pro Ala Ala Gly Gly Ala Val His Thr Arg Gly Leu Asp Phe Ala
    370                 375                 380

Ser Asp Ile Tyr Ile Trp Ala Pro Leu Ala Gly Thr Cys Gly Val Leu
385                 390                 395                 400

Leu Leu Ser Leu Val Ile Thr Leu Tyr Cys Asn His Arg Asn Arg Ser
                405                 410                 415

Lys Arg Ser Arg Gly Gly His Ser Asp Tyr Met Asn Met Thr Pro Arg
            420                 425                 430

Arg Pro Gly Pro Thr Arg Lys His Tyr Gln Pro Tyr Ala Pro Pro Arg
        435                 440                 445

Asp Phe Ala Ala Tyr Arg Ser Arg Val Lys Phe Ser Arg Ser Ala Asp
    450                 455                 460

Ala Pro Ala Tyr Gln Gln Gly Gln Asn Gln Leu Tyr Asn Glu Leu Asn
465                 470                 475                 480

Leu Gly Arg Arg Glu Glu Tyr Asp Val Leu Asp Lys Arg Arg Gly Arg
                485                 490                 495
```

```
Asp Pro Glu Met Gly Gly Lys Pro Arg Arg Lys Asn Pro Gln Glu Gly
            500                 505                 510

Leu Tyr Asn Glu Leu Gln Lys Asp Lys Met Ala Glu Ala Tyr Ser Glu
        515                 520                 525

Ile Gly Met Lys Gly Glu Arg Arg Arg Gly Lys Gly His Asp Gly Leu
    530                 535                 540

Tyr Gln Gly Leu Ser Thr Ala Thr Lys Asp Thr Tyr Asp Ala Leu His
545                 550                 555                 560

Met Gln Ala Leu Pro Pro Arg
                565


<210> SEQ ID NO 60
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Lys Pro Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Ser Arg Pro Ala Ala Gly Gly Ala Val His Thr Arg Gly Leu Asp
```

275 280 285

Phe Ala Ser Asp Lys Pro Thr Thr Thr Pro Ala Pro Arg Pro Pro Thr
290 295 300

Pro Ala Pro Thr Ile Ala Ser Gln Pro Leu Ser Leu Arg Pro Glu Ala
305 310 315 320

Ser Arg Pro Ala Ala Gly Gly Ala Val His Thr Arg Gly Leu Asp Phe
325 330 335

Ala Ser Asp Lys Pro Thr Thr Thr Pro Ala Pro Arg Pro Pro Thr Pro
340 345 350

Ala Pro Thr Ile Ala Ser Gln Pro Leu Ser Leu Arg Pro Glu Ala Ser
355 360 365

Arg Pro Ala Ala Gly Gly Ala Val His Thr Arg Gly Leu Asp Phe Ala
370 375 380

Ser Asp Lys Pro Thr Thr Thr Pro Ala Pro Arg Pro Pro Thr Pro Ala
385 390 395 400

Pro Thr Ile Ala Ser Gln Pro Leu Ser Leu Arg Pro Glu Ala Cys Arg
405 410 415

Pro Ala Ala Gly Gly Ala Val His Thr Arg Gly Leu Asp Phe Ala Cys
420 425 430

Asp Ile Tyr Ile Trp Ala Pro Leu Ala Gly Thr Cys Gly Val Leu Leu
435 440 445

Leu Ser Leu Val Ile Thr Leu Tyr Cys Asn His Arg Asn Arg Ser Lys
450 455 460

Arg Ser Arg Gly Gly His Ser Asp Tyr Met Asn Met Thr Pro Arg Arg
465 470 475 480

Pro Gly Pro Thr Arg Lys His Tyr Gln Pro Tyr Ala Pro Pro Arg Asp
485 490 495

Phe Ala Ala Tyr Arg Ser Arg Val Lys Phe Ser Arg Ser Ala Asp Ala
500 505 510

Pro Ala Tyr Gln Gln Gly Gln Asn Gln Leu Tyr Asn Glu Leu Asn Leu
515 520 525

Gly Arg Arg Glu Glu Tyr Asp Val Leu Asp Lys Arg Arg Gly Arg Asp
530 535 540

Pro Glu Met Gly Gly Lys Pro Arg Arg Lys Asn Pro Gln Glu Gly Leu
545 550 555 560

Tyr Asn Glu Leu Gln Lys Asp Lys Met Ala Glu Ala Tyr Ser Glu Ile
565 570 575

Gly Met Lys Gly Glu Arg Arg Arg Gly Lys Gly His Asp Gly Leu Tyr
580 585 590

Gln Gly Leu Ser Thr Ala Thr Lys Asp Thr Tyr Asp Ala Leu His Met
595 600 605

Gln Ala Leu Pro Pro Arg
610

<210> SEQ ID NO 61
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asp Asn Tyr
20 25 30

Gly Ile Ser Phe Met Asn Trp Phe Gln Gln Lys Pro Gly Lys Ala Pro
35 40 45

Lys Leu Leu Ile Tyr Ala Ala Ser Asn Gln Gly Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys
100 105 110

<210> SEQ ID NO 62
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Asn Met His Trp Val Arg Gln Ala Pro Gly Gln Gly Leu Glu Trp Ile
35 40 45

Gly Tyr Ile Tyr Pro Tyr Asn Gly Gly Thr Gly Tyr Asn Gln Lys Phe
50 55 60

Lys Ser Lys Ala Thr Ile Thr Ala Asp Glu Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Gly Arg Pro Ala Met Asp Tyr Trp Gly Gln Gly Thr Leu Val
100 105 110

Thr Val Ser Ser
115

<210> SEQ ID NO 63
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asp Asn Tyr
20 25 30

Gly Ile Ser Phe Met Asn Trp Phe Gln Gln Lys Pro Gly Lys Ala Pro
35 40 45

Lys Leu Leu Ile Tyr Ala Ala Ser Asn Gln Gly Ser Gly Val Pro Ser
50 55 60

Arg Phe Ser Gly Ser Gly Ser Gly Thr Asp Phe Thr Leu Thr Ile Ser
65 70 75 80

-continued

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys Gly
100 105 110

Gly Gly Gly Ser Gly Gly Gly Gly Ser Gly Gly Gly Gly Ser Gln Val
115 120 125

Gln Leu Val Gln Ser Gly Ala Glu Val Lys Lys Pro Gly Ser Ser Val
130 135 140

Lys Val Ser Cys Lys Ala Ser Gly Tyr Thr Phe Thr Asp Tyr Asn Met
145 150 155 160

His Trp Val Arg Gln Ala Pro Gly Gln Gly Leu Glu Trp Ile Gly Tyr
165 170 175

Ile Tyr Pro Tyr Asn Gly Gly Thr Gly Tyr Asn Gln Lys Phe Lys Ser
180 185 190

Lys Ala Thr Ile Thr Ala Asp Glu Ser Thr Asn Thr Ala Tyr Met Glu
195 200 205

Leu Ser Ser Leu Arg Ser Glu Asp Thr Ala Val Tyr Tyr Cys Ala Arg
210 215 220

Gly Arg Pro Ala Met Asp Tyr Trp Gly Gln Gly Thr Leu Val Thr Val
225 230 235 240

Ser Ser

<210> SEQ ID NO 64
<211> LENGTH: 471
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asp Asn Tyr
20 25 30

Gly Ile Ser Phe Met Asn Trp Phe Gln Gln Lys Pro Gly Lys Ala Pro
35 40 45

Lys Leu Leu Ile Tyr Ala Ala Ser Asn Gln Gly Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys Gly
100 105 110

Gly Gly Gly Ser Gly Gly Gly Gly Ser Gly Gly Gly Gly Ser Gln Val
115 120 125

Gln Leu Val Gln Ser Gly Ala Glu Val Lys Lys Pro Gly Ser Ser Val
130 135 140

Lys Val Ser Cys Lys Ala Ser Gly Tyr Thr Phe Thr Asp Tyr Asn Met
145 150 155 160

His Trp Val Arg Gln Ala Pro Gly Gln Gly Leu Glu Trp Ile Gly Tyr
165 170 175

Ile Tyr Pro Tyr Asn Gly Gly Thr Gly Tyr Asn Gln Lys Phe Lys Ser
180 185 190

```
Lys Ala Thr Ile Thr Ala Asp Glu Ser Thr Asn Thr Ala Tyr Met Glu
        195                 200                 205

Leu Ser Ser Leu Arg Ser Glu Asp Thr Ala Val Tyr Tyr Cys Ala Arg
    210                 215                 220

Gly Arg Pro Ala Met Asp Tyr Trp Gly Gln Gly Thr Leu Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470


<210> SEQ ID NO 65
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80
```

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys Gly
100 105 110

Gly Gly Gly Ser Gly Gly Gly Gly Ser Gly Gly Gly Gly Ser Gln Val
115 120 125

Gln Leu Val Gln Ser Gly Ala Glu Val Lys Lys Pro Gly Ser Ser Val
130 135 140

Lys Val Ser Cys Lys Ala Ser Gly Tyr Thr Phe Thr Asp Tyr Asn Met
145 150 155 160

His Trp Val Arg Gln Ala Pro Gly Gln Gly Leu Glu Trp Ile Gly Tyr
165 170 175

Ile Tyr Pro Tyr Asn Gly Gly Thr Gly Tyr Asn Gln Lys Phe Lys Ser
180 185 190

Lys Ala Thr Ile Thr Ala Asp Glu Ser Thr Asn Thr Ala Tyr Met Glu
195 200 205

Leu Ser Ser Leu Arg Ser Glu Asp Thr Ala Val Tyr Tyr Cys Ala Arg
210 215 220

Gly Arg Pro Ala Met Asp Tyr Trp Gly Gln Gly Thr Leu Val Thr Val
225 230 235 240

Ser Ser Lys Pro Thr Thr Thr Pro Ala Pro Arg Pro Pro Thr Pro Ala
245 250 255

Pro Thr Ile Ala Ser Gln Pro Leu Ser Leu Arg Pro Glu Ala Ser Arg
260 265 270

Pro Ala Ala Gly Gly Ala Val His Thr Arg Gly Leu Asp Phe Ala Ser
275 280 285

Asp Lys Pro Thr Thr Thr Pro Ala Pro Arg Pro Pro Thr Pro Ala Pro
290 295 300

Thr Ile Ala Ser Gln Pro Leu Ser Leu Arg Pro Glu Ala Cys Arg Pro
305 310 315 320

Ala Ala Gly Gly Ala Val His Thr Arg Gly Leu Asp Phe Ala Cys Asp
325 330 335

Ile Tyr Ile Trp Ala Pro Leu Ala Gly Thr Cys Gly Val Leu Leu Leu
340 345 350

Ser Leu Val Ile Thr Leu Tyr Cys Asn His Arg Asn Lys Arg Gly Arg
355 360 365

Lys Lys Leu Leu Tyr Ile Phe Lys Gln Pro Phe Met Arg Pro Val Gln
370 375 380

Thr Thr Gln Glu Glu Asp Gly Cys Ser Cys Arg Phe Pro Glu Glu Glu
385 390 395 400

Glu Gly Gly Cys Glu Leu Arg Val Lys Phe Ser Arg Ser Ala Asp Ala
405 410 415

Pro Ala Tyr Gln Gln Gly Gln Asn Gln Leu Tyr Asn Glu Leu Asn Leu
420 425 430

Gly Arg Arg Glu Glu Tyr Asp Val Leu Asp Lys Arg Arg Gly Arg Asp
435 440 445

Pro Glu Met Gly Gly Lys Pro Arg Arg Lys Asn Pro Gln Glu Gly Leu
450 455 460

Tyr Asn Glu Leu Gln Lys Asp Lys Met Ala Glu Ala Tyr Ser Glu Ile
465 470 475 480

Gly Met Lys Gly Glu Arg Arg Arg Gly Lys Gly His Asp Gly Leu Tyr
485 490 495

Gln Gly Leu Ser Thr Ala Thr Lys Asp Thr Tyr Asp Ala Leu His Met
500 505 510

Gln Ala Leu Pro Pro Arg
515

<210> SEQ ID NO 66
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asp Asn Tyr
20 25 30

Gly Ile Ser Phe Met Asn Trp Phe Gln Gln Lys Pro Gly Lys Ala Pro
35 40 45

Lys Leu Leu Ile Tyr Ala Ala Ser Asn Gln Gly Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys Gly
100 105 110

Gly Gly Gly Ser Gly Gly Gly Gly Ser Gly Gly Gly Gly Ser Gln Val
115 120 125

Gln Leu Val Gln Ser Gly Ala Glu Val Lys Lys Pro Gly Ser Ser Val
130 135 140

Lys Val Ser Cys Lys Ala Ser Gly Tyr Thr Phe Thr Asp Tyr Asn Met
145 150 155 160

His Trp Val Arg Gln Ala Pro Gly Gln Gly Leu Glu Trp Ile Gly Tyr
165 170 175

Ile Tyr Pro Tyr Asn Gly Gly Thr Gly Tyr Asn Gln Lys Phe Lys Ser
180 185 190

Lys Ala Thr Ile Thr Ala Asp Glu Ser Thr Asn Thr Ala Tyr Met Glu
195 200 205

Leu Ser Ser Leu Arg Ser Glu Asp Thr Ala Val Tyr Tyr Cys Ala Arg
210 215 220

Gly Arg Pro Ala Met Asp Tyr Trp Gly Gln Gly Thr Leu Val Thr Val
225 230 235 240

Ser Ser Lys Pro Thr Thr Thr Pro Ala Pro Arg Pro Pro Thr Pro Ala
245 250 255

Pro Thr Ile Ala Ser Gln Pro Leu Ser Leu Arg Pro Glu Ala Ser Arg
260 265 270

Pro Ala Ala Gly Gly Ala Val His Thr Arg Gly Leu Asp Phe Ala Ser
275 280 285

Asp Lys Pro Thr Thr Thr Pro Ala Pro Arg Pro Pro Thr Pro Ala Pro
290 295 300

Thr Ile Ala Ser Gln Pro Leu Ser Leu Arg Pro Glu Ala Ser Arg Pro
305 310 315 320

Ala Ala Gly Gly Ala Val His Thr Arg Gly Leu Asp Phe Ala Ser Asp
325 330 335

Lys Pro Thr Thr Thr Pro Ala Pro Arg Pro Pro Thr Pro Ala Pro Thr
340 345 350

Ile Ala Ser Gln Pro Leu Ser Leu Arg Pro Glu Ala Cys Arg Pro Ala
355 360 365

Ala Gly Gly Ala Val His Thr Arg Gly Leu Asp Phe Ala Cys Asp Ile
370 375 380

Tyr Ile Trp Ala Pro Leu Ala Gly Thr Cys Gly Val Leu Leu Leu Ser
385 390 395 400

Leu Val Ile Thr Leu Tyr Cys Asn His Arg Asn Lys Arg Gly Arg Lys
405 410 415

Lys Leu Leu Tyr Ile Phe Lys Gln Pro Phe Met Arg Pro Val Gln Thr
420 425 430

Thr Gln Glu Glu Asp Gly Cys Ser Cys Arg Phe Pro Glu Glu Glu Glu
435 440 445

Gly Gly Cys Glu Leu Arg Val Lys Phe Ser Arg Ser Ala Asp Ala Pro
450 455 460

Ala Tyr Gln Gln Gly Gln Asn Gln Leu Tyr Asn Glu Leu Asn Leu Gly
465 470 475 480

Arg Arg Glu Glu Tyr Asp Val Leu Asp Lys Arg Arg Gly Arg Asp Pro
485 490 495

Glu Met Gly Gly Lys Pro Arg Arg Lys Asn Pro Gln Glu Gly Leu Tyr
500 505 510

Asn Glu Leu Gln Lys Asp Lys Met Ala Glu Ala Tyr Ser Glu Ile Gly
515 520 525

Met Lys Gly Glu Arg Arg Arg Gly Lys Gly His Asp Gly Leu Tyr Gln
530 535 540

Gly Leu Ser Thr Ala Thr Lys Asp Thr Tyr Asp Ala Leu His Met Gln
545 550 555 560

Ala Leu Pro Pro Arg
565

<210> SEQ ID NO 67
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asp Asn Tyr
20 25 30

Gly Ile Ser Phe Met Asn Trp Phe Gln Gln Lys Pro Gly Lys Ala Pro
35 40 45

Lys Leu Leu Ile Tyr Ala Ala Ser Asn Gln Gly Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys Gly
100 105 110

Gly Gly Gly Ser Gly Gly Gly Gly Ser Gly Gly Gly Gly Ser Gln Val

```
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Asp Tyr Asn Met
145                 150                 155                 160

His Trp Val Arg Gln Ala Pro Gly Gln Gly Leu Glu Trp Ile Gly Tyr
                165                 170                 175

Ile Tyr Pro Tyr Asn Gly Gly Thr Gly Tyr Asn Gln Lys Phe Lys Ser
            180                 185                 190

Lys Ala Thr Ile Thr Ala Asp Glu Ser Thr Asn Thr Ala Tyr Met Glu
        195                 200                 205

Leu Ser Ser Leu Arg Ser Glu Asp Thr Ala Val Tyr Tyr Cys Ala Arg
    210                 215                 220

Gly Arg Pro Ala Met Asp Tyr Trp Gly Gln Gly Thr Leu Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Ser Arg Pro Ala
        355                 360                 365

Ala Gly Gly Ala Val His Thr Arg Gly Leu Asp Phe Ala Ser Asp Ile
    370                 375                 380

Tyr Ile Trp Ala Pro Leu Ala Gly Thr Cys Gly Val Leu Leu Leu Ser
385                 390                 395                 400

Leu Val Ile Thr Leu Tyr Cys Asn His Arg Asn Lys Arg Gly Arg Lys
                405                 410                 415

Lys Leu Leu Tyr Ile Phe Lys Gln Pro Phe Met Arg Pro Val Gln Thr
            420                 425                 430

Thr Gln Glu Glu Asp Gly Cys Ser Cys Arg Phe Pro Glu Glu Glu Glu
        435                 440                 445

Gly Gly Cys Glu Leu Arg Val Lys Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Arg Arg Lys Asn Pro Gln Glu Gly Leu Tyr
            500                 505                 510

Asn Glu Leu Gln Lys Asp Lys Met Ala Glu Ala Tyr Ser Glu Ile Gly
        515                 520                 525

Met Lys Gly Glu Arg Arg Arg Gly Lys Gly His Asp Gly Leu Tyr Gln
    530                 535                 540
```

```
Gly Leu Ser Thr Ala Thr Lys Asp Thr Tyr Asp Ala Leu His Met Gln
545                 550                 555                 560

Ala Leu Pro Pro Arg
                565


<210> SEQ ID NO 68
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys Gly
            100                 105                 110

Gly Gly Gly Ser Gly Gly Gly Gly Ser Gly Gly Gly Gly Ser Gln Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Asp Tyr Asn Met
145                 150                 155                 160

His Trp Val Arg Gln Ala Pro Gly Gln Gly Leu Glu Trp Ile Gly Tyr
                165                 170                 175

Ile Tyr Pro Tyr Asn Gly Gly Thr Gly Tyr Asn Gln Lys Phe Lys Ser
            180                 185                 190

Lys Ala Thr Ile Thr Ala Asp Glu Ser Thr Asn Thr Ala Tyr Met Glu
        195                 200                 205

Leu Ser Ser Leu Arg Ser Glu Asp Thr Ala Val Tyr Tyr Cys Ala Arg
    210                 215                 220

Gly Arg Pro Ala Met Asp Tyr Trp Gly Gln Gly Thr Leu Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
```

```
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Ser Arg Pro Ala
        355                 360                 365

Ala Gly Gly Ala Val His Thr Arg Gly Leu Asp Phe Ala Ser Asp Lys
    370                 375                 380

Pro Thr Thr Thr Pro Ala Pro Arg Pro Pro Thr Pro Ala Pro Thr Ile
385                 390                 395                 400

Ala Ser Gln Pro Leu Ser Leu Arg Pro Glu Ala Cys Arg Pro Ala Ala
            405                 410                 415

Gly Gly Ala Val His Thr Arg Gly Leu Asp Phe Ala Cys Asp Ile Tyr
            420                 425                 430

Ile Trp Ala Pro Leu Ala Gly Thr Cys Gly Val Leu Leu Leu Ser Leu
        435                 440                 445

Val Ile Thr Leu Tyr Cys Asn His Arg Asn Lys Arg Gly Arg Lys Lys
    450                 455                 460

Leu Leu Tyr Ile Phe Lys Gln Pro Phe Met Arg Pro Val Gln Thr Thr
465                 470                 475                 480

Gln Glu Glu Asp Gly Cys Ser Cys Arg Phe Pro Glu Glu Glu Glu Gly
            485                 490                 495

Gly Cys Glu Leu Arg Val Lys Phe Ser Arg Ser Ala Asp Ala Pro Ala
            500                 505                 510

Tyr Gln Gln Gly Gln Asn Gln Leu Tyr Asn Glu Leu Asn Leu Gly Arg
        515                 520                 525

Arg Glu Glu Tyr Asp Val Leu Asp Lys Arg Arg Gly Arg Asp Pro Glu
    530                 535                 540

Met Gly Gly Lys Pro Arg Arg Lys Asn Pro Gln Glu Gly Leu Tyr Asn
545                 550                 555                 560

Glu Leu Gln Lys Asp Lys Met Ala Glu Ala Tyr Ser Glu Ile Gly Met
            565                 570                 575

Lys Gly Glu Arg Arg Arg Gly Lys Gly His Asp Gly Leu Tyr Gln Gly
            580                 585                 590

Leu Ser Thr Ala Thr Lys Asp Thr Tyr Asp Ala Leu His Met Gln Ala
        595                 600                 605

Leu Pro Pro Arg
    610


<210> SEQ ID NO 69
<211> LENGTH: 142
<212> TYPE: PRT
<213> ORGANISM: Homo sapiens

<400> SEQUENCE: 69

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80
```

Ser Ile Ile Pro Glu Asp Thr Phe Phe Pro Ser Pro Glu Ser Ser Cys
85 90 95

Asp Val Lys Leu Val Glu Lys Ser Phe Glu Thr Asp Thr Asn Leu Asn
100 105 110

Phe Gln Asn Leu Ser Val Ile Gly Phe Arg Ile Leu Leu Leu Lys Val
115 120 125

Ala Gly Phe Asn Leu Leu Met Thr Leu Arg Leu Trp Ser Ser
130 135 140

<210> SEQ ID NO 70
<211> LENGTH: 117
<212> TYPE: PRT
<213> ORGANISM: Homo sapiens

<400> SEQUENCE: 70

Pro Asn Ile Gln Asn Pro Asp Pro Ala Val Tyr Gln Leu Arg Asp Ser
1 5 10 15

Lys Ser Ser Asp Lys Ser Val Cys Leu Phe Thr Asp Phe Asp Ser Gln
20 25 30

Thr Asn Val Ser Gln Ser Lys Asp Ser Asp Val Tyr Ile Thr Asp Lys
35 40 45

Thr Val Leu Asp Met Arg Ser Met Asp Phe Lys Ser Asn Ser Ala Val
50 55 60

Ala Trp Ser Asn Lys Ser Asp Phe Ala Cys Ala Asn Ala Phe Asn Asn
65 70 75 80

Ser Ile Ile Pro Glu Asp Thr Phe Phe Pro Ser Pro Glu Ser Ser Cys
85 90 95

Asp Val Lys Leu Val Glu Lys Ser Phe Glu Thr Asp Thr Asn Leu Asn
100 105 110

Phe Gln Asn Leu Ser
115

<210> SEQ ID NO 71
<211> LENGTH: 20
<212> TYPE: PRT
<213> ORGANISM: Homo sapiens

<400> SEQUENCE: 71

Val Ile Gly Phe Arg Ile Leu Leu Leu Lys Val Ala Gly Phe Asn Leu
1 5 10 15

Leu Met Thr Leu
20

<210> SEQ ID NO 72
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Cys Asp Val Lys Leu Val Glu Lys Ser Phe Glu Thr Asp Thr Asn Leu
1 5 10 15

Asn Phe Gln Asn Leu Ser
20

<210> SEQ ID NO 73
<211> LENGTH: 22
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 73

Ser Asp Val Lys Leu Val Glu Lys Ser Phe Glu Thr Asp Thr Asn Leu
1 5 10 15

Asn Phe Gln Asn Leu Ser
20

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

Cys Asp Val Lys Leu Val Glu Lys Ser Phe Glu Thr Asp Thr Asn Leu
1 5 10 15

Asn Phe Gln Asn Leu Ser Gly Gly Gly Gly Ser Gly Gly Gly Gly Ser
20 25 30

Gly Gly Gly Gly Ser
35

<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 75

Gly Gly Gly Gly Ser Gly Gly Gly Gly Ser Gly Gly Gly Gly Ser Cys
1 5 10 15

Asp Val Lys Leu Val Glu Lys Ser Phe Glu Thr Asp Thr Asn Leu Asn
20 25 30

Phe Gln Asn Leu Ser
35

<210> SEQ ID NO 76
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 76

Gly Ser Thr Ser Gly Ser Gly Lys Pro Gly Ser Gly Glu Gly Ser Thr
1 5 10 15

Lys Gly Cys Asp Val Lys Leu Val Glu Lys Ser Phe Glu Thr Asp Thr
20 25 30

Asn Leu Asn Phe Gln Asn Leu Ser
35 40

<210> SEQ ID NO 77
<211> LENGTH: 44
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 77

Ser Asp Val Lys Leu Val Glu Lys Ser Phe Glu Thr Asp Thr Asn Leu
1               5                   10                  15

Asn Phe Gln Asn Leu Ser Cys Asp Val Lys Leu Val Glu Lys Ser Phe
            20                  25                  30

Glu Thr Asp Thr Asn Leu Asn Phe Gln Asn Leu Ser
        35                  40


<210> SEQ ID NO 78
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ser Asp Val Lys Leu Val Glu Lys Ser Phe Glu Thr Asp Thr Asn Leu
1               5                   10                  15

Asn Phe Gln Asn Leu Ser Ser Asp Val Lys Leu Val Glu Lys Ser Phe
            20                  25                  30

Glu Thr Asp Thr Asn Leu Asn Phe Gln Asn Leu Ser Cys Asp Val Lys
        35                  40                  45

Leu Val Glu Lys Ser Phe Glu Thr Asp Thr Asn Leu Asn Phe Gln Asn
    50                  55                  60

Leu Ser
65


<210> SEQ ID NO 79
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ser Asp Val Lys Leu Val Glu Lys Ser Phe Glu Thr Asp Thr Asn Leu
1               5                   10                  15

Asn Phe Gln Asn Leu Ser Ser Asp Val Lys Leu Val Glu Lys Ser Phe
            20                  25                  30

Glu Thr Asp Thr Asn Leu Asn Phe Gln Asn Leu Ser Ser Asp Val Lys
        35                  40                  45

Leu Val Glu Lys Ser Phe Glu Thr Asp Thr Asn Leu Asn Phe Gln Asn
    50                  55                  60

Leu Ser Cys Asp Val Lys Leu Val Glu Lys Ser Phe Glu Thr Asp Thr
65                  70                  75                  80

Asn Leu Asn Phe Gln Asn Leu Ser
                85


<210> SEQ ID NO 80
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80
```

```
Cys Asp Val Lys Leu Val Glu Lys Ser Phe Glu Thr Asp Thr Asn Leu
1               5                   10                  15

Asn Phe Gln Asn Leu Ser Ser Asp Val Lys Leu Val Glu Lys Ser Phe
            20                  25                  30

Glu Thr Asp Thr Asn Leu Asn Phe Gln Asn Leu Ser
        35                  40
```

<210> SEQ ID NO 81
<211> LENGTH: 66
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

```
Cys Asp Val Lys Leu Val Glu Lys Ser Phe Glu Thr Asp Thr Asn Leu
1               5                   10                  15

Asn Phe Gln Asn Leu Ser Ser Asp Val Lys Leu Val Glu Lys Ser Phe
            20                  25                  30

Glu Thr Asp Thr Asn Leu Asn Phe Gln Asn Leu Ser Ser Asp Val Lys
        35                  40                  45

Leu Val Glu Lys Ser Phe Glu Thr Asp Thr Asn Leu Asn Phe Gln Asn
    50                  55                  60

Leu Ser
65
```

<210> SEQ ID NO 82
<211> LENGTH: 88
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Cys Asp Val Lys Leu Val Glu Lys Ser Phe Glu Thr Asp Thr Asn Leu
1               5                   10                  15

Asn Phe Gln Asn Leu Ser Ser Asp Val Lys Leu Val Glu Lys Ser Phe
            20                  25                  30

Glu Thr Asp Thr Asn Leu Asn Phe Gln Asn Leu Ser Ser Asp Val Lys
        35                  40                  45

Leu Val Glu Lys Ser Phe Glu Thr Asp Thr Asn Leu Asn Phe Gln Asn
    50                  55                  60

Leu Ser Ser Asp Val Lys Leu Val Glu Lys Ser Phe Glu Thr Asp Thr
65                  70                  75                  80

Asn Leu Asn Phe Gln Asn Leu Ser
                85
```

<210> SEQ ID NO 83
<211> LENGTH: 177
<212> TYPE: PRT
<213> ORGANISM: Homo sapiens

<400> SEQUENCE: 83

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30
```

```
Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe


<210> SEQ ID NO 84
<211> LENGTH: 150
<212> TYPE: PRT
<213> ORGANISM: Homo sapiens

<400> SEQUENCE: 84

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu
145                 150


<210> SEQ ID NO 85
<211> LENGTH: 21
<212> TYPE: PRT
<213> ORGANISM: Homo sapiens

<400> SEQUENCE: 85

Ile Leu Leu Gly Lys Ala Thr Leu Tyr Ala Val Leu Val Ser Ala Leu
1               5                   10                  15

Val Leu Met Ala Met
```

20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Cys Gly Phe Thr Ser Val Ser Tyr Gln Gln Gly Val Leu Ser Ala Thr
1 5 10 15

Ile Leu Tyr Glu
20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Ser Gly Phe Thr Ser Val Ser Tyr Gln Gln Gly Val Leu Ser Ala Thr
1 5 10 15

Ile Leu Tyr Glu
20

<210> SEQ ID NO 88
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 88

Cys Gly Phe Thr Ser Val Ser Tyr Gln Gln Gly Val Leu Ser Ala Thr
1 5 10 15

Ile Leu Tyr Glu Gly Gly Gly Gly Ser Gly Gly Gly Gly Ser Gly Gly
20 25 30

Gly Gly Ser
35

<210> SEQ ID NO 89
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 89

Gly Gly Gly Gly Ser Gly Gly Gly Gly Ser Gly Gly Gly Gly Ser Cys
1 5 10 15

Gly Phe Thr Ser Val Ser Tyr Gln Gln Gly Val Leu Ser Ala Thr Ile
20 25 30

Leu Tyr Glu
35

<210> SEQ ID NO 90
<211> LENGTH: 38

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 90

```
Gly Ser Thr Ser Gly Ser Gly Lys Pro Gly Ser Gly Glu Gly Ser Thr
1               5                   10                  15

Lys Gly Cys Gly Phe Thr Ser Val Ser Tyr Gln Gln Gly Val Leu Ser
            20                  25                  30

Ala Thr Ile Leu Tyr Glu
        35
```

<210> SEQ ID NO 91
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 91

```
Ser Gly Phe Thr Ser Val Ser Tyr Gln Gln Gly Val Leu Ser Ala Thr
1               5                   10                  15

Ile Leu Tyr Glu Cys Gly Phe Thr Ser Val Ser Tyr Gln Gln Gly Val
            20                  25                  30

Leu Ser Ala Thr Ile Leu Tyr Glu
        35                  40
```

<210> SEQ ID NO 92
<211> LENGTH: 60
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 92

```
Ser Gly Phe Thr Ser Val Ser Tyr Gln Gln Gly Val Leu Ser Ala Thr
1               5                   10                  15

Ile Leu Tyr Glu Ser Gly Phe Thr Ser Val Ser Tyr Gln Gln Gly Val
            20                  25                  30

Leu Ser Ala Thr Ile Leu Tyr Glu Cys Gly Phe Thr Ser Val Ser Tyr
        35                  40                  45

Gln Gln Gly Val Leu Ser Ala Thr Ile Leu Tyr Glu
    50                  55                  60
```

<210> SEQ ID NO 93
<211> LENGTH: 80
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 93

```
Ser Gly Phe Thr Ser Val Ser Tyr Gln Gln Gly Val Leu Ser Ala Thr
1               5                   10                  15

Ile Leu Tyr Glu Ser Gly Phe Thr Ser Val Ser Tyr Gln Gln Gly Val
            20                  25                  30

Leu Ser Ala Thr Ile Leu Tyr Glu Ser Gly Phe Thr Ser Val Ser Tyr
        35                  40                  45
```

Gln Gln Gly Val Leu Ser Ala Thr Ile Leu Tyr Glu Cys Gly Phe Thr
    50                  55                  60

Ser Val Ser Tyr Gln Gln Gly Val Leu Ser Ala Thr Ile Leu Tyr Glu
65                  70                  75                  80

<210> SEQ ID NO 94
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Cys Gly Phe Thr Ser Val Ser Tyr Gln Gln Gly Val Leu Ser Ala Thr
1               5                   10                  15

Ile Leu Tyr Glu Ser Gly Phe Thr Ser Val Ser Tyr Gln Gln Gly Val
            20                  25                  30

Leu Ser Ala Thr Ile Leu Tyr Glu
        35                  40

<210> SEQ ID NO 95
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Cys Gly Phe Thr Ser Val Ser Tyr Gln Gln Gly Val Leu Ser Ala Thr
1               5                   10                  15

Ile Leu Tyr Glu Ser Gly Phe Thr Ser Val Ser Tyr Gln Gln Gly Val
            20                  25                  30

Leu Ser Ala Thr Ile Leu Tyr Glu Ser Gly Phe Thr Ser Val Ser Tyr
        35                  40                  45

Gln Gln Gly Val Leu Ser Ala Thr Ile Leu Tyr Glu
    50                  55                  60

<210> SEQ ID NO 96
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Cys Gly Phe Thr Ser Val Ser Tyr Gln Gln Gly Val Leu Ser Ala Thr
1               5                   10                  15

Ile Leu Tyr Glu Ser Gly Phe Thr Ser Val Ser Tyr Gln Gln Gly Val
            20                  25                  30

Leu Ser Ala Thr Ile Leu Tyr Glu Ser Gly Phe Thr Ser Val Ser Tyr
        35                  40                  45

Gln Gln Gly Val Leu Ser Ala Thr Ile Leu Tyr Glu Ser Gly Phe Thr
    50                  55                  60

Ser Val Ser Tyr Gln Gln Gly Val Leu Ser Ala Thr Ile Leu Tyr Glu
65                  70                  75                  80

<210> SEQ ID NO 97
<211> LENGTH: 178

<212> TYPE: PRT
<213> ORGANISM: Homo sapiens

<400> SEQUENCE: 97

Asp Leu Lys Asn Val Phe Pro Pro Glu Val Ala Val Phe Glu Pro Ser
1 5 10 15

Glu Ala Glu Ile Ser His Thr Gln Lys Ala Thr Leu Val Cys Leu Ala
20 25 30

Thr Gly Phe Tyr Pro Asp His Val Glu Leu Ser Trp Trp Val Asn Gly
35 40 45

Lys Glu Val His Ser Gly Val Ser Thr Asp Pro Gln Pro Leu Lys Glu
50 55 60

Gln Pro Ala Leu Asn Asp Ser Arg Tyr Cys Leu Ser Ser Arg Leu Arg
65 70 75 80

Val Ser Ala Thr Phe Trp Gln Asn Pro Arg Asn His Phe Arg Cys Gln
85 90 95

Val Gln Phe Tyr Gly Leu Ser Glu Asn Asp Glu Trp Thr Gln Asp Arg
100 105 110

Ala Lys Pro Val Thr Gln Ile Val Ser Ala Glu Ala Trp Gly Arg Ala
115 120 125

Asp Cys Gly Phe Thr Ser Glu Ser Tyr Gln Gln Gly Val Leu Ser Ala
130 135 140

Thr Ile Leu Tyr Glu Ile Leu Leu Gly Lys Ala Thr Leu Tyr Ala Val
145 150 155 160

Leu Val Ser Ala Leu Val Leu Met Ala Met Val Lys Arg Lys Asp Ser
165 170 175

Arg Gly

<210> SEQ ID NO 98
<211> LENGTH: 144
<212> TYPE: PRT
<213> ORGANISM: Homo sapiens

<400> SEQUENCE: 98

Asp Leu Lys Asn Val Phe Pro Pro Glu Val Ala Val Phe Glu Pro Ser
1 5 10 15

Glu Ala Glu Ile Ser His Thr Gln Lys Ala Thr Leu Val Cys Leu Ala
20 25 30

Thr Gly Phe Tyr Pro Asp His Val Glu Leu Ser Trp Trp Val Asn Gly
35 40 45

Lys Glu Val His Ser Gly Val Ser Thr Asp Pro Gln Pro Leu Lys Glu
50 55 60

Gln Pro Ala Leu Asn Asp Ser Arg Tyr Cys Leu Ser Ser Arg Leu Arg
65 70 75 80

Val Ser Ala Thr Phe Trp Gln Asn Pro Arg Asn His Phe Arg Cys Gln
85 90 95

Val Gln Phe Tyr Gly Leu Ser Glu Asn Asp Glu Trp Thr Gln Asp Arg
100 105 110

Ala Lys Pro Val Thr Gln Ile Val Ser Ala Glu Ala Trp Gly Arg Ala
115 120 125

Asp Cys Gly Phe Thr Ser Glu Ser Tyr Gln Gln Gly Val Leu Ser Ala
130 135 140

<210> SEQ ID NO 99
<211> LENGTH: 173
<212> TYPE: PRT

<213> ORGANISM: Homo sapiens

<400> SEQUENCE: 99

Asp Lys Gln Leu Asp Ala Asp Val Ser Pro Lys Pro Thr Ile Phe Leu
1 5 10 15

Pro Ser Ile Ala Glu Thr Lys Leu Gln Lys Ala Gly Thr Tyr Leu Cys
20 25 30

Leu Leu Glu Lys Phe Phe Pro Asp Val Ile Lys Ile His Trp Gln Glu
35 40 45

Lys Lys Ser Asn Thr Ile Leu Gly Ser Gln Glu Gly Asn Thr Met Lys
50 55 60

Thr Asn Asp Thr Tyr Met Lys Phe Ser Trp Leu Thr Val Pro Glu Lys
65 70 75 80

Ser Leu Asp Lys Glu His Arg Cys Ile Val Arg His Glu Asn Asn Lys
85 90 95

Asn Gly Val Asp Gln Glu Ile Ile Phe Pro Pro Ile Lys Thr Asp Val
100 105 110

Ile Thr Met Asp Pro Lys Asp Asn Cys Ser Lys Asp Ala Asn Asp Thr
115 120 125

Leu Leu Leu Gln Leu Thr Asn Thr Ser Ala Tyr Tyr Met Tyr Leu Leu
130 135 140

Leu Leu Leu Lys Ser Val Val Tyr Phe Ala Ile Ile Thr Cys Cys Leu
145 150 155 160

Leu Arg Arg Thr Ala Phe Cys Cys Asn Gly Glu Lys Ser
165 170

<210> SEQ ID NO 100
<211> LENGTH: 138
<212> TYPE: PRT
<213> ORGANISM: Homo sapiens

<400> SEQUENCE: 100

Asp Lys Gln Leu Asp Ala Asp Val Ser Pro Lys Pro Thr Ile Phe Leu
1 5 10 15

Pro Ser Ile Ala Glu Thr Lys Leu Gln Lys Ala Gly Thr Tyr Leu Cys
20 25 30

Leu Leu Glu Lys Phe Phe Pro Asp Val Ile Lys Ile His Trp Gln Glu
35 40 45

Lys Lys Ser Asn Thr Ile Leu Gly Ser Gln Glu Gly Asn Thr Met Lys
50 55 60

Thr Asn Asp Thr Tyr Met Lys Phe Ser Trp Leu Thr Val Pro Glu Lys
65 70 75 80

Ser Leu Asp Lys Glu His Arg Cys Ile Val Arg His Glu Asn Asn Lys
85 90 95

Asn Gly Val Asp Gln Glu Ile Ile Phe Pro Pro Ile Lys Thr Asp Val
100 105 110

Ile Thr Met Asp Pro Lys Asp Asn Cys Ser Lys Asp Ala Asn Asp Thr
115 120 125

Leu Leu Leu Gln Leu Thr Asn Thr Ser Ala
130 135

<210> SEQ ID NO 101
<211> LENGTH: 23
<212> TYPE: PRT
<213> ORGANISM: Homo sapiens

<400> SEQUENCE: 101

```
Tyr Tyr Met Tyr Leu Leu Leu Leu Leu Lys Ser Val Val Tyr Phe Ala
1               5                   10                  15

Ile Ile Thr Cys Cys Leu Leu
            20
```

<210> SEQ ID NO 102
<211> LENGTH: 189
<212> TYPE: PRT
<213> ORGANISM: Homo sapiens

<400> SEQUENCE: 102

```
Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Ile Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Glu
65                  70                  75                  80

Ser Leu Asp Lys Glu His Arg Cys Ile Val Arg His Glu Asn Asn Lys
                85                  90                  95

Asn Gly Ile Asp Gln Glu Ile Ile Phe Pro Pro Ile Lys Thr Asp Val
            100                 105                 110

Thr Thr Val Asp Pro Lys Asp Ser Tyr Ser Lys Asp Ala Asn Asp Val
        115                 120                 125

Ile Thr Met Asp Pro Lys Asp Asn Trp Ser Lys Asp Ala Asn Asp Thr
    130                 135                 140

Leu Leu Leu Gln Leu Thr Asn Thr Ser Ala Tyr Tyr Met Tyr Leu Leu
145                 150                 155                 160

Leu Leu Leu Lys Ser Val Val Tyr Phe Ala Ile Ile Thr Cys Cys Leu
                165                 170                 175

Leu Gly Arg Thr Ala Phe Cys Cys Asn Gly Glu Lys Ser
            180                 185
```

<210> SEQ ID NO 103
<211> LENGTH: 156
<212> TYPE: PRT
<213> ORGANISM: Homo sapiens

<400> SEQUENCE: 103

```
Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Ile Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Glu
65                  70                  75                  80

Ser Leu Asp Lys Glu His Arg Cys Ile Val Arg His Glu Asn Asn Lys
                85                  90                  95

Asn Gly Ile Asp Gln Glu Ile Ile Phe Pro Pro Ile Lys Thr Asp Val
            100                 105                 110
```

Thr Thr Val Asp Pro Lys Asp Ser Tyr Ser Lys Asp Ala Asn Asp Val
115 120 125

Ile Thr Met Asp Pro Lys Asp Asn Trp Ser Lys Asp Ala Asn Asp Thr
130 135 140

Leu Leu Leu Gln Leu Thr Asn Thr Ser Ala Tyr Tyr
145 150 155

<210> SEQ ID NO 104
<211> LENGTH: 153
<212> TYPE: PRT
<213> ORGANISM: Homo sapiens

<400> SEQUENCE: 104

Ser Gln Pro His Thr Lys Pro Ser Val Phe Val Met Lys Asn Gly Thr
1 5 10 15

Asn Val Ala Cys Leu Val Lys Glu Phe Tyr Pro Lys Asp Ile Arg Ile
20 25 30

Asn Leu Val Ser Ser Lys Lys Ile Thr Glu Phe Asp Pro Ala Ile Val
35 40 45

Ile Ser Pro Ser Gly Lys Tyr Asn Ala Val Lys Leu Gly Lys Tyr Glu
50 55 60

Asp Ser Asn Ser Val Thr Cys Ser Val Gln His Asp Asn Lys Thr Val
65 70 75 80

His Ser Thr Asp Phe Glu Val Lys Thr Asp Ser Thr Asp His Val Lys
85 90 95

Pro Lys Glu Thr Glu Asn Thr Lys Gln Pro Ser Lys Ser Cys His Lys
100 105 110

Pro Lys Ala Ile Val His Thr Glu Lys Val Asn Met Met Ser Leu Thr
115 120 125

Val Leu Gly Leu Arg Met Leu Phe Ala Lys Thr Val Ala Val Asn Phe
130 135 140

Leu Leu Thr Ala Lys Leu Phe Phe Leu
145 150

<210> SEQ ID NO 105
<211> LENGTH: 129
<212> TYPE: PRT
<213> ORGANISM: Homo sapiens

<400> SEQUENCE: 105

Ser Gln Pro His Thr Lys Pro Ser Val Phe Val Met Lys Asn Gly Thr
1 5 10 15

Asn Val Ala Cys Leu Val Lys Glu Phe Tyr Pro Lys Asp Ile Arg Ile
20 25 30

Asn Leu Val Ser Ser Lys Lys Ile Thr Glu Phe Asp Pro Ala Ile Val
35 40 45

Ile Ser Pro Ser Gly Lys Tyr Asn Ala Val Lys Leu Gly Lys Tyr Glu
50 55 60

Asp Ser Asn Ser Val Thr Cys Ser Val Gln His Asp Asn Lys Thr Val
65 70 75 80

His Ser Thr Asp Phe Glu Val Lys Thr Asp Ser Thr Asp His Val Lys
85 90 95

Pro Lys Glu Thr Glu Asn Thr Lys Gln Pro Ser Lys Ser Cys His Lys
100 105 110

Pro Lys Ala Ile Val His Thr Glu Lys Val Asn Met Met Ser Leu Thr
115 120 125

Val

<210> SEQ ID NO 106
<211> LENGTH: 23
<212> TYPE: PRT
<213> ORGANISM: Homo sapiens

<400> SEQUENCE: 106

Leu Gly Leu Arg Met Leu Phe Ala Lys Thr Val Ala Val Asn Phe Leu
1               5                   10                  15

Leu Thr Ala Lys Leu Phe Phe
            20

<210> SEQ ID NO 107
<211> LENGTH: 705
<212> TYPE: DNA
<213> ORGANISM: Homo sapiens

<400> SEQUENCE: 107
atggccttac cagtgaccgc cttgctcctg ccgctggcct tgctgctcca cgccgccagg 60
ccgagccagt tccgggtgtc gccgctggat cggacctgga acctgggcga gacagtggag 120
ctgaagtgcc aggtgctgct gtccaacccg acgtcgggct gctcgtggct cttccagccg 180
cgcggcgccg ccgccagtcc caccttcctc ctatacctct cccaaaacaa gcccaaggcg 240
gccgaggggc tggacaccca gcggttctcg ggcaagaggt tgggggacac cttcgtcctc 300
accctgagcg acttccgccg agagaacgag ggctactatt tctgctcggc cctgagcaac 360
tccatcatgt acttcagcca cttcgtgccg gtcttcctgc cagcgaagcc caccacgacg 420
ccagcgccgc gaccaccaac accggcgccc accatcgcgt cgcagcccct gtccctgcgc 480
ccagaggcgt gccggccagc ggcggggggc gcagtgcaca cgagggggct ggacttcgcc 540
tgtgatatct acatctgggc gcccttggcc gggacttgtg gggtccttct cctgtcactg 600
gttatcaccc tttactgcaa ccacaggaac cgaagacgtg tttgcaaatg tccccggcct 660
gtggtcaaat cgggagacaa gcccagcctt tcggcgagat acgtc 705

<210> SEQ ID NO 108
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
aaacctacta ccactccagc cccaaggccc ccaaccccag caccgactat cgcatcacag 60
cctttgtcac tgcgtcctga agccagccgg ccagctgcag gggggggcgt ccacacaagg 120
ggactcgact ttgcgagtga t 141

<210> SEQ ID NO 109
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
aagcccacca ccacccctgc ccctagacct ccaaccccag cccctacaat cgccagccag 60
cccctgagcc tgaggcccga agcctgtaga cctgccgctg gcggagccgt gcacaccaga 120
ggcctggatt tcgcctgcga c 141

<210> SEQ ID NO 110
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110
aaacctacta caactcctgc cccccggcct cctacaccag ctcctactat cgcctcccag 60
ccactcagtc tcagacccga ggcttctagg ccagcggccg gaggcgcggt ccacacccgc 120
gggctggact ttgcatccga taagcccacc accacccctg ccccctagacc tccaacccca 180 gcccctacaa tcgccagcca gcccctgagc ctgaggcccg aagcctgtag acctgccgct 240
ggcggagccg tgcacaccag aggcctggat ttcgcctgcg ac 282

<210> SEQ ID NO 111
<211> LENGTH: 423
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111
aagcctacca ccacccccgc acctcgtcct ccaacccctg cacctacgat tgccagtcag 60
cctctttcac tgcggcctga ggccagcaga ccagctgccg gcggtgccgt ccatacaaga 120
ggactggact tcgcgtccga taaacctact accactccag ccccaaggcc cccaacccca 180
gcaccgacta tcgcatcaca gcctttgtca ctgcgtcctg aagccagccg gccagctgca 240 ggggggggccg tccacacaag gggactcgac tttgcgagtg ataagcccac caccacccct 300
gcccctagac ctccaacccc agcccctaca atcgccagcc agcccctgag cctgaggccc 360
gaagcctgta gacctgccgc tggcggagcc gtgcacacca gaggcctgga tttcgcctgc 420
gac 423

<210> SEQ ID NO 112
<211> LENGTH: 423
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112
aagcccacca ccacccctgc ccctagacct ccaaccccag cccctacaat cgccagccag 60
cccctgagcc tgaggcccga agcctgtaga cctgccgctg gcggagccgt gcacaccaga 120
ggcctggatt tcgcctgcga caagcctacc accacccccg cacctcgtcc tccaacccct 180
gcacctacga ttgccagtca gcctctttca ctgcggcctg aggccagcag accagctgcc 240
ggcggtgccg tccatacaag aggactggac ttcgcgtccg ataaacctac taccactcca 300
gccccaaggc ccccaacccc agcaccgact atcgcatcac agcctttgtc actgcgtcct 360
gaagccagcc ggccagctgc aggggggggcc gtccacacaa ggggactcga ctttgcgagt 420
gat 423

<210> SEQ ID NO 113
<211> LENGTH: 564
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 113
aagcctacca ccaccccgc acctcgtcct ccaacccctg cacctacgat tgccagtcag 60
cctctttcac tgcggcctga ggccagcaga ccagctgccg gcggtgccgt ccatacaaga 120
ggactggact tcgcgtccga taaacctact accactccag ccccaaggcc cccaacccca 180
gcaccgacta tcgcatcaca gcctttgtca ctgcgtcctg aagccagccg gccagctgca 240
gggggggccg tccacacaag ggactcgac tttgcgagtg ataaacctac tacaactcct 300
gccccccggc ctcctacacc agctcctact atcgcctccc agccactcag tctcagaccc 360
gaggcttcta ggccagcggc cggaggcgcg gtccacaccc gcgggctgga ctttgcatcc 420
gataagccca ccaccacccc tgcccctaga cctccaaccc cagcccctac aatcgccagc 480
cagcccctga gcctgaggcc cgaagcctgt agacctgccg ctggcggagc cgtgcacacc 540
agaggcctgg atttcgcctg cgac 564

<210> SEQ ID NO 114
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
ggcagcacct ccggcagcgg caagcctggc agcggcgagg gcagcaccaa gggc 54

<210> SEQ ID NO 115
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115 ggaagcgga 9

<210> SEQ ID NO 116
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
agtggcagcg gc 12

<210> SEQ ID NO 117
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
ggcggaggcg gaagcggagg cggaggctcc ggcggaggcg gaagc 45

<210> SEQ ID NO 118
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 118
ggcggaggcg gaagcggagg cggaggctcc ggcggaggcg gaagcaagcc caccaccacc 60
cctgccccta gacctccaac cccagcccct acaatcgcca gccagcccct gagcctgagg 120
cccgaagcct gtagacctgc cgctggcgga gccgtgcaca ccagaggcct ggatttcgcc 180
tgcgac 186

<210> SEQ ID NO 119
<211> LENGTH: 195
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 119
ggcagcacct ccggcagcgg caagcctggc agcggcgagg gcagcaccaa gggcaagccc 60
accaccaccc ctgcccctag acctccaacc ccagccccta caatcgccag ccagcccctg 120
agcctgaggc ccgaagcctg tagacctgcc gctggcggag ccgtgcacac cagaggcctg 180
gatttcgcct gcgac 195

<210> SEQ ID NO 120
<211> LENGTH: 249
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 120
ggcagcacct ccggcagcgg caagcctggc agcggcgagg gcagcaccaa gggcggcagc 60
acctccggca gcggcaagcc tggcagcggc gagggcagca ccaagggcaa gcccaccacc 120
acccctgccc ctagacctcc aaccccagcc cctacaatcg ccagccagcc cctgagcctg 180
aggcccgaag cctgtagacc tgccgctggc ggagccgtgc acaccagagg cctggatttc 240
gcctgcgac 249

<210> SEQ ID NO 121
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 121
ggcagcacct ccggcagcgg caagcctggc agcggcgagg gcagcaccaa gggcaaacct 60
actacaactc ctgccccccg gcctcctaca ccagctccta ctatcgcctc ccagccactc 120
agtctcagac ccgaggcttc taggccagcg gccggaggcg cggtccacac ccgcgggctg 180

```
gactttgcat ccgataagcc caccaccacc cctgccccta gacctccaac cccagcccct    240

acaatcgcca gccagcccct gagcctgagg cccgaagcct gtagacctgc cgctggcgga    300

gccgtgcaca ccagaggcct ggatttcgcc tgcgac                              336
```

<210> SEQ ID NO 122
<211> LENGTH: 666
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 122

```
aaggaggcat gccccacagg cctgtacaca cacagcggtg agtgctgcaa agcctgcaac     60

ctgggcgagg gtgtggccca gccttgtgga gccaaccaga ccgtgtgtga gccctgcctg    120

gacagcgtga cgttctccga cgtggtgagc gcgaccgagc cgtgcaagcc gtgcaccgag    180

tgcgtggggc tccagagcat gtcggcgccg tgcgtggagg ccgacgacgc cgtgtgccgc    240

tgcgcctacg gctactacca ggatgagacg actgggcgct gcgaggcgtg ccgcgtgtgc    300

gaggcgggct cgggcctcgt gttctcctgc caggacaagc agaacaccgt gtgcgaggag    360

tgccccgacg gcacgtattc cgacgaggcc aaccacgtgg acccgtgcct gccctgcacc    420

gtgtgcgagg acaccgagcg ccagctccgc gagtgcacac gctgggccga cgccgagtgc    480

gaggagatcc ctggccgttg gattacacgg tccacacccc cagagggctc ggacagcaca    540

gcccccagca cccaggagcc tgaggcacct ccagaacaag acctcatagc cagcacggtg    600

gcaggtgtgg tgaccacagt gatgggcagc tcccagcccg tggtgacccg aggcaccacc    660

gacaac                                                               666
```

<210> SEQ ID NO 123
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
aaggaggcat gccccacagg cctgtacaca cacagcggtg agtgctgcaa agcctgcaac     60

ctgggcgagg gtgtggccca gccttgtgga gccaaccaga ccgtgtgtga gccctgcctg    120

gacagcgtga cgttctccga cgtggtgagc gcgaccgagc cgtgcaagcc gtgcaccgag    180

tgcgtggggc tccagagcat gtcggcgccg tgcgtggagg ccgacgacgc cgtgtgccgc    240

tgcgcctacg gctactacca ggatgagacg actgggcgct gcgaggcgtg ccgcgtgtgc    300

gaggcgggct cgggcctcgt gttctcctgc caggacaagc agaacaccgt gtgcgaggag    360

tgccccgacg gcacgtattc cgacgaggcc aaccacgtgg acccgtgcct gccctgcacc    420

gtgtgcgagg acaccgagcg ccagctccgc gagtgcacac gctgggccga cgccgagtgc    480

gaggagatcc ctggccgttg gattacacgg tccacacccc cagagggctc ggacagcaca    540

gcccccagca cccaggagcc tgaggcacct ccagaacaag acctcatagc cagcacggtg    600

gcaggtgtgg tgaccacagt gatgggcagc tcccagcccg tggtgacccg aggcaccacc    660

gacaacaagg aggcatgccc cacaggcctg tacacacaca gcggtgagtg ctgcaaagcc    720

tgcaacctgg gcgagggtgt ggcccagcct tgtggagcca accagaccgt gtgtgagccc    780
```

tgcctggaca gcgtgacgtt ctccgacgtg gtgagcgcga ccgagccgtg caagccgtgc 840
accgagtgcg tggggctcca gagcatgtcg gcgccgtgcg tggaggccga cgacgccgtg 900
tgccgctgcg cctacggcta ctaccaggat gagacgactg ggcgctgcga ggcgtgccgc 960
gtgtgcgagg cgggctcggg cctcgtgttc tcctgccagg acaagcagaa caccgtgtgc 1020
gaggagtgcc ccgacggcac gtattccgac gaggccaacc acgtggaccc gtgcctgccc 1080
tgcaccgtgt gcgaggacac cgagcgccag ctccgcgagt gcacacgctg ggccgacgcc 1140
gagtgcgagg agatccctgg ccgttggatt acacggtcca cacccccaga gggctcggac 1200
agcacagccc ccagcaccca ggagcctgag gcacctccag aacaagacct catagccagc 1260
acggtggcag gtgtggtgac cacagtgatg ggcagctccc agcccgtggt gacccgaggc 1320
accaccgaca ac 1332

<210> SEQ ID NO 124
<211> LENGTH: 558
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124
gagccctgcc tggacagcgt gacgttctcc gacgtggtga gcgcgaccga gccgtgcaag 60
ccgtgcaccg agtgcgtggg gctccagagc atgtcggcgc cgtgcgtgga ggccgacgac 120
gccgtgtgcc gctgcgccta cggctactac caggatgaga cgactgggcg ctgcgaggcg 180
tgccgcgtgt gcgaggcggg ctcgggcctc gtgttctcct gccaggacaa gcagaacacc 240
gtgtgcgagg agtgccccga cggcacgtat tccgacgagg ccaaccacgt ggacccgtgc 300
ctgccctgca ccgtgtgcga ggacaccgag cgccagctcc gcgagtgcac acgctgggcc 360
gacgccgagt gcgaggagat ccctggccgt tggattacac ggtccacacc cccagagggc 420
tcggacagca cagcccccag cacccaggag cctgaggcac ctccagaaca agacctcata 480
gccagcacgg tggcaggtgt ggtgaccaca gtgatgggca gctcccagcc cgtggtgacc 540
cgaggcacca ccgacaac 558

<210> SEQ ID NO 125
<211> LENGTH: 1116
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125
gagccctgcc tggacagcgt gacgttctcc gacgtggtga gcgcgaccga gccgtgcaag 60
ccgtgcaccg agtgcgtggg gctccagagc atgtcggcgc cgtgcgtgga ggccgacgac 120
gccgtgtgcc gctgcgccta cggctactac caggatgaga cgactgggcg ctgcgaggcg 180
tgccgcgtgt gcgaggcggg ctcgggcctc gtgttctcct gccaggacaa gcagaacacc 240
gtgtgcgagg agtgccccga cggcacgtat tccgacgagg ccaaccacgt ggacccgtgc 300
ctgccctgca ccgtgtgcga ggacaccgag cgccagctcc gcgagtgcac acgctgggcc 360
gacgccgagt gcgaggagat ccctggccgt tggattacac ggtccacacc cccagagggc 420
tcggacagca cagcccccag cacccaggag cctgaggcac ctccagaaca agacctcata 480
gccagcacgg tggcaggtgt ggtgaccaca gtgatgggca gctcccagcc cgtggtgacc 540
cgaggcacca ccgacaacga gccctgcctg gacagcgtga cgttctccga cgtggtgagc 600
gcgaccgagc cgtgcaagcc gtgcaccgag tgcgtggggc tccagagcat gtcggcgccg 660
tgcgtggagg ccgacgacgc cgtgtgccgc tgcgcctacg gctactacca ggatgagacg 720
actgggcgct gcgaggcgtg ccgcgtgtgc gaggcgggct cgggcctcgt gttctcctgc 780
caggacaagc agaacaccgt gtgcgaggag tgccccgacg gcacgtattc cgacgaggcc 840
aaccacgtgg acccgtgcct gccctgcacc gtgtgcgagg acaccgagcg ccagctccgc 900
gagtgcacac gctgggccga cgccgagtgc gaggagatcc ctggccgttg gattacacgg 960
tccacacccc cagagggctc ggacagcaca gcccccagca cccaggagcc tgaggcacct 1020
ccagaacaag acctcatagc cagcacggtg gcaggtgtgg tgaccacagt gatgggcagc 1080
tcccagcccg tggtgacccg aggcaccacc gacaac 1116

<210> SEQ ID NO 126
<211> LENGTH: 429
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126
cgctgcgcct acggctacta ccaggatgag acgactgggc gctgcgaggc gtgccgcgtg 60
tgcgaggcgg gctcgggcct cgtgttctcc tgccaggaca agcagaacac cgtgtgcgag 120
gagtgccccg acggcacgta ttccgacgag gccaaccacg tggacccgtg cctgccctgc 180
accgtgtgcg aggacaccga gcgccagctc cgcgagtgca cacgctgggc cgacgccgag 240
tgcgaggaga tccctggccg ttggattaca cggtccacac ccccagaggg ctcggacagc 300
acagccccca gcacccagga gcctgaggca cctccagaac aagacctcat agccagcacg 360
gtggcaggtg tggtgaccac agtgatgggc agctcccagc ccgtggtgac ccgaggcacc 420
accgacaac 429

<210> SEQ ID NO 127
<211> LENGTH: 858
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127
cgctgcgcct acggctacta ccaggatgag acgactgggc gctgcgaggc gtgccgcgtg 60
tgcgaggcgg gctcgggcct cgtgttctcc tgccaggaca agcagaacac cgtgtgcgag 120
gagtgccccg acggcacgta ttccgacgag gccaaccacg tggacccgtg cctgccctgc 180
accgtgtgcg aggacaccga gcgccagctc cgcgagtgca cacgctgggc cgacgccgag 240
tgcgaggaga tccctggccg ttggattaca cggtccacac ccccagaggg ctcggacagc 300
acagccccca gcacccagga gcctgaggca cctccagaac aagacctcat agccagcacg 360
gtggcaggtg tggtgaccac agtgatgggc agctcccagc ccgtggtgac ccgaggcacc 420
accgacaacc gctgcgccta cggctactac caggatgaga cgactgggcg ctgcgaggcg 480
tgccgcgtgt gcgaggcggg ctcgggcctc gtgttctcct gccaggacaa gcagaacacc 540
gtgtgcgagg agtgccccga cggcacgtat tccgacgagg ccaaccacgt ggacccgtgc 600

```
ctgccctgca ccgtgtgcga ggacaccgag cgccagctcc gcgagtgcac acgctgggcc    660

gacgccgagt gcgaggagat ccctggccgt tggattacac ggtccacacc cccagagggc    720

tcggacagca cagcccccag cacccaggag cctgaggcac ctccagaaca agacctcata    780

gccagcacgg tggcaggtgt ggtgaccaca gtgatgggca gctcccagcc cgtggtgacc    840

cgaggcacca ccgacaac                                                  858


<210> SEQ ID NO 128
<211> LENGTH: 1287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

cgctgcgcct acggctacta ccaggatgag acgactgggc gctgcgaggc gtgccgcgtg     60

tgcgaggcgg gctcgggcct cgtgttctcc tgccaggaca agcagaacac cgtgtgcgag    120

gagtgccccg acggcacgta ttccgacgag gccaaccacg tggacccgtg cctgccctgc    180

accgtgtgcg aggacaccga gcgccagctc cgcgagtgca cacgctgggc cgacgccgag    240

tgcgaggaga tccctggccg ttggattaca cggtccacac ccccagaggg ctcggacagc    300

acagccccca gcacccagga gcctgaggca cctccagaac aagacctcat agccagcacg    360

gtggcaggtg tggtgaccac agtgatgggc agctcccagc ccgtggtgac ccgaggcacc    420

accgacaacc gctgcgccta cggctactac caggatgaga cgactgggcg ctgcgaggcg    480

tgccgcgtgt gcgaggcggg ctcgggcctc gtgttctcct gccaggacaa gcagaacacc    540

gtgtgcgagg agtgccccga cggcacgtat tccgacgagg ccaaccacgt ggacccgtgc    600

ctgccctgca ccgtgtgcga ggacaccgag cgccagctcc gcgagtgcac acgctgggcc    660

gacgccgagt gcgaggagat ccctggccgt tggattacac ggtccacacc cccagagggc    720

tcggacagca cagcccccag cacccaggag cctgaggcac ctccagaaca agacctcata    780

gccagcacgg tggcaggtgt ggtgaccaca gtgatgggca gctcccagcc cgtggtgacc    840

cgaggcacca ccgacaaccg ctgcgcctac ggctactacc aggatgagac gactgggcgc    900

tgcgaggcgt gccgcgtgtg cgaggcgggc tcgggcctcg tgttctcctg ccaggacaag    960

cagaacaccg tgtgcgagga gtgccccgac ggcacgtatt ccgacgaggc caaccacgtg   1020

gacccgtgcc tgccctgcac cgtgtgcgag gacaccgagc gccagctccg cgagtgcaca   1080

cgctgggccg acgccgagtg cgaggagatc cctggccgtt ggattacacg gtccacaccc   1140

ccagagggct cggacagcac agcccccagc acccaggagc ctgaggcacc tccagaacaa   1200

gacctcatag ccagcacggt ggcaggtgtg gtgaccacag tgatgggcag ctcccagccc   1260

gtggtgaccc gaggcaccac cgacaac                                       1287


<210> SEQ ID NO 129
<211> LENGTH: 1716
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

cgctgcgcct acggctacta ccaggatgag acgactgggc gctgcgaggc gtgccgcgtg     60

tgcgaggcgg gctcgggcct cgtgttctcc tgccaggaca agcagaacac cgtgtgcgag    120
```

-continued gagtgccccg acggcacgta ttccgacgag gccaaccacg tggacccgtg cctgccctgc 180
accgtgtgcg aggacaccga gcgccagctc cgcgagtgca cacgctgggc cgacgccgag 240
tgcgaggaga tccctggccg ttggattaca cggtccacac ccccagaggg ctcggacagc 300
acagccccca gcacccagga gcctgaggca cctccagaac aagacctcat agccagcacg 360
gtggcaggtg tggtgaccac agtgatgggc agctcccagc ccgtggtgac ccgaggcacc 420
accgacaacc gctgcgccta cggctactac caggatgaga cgactgggcg ctgcgaggcg 480
tgccgcgtgt gcgaggcggg ctcgggcctc gtgttctcct gccaggacaa gcagaacacc 540
gtgtgcgagg agtgccccga cggcacgtat tccgacgagg ccaaccacgt ggacccgtgc 600
ctgccctgca ccgtgtgcga ggacaccgag cgccagctcc gcgagtgcac acgctgggcc 660
gacgccgagt gcgaggagat ccctggccgt tggattacac ggtccacacc cccagagggc 720
tcggacagca cagcccccag cacccaggag cctgaggcac ctccagaaca agacctcata 780
gccagcacgg tggcaggtgt ggtgaccaca gtgatgggca gctcccagcc cgtggtgacc 840
cgaggcacca ccgacaaccg ctgcgcctac ggctactacc aggatgagac gactgggcgc 900
tgcgaggcgt gccgcgtgtg cgaggcgggc tcgggcctcg tgttctcctg ccaggacaag 960
cagaacaccg tgtgcgagga gtgccccgac ggcacgtatt ccgacgaggc caaccacgtg 1020
gacccgtgcc tgccctgcac cgtgtgcgag gacaccgagc gccagctccg cgagtgcaca 1080
cgctgggccg acgccgagtg cgaggagatc cctggccgtt ggattacacg gtccacaccc 1140
ccagagggct cggacagcac agcccccagc acccaggagc ctgaggcacc tccagaacaa 1200
gacctcatag ccagcacggt ggcaggtgtg gtgaccacag tgatgggcag ctcccagccc 1260
gtggtgaccc gaggcaccac cgacaaccgc tgcgcctacg gctactacca ggatgagacg 1320
actgggcgct gcgaggcgtg ccgcgtgtgc gaggcgggct cgggcctcgt gttctcctgc 1380
caggacaagc agaacaccgt gtgcgaggag tgccccgacg gcacgtattc cgacgaggcc 1440
aaccacgtgg acccgtgcct gccctgcacc gtgtgcgagg acaccgagcg ccagctccgc 1500
gagtgcacac gctgggccga cgccgagtgc gaggagatcc ctggccgttg gattacacgg 1560
tccacacccc cagagggctc ggacagcaca gcccccagca cccaggagcc tgaggcacct 1620
ccagaacaag acctcatagc cagcacggtg gcaggtgtgg tgaccacagt gatgggcagc 1680
tcccagcccg tggtgacccg aggcaccacc gacaac 1716

<210> SEQ ID NO 130
<211> LENGTH: 84
<212> TYPE: DNA
<213> ORGANISM: Homo sapiens

<400> SEQUENCE: 130
atctacatct gggcccctct ggccggcacc tgtggcgtgc tgctgctgag cctggtcatc 60
accctgtact gcaaccaccg gaat 84

<210> SEQ ID NO 131
<211> LENGTH: 81
<212> TYPE: DNA
<213> ORGANISM: Homo sapiens

<400> SEQUENCE: 131
ttttgggtgc tggtggtggt tggtggagtc ctggcttgct atagcttgct agtaacagtg 60
gcctttatta ttttctgggt g 81

<210> SEQ ID NO 132
<211> LENGTH: 123
<212> TYPE: DNA
<213> ORGANISM: Unknown
<220> FEATURE:
<223> OTHER INFORMATION: Description of Unknown:
CD28 co-stimulatory endodomain sequence

<400> SEQUENCE: 132
aggagcaagc ggagcagagg cggccacagc gactacatga acatgacccc ccggaggcct 60
ggccccaccc ggaagcacta ccagccctac gccccctccca gggacttcgc cgcctaccgg 120
agc 123

<210> SEQ ID NO 133
<211> LENGTH: 126
<212> TYPE: DNA
<213> ORGANISM: Unknown
<220> FEATURE:
<223> OTHER INFORMATION: Description of Unknown:
4-1BB (CD137) co-stimulatory endodomain sequence

<400> SEQUENCE: 133
aagagaggcc ggaagaaact gctgtacatc ttcaagcagc ccttcatgcg gcccgtgcag 60
accacccagg aagaggacgg ctgcagctgc cggttccccg aggaagagga aggcggctgc 120
gaactg 126

<210> SEQ ID NO 134
<211> LENGTH: 336
<212> TYPE: DNA
<213> ORGANISM: Unknown
<220> FEATURE:
<223> OTHER INFORMATION: Description of Unknown:
CD3 zetaz stimulatory endodomain sequence

<400> SEQUENCE: 134
cgggtgaagt tcagccggag cgccgacgcc cctgcctacc agcagggcca gaaccagctg 60
tacaacgagc tgaacctggg ccggagggag gagtacgacg tgctggacaa gcggagaggc 120
cgggaccctg agatgggcgg caagccccgg agaaagaacc ctcaggaggg cctgtataac 180
gaactgcaga aagacaagat ggccgaggcc tacagcgaga tcggcatgaa gggcgagcgg 240
cggaggggca agggccacga cggcctgtac cagggcctga gcaccgccac caaggatacc 300
tacgacgccc tgcacatgca ggccctgccc cccaga 336

<210> SEQ ID NO 135
<211> LENGTH: 72
<212> TYPE: DNA
<213> ORGANISM: Unknown
<220> FEATURE:
<223> OTHER INFORMATION: Description of Unknown:
DNAX-activation protein 10 (DAP 10) Signaling Domain sequence

<400> SEQUENCE: 135
ctgtgcgcac gcccacgccg cagccccgcc caagaagatg gcaaagtcta catcaacatg 60
ccaggcaggg gc 72

<210> SEQ ID NO 136
<211> LENGTH: 156
<212> TYPE: DNA
<213> ORGANISM: Unknown
<220> FEATURE:
<223> OTHER INFORMATION: Description of Unknown:

DNAX-activation protein 12 (DAP12) Signaling Domain sequence

<400> SEQUENCE: 136
tacttcctgg gccggctggt ccctcggggg cgaggggctg cggaggcagc gacccggaaa 60
cagcgtatca ctgagaccga gtcgccttat caggagctcc agggtcagag gtcggatgtc 120
tacagcgacc tcaacacaca gaggccgtat tacaaa 156

<210> SEQ ID NO 137
<211> LENGTH: 660
<212> TYPE: DNA
<213> ORGANISM: Homo sapiens

<400> SEQUENCE: 137
atgctcaggc tgctcttggc tctcaactta ttcccttcaa ttcaagtaac aggaaacaag 60
attttggtga agcagtcgcc catgcttgta gcgtacgaca atgcggtcaa ccttagctgc 120
aagtattcct acaatctctt ctcaagggag ttccgggcat cccttcacaa aggactggat 180
agtgctgtgg aagtctgtgt tgtatatggg aattactccc agcagcttca ggtttactca 240
aaaacggggt tcaactgtga tgggaaattg ggcaatgaat cagtgacatt ctacctccag 300
aatttgtatg ttaaccaaac agatatttac ttctgcaaaa ttgaagttat gtatcctcct 360
ccttacctag acaatgagaa gagcaatgga accattatcc atgtgaaagg gaaacacctt 420
tgtccaagtc ccctatttcc cggaccttct aagccctttt gggtgctggt ggtggttggt 480
ggagtcctgg cttgctatag cttgctagta acagtggcct ttattatttt ctgggtgagg 540
agtaagagga gcaggctcct gcacagtgac tacatgaaca tgactccccg ccgccccggg 600
cccacccgca agcattacca gccctatgcc ccaccacgcg acttcgcagc ctatcgctcc 660

<210> SEQ ID NO 138
<211> LENGTH: 117
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 138
attgaagtta tgtatcctcc tccttaccta gacaatgaga agagcaatgg aaccattatc 60
catgtgaaag ggaaacacct ttgtccaagt cccctatttc ccggaccttc taagccc 117

<210> SEQ ID NO 139
<211> LENGTH: 234
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
attgaagtta tgtatcctcc tccttaccta gacaatgaga agagcaatgg aaccattatc 60
catgtgaaag ggaaacacct tagtccaagt cccctatttc ccggaccttc taagcccatt 120
gaagttatgt atcctcctcc ttacctagac aatgagaaga gcaatggaac cattatccat 180
gtgaaaggga aacacctttg tccaagtccc ctatttcccg gaccttctaa gccc 234

<210> SEQ ID NO 140
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140
attgaagtta tgtatcctcc tccttaccta gacaatgaga agagcaatgg aaccattatc 60
catgtgaaag ggaaacacct tagtccaagt cccctatttc ccggaccttc taagcccatt 120
gaagttatgt atcctcctcc ttacctagac aatgagaaga gcaatggaac cattatccat 180
gtgaaaggga aacaccttag tccaagtccc ctatttcccg gaccttctaa gcccattgaa 240
gttatgtatc ctcctcctta cctagacaat gagaagagca atggaaccat tatccatgtg 300
aaagggaaac acctttgtcc aagtccccta tttcccggac cttctaagcc c 351

<210> SEQ ID NO 141
<211> LENGTH: 468
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141
attgaagtta tgtatcctcc tccttaccta gacaatgaga agagcaatgg aaccattatc 60
catgtgaaag ggaaacacct tagtccaagt cccctatttc ccggaccttc taagcccatt 120
gaagttatgt atcctcctcc ttacctagac aatgagaaga gcaatggaac cattatccat 180
gtgaaaggga aacaccttag tccaagtccc ctatttcccg gaccttctaa gcccattgaa 240
gttatgtatc ctcctcctta cctagacaat gagaagagca atggaaccat tatccatgtg 300
aaagggaaac accttagtcc aagtccccta tttcccggac cttctaagcc cattgaagtt 360
atgtatcctc ctccttacct agacaatgag aagagcaatg gaaccattat ccatgtgaaa 420
gggaaacacc tttgtccaag tcccctattt cccggacctt ctaagccc 468

<210> SEQ ID NO 142
<211> LENGTH: 669
<212> TYPE: DNA
<213> ORGANISM: Homo sapiens

<400> SEQUENCE: 142
atggcttgcc ttggatttca gcggcacaag gctcagctga acctggctac caggacctgg 60
ccctgcactc tcctgttttt tcttctcttc atccctgtct tctgcaaagc aatgcacgtg 120
gcccagcctg ctgtggtact ggccagcagc cgaggcatcg ccagctttgt gtgtgagtat 180
gcatctccag gcaaagccac tgaggtccgg gtgacagtgc ttcggcaggc tgacagccag 240
gtgactgaag tctgtgcggc aacctacatg atggggaatg agttgacctt cctagatgat 300
tccatctgca cgggcacctc cagtggaaat caagtgaacc tcactatcca aggactgagg 360
gccatggaca cgggactcta catctgcaag gtggagctca tgtacccacc gccatactac 420
ctgggcatag gcaacggaac ccagatttat gtaattgatc cagaaccgtg cccagattct 480
gacttcctcc tctggatcct tgcagcagtt agttcggggt tgttttttta tagctttctc 540
ctcacagctg tttctttgag caaaatgcta aagaaaagaa gccctcttac aacaggggtc 600
tatgtgaaaa tgcccccaac agagccagaa tgtgaaaagc aatttcagcc ttattttatt 660
cccatcaat 669

<210> SEQ ID NO 143

<400> SEQUENCE: 143

000

<210> SEQ ID NO 144
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
gagagcaagt acggccctcc ctgccccct tgccct 36

<210> SEQ ID NO 145
<211> LENGTH: 687
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145
gagagcaagt acggccctcc ctgccccct tgccctgccc ccgagttcct gggcggaccc 60
agcgtgttcc tgttcccccc caagcccaag gacaccctga tgatcagccg gacccccgag 120
gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaatc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc aggctgaccg tggacaagag ccggtggcag 600
gagggcaacg tctttagctg ctccgtgatg cacgaggccc tgcacaacca ctacacccag 660
aagagcctgt ccctgagcct gggcaag 687

<210> SEQ ID NO 146
<211> LENGTH: 66
<212> TYPE: DNA
<213> ORGANISM: Unknown
<220> FEATURE:
<223> OTHER INFORMATION: Description of Unknown: Granulocyte macrophage colony-stimulating factor receptor alpha Signal Peptide sequence

<400> SEQUENCE: 146
atgctgctgc tggtgaccag cctgctgctg tgtgagctgc cccaccccgc ctttctgctg 60
atcccc 66

<210> SEQ ID NO 147
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 147
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggagcag 240
gaggacatcg ccacctactt ttgccagcag ggcaacacac tgccctacac ctttggcggc 300
ggaacaaagc tggagatcac c 321

<210> SEQ ID NO 148
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 148
gaggtgaagc tgcaggagag cggccctggc ctggtggccc ccagccagag cctgagcgtg 60
acctgtaccg tgtccggcgt gtccctgccc gactacggcg tgtcctggat ccggcagccc 120
cctaggaagg gcctggagtg gctgggcgtg atctggggca gcgagaccac ctactacaac 180
agcgccctga agagccggct gaccatcatc aaggacaaca gcaagagcca ggtgttcctg 240
aagatgaaca gcctgcagac cgacgacacc gccatctact actgtgccaa gcactactac 300
tacggcggca gctacgccat ggactactgg ggccagggca ccagcgtgac cgtgtccagc 360

<210> SEQ ID NO 149
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 149
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggagcag 240
gaggacatcg ccacctactt ttgccagcag ggcaacacac tgccctacac ctttggcggc 300
ggaacaaagc tggagatcac cggcagcacc tccggcagcg gcaagcctgg cagcggcgag 360
ggcagcacca agggcgaggt gaagctgcag gagagcggcc ctggcctggt ggcccccagc 420
cagagcctga gcgtgacctg taccgtgtcc ggcgtgtccc tgcccgacta cggcgtgtcc 480
tggatccggc agccccctag gaagggcctg gagtggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgt 660
gccaagcact actactacgg cggcagctac gccatggact actggggcca gggcaccagc 720
gtgaccgtgt ccagc 735

<210> SEQ ID NO 150
<211> LENGTH: 1419
<212> TYPE: DNA
<213> ORGANISM: Artificial Sequence
<220> FEATURE:

-continued

<223> OTHER INFORMATION: Description of Artificial Sequence: Synthetic
polynucleotide

<400> SEQUENCE: 150
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggagcag 240
gaggacatcg ccacctactt ttgccagcag ggcaacacac tgccctacac ctttggcggc 300
ggaacaaagc tggagatcac cggcagcacc tccggcagcg gcaagcctgg cagcggcgag 360
ggcagcacca agggcgaggt gaagctgcag gagagcggcc ctggcctggt ggcccccagc 420
cagagcctga gcgtgacctg taccgtgtcc ggcgtgtccc tgcccgacta cggcgtgtcc 480
tggatccggc agccccctag gaagggcctg gagtggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgt 660
gccaagcact actactacgg cggcagctac gccatggact actggggcca gggcaccagc 720
gtgaccgtgt ccagcaagcc caccaccacc cctgccccta gacctccaac cccagcccct 780
acaatcgcca gccagcccct gagcctgagg cccgaagcct gtagacctgc cgctggcgga 840
gccgtgcaca ccagaggcct ggatttcgcc tgcgacatct acatctgggc ccctctggcc 900
ggcacctgtg gcgtgctgct gctgagcctg gtcatcaccc tgtactgcaa ccaccggaat 960
aggagcaagc ggagcagagg cggccacagc gactacatga acatgacccc ccggaggcct 1020
ggccccaccc ggaagcacta ccagccctac gcccctccca gggacttcgc cgcctaccgg 1080
agccgggtga agttcagccg gagcgccgac gcccctgcct accagcaggg ccagaaccag 1140
ctgtacaacg agctgaacct gggccggagg gaggagtacg acgtgctgga caagcggaga 1200
ggccgggacc ctgagatggg cggcaagccc cggagaaaga accctcagga gggcctgtat 1260
aacgaactgc agaaagacaa gatggccgag gcctacagcg agatcggcat gaagggcgag 1320
cggcggaggg gcaagggcca cgacggcctg taccagggcc tgagcaccgc caccaaggat 1380
acctacgacg ccctgcacat gcaggccctg cccccccaga 1419

<210> SEQ ID NO 151
<211> LENGTH: 1560
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 151
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggagcag 240
gaggacatcg ccacctactt ttgccagcag ggcaacacac tgccctacac ctttggcggc 300
ggaacaaagc tggagatcac cggcagcacc tccggcagcg gcaagcctgg cagcggcgag 360
ggcagcacca agggcgaggt gaagctgcag gagagcggcc ctggcctggt ggcccccagc 420
cagagcctga gcgtgacctg taccgtgtcc ggcgtgtccc tgcccgacta cggcgtgtcc 480

```
tggatccggc agccccctag gaagggcctg gagtggctgg gcgtgatctg ggcagcgag    540
accacctact acaacagcgc cctgaagagc cggctgacca tcatcaagga caacagcaag    600
agccaggtgt tcctgaagat gaacagcctg cagaccgacg acaccgccat ctactactgt    660
gccaagcact actactacgg cggcagctac gccatggact actggggcca gggcaccagc    720
gtgaccgtgt ccagcaaacc tactacaact cctgcccccc ggcctcctac accagctcct    780
actatcgcct cccagccact cagtctcaga cccgaggctt ctaggccagc ggccggaggc    840
gcggtccaca cccgcgggct ggactttgca tccgataagc ccaccaccac ccctgcccct    900
agacctccaa ccccagcccc tacaatcgcc agccagcccc tgagcctgag gcccgaagcc    960
tgtagacctg ccgctggcgg agccgtgcac accagaggcc tggatttcgc ctgcgacatc   1020
tacatctggg cccctctggc cggcacctgt ggcgtgctgc tgctgagcct ggtcatcacc   1080
ctgtactgca accaccggaa taggagcaag cggagcagag gcggccacag cgactacatg   1140
aacatgaccc cccggaggcc tggccccacc cggaagcact accagcccta cgcccctccc   1200
agggacttcg ccgcctaccg gagccgggtg aagttcagcc ggagcgccga cgcccctgcc   1260
taccagcagg gccagaacca gctgtacaac gagctgaacc tgggccggag ggaggagtac   1320
gacgtgctgg acaagcggag aggccgggac cctgagatgg gcggcaagcc ccggagaaag   1380
aaccctcagg agggcctgta taacgaactg cagaaagaca agatggccga ggcctacagc   1440
gagatcggca tgaagggcga gcggcggagg ggcaagggcc acgacggcct gtaccagggc   1500
ctgagcaccg ccaccaagga tacctacgac gccctgcaca tgcaggccct gccccccaga   1560
```

<210> SEQ ID NO 152
<211> LENGTH: 1701
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152

```
gacatccaga tgacccagac cacctccagc ctgagcgcca gcctgggcga ccgggtgacc     60
atcagctgcc gggccagcca ggacatcagc aagtacctga actggtatca gcagaagccc    120
gacggcaccg tcaagctgct gatctaccac accagccggc tgcacagcgg cgtgcccagc    180
cggtttagcg gcagcggctc cggcaccgac tacagcctga ccatctccaa cctggagcag    240
gaggacatcg ccacctactt ttgccagcag ggcaacacac tgccctacac ctttggcggc    300
ggaacaaagc tggagatcac cggcagcacc tccggcagcg gcaagcctgg cagcggcgag    360
ggcagcacca agggcgaggt gaagctgcag gagagcggcc ctggcctggt ggccccccagc   420
cagagcctga gcgtgacctg taccgtgtcc ggcgtgtccc tgcccgacta cggcgtgtcc    480
tggatccggc agccccctag gaagggcctg gagtggctgg gcgtgatctg gggcagcgag    540
accacctact acaacagcgc cctgaagagc cggctgacca tcatcaagga caacagcaag    600
agccaggtgt tcctgaagat gaacagcctg cagaccgacg acaccgccat ctactactgt    660
gccaagcact actactacgg cggcagctac gccatggact actggggcca gggcaccagc    720
gtgaccgtgt ccagcaagcc taccaccacc cccgcacctc gtcctccaac ccctgcacct    780
acgattgcca gtcagcctct ttcactgcgg cctgaggcca gcagaccagc tgccggcggt    840
gccgtccata caagaggact ggacttcgcg tccgataaac ctactaccac tccagcccca    900
aggcccccaa ccccagcacc gactatcgca tcacagcctt tgtcactgcg tcctgaagcc    960
```

agccggccag ctgcaggggg ggccgtccac acaaggggac tcgactttgc gagtgataag 1020
cccaccacca cccctgcccc tagacctcca accccagccc ctacaatcgc cagccagccc 1080
ctgagcctga ggcccgaagc ctgtagacct gccgctggcg gagccgtgca caccagaggc 1140
ctggatttcg cctgcgacat ctacatctgg gcccctctgg ccggcacctg tggcgtgctg 1200
ctgctgagcc tggtcatcac cctgtactgc aaccaccgga ataggagcaa gcggagcaga 1260
ggcggccaca gcgactacat gaacatgacc ccccggaggc ctggccccac ccggaagcac 1320
taccagccct acgcccctcc cagggacttc gccgcctacc ggagccgggt gaagttcagc 1380
cggagcgccg acgcccctgc ctaccagcag ggccagaacc agctgtacaa cgagctgaac 1440
ctgggccgga gggaggagta cgacgtgctg gacaagcgga gaggccggga ccctgagatg 1500
ggcggcaagc cccggagaaa gaaccctcag gagggcctgt ataacgaact gcagaaagac 1560
aagatggccg aggcctacag cgagatcggc atgaagggcg agcggcggag gggcaagggc 1620
cacgacggcc tgtaccaggg cctgagcacc gccaccaagg atacctacga cgccctgcac 1680
atgcaggccc tgccccccag a 1701

<210> SEQ ID NO 153
<211> LENGTH: 1701
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 153
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggagcag 240
gaggacatcg ccacctactt ttgccagcag ggcaacacac tgccctacac ctttggcggc 300
ggaacaaagc tggagatcac cggcagcacc tccggcagcg gcaagcctgg cagcggcgag 360
ggcagcacca agggcgaggt gaagctgcag gagagcggcc ctggcctggt ggcccccagc 420
cagagcctga gcgtgacctg taccgtgtcc ggcgtgtccc tgcccgacta cggcgtgtcc 480
tggatccggc agccccctag gaagggcctg gagtggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgt 660
gccaagcact actactacgg cggcagctac gccatggact actggggcca gggcaccagc 720
gtgaccgtgt ccagcaagcc caccaccacc cctgccccta gacctccaac cccagcccct 780
acaatcgcca gccagcccct gagcctgagg cccgaagcct gtagacctgc cgctggcgga 840
gccgtgcaca ccagaggcct ggatttcgcc tgcgacaagc ctaccaccac ccccgcacct 900
cgtcctccaa cccctgcacc tacgattgcc agtcagcctc tttcactgcg gcctgaggcc 960
agcagaccag ctgccggcgg tgccgtccat acaagaggac tggacttcgc gtccgataaa 1020
cctactacca ctccagcccc aaggccccca accccagcac cgactatcgc atcacagcct 1080
ttgtcactgc gtcctgaagc cagccggcca gctgcagggg gggccgtcca cacaagggga 1140
ctcgactttg cgagtgatat ctacatctgg gcccctctgg ccggcacctg tggcgtgctg 1200
ctgctgagcc tggtcatcac cctgtactgc aaccaccgga ataggagcaa gcggagcaga 1260
ggcggccaca gcgactacat gaacatgacc ccccggaggc ctggccccac ccggaagcac 1320
taccagccct acgcccctcc cagggacttc gccgcctacc ggagccgggt gaagttcagc 1380
cggagcgccg acgcccctgc ctaccagcag ggccagaacc agctgtacaa cgagctgaac 1440
ctgggccgga gggaggagta cgacgtgctg gacaagcgga gaggccggga ccctgagatg 1500
ggcggcaagc cccggagaaa gaaccctcag gagggcctgt ataacgaact gcagaaagac 1560
aagatggccg aggcctacag cgagatcggc atgaagggcg agcggcggag gggcaagggc 1620
cacgacggcc tgtaccaggg cctgagcacc gccaccaagg atacctacga cgccctgcac 1680
atgcaggccc tgccccccag a 1701

<210> SEQ ID NO 154
<211> LENGTH: 1842
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 154
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggagcag 240
gaggacatcg ccacctactt ttgccagcag ggcaacacac tgccctacac ctttggcggc 300
ggaacaaagc tggagatcac cggcagcacc tccggcagcg gcaagcctgg cagcggcgag 360
ggcagcacca agggcgaggt gaagctgcag gagagcggcc ctggcctggt ggcccccagc 420
cagagcctga gcgtgacctg taccgtgtcc ggcgtgtccc tgcccgacta cggcgtgtcc 480
tggatccggc agccccctag gaagggcctg gagtggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgt 660
gccaagcact actactacgg cggcagctac gccatggact actggggcca gggcaccagc 720
gtgaccgtgt ccagcaagcc taccaccacc cccgcacctc gtcctccaac ccctgcacct 780
acgattgcca gtcagcctct ttcactgcgg cctgaggcca gcagaccagc tgccggcggt 840
gccgtccata caagaggact ggacttcgcg tccgataaac ctactaccac tccagcccca 900
aggcccccaa ccccagcacc gactatcgca tcacagcctt tgtcactgcg tcctgaagcc 960
agccggccag ctgcaggggg ggccgtccac acaaggggac tcgactttgc gagtgataaa 1020
cctactacaa ctcctgcccc ccggcctcct acaccagctc ctactatcgc ctcccagcca 1080
ctcagtctca gacccgaggc ttctaggcca gcggccggag gcgcggtcca cacccgcggg 1140
ctggactttg catccgataa gcccaccacc acccctgccc ctagacctcc aaccccagcc 1200
cctacaatcg ccagccagcc cctgagcctg aggcccgaag cctgtagacc tgccgctggc 1260
ggagccgtgc acaccagagg cctggatttc gcctgcgaca tctacatctg ggcccctctg 1320
gccggcacct gtggcgtgct gctgctgagc ctggtcatca ccctgtactg caaccaccgg 1380
aataggagca agcggagcag aggcggccac agcgactaca tgaacatgac cccccggagg 1440
cctggcccca cccggaagca ctaccagccc tacgcccctc ccagggactt cgccgcctac 1500
cggagccggg tgaagttcag ccggagcgcc gacgcccctg cctaccagca gggccagaac 1560
cagctgtaca acgagctgaa cctgggccgg agggaggagt acgacgtgct ggacaagcgg 1620
agaggccggg accctgagat gggcggcaag ccccggagaa agaaccctca ggagggcctg 1680
tataacgaac tgcagaaaga caagatggcc gaggcctaca gcgagatcgg catgaagggc 1740
gagcggcgga ggggcaaggg ccacgacggc ctgtaccagg gcctgagcac cgccaccaag 1800
gatacctacg acgccctgca catgcaggcc ctgcccccca ga 1842

<210> SEQ ID NO 155
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155
gacattcaga tgacccagtc tccgagctct ctgtccgcat cagtaggaga cagggtcacc 60
atcacatgca gagccagcga aagtgtcgac aattatggca ttagctttat gaactggttc 120
caacagaaac ccgggaaggc tcctaagctt ctgatttacg ctgcatccaa ccaaggctcc 180
ggggtaccct ctcgcttctc aggcagtgga tctgggacag acttcactct caccatttca 240
tctctgcagc ctgatgactt cgcaacctat tactgtcagc aaagtaagga ggttccgtgg 300
acgttcggtc aagggaccaa ggtggagatc aaa 333

<210> SEQ ID NO 156
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156
caggttcagc tggtgcagtc tggagctgag gtgaagaagc ctgggagctc agtgaaggtt 60
tcctgcaaag cttctggcta caccttcact gactacaaca tgcactgggt gaggcaggct 120
cctggccaag gcctggaatg gattggatat atttatcctt acaatggtgg taccggctac 180
aaccagaagt tcaagagcaa ggccacaatt acagcagacg agagtactaa cacagcctac 240
atggaactct ccagcctgag gtctgaggac actgcagtct attactgcgc aagagggcgc 300
cccgctatgg actactgggg ccaagggact ctggtcactg tctcttca 348

<210> SEQ ID NO 157
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157
gacattcaga tgacccagtc tccgagctct ctgtccgcat cagtaggaga cagggtcacc 60
atcacatgca gagccagcga aagtgtcgac aattatggca ttagctttat gaactggttc 120
caacagaaac ccgggaaggc tcctaagctt ctgatttacg ctgcatccaa ccaaggctcc 180
ggggtaccct ctcgcttctc aggcagtgga tctgggacag acttcactct caccatttca 240
tctctgcagc ctgatgactt cgcaacctat tactgtcagc aaagtaagga ggttccgtgg 300
acgttcggtc aagggaccaa ggtggagatc aaaggtggcg gtggctcggg cggtggtggg 360
tcgggtggcg gcggatctca ggttcagctg gtgcagtctg gagctgaggt gaagaagcct 420
gggagctcag tgaaggtttc ctgcaaagct tctggctaca ccttcactga ctacaacatg 480
cactgggtga ggcaggctcc tggccaaggc ctggaatgga ttggatatat ttatccttac 540
aatggtggta ccggctacaa ccagaagttc aagagcaagg ccacaattac agcagacgag 600
agtactaaca cagcctacat ggaactctcc agcctgaggt ctgaggacac tgcagtctat 660
tactgcgcaa gagggcgccc cgctatggac tactggggcc aagggactct ggtcactgtc 720
tcttca 726

<210> SEQ ID NO 158
<211> LENGTH: 1413
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158
gacattcaga tgacccagtc tccgagctct ctgtccgcat cagtaggaga cagggtcacc 60
atcacatgca gagccagcga aagtgtcgac aattatggca ttagctttat gaactggttc 120
caacagaaac ccgggaaggc tcctaagctt ctgatttacg ctgcatccaa ccaaggctcc 180
ggggtaccct ctcgcttctc aggcagtgga tctgggacag acttcactct caccatttca 240
tctctgcagc ctgatgactt cgcaacctat tactgtcagc aaagtaagga ggttccgtgg 300
acgttcggtc aagggaccaa ggtggagatc aaaggtggcg gtggctcggg cggtggtggg 360
tcgggtggcg gcggatctca ggttcagctg gtgcagtctg gagctgaggt gaagaagcct 420
gggagctcag tgaaggtttc ctgcaaagct tctggctaca ccttcactga ctacaacatg 480
cactgggtga ggcaggctcc tggccaaggc ctggaatgga ttggatatat ttatccttac 540
aatggtggta ccggctacaa ccagaagttc aagagcaagg ccacaattac agcagacgag 600
agtactaaca cagcctacat ggaactctcc agcctgaggt ctgaggacac tgcagtctat 660
tactgcgcaa gagggcgccc cgctatggac tactggggcc aagggactct ggtcactgtc 720
tcttcaaagc ccaccaccac ccctgcccct agacctccaa ccccagcccc tacaatcgcc 780
agccagcccc tgagcctgag gcccgaagcc tgtagacctg ccgctggcgg agccgtgcac 840
accagaggcc tggatttcgc ctgcgacatc tacatctggg cccctctggc cggcacctgt 900
ggcgtgctgc tgctgagcct ggtcatcacc ctgtactgca accaccggaa taagagaggc 960
cggaagaaac tgctgtacat cttcaagcag cccttcatgc ggcccgtgca gaccacccag 1020
gaagaggacg gctgcagctg ccggttcccc gaggaagagg aaggcggctg cgaactgcgg 1080
gtgaagttca gccggagcgc cgacgcccct gcctaccagc agggccagaa ccagctgtac 1140
aacgagctga acctgggccg gagggaggag tacgacgtgc tggacaagcg gagaggccgg 1200
gaccctgaga tgggcggcaa gccccggaga aagaaccctc aggagggcct gtataacgaa 1260
ctgcagaaag acaagatggc cgaggcctac agcgagatcg gcatgaaggg cgagcggcgg 1320
aggggcaagg gccacgacgg cctgtaccag ggcctgagca ccgccaccaa ggatacctac 1380
gacgccctgc acatgcaggc cctgcccccc aga 1413

<210> SEQ ID NO 159
<211> LENGTH: 1554
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159

```
gacattcaga tgacccagtc tccgagctct ctgtccgcat cagtaggaga cagggtcacc     60
atcacatgca gagccagcga aagtgtcgac aattatggca ttagctttat gaactggttc    120
caacagaaac ccgggaaggc tcctaagctt ctgatttacg ctgcatccaa ccaaggctcc    180
ggggtaccct ctcgcttctc aggcagtgga tctgggacag acttcactct caccatttca    240
tctctgcagc ctgatgactt cgcaacctat tactgtcagc aaagtaagga ggttccgtgg    300
acgttcggtc aagggaccaa ggtggagatc aaaggtggcg gtggctcggg cggtggtggg    360
tcgggtggcg gcggatctca ggttcagctg gtgcagtctg gagctgaggt gaagaagcct    420
gggagctcag tgaaggtttc ctgcaaagct tctggctaca ccttcactga ctacaacatg    480
cactgggtga ggcaggctcc tggccaaggc ctggaatgga ttggatatat ttatccttac    540
aatggtggta ccggctacaa ccagaagttc aagagcaagg ccacaattac agcagacgag    600
agtactaaca cagcctacat ggaactctcc agcctgaggt ctgaggacac tgcagtctat    660
tactgcgcaa gagggcgccc cgctatggac tactggggcc aagggactct ggtcactgtc    720
tcttcaaaac ctactacaac tcctgccccc cggcctccta caccagctcc tactatcgcc    780
tcccagccac tcagtctcag acccgaggct tctaggccag cggccggagg cgcggtccac    840
acccgcgggc tggactttgc atccgataag cccaccacca cccctgcccc tagacctcca    900
accccagccc ctacaatcgc cagccagccc ctgagcctga ggcccgaagc ctgtagacct    960
gccgctggcg gagccgtgca caccagaggc ctggatttcg cctgcgacat ctacatctgg   1020
gcccctctgg ccggcacctg tggcgtgctg ctgctgagcc tggtcatcac cctgtactgc   1080
aaccaccgga ataagagagg ccggaagaaa ctgctgtaca tcttcaagca gcccttcatg   1140
cggcccgtgc agaccaccca ggaagaggac ggctgcagct gccggttccc cgaggaagag   1200
gaaggcggct gcgaactgcg ggtgaagttc agccggagcg ccgacgcccc tgcctaccag   1260
cagggccaga accagctgta caacgagctg aacctgggcc ggagggagga gtacgacgtg   1320
ctggacaagc ggagaggccg ggaccctgag atgggcggca agccccggag aaagaaccct   1380
caggagggcc tgtataacga actgcagaaa gacaagatgg ccgaggccta cagcgagatc   1440
ggcatgaagg gcgagcggcg gaggggcaag ggccacgacg gcctgtacca gggcctgagc   1500
accgccacca aggataccta cgacgccctg cacatgcagg ccctgccccc caga          1554
```

<210> SEQ ID NO 160
<211> LENGTH: 1695
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 160

```
gacattcaga tgacccagtc tccgagctct ctgtccgcat cagtaggaga cagggtcacc     60
atcacatgca gagccagcga aagtgtcgac aattatggca ttagctttat gaactggttc    120
caacagaaac ccgggaaggc tcctaagctt ctgatttacg ctgcatccaa ccaaggctcc    180
ggggtaccct ctcgcttctc aggcagtgga tctgggacag acttcactct caccatttca    240
tctctgcagc ctgatgactt cgcaacctat tactgtcagc aaagtaagga ggttccgtgg    300
```

```
acgttcggtc aagggaccaa ggtggagatc aaaggtggcg gtggctcggg cggtggtggg    360
tcgggtggcg gcggatctca ggttcagctg gtgcagtctg gagctgaggt gaagaagcct    420
gggagctcag tgaaggtttc ctgcaaagct tctggctaca ccttcactga ctacaacatg    480
cactgggtga ggcaggctcc tggccaaggc ctggaatgga ttggatatat ttatccttac    540
aatggtggta ccggctacaa ccagaagttc aagagcaagg ccacaattac agcagacgag    600
agtactaaca cagcctacat ggaactctcc agcctgaggt ctgaggacac tgcagtctat    660
tactgcgcaa gagggcgccc cgctatggac tactggggcc aagggactct ggtcactgtc    720
tcttcaaagc ctaccaccac ccccgcacct cgtcctccaa cccctgcacc tacgattgcc    780
agtcagcctc tttcactgcg gcctgaggcc agcagaccag ctgccggcgg tgccgtccat    840
acaagaggac tggacttcgc gtccgataaa cctactacca ctccagcccc aaggccccca    900
accccagcac cgactatcgc atcacagcct ttgtcactgc gtcctgaagc cagccggcca    960
gctgcagggg gggccgtcca cacaagggga ctcgactttg cgagtgataa gcccaccacc   1020
acccctgccc ctagacctcc aaccccagcc cctacaatcg ccagccagcc cctgagcctg   1080
aggcccgaag cctgtagacc tgccgctggc ggagccgtgc acaccagagg cctggatttc   1140
gcctgcgaca tctacatctg ggcccctctg gccggcacct gtggcgtgct gctgctgagc   1200
ctggtcatca ccctgtactg caaccaccgg aataagagag gccggaagaa actgctgtac   1260
atcttcaagc agcccttcat gcggcccgtg cagaccaccc aggaagagga cggctgcagc   1320
tgccggttcc ccgaggaaga ggaaggcggc tgcgaactgc gggtgaagtt cagccggagc   1380
gccgacgccc ctgcctacca gcagggccag aaccagctgt acaacgagct gaacctgggc   1440
cggagggagg agtacgacgt gctggacaag cggagaggcc gggaccctga gatgggcggc   1500
aagccccgga gaaagaaccc tcaggagggc ctgtataacg aactgcagaa agacaagatg   1560
gccgaggcct acagcgagat cggcatgaag ggcgagcggc ggaggggcaa gggccacgac   1620
ggcctgtacc agggcctgag caccgccacc aaggatacct acgacgccct gcacatgcag   1680
gccctgcccc ccaga                                                    1695
```

<210> SEQ ID NO 161
<211> LENGTH: 1695
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161

```
gacattcaga tgacccagtc tccgagctct ctgtccgcat cagtaggaga cagggtcacc     60
atcacatgca gagccagcga aagtgtcgac aattatggca ttagctttat gaactggttc    120
caacagaaac ccgggaaggc tcctaagctt ctgatttacg ctgcatccaa ccaaggctcc    180
ggggtaccct ctcgcttctc aggcagtgga tctgggacag acttcactct caccatttca    240
tctctgcagc ctgatgactt cgcaacctat tactgtcagc aaagtaagga ggttccgtgg    300
acgttcggtc aagggaccaa ggtggagatc aaaggtggcg gtggctcggg cggtggtggg    360
tcgggtggcg gcggatctca ggttcagctg gtgcagtctg gagctgaggt gaagaagcct    420
gggagctcag tgaaggtttc ctgcaaagct tctggctaca ccttcactga ctacaacatg    480
cactgggtga ggcaggctcc tggccaaggc ctggaatgga ttggatatat ttatccttac    540
aatggtggta ccggctacaa ccagaagttc aagagcaagg ccacaattac agcagacgag    600
```

```
agtactaaca cagcctacat ggaactctcc agcctgaggt ctgaggacac tgcagtctat    660

tactgcgcaa gagggcgccc cgctatggac tactggggcc aagggactct ggtcactgtc    720

tcttcaaagc ccaccaccac ccctgcccct agacctccaa ccccagcccc tacaatcgcc    780

agccagcccc tgagcctgag gcccgaagcc tgtagacctg ccgctggcgg agccgtgcac    840

accagaggcc tggatttcgc ctgcgacaag cctaccacca cccccgcacc tcgtcctcca    900

acccctgcac ctacgattgc cagtcagcct ctttcactgc ggcctgaggc cagcagacca    960

gctgccggcg gtgccgtcca tacaagagga ctggacttcg cgtccgataa acctactacc   1020

actccagccc caaggccccc aaccccagca ccgactatcg catcacagcc tttgtcactg   1080

cgtcctgaag ccagccggcc agctgcaggg ggggccgtcc acacaagggg actcgacttt   1140

gcgagtgata tctacatctg ggcccctctg gccggcacct gtggcgtgct gctgctgagc   1200

ctggtcatca ccctgtactg caaccaccgg aataagagag gccggaagaa actgctgtac   1260

atcttcaagc agcccttcat gcggcccgtg cagaccaccc aggaagagga cggctgcagc   1320

tgccggttcc ccgaggaaga ggaaggcggc tgcgaactgc gggtgaagtt cagccggagc   1380

gccgacgccc ctgcctacca gcagggccag aaccagctgt acaacgagct gaacctgggc   1440

cggagggagg agtacgacgt gctggacaag cggagaggcc gggaccctga gatgggcggc   1500

aagccccgga gaaagaaccc tcaggagggc ctgtataacg aactgcagaa agacaagatg   1560

gccgaggcct acagcgagat cggcatgaag ggcgagcggc ggaggggcaa gggccacgac   1620

ggcctgtacc agggcctgag caccgccacc aaggatacct acgacgccct gcacatgcag   1680

gccctgcccc ccaga                                                    1695
```

<210> SEQ ID NO 162
<211> LENGTH: 1836
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162

```
gacattcaga tgacccagtc tccgagctct ctgtccgcat cagtaggaga cagggtcacc     60

atcacatgca gagccagcga aagtgtcgac aattatggca ttagctttat gaactggttc    120

caacagaaac ccgggaaggc tcctaagctt ctgatttacg ctgcatccaa ccaaggctcc    180

ggggtaccct ctcgcttctc aggcagtgga tctgggacag acttcactct caccatttca    240

tctctgcagc ctgatgactt cgcaacctat tactgtcagc aaagtaagga ggttccgtgg    300

acgttcggtc aagggaccaa ggtggagatc aaaggtggcg gtggctcggg cggtggtggg    360

tcgggtggcg gcggatctca ggttcagctg gtgcagtctg gagctgaggt gaagaagcct    420

gggagctcag tgaaggtttc ctgcaaagct tctggctaca ccttcactga ctacaacatg    480

cactgggtga ggcaggctcc tggccaaggc ctggaatgga ttggatatat ttatccttac    540

aatggtggta ccggctacaa ccagaagttc aagagcaagg ccacaattac agcagacgag    600

agtactaaca cagcctacat ggaactctcc agcctgaggt ctgaggacac tgcagtctat    660

tactgcgcaa gagggcgccc cgctatggac tactggggcc aagggactct ggtcactgtc    720

tcttcaaagc ctaccaccac ccccgcacct cgtcctccaa cccctgcacc tacgattgcc    780

agtcagcctc tttcactgcg gcctgaggcc agcagaccag ctgccggcgg tgccgtccat    840

acaagaggac tggacttcgc gtccgataaa cctactacca ctccagcccc aaggccccca    900
```

-continued

```
accccagcac cgactatcgc atcacagcct ttgtcactgc gtcctgaagc cagccggcca    960

gctgcagggg gggccgtcca cacaagggga ctcgactttg cgagtgataa acctactaca   1020

actcctgccc cccggcctcc tacaccagct cctactatcg cctcccagcc actcagtctc   1080

agacccgagg cttctaggcc agcggccgga ggcgcggtcc acacccgcgg gctggacttt   1140

gcatccgata agcccaccac cacccctgcc cctagacctc caaccccagc ccctacaatc   1200

gccagccagc ccctgagcct gaggcccgaa gcctgtagac ctgccgctgg cggagccgtg   1260

cacaccagag gcctggattt cgcctgcgac atctacatct gggcccctct ggccggcacc   1320

tgtggcgtgc tgctgctgag cctggtcatc accctgtact gcaaccaccg gaataagaga   1380

ggccggaaga aactgctgta catcttcaag cagcccttca tgcggcccgt gcagaccacc   1440

caggaagagg acggctgcag ctgccggttc cccgaggaag aggaaggcgg ctgcgaactg   1500

cgggtgaagt tcagccggag cgccgacgcc cctgcctacc agcagggcca gaaccagctg   1560

tacaacgagc tgaacctggg ccggagggag gagtacgacg tgctggacaa gcggagaggc   1620

cgggaccctg agatgggcgg caagccccgg agaaagaacc ctcaggaggg cctgtataac   1680

gaactgcaga aagacaagat ggccgaggcc tacagcgaga tcggcatgaa gggcgagcgg   1740

cggaggggca agggccacga cggcctgtac cagggcctga gcaccgccac caaggatacc   1800

tacgacgccc tgcacatgca ggccctgccc cccaga                             1836
```

<210> SEQ ID NO 163
<211> LENGTH: 426
<212> TYPE: DNA
<213> ORGANISM: Homo sapiens

<400> SEQUENCE: 163

```
ccaaatatcc agaaccctga ccctgccgtg taccagctga gagactctaa atccagtgac     60

aagtctgtct gcctattcac cgattttgat tctcaaacaa atgtgtcaca aagtaaggat    120

tctgatgtgt atatcacaga caaaactgtg ctagacatga ggtctatgga cttcaagagc    180

aacagtgctg tggcctggag caacaaatct gactttgcat gtgcaaacgc cttcaacaac    240

agcattattc cagaagacac cttcttcccc agcccagaaa gttcctgtga tgtcaagctg    300

gtcgagaaaa gctttgaaac agatacgaac ctaaactttc aaaacctgtc agtgattggg    360

ttccgaatcc tcctcctgaa agtggccggg tttaatctgc tcatgacgct gcggctgtgg    420

tccagc                                                               426
```

<210> SEQ ID NO 164
<211> LENGTH: 351
<212> TYPE: DNA
<213> ORGANISM: Homo sapiens

<400> SEQUENCE: 164

```
ccaaatatcc agaaccctga ccctgccgtg taccagctga gagactctaa atccagtgac     60

aagtctgtct gcctattcac cgattttgat tctcaaacaa atgtgtcaca aagtaaggat    120

tctgatgtgt atatcacaga caaaactgtg ctagacatga ggtctatgga cttcaagagc    180

aacagtgctg tggcctggag caacaaatct gactttgcat gtgcaaacgc cttcaacaac    240

agcattattc cagaagacac cttcttcccc agcccagaaa gttcctgtga tgtcaagctg    300

gtcgagaaaa gctttgaaac agatacgaac ctaaactttc aaaacctgtc a            351
```

<210> SEQ ID NO 165
<211> LENGTH: 60

<212> TYPE: DNA
<213> ORGANISM: Homo sapiens

<400> SEQUENCE: 165
gtgattgggt tccgaatcct cctcctgaaa gtggccgggt ttaatctgct catgacgctg 60

<210> SEQ ID NO 166
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 166
tgtgatgtca agctggtcga gaaaagcttt gaaacagata cgaacctaaa ctttcaaaac 60
ctgtca 66

<210> SEQ ID NO 167
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
tgtgatgtca agctggtcga gaaaagcttt gaaacagata cgaacctaaa ctttcaaaac 60
ctgtca 66

<210> SEQ ID NO 168
<211> LENGTH: 111
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168
tgtgatgtca agctggtcga gaaaagcttt gaaacagata cgaacctaaa ctttcaaaac 60
ctgtcaggcg gaggcggaag cggaggcgga ggctccggcg gaggcggaag c 111

<210> SEQ ID NO 169
<211> LENGTH: 111
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 169
ggcggaggcg gaagcggagg cggaggctcc ggcggaggcg gaagctgtga tgtcaagctg 60
gtcgagaaaa gctttgaaac agatacgaac ctaaactttc aaaacctgtc a 111

<210> SEQ ID NO 170
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 170
ggcagcacct ccggcagcgg caagcctggc agcggcgagg gcagcaccaa gggctgtgat 60
gtcaagctgg tcgagaaaag ctttgaaaca gatacgaacc taaactttca aaacctgtca 120

<210> SEQ ID NO 171
<211> LENGTH: 132
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 171
agtgatgtca agctggtcga gaaaagcttt gaaacagata cgaacctaaa ctttcaaaac 60
ctgtcatgtg atgtcaagct ggtcgagaaa agctttgaaa cagatacgaa cctaaacttt 120
caaaacctgt ca 132

<210> SEQ ID NO 172
<211> LENGTH: 198
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 172
agtgatgtca agctggtcga gaaaagcttt gaaacagata cgaacctaaa ctttcaaaac 60
ctgtcaagtg atgtcaagct ggtcgagaaa agctttgaaa cagatacgaa cctaaacttt 120
caaaacctgt catgtgatgt caagctggtc gagaaaagct ttgaaacaga tacgaaccta 180
aactttcaaa acctgtca 198

<210> SEQ ID NO 173
<211> LENGTH: 264
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 173
agtgatgtca agctggtcga gaaaagcttt gaaacagata cgaacctaaa ctttcaaaac 60
ctgtcaagtg atgtcaagct ggtcgagaaa agctttgaaa cagatacgaa cctaaacttt 120
caaaacctgt caagtgatgt caagctggtc gagaaaagct ttgaaacaga tacgaaccta 180
aactttcaaa acctgtcatg tgatgtcaag ctggtcgaga aaagctttga aacagatacg 240
aacctaaact ttcaaaacct gtca 264

<210> SEQ ID NO 174
<211> LENGTH: 132
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 174
tgtgatgtca agctggtcga gaaaagcttt gaaacagata cgaacctaaa ctttcaaaac 60
ctgtcaagtg atgtcaagct ggtcgagaaa agctttgaaa cagatacgaa cctaaacttt 120
caaaacctgt ca 132

<210> SEQ ID NO 175

<211> LENGTH: 198
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 175
tgtgatgtca agctggtcga gaaaagcttt gaaacagata cgaacctaaa ctttcaaaac 60
ctgtcaagtg atgtcaagct ggtcgagaaa agctttgaaa cagatacgaa cctaaacttt 120
caaaacctgt caagtgatgt caagctggtc gagaaaagct ttgaaacaga tacgaaccta 180
aactttcaaa acctgtca 198

<210> SEQ ID NO 176
<211> LENGTH: 264
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176
tgtgatgtca agctggtcga gaaaagcttt gaaacagata cgaacctaaa ctttcaaaac 60
ctgtcaagtg atgtcaagct ggtcgagaaa agctttgaaa cagatacgaa cctaaacttt 120
caaaacctgt caagtgatgt caagctggtc gagaaaagct ttgaaacaga tacgaaccta 180
aactttcaaa acctgtcaag tgatgtcaag ctggtcgaga aaagctttga aacagatacg 240
aacctaaact ttcaaaacct gtca 264

<210> SEQ ID NO 177
<211> LENGTH: 531
<212> TYPE: DNA
<213> ORGANISM: Homo sapiens

<400> SEQUENCE: 177
gaggacctga acaaggtgtt cccacccgag gtcgctgtgt ttgagccatc agaagcagag 60
atctcccaca cccaaaaggc cacactggtg tgcctggcca caggcttctt ccccgaccac 120
gtggagctga gctggtgggt gaatgggaag gaggtgcaca gtggggtcag cacagacccg 180
cagcccctca aggagcagcc cgccctcaat gactccagat actgcctgag cagccgcctg 240
agggtctcgg ccaccttctg gcagaacccc cgcaaccact tccgctgtca agtccagttc 300
tacgggctct cggagaatga cgagtggacc caggataggg ccaaacccgt cacccagatc 360
gtcagcgccg aggcctgggg tagagcagac tgtggcttta cctcggtgtc ctaccagcaa 420
ggggtcctgt ctgccaccat cctctatgag atcctgctag ggaaggccac cctgtatgct 480
gtgctggtca gcgcccttgt gttgatggcc atggtcaaga gaaaggattt c 531

<210> SEQ ID NO 178
<211> LENGTH: 450
<212> TYPE: DNA
<213> ORGANISM: Homo sapiens

<400> SEQUENCE: 178
gaggacctga acaaggtgtt cccacccgag gtcgctgtgt ttgagccatc agaagcagag 60
atctcccaca cccaaaaggc cacactggtg tgcctggcca caggcttctt ccccgaccac 120
gtggagctga gctggtgggt gaatgggaag gaggtgcaca gtggggtcag cacagacccg 180
cagcccctca aggagcagcc cgccctcaat gactccagat actgcctgag cagccgcctg 240
agggtctcgg ccaccttctg gcagaacccc cgcaaccact tccgctgtca agtccagttc 300
tacgggctct cggagaatga cgagtggacc caggataggg ccaaacccgt cacccagatc 360
gtcagcgccg aggcctgggg tagagcagac tgtggcttta cctcggtgtc ctaccagcaa 420
ggggtcctgt ctgccaccat cctctatgag 450

<210> SEQ ID NO 179
<211> LENGTH: 63
<212> TYPE: DNA
<213> ORGANISM: Homo sapiens

<400> SEQUENCE: 179
atcctgctag ggaaggccac cctgtatgct gtgctggtca gcgcccttgt gttgatggcc 60
atg 63

<210> SEQ ID NO 180
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 180
tgtggcttta cctcggtgtc ctaccagcaa ggggtcctgt ctgccaccat cctctatgag 60

<210> SEQ ID NO 181
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 181
agtggcttta cctcggtgtc ctaccagcaa ggggtcctgt ctgccaccat cctctatgag 60

<210> SEQ ID NO 182
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 182
tgtggcttta cctcggtgtc ctaccagcaa ggggtcctgt ctgccaccat cctctatgag 60
ggcggaggcg gaagcggagg cggaggctcc ggcggaggcg gaagc 105

<210> SEQ ID NO 183
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183
ggcggaggcg gaagcggagg cggaggctcc ggcggaggcg gaagctgtgg ctttacctcg 60
gtgtcctacc agcaaggggt cctgtctgcc accatcctct atgag 105

<210> SEQ ID NO 184

<211> LENGTH: 114
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184
ggcagcacct ccggcagcgg caagcctggc agcggcgagg gcagcaccaa gggctgtggc 60
tttacctcgg tgtcctacca gcaaggggtc ctgtctgcca ccatcctcta tgag 114

<210> SEQ ID NO 185
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 185
agtggcttta cctcggtgtc ctaccagcaa ggggtcctgt ctgccaccat cctctatgag 60
tgtggcttta cctcggtgtc ctaccagcaa ggggtcctgt ctgccaccat cctctatgag 120

<210> SEQ ID NO 186
<211> LENGTH: 180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 186
agtggcttta cctcggtgtc ctaccagcaa ggggtcctgt ctgccaccat cctctatgag 60
agtggcttta cctcggtgtc ctaccagcaa ggggtcctgt ctgccaccat cctctatgag 120
tgtggcttta cctcggtgtc ctaccagcaa ggggtcctgt ctgccaccat cctctatgag 180

<210> SEQ ID NO 187
<211> LENGTH: 240
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187
agtggcttta cctcggtgtc ctaccagcaa ggggtcctgt ctgccaccat cctctatgag 60
agtggcttta cctcggtgtc ctaccagcaa ggggtcctgt ctgccaccat cctctatgag 120
agtggcttta cctcggtgtc ctaccagcaa ggggtcctgt ctgccaccat cctctatgag 180
tgtggcttta cctcggtgtc ctaccagcaa ggggtcctgt ctgccaccat cctctatgag 240

<210> SEQ ID NO 188
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 188
tgtggcttta cctcggtgtc ctaccagcaa ggggtcctgt ctgccaccat cctctatgag 60
agtggcttta cctcggtgtc ctaccagcaa ggggtcctgt ctgccaccat cctctatgag 120

<210> SEQ ID NO 189
<211> LENGTH: 180
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 189
tgtggcttta cctcggtgtc ctaccagcaa ggggtcctgt ctgccaccat cctctatgag 60
agtggcttta cctcggtgtc ctaccagcaa ggggtcctgt ctgccaccat cctctatgag 120
agtggcttta cctcggtgtc ctaccagcaa ggggtcctgt ctgccaccat cctctatgag 180

<210> SEQ ID NO 190
<211> LENGTH: 240
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 190
tgtggcttta cctcggtgtc ctaccagcaa ggggtcctgt ctgccaccat cctctatgag 60
agtggcttta cctcggtgtc ctaccagcaa ggggtcctgt ctgccaccat cctctatgag 120
agtggcttta cctcggtgtc ctaccagcaa ggggtcctgt ctgccaccat cctctatgag 180
agtggcttta cctcggtgtc ctaccagcaa ggggtcctgt ctgccaccat cctctatgag 240

<210> SEQ ID NO 191
<211> LENGTH: 537
<212> TYPE: DNA
<213> ORGANISM: Homo sapiens

<400> SEQUENCE: 191
gatctgaaga acgtgttccc tcccgaggtg gctgttttcg aaccaagtga ggctgaaatc 60
tctcatacac agaaggccac tctggtctgt ctcgccacag ggttttaccc tgaccatgtg 120
gagctgtcat ggtgggttaa cggcaaagag gtacactcag gtgtcagtac agatccgcaa 180
ccccttaaag agcagccagc cctgaacgat tcacgttact gtttatctag ccggctgaga 240
gtttctgcaa cattctggca aaaccccgt aaccacttca gatgccaggt ccagttttac 300
ggactgagcg agaatgacga atggacccag gatcgagcaa aacctgttac tcagatagtt 360
tcagccgaag catggggtcg tgccgattgt ggtttcacct ccgaatcata ccagcaggga 420
gtgctaagcg ctactattct ttatgaaatc ttattgggca aagccacact ttatgcagtc 480
ttggtgtccg ctctggtgct gatggctatg gtgaagcgca aggatagcag aggatga 537

<210> SEQ ID NO 192
<211> LENGTH: 432
<212> TYPE: DNA
<213> ORGANISM: Homo sapiens

<400> SEQUENCE: 192
gatctgaaga acgtgttccc tcccgaggtg gctgttttcg aaccaagtga ggctgaaatc 60
tctcatacac agaaggccac tctggtctgt ctcgccacag ggttttaccc tgaccatgtg 120
gagctgtcat ggtgggttaa cggcaaagag gtacactcag gtgtcagtac agatccgcaa 180
ccccttaaag agcagccagc cctgaacgat tcacgttact gtttatctag ccggctgaga 240
gtttctgcaa cattctggca aaaccccgt aaccacttca gatgccaggt ccagttttac 300
ggactgagcg agaatgacga atggacccag gatcgagcaa aacctgttac tcagatagtt 360
tcagccgaag catggggtcg tgccgattgt ggtttcacct ccgaatcata ccagcaggga 420
gtgctaagcg ct 432

<210> SEQ ID NO 193
<211> LENGTH: 519
<212> TYPE: DNA
<213> ORGANISM: Homo sapiens

<400> SEQUENCE: 193
gacaagcagc tcgacgctga tgtgtctccc aagcccacca tcttccttcc cagtatcgct 60
gaaaccaagc tgcagaaagc agggacgtac ctttgtttgc ttgagaagtt tttccctgat 120
gtgattaaga ttcattggca ggaaaagaag tctaacacta ttctggggtc ccaagaagga 180
aatactatga aaaccaacga cacgtatatg aagtttagct ggttgactgt gcctgaaaaa 240
tccctggaca aagagcacag gtgcatcgta cggcacgaaa acaacaagaa cggcgtggac 300
caggaaatca tttttcctcc tattaagacc gatgttatta ctatggatcc taaggacaac 360
tgtagcaaag atgcaaatga cacgcttctc ttgcagttaa ccaacacgtc tgcatactac 420
atgtatctgt tgctgcttct gaagtctgtg gtgtacttcg ccattattac gtgctgtctg 480
ctacggcgca ccgccttctg ctgcaacggg gaaaagtcg 519

<210> SEQ ID NO 194
<211> LENGTH: 414
<212> TYPE: DNA
<213> ORGANISM: Homo sapiens

<400> SEQUENCE: 194
gataaacaac tggatgccga tgtctcccca aaaccgacta tttttttacc atcgatcgca 60
gagaccaagc tccaaaaggc cggcacctac ctctgtttgc tggaaaaatt ctttccagat 120
gtaattaaaa tccattggca ggaaaaaaag agcaacacta tactgggttc gcaggaaggt 180
aatacgatga agacaaatga cacatacatg aagttctcgt ggcttactgt gcctgagaaa 240
tcactggata aggagcaccg gtgcattgtc cggcatgaaa acaacaagaa cggagtggac 300
caggagatca tctttccgcc gatcaagaca gacgtcatta caatggatcc taaggataac 360
tgttctaagg atgcgaacga cacactgcta ctgcagctca ctaacacctc ggca 414

<210> SEQ ID NO 195
<211> LENGTH: 69
<212> TYPE: DNA
<213> ORGANISM: Homo sapiens

<400> SEQUENCE: 195
tactatatgt atctgttgct gctgttaaag tccgtggttt acttcgcaat tatcacatgc 60
tgcctgttg 69

<210> SEQ ID NO 196
<211> LENGTH: 567
<212> TYPE: DNA
<213> ORGANISM: Homo sapiens

<400> SEQUENCE: 196
gataaacaac tagacgcgga tgtctctcct aaacctacta tcttcttgcc atcaattgcc 60
gaaactaagc tgcagaaggc aggcacttac ctctgtttgc tggaaaagtt tttccctgat 120
attataaaga ttcattggca agagaaaaaa agcaatacga ttcttggatc ccaggaagga 180
aacacaatga agaccaatga cacctatatg aagttttctt ggctgaccgt acctgaggaa 240
agcctcgata aggagcacag gtgcatcgtg cgccatgaga ataacaagaa tggcatcgat 300
caggaaatca tattcccacc cattaaaacc gatgtgacaa cagtcgaccc caaagactcc 360
tacagcaaag acgctaatga cgtcatcacc atggatccta aagataattg gtccaaggac 420
gcaaatgaca ctcttctcct gcagctcaca aatacctcag cgtattatat gtatctcctg 480
ctactgctga agtcagttgt ttacttcgcc attatcacct gttgcctcct gggcagaact 540
gctttctgct gtaatggcga gaaaagt 567

<210> SEQ ID NO 197
<211> LENGTH: 468
<212> TYPE: DNA
<213> ORGANISM: Homo sapiens

<400> SEQUENCE: 197
gataaacaac tggacgctga tgtgtctcca aaaccaacta tcttcttgcc cagcatagct 60
gaaaccaagc tccagaaagc tggcacatac ctgtgtctct tagaaaagtt cttccccgac 120
atcatcaaga ttcattggca ggagaagaag agcaacacga tactgggcag ccaggaagga 180
aatactatga aaaccaacga tacctatatg aagtttagtt ggctcactgt tccagaggaa 240
agtctggata aggaacatcg gtgtattgtc cgccatgaga ataataaaaa cgggattgat 300
caagagatca tctttccacc catcaaaacc gacgtaacta ctgtagatcc taaggattcc 360
tactctaagg acgcgaacga cgtaatcacc atggatccca aagataactg gtcaaaggac 420
gcgaatgata ctttactcct ccagctgact aatacttcgg cctactat 468

<210> SEQ ID NO 198
<211> LENGTH: 459
<212> TYPE: DNA
<213> ORGANISM: Homo sapiens

<400> SEQUENCE: 198
tctcaaccgc ataccaaacc cagcgtcttt gtgatgaaga atggcacaaa cgtcgcttgc 60
ttggttaaag aattttaccc taaggacatt aggatcaatc tcgtaagcag caaaaaaatc 120
acggagttcg atcctgctat cgtgataagc ccttcaggaa agtacaacgc cgtgaaactg 180
ggcaagtatg aggatagcaa tagcgtgact tgtagcgtgc aacacgataa caaaaaccgta 240 cacagcaccg atttcgaagt taaaaccgac tcaactgatc acgttaaacc caaagagacc 300
gaaaatacca aacagccgtc taagagttgc cacaagccta aggcaattgt ccatactgaa 360
aaggtcaaca tgatgagttt gactgtcctc ggcttgagaa tgctgtttgc taagacggtc 420
gccgttaact tcttgctgac cgccaagctg ttctttcta 459

<210> SEQ ID NO 199
<211> LENGTH: 387
<212> TYPE: DNA
<213> ORGANISM: Homo sapiens

<400> SEQUENCE: 199
agccagccac atactaaacc cagcgtgttt gtgatgaaga acggaaccaa cgtcgcttgc 60
ctggtgaaag aattctaccc aaaagacatc aggataaacc tggtgagttc caagaaaatc 120
actgagtttg atcccgcgat agttatttcc ccgtcaggca agtacaacgc cgttaagctc 180
ggcaaatatg aggatagtaa ctccgttacg tgttctgtgc agcacgataa caagactgtc 240
cacagcaccg attttgaagt taagacagat agtaccgacc atgtcaaacc taaggagact 300
gagaacacca aacagccgtc taaaagttgc cacaaaccca aagccattgt tcatacagag 360
aaggtaaata tgatgtcgct gaccgtc 387

<210> SEQ ID NO 200
<211> LENGTH: 69
<212> TYPE: DNA
<213> ORGANISM: Homo sapiens

<400> SEQUENCE: 200
ttaggactgc gaatgttgtt tgccaaaaca gtggcagtga acttcctgtt gactgccaag 60
ctcttcttt 69

<210> SEQ ID NO 201
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 201
gaagtgcagg tgctggaaag cggcggagga ctggtgcagc ctggcggatc tctgagactg 60
agctgtgccg ccagcggctt caccttcagc agctacgcca tgagctgggt gcgccaggcc 120
cctggaaaag gcctggaatg ggtgtccgcc atctctggct ccggcggcag caccaattac 180
gccgatagcg tgaagggccg gttcaccatc agccgggaca acagcaagaa caccctgtac 240
ctgcagatga acagcctgag agccgaggac accgccgtgt actactgtgc cggaagctct 300
gggtggagcg agtattgggg ccagggcaca ctcgtgaccg tgtccagc 348

<210> SEQ ID NO 202
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 202

Glu Val Gln Val Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Asn Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Gly Ser Ser Gly Trp Ser Glu Tyr Trp Gly Gln Gly Thr Leu Val
100 105 110

Thr Val Ser Ser
115

<210> SEQ ID NO 203

<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 203
gacatccaga tgacccagag ccccagcagc ctgtctgcca gcgtgggcga cagagtgacc 60
atcacctgta gagccagcca gggcatccgg aacaacctgg cctggtatca gcagaagccc 120
ggcaaggccc ccaagcggct gatctacgcc gccagcaatc tgcagagcgg cgtgccctct 180
agattcaccg gctctggcag cggcaccgag ttcaccctga tcgtgtctag cctgcagccc 240
gaggacttcg ccacctacta ctgcctgcag caccacagct accccctgac atctggcgga 300
ggcaccaagg tggaaatcaa g 321

<210> SEQ ID NO 204
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 204

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asn
20 25 30

Leu Ala Trp Tyr Gln Gln Lys Pro Gly Lys Ala Pro Lys Arg Leu Ile
35 40 45

Tyr Ala Ala Ser Asn Leu Gln Ser Gly Val Pro Ser Arg Phe Thr Gly
50 55 60

Ser Gly Ser Gly Thr Glu Phe Thr Leu Ile Val Ser Ser Leu Gln Pro
65 70 75 80

Glu Asp Phe Ala Thr Tyr Tyr Cys Leu Gln His His Ser Tyr Pro Leu
85 90 95

Thr Ser Gly Gly Gly Thr Lys Val Glu Ile Lys
100 105

<210> SEQ ID NO 205
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 205
caagtgaagc tgcagcagtc tggcggaggc ctcgtgaaac ctggcgcctc tctgaagctg 60
agctgcgtga ccagcggctt caccttcaga aagttcggca tgagctgggt gcgccagacc 120
agcgacaagc ggctggaatg ggtggccagc atcagcaccg gcggctacaa cacctactac 180
agcgacaacg tgaagggcag attcaccatc agcagagaga acgccaagaa taccctgtac 240
ctgcagatga gcagcctgaa gtccgaggac accgccctgt actactgcac cagaggctac 300
agcagcacca gctacgccat ggactattgg ggccagggca ccaccgtgac cgtgtctagt 360

<210> SEQ ID NO 206
<211> LENGTH: 120

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 206

Gln Val Lys Leu Gln Gln Ser Gly Gly Gly Leu Val Lys Pro Gly Ala
1 5 10 15

Ser Leu Lys Leu Ser Cys Val Thr Ser Gly Phe Thr Phe Arg Lys Phe
20 25 30

Gly Met Ser Trp Val Arg Gln Thr Ser Asp Lys Arg Leu Glu Trp Val
35 40 45

Ala Ser Ile Ser Thr Gly Gly Tyr Asn Thr Tyr Tyr Ser Asp Asn Val
50 55 60

Lys Gly Arg Phe Thr Ile Ser Arg Glu Asn Ala Lys Asn Thr Leu Tyr
65 70 75 80

Leu Gln Met Ser Ser Leu Lys Ser Glu Asp Thr Ala Leu Tyr Tyr Cys
85 90 95

Thr Arg Gly Tyr Ser Ser Thr Ser Tyr Ala Met Asp Tyr Trp Gly Gln
100 105 110

Gly Thr Thr Val Thr Val Ser Ser
115 120

<210> SEQ ID NO 207
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 207
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agcttcaacg tgcccctgac ctttggcgac 300
ggcaccaagc tggaaatcaa g 321

<210> SEQ ID NO 208
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 208

Asp Ile Glu Leu Thr Gln Ser Pro Ala Ser Leu Ser Val Ala Thr Gly
1 5 10 15

Glu Lys Val Thr Ile Arg Cys Met Thr Ser Thr Asp Ile Asp Asp Asp
20 25 30

Met Asn Trp Tyr Gln Gln Lys Pro Gly Glu Pro Pro Lys Phe Leu Ile
35 40 45

Ser Glu Gly Asn Thr Leu Arg Pro Gly Val Pro Ser Arg Phe Ser Ser
50 55 60

Ser Gly Thr Gly Thr Asp Phe Val Phe Thr Ile Glu Asn Thr Leu Ser

```
65                  70                  75                  80

Glu Asp Val Gly Asp Tyr Tyr Cys Leu Gln Ser Phe Asn Val Pro Leu
                85                  90                  95

Thr Phe Gly Asp Gly Thr Lys Leu Glu Ile Lys
            100                 105


<210> SEQ ID NO 209
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

caagtgaagc tgcagcagtc tggcggaggc ctcgtgaaac ctggcgcctc tctgaagctg      60

agctgcgtga ccagcggctt caccttcaga aagttcggca tgagctgggt gcgccagacc     120

agcgacaagc ggctggaatg ggtggccagc atcagcaccg gcggctacaa cacctactac     180

agcgacaacg tgaagggcag attcaccatc agcagagaga acgccaagaa taccctgtac     240

ctgcagatga gcagcctgaa gtccgaggac accgccctgt actactgcac cagaggctac     300

agcccctaca gctacgccat ggactattgg ggccagggca ccaccgtgac cgtgtctagt     360


<210> SEQ ID NO 210
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Pro Tyr Ser Tyr Ala Met Asp Tyr Trp Gly Gln
            100                 105                 110

Gly Thr Thr Val Thr Val Ser Ser
        115                 120


<210> SEQ ID NO 211
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

gacatcgagc tgacacagag ccctgccagc ctgtctgtgg ccaccggcga gaaagtgacc      60
```

atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agctggaacg tgcccctgac ctttggcgac 300
ggcaccaagc tggaaatcaa g 321

<210> SEQ ID NO 212
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Asp Ile Glu Leu Thr Gln Ser Pro Ala Ser Leu Ser Val Ala Thr Gly
1 5 10 15

Glu Lys Val Thr Ile Arg Cys Met Thr Ser Thr Asp Ile Asp Asp Asp
20 25 30

Met Asn Trp Tyr Gln Gln Lys Pro Gly Glu Pro Pro Lys Phe Leu Ile
35 40 45

Ser Glu Gly Asn Thr Leu Arg Pro Gly Val Pro Ser Arg Phe Ser Ser
50 55 60

Ser Gly Thr Gly Thr Asp Phe Val Phe Thr Ile Glu Asn Thr Leu Ser
65 70 75 80

Glu Asp Val Gly Asp Tyr Tyr Cys Leu Gln Ser Trp Asn Val Pro Leu
85 90 95

Thr Phe Gly Asp Gly Thr Lys Leu Glu Ile Lys
100 105

<210> SEQ ID NO 213
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213
caggtgcagc tgcaggaatc tggcggaggg ctcgtgaagc ctggcggaag cctgaagctg 60
agctgtgccg ccagcggctt caccttcagc aagttcggca tgagctgggt gcgccagacc 120
cccgacaaga gactggaatg ggtggccagc atcagcaccg gcggctacaa tacctactac 180
agcgacaacg tgaagggccg gttcaccatc tcccgggaca acgccaagaa caccctgtac 240
ctgcagatga gcagcctgaa gtccgaggac accgccatgt actactgtgc cagaggctac 300
agcccctaca gctacgccat ggattactgg ggccagggca caatggtcac cgtgtcctct 360

<210> SEQ ID NO 214
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

Gln Val Gln Leu Gln Glu Ser Gly Gly Gly Leu Val Lys Pro Gly Gly
1 5 10 15

Ser Leu Lys Leu Ser Cys Ala Ala Ser Gly Phe Thr Phe Ser Lys Phe
20 25 30

Gly Met Ser Trp Val Arg Gln Thr Pro Asp Lys Arg Leu Glu Trp Val
35 40 45

Ala Ser Ile Ser Thr Gly Gly Tyr Asn Thr Tyr Tyr Ser Asp Asn Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Tyr Cys
85 90 95

Ala Arg Gly Tyr Ser Pro Tyr Ser Tyr Ala Met Asp Tyr Trp Gly Gln
100 105 110

Gly Thr Met Val Thr Val Ser Ser
115 120

<210> SEQ ID NO 215
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 215
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180 agatttctg gcagcggctc cggcaccgac ttcatcttca ccatcagctc cctgcagccc 240
gaggatatcg ccacctacta ctgcctgcag agctggaacg tgcccctgac ctttggcgga 300
ggcaccaagg tggaaatcaa g 321

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

Asp Ile Gln Met Thr Gln Ser Pro Ser Ser Leu Ser Ala Ser Val Gly
1 5 10 15

Asp Arg Val Thr Ile Thr Cys Met Thr Ser Thr Asp Ile Asp Asp Asp
20 25 30

Met Asn Trp Tyr Gln Gln Lys Pro Gly Lys Thr Pro Lys Leu Leu Ile
35 40 45

Tyr Glu Gly Asn Thr Leu Arg Pro Gly Val Pro Ser Arg Phe Ser Gly
50 55 60

Ser Gly Ser Gly Thr Asp Phe Ile Phe Thr Ile Ser Ser Leu Gln Pro
65 70 75 80

Glu Asp Ile Ala Thr Tyr Tyr Cys Leu Gln Ser Trp Asn Val Pro Leu
85 90 95

Thr Phe Gly Gly Gly Thr Lys Val Glu Ile Lys
100 105

<210> SEQ ID NO 217
<211> LENGTH: 360

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 217

```
caggtgcagc tgcaggaatc tggcggaggg ctcgtgaagc ctggcggaag cctgaagctg     60

agctgtgccg ccagcggctt caccttcagc aagttcggca tgagctgggt gcgccagacc    120

cccgacaaga gactggaatg ggtggccagc atcagcaccg gcggctacaa caccttctac    180

agcgacaacg tgaagggccg gttcaccatc tcccgggaca acgccaagaa caccctgtac    240

ctgcagatga gcagcctgaa gtccgaggac accgccatgt actactgtgc cagaggctac    300

agcccctaca gcttcgccat ggattactgg ggccagggca caatggtcac cgtgtcctct    360
```

<210> SEQ ID NO 218
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 218

```
Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Lys Phe
            20                  25                  30

Gly Met Ser Trp Val Arg Gln Thr Pro Asp Lys Arg Leu Glu Trp Val
        35                  40                  45

Ala Ser Ile Ser Thr Gly Gly Tyr Asn Thr Phe Tyr Ser Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gly Tyr Ser Pro Tyr Ser Phe Ala Met Asp Tyr Trp Gly Gln
            100                 105                 110

Gly Thr Met Val Thr Val Ser Ser
        115                 120
```

<210> SEQ ID NO 219
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 219

```
gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agatttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa g                                              321
```

<210> SEQ ID NO 220
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 220

```
Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys
            100                 105
```

<210> SEQ ID NO 221
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 221

```
gacatccaga tgacccagag ccccagcagc ctgtctgcca gcgtgggcga cagagtgacc     60

atcacctgta gagccagcca gggcatccgg aacaacctgg cctggtatca gcagaagccc    120

ggcaaggccc ccaagcggct gatctacgcc gccagcaatc tgcagagcgg cgtgccctct    180

agattcaccg gctctggcag cggcaccgag ttcaccctga tcgtgtctag cctgcagccc    240

gaggacttcg ccacctacta ctgcctgcag caccacagct accccctgac atctggcgga    300

ggcaccaagg tggaaatcaa gggcagcaca agcggcagcg gaaaacctgg atctggcgag    360

ggctctacca agggcgaagt gcaggtgctg gaaagcggcg gaggactggt gcagcctggc    420

ggatctctga gactgagctg tgccgccagc ggcttcacct tcagcagcta cgccatgagc    480

tgggtgcgcc aggcccctgg aaaaggcctg gaatgggtgt ccgccatctc tggctccggc    540

ggcagcacca attacgccga tagcgtgaag ggccggttca ccatcagccg ggacaacagc    600

aagaacaccc tgtacctgca gatgaacagc ctgagagccg aggacaccgc cgtgtactac    660

tgtgccggaa gctctgggtg gagcgagtat tggggccagg gcacactcgt gaccgtgtcc    720

agc                                                                  723
```

<210> SEQ ID NO 222
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 222

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Val Leu Glu Ser Gly Gly Gly Leu Val Gln Pro Gly Gly Ser Leu Arg
    130                 135                 140

Leu Ser Cys Ala Ala Ser Gly Phe Thr Phe Ser Ser Tyr Ala Met Ser
145                 150                 155                 160

Trp Val Arg Gln Ala Pro Gly Lys Gly Leu Glu Trp Val Ser Ala Ile
                165                 170                 175

Ser Gly Ser Gly Gly Ser Thr Asn Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Gly Ser
    210                 215                 220

Ser Gly Trp Ser Glu Tyr Trp Gly Gln Gly Thr Leu Val Thr Val Ser
225                 230                 235                 240

Ser
```

<210> SEQ ID NO 223
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 223

```
gacatcgagc tgacacagag ccctgccagc ctgtctgtgg ccaccggcga gaaagtgacc     60

atccggtgca tgaccagcac cgacatcgac gacgacatga actggtatca gcagaagccc    120

ggcgagcccc ccaagttcct gatcagcgag ggcaacacac tgcggcctgg cgtgccaagc    180

agattcagca gctctggcac cggcaccgac ttcgtgttca ccatcgagaa caccctgagc    240

gaggacgtgg gcgactacta ctgcctgcag agcttcaacg tgcccctgac ctttggcgac    300

ggcaccaagc tggaaatcaa gggcggaggc ggatctggcg gcggaggatc tgggggaggc    360

ggctctcaag tgaagctgca gcagtctggc ggaggcctcg tgaaacctgg cgcctctctg    420

aagctgagct gcgtgaccag cggcttcacc ttcagaaagt tcggcatgag ctgggtgcgc    480

cagaccagcg acaagcggct ggaatgggtg gccagcatca gcaccggcgg ctacaacacc    540

tactacagcg acaacgtgaa gggcagattc accatcagca gagagaacgc caagaatacc    600

ctgtacctgc agatgagcag cctgaagtcc gaggacaccg ccctgtacta ctgcaccaga    660
```

ggctacagca gcaccagcta cgccatggac tattggggcc agggcaccac cgtgaccgtg 720
tctagt 726

<210> SEQ ID NO 224
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

Asp Ile Glu Leu Thr Gln Ser Pro Ala Ser Leu Ser Val Ala Thr Gly
1 5 10 15

Glu Lys Val Thr Ile Arg Cys Met Thr Ser Thr Asp Ile Asp Asp Asp
20 25 30

Met Asn Trp Tyr Gln Gln Lys Pro Gly Glu Pro Pro Lys Phe Leu Ile
35 40 45

Ser Glu Gly Asn Thr Leu Arg Pro Gly Val Pro Ser Arg Phe Ser Ser
50 55 60

Ser Gly Thr Gly Thr Asp Phe Val Phe Thr Ile Glu Asn Thr Leu Ser
65 70 75 80

Glu Asp Val Gly Asp Tyr Tyr Cys Leu Gln Ser Phe Asn Val Pro Leu
85 90 95

Thr Phe Gly Asp Gly Thr Lys Leu Glu Ile Lys Gly Gly Gly Gly Ser
100 105 110

Gly Gly Gly Gly Ser Gly Gly Gly Gly Ser Gln Val Lys Leu Gln Gln
115 120 125

Ser Gly Gly Gly Leu Val Lys Pro Gly Ala Ser Leu Lys Leu Ser Cys
130 135 140

Val Thr Ser Gly Phe Thr Phe Arg Lys Phe Gly Met Ser Trp Val Arg
145 150 155 160

Gln Thr Ser Asp Lys Arg Leu Glu Trp Val Ala Ser Ile Ser Thr Gly
165 170 175

Gly Tyr Asn Thr Tyr Tyr Ser Asp Asn Val Lys Gly Arg Phe Thr Ile
180 185 190

Ser Arg Glu Asn Ala Lys Asn Thr Leu Tyr Leu Gln Met Ser Ser Leu
195 200 205

Lys Ser Glu Asp Thr Ala Leu Tyr Tyr Cys Thr Arg Gly Tyr Ser Ser
210 215 220

Thr Ser Tyr Ala Met Asp Tyr Trp Gly Gln Gly Thr Thr Val Thr Val
225 230 235 240

Ser Ser

<210> SEQ ID NO 225
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 225
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180

```
agattcagca gctctggcac cggcaccgac ttcgtgttca ccatcgagaa caccctgagc    240

gaggacgtgg gcgactacta ctgcctgcag agctggaacg tgcccctgac ctttggcgac    300

ggcaccaagc tggaaatcaa gggcggaggc ggatctggcg gcggaggatc tgggggaggc    360

ggctctcaag tgaagctgca gcagtctggc ggaggcctcg tgaaacctgg cgcctctctg    420

aagctgagct gcgtgaccag cggcttcacc ttcagaaagt tcggcatgag ctgggtgcgc    480

cagaccagcg acaagcggct ggaatgggtg gccagcatca gcaccggcgg ctacaacacc    540

tactacagcg acaacgtgaa gggcagattc accatcagca gagagaacgc caagaatacc    600

ctgtacctgc agatgagcag cctgaagtcc gaggacaccg ccctgtacta ctgcaccaga    660

ggctacagcc cctacagcta cgccatggac tattggggcc agggcaccac cgtgaccgtg    720

tctagt                                                               726
```

```
<210> SEQ ID NO 226
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220

Tyr Ser Tyr Ala Met Asp Tyr Trp Gly Gln Gly Thr Thr Val Thr Val
225                 230                 235                 240

Ser Ser
```

<210> SEQ ID NO 227
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 227

```
gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480

cagacccccg acaagagact ggaatgggtg gccagcatca gcaccggcgg ctacaatacc    540

tactacagcg acaacgtgaa gggccggttc accatctccc gggacaacgc caagaacacc    600

ctgtacctgc agatgagcag cctgaagtcc gaggacaccg ccatgtacta ctgtgccaga    660

ggctacagcc cctacagcta cgccatggat tactggggcc agggcacaat ggtcaccgtg    720

tcctct                                                               726
```

<210> SEQ ID NO 228
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

```
Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
```

```
                165                 170                 175

Gly Tyr Asn Thr Tyr Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Tyr Ala Met Asp Tyr Trp Gly Gln Gly Thr Met Val Thr Val
225                 230                 235                 240

Ser Ser


<210> SEQ ID NO 229
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229

gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480

cagacccccg acaagagact ggaatgggtg gccagcatca gcaccggcgg ctacaacacc    540

ttctacagcg acaacgtgaa gggccggttc accatctccc gggacaacgc caagaacacc    600

ctgtacctgc agatgagcag cctgaagtcc gaggacaccg ccatgtacta ctgtgccaga    660

ggctacagcc cctacagctt cgccatggat tactggggcc agggcacaat ggtcaccgtg    720

tcctct                                                               726


<210> SEQ ID NO 230
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80
```

```
Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Phe Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Phe Ala Met Asp Tyr Trp Gly Gln Gly Thr Met Val Thr Val
225                 230                 235                 240

Ser Ser
```

<210> SEQ ID NO 231
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 231

```
gacatccaga tgacccagag ccccagcagc ctgtctgcca gcgtgggcga cagagtgacc     60

atcacctgta gagccagcca gggcatccgg aacaacctgg cctggtatca gcagaagccc    120

ggcaaggccc ccaagcggct gatctacgcc gccagcaatc tgcagagcgg cgtgccctct    180

agattcaccg gctctggcag cggcaccgag ttcaccctga tcgtgtctag cctgcagccc    240

gaggacttcg ccacctacta ctgcctgcag caccacagct accccctgac atctggcgga    300

ggcaccaagg tggaaatcaa gggcagcaca agcggcagcg gaaaacctgg atctggcgag    360

ggctctacca agggcgaagt gcaggtgctg gaaagcggcg gaggactggt gcagcctggc    420

ggatctctga gactgagctg tgccgccagc ggcttcacct tcagcagcta cgccatgagc    480

tgggtgcgcc aggcccctgg aaaaggcctg gaatgggtgt ccgccatctc tggctccggc    540

ggcagcacca attacgccga tagcgtgaag ggccggttca ccatcagccg ggacaacagc    600

aagaacaccc tgtacctgca gatgaacagc ctgagagccg aggacaccgc cgtgtactac    660

tgtgccggaa gctctgggtg gagcgagtat tggggccagg gcacactcgt gaccgtgtcc    720

agcaagccca ccaccacccc tgcccctaga cctccaaccc cagcccctac aatcgccagc    780

cagcccctga gcctgaggcc cgaagcctgt agacctgccg ctggcggagc cgtgcacacc    840

agaggcctgg atttcgcctg cgacatctac atctgggccc ctctggccgg cacctgtggc    900

gtgctgctgc tgagcctggt catcaccctg tactgcaacc accggaataa gagaggccgg    960

aagaaactgc tgtacatctt caagcagccc ttcatgcggc ccgtgcagac cacccaggaa   1020

gaggacggct gcagctgccg gttccccgag gaagaggaag gcggctgcga actgcgggtg   1080
```

aagttcagcc ggagcgccga cgcccctgcc taccagcagg gccagaacca gctgtacaac 1140
gagctgaacc tgggccggag ggaggagtac gacgtgctgg acaagcggag aggccgggac 1200
cctgagatgg gcggcaagcc ccggagaaag aaccctcagg agggcctgta taacgaactg 1260
cagaaagaca agatggccga ggcctacagc gagatcggca tgaagggcga gcggcggagg 1320
ggcaagggcc acgacggcct gtaccagggc ctgagcaccg ccaccaagga tacctacgac 1380
gccctgcaca tgcaggccct gccccccaga 1410

<210> SEQ ID NO 232
<211> LENGTH: 470
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 232

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asn
20 25 30

Leu Ala Trp Tyr Gln Gln Lys Pro Gly Lys Ala Pro Lys Arg Leu Ile
35 40 45

Tyr Ala Ala Ser Asn Leu Gln Ser Gly Val Pro Ser Arg Phe Thr Gly
50 55 60

Ser Gly Ser Gly Thr Glu Phe Thr Leu Ile Val Ser Ser Leu Gln Pro
65 70 75 80

Glu Asp Phe Ala Thr Tyr Tyr Cys Leu Gln His His Ser Tyr Pro Leu
85 90 95

Thr Ser Gly Gly Gly Thr Lys Val Glu Ile Lys Gly Ser Thr Ser Gly
100 105 110

Ser Gly Lys Pro Gly Ser Gly Glu Gly Ser Thr Lys Gly Glu Val Gln
115 120 125

Val Leu Glu Ser Gly Gly Gly Leu Val Gln Pro Gly Gly Ser Leu Arg
130 135 140

Leu Ser Cys Ala Ala Ser Gly Phe Thr Phe Ser Ser Tyr Ala Met Ser
145 150 155 160

Trp Val Arg Gln Ala Pro Gly Lys Gly Leu Glu Trp Val Ser Ala Ile
165 170 175

Ser Gly Ser Gly Gly Ser Thr Asn Tyr Ala Asp Ser Val Lys Gly Arg
180 185 190

Phe Thr Ile Ser Arg Asp Asn Ser Lys Asn Thr Leu Tyr Leu Gln Met
195 200 205

Asn Ser Leu Arg Ala Glu Asp Thr Ala Val Tyr Tyr Cys Ala Gly Ser
210 215 220

Ser Gly Trp Ser Glu Tyr Trp Gly Gln Gly Thr Leu Val Thr Val Ser
225 230 235 240

Ser Lys Pro Thr Thr Thr Pro Ala Pro Arg Pro Pro Thr Pro Ala Pro
245 250 255

Thr Ile Ala Ser Gln Pro Leu Ser Leu Arg Pro Glu Ala Cys Arg Pro
260 265 270

Ala Ala Gly Gly Ala Val His Thr Arg Gly Leu Asp Phe Ala Cys Asp
275 280 285

Ile Tyr Ile Trp Ala Pro Leu Ala Gly Thr Cys Gly Val Leu Leu Leu
290 295 300

```
Ser Leu Val Ile Thr Leu Tyr Cys Asn His Arg Asn Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470
```

```
<210> SEQ ID NO 233
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233

gacatcgagc tgacacagag ccctgccagc ctgtctgtgg ccaccggcga gaaagtgacc     60

atccggtgca tgaccagcac cgacatcgac gacgacatga actggtatca gcagaagccc    120

ggcgagcccc ccaagttcct gatcagcgag ggcaacacac tgcggcctgg cgtgccaagc    180

agattcagca gctctggcac cggcaccgac ttcgtgttca ccatcgagaa caccctgagc    240

gaggacgtgg gcgactacta ctgcctgcag agcttcaacg tgcccctgac ctttggcgac    300

ggcaccaagc tggaaatcaa gggcggaggc ggatctggcg gcggaggatc tgggggaggc    360

ggctctcaag tgaagctgca gcagtctggc ggaggcctcg tgaaacctgg cgcctctctg    420

aagctgagct gcgtgaccag cggcttcacc ttcagaaagt tcggcatgag ctgggtgcgc    480

cagaccagcg acaagcggct ggaatgggtg gccagcatca gcaccggcgg ctacaacacc    540

tactacagcg acaacgtgaa gggcagattc accatcagca gagagaacgc caagaatacc    600

ctgtacctgc agatgagcag cctgaagtcc gaggacaccg ccctgtacta ctgcaccaga    660

ggctacagca gcaccagcta cgccatggac tattggggcc agggcaccac cgtgaccgtg    720

tctagtaagc ccaccaccac ccctgcccct agacctccaa ccccagcccc tacaatcgcc    780

agccagcccc tgagcctgag gcccgaagcc tgtagacctg ccgctggcgg agccgtgcac    840

accagaggcc tggatttcgc ctgcgacatc tacatctggg cccctctggc cggcacctgt    900

ggcgtgctgc tgctgagcct ggtcatcacc ctgtactgca accaccggaa taagagaggc    960

cggaagaaac tgctgtacat cttcaagcag cccttcatgc ggcccgtgca gaccacccag   1020
```

```
gaagaggacg gctgcagctg ccggttcccc gaggaagagg aaggcggctg cgaactgcgg   1080

gtgaagttca gccggagcgc cgacgcccct gcctaccagc agggccagaa ccagctgtac   1140

aacgagctga acctgggccg gagggaggag tacgacgtgc tggacaagcg gagaggccgg   1200

gaccctgaga tgggcggcaa gccccggaga aagaaccctc aggagggcct gtataacgaa   1260

ctgcagaaag acaagatggc cgaggcctac agcgagatcg gcatgaaggg cgagcggcgg   1320

aggggcaagg gccacgacgg cctgtaccag ggcctgagca ccgccaccaa ggatacctac   1380

gacgccctgc acatgcaggc cctgcccccc aga                                1413
```

```
<210> SEQ ID NO 234
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Phe Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Ser
    210                 215                 220

Thr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285
```

```
Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 235
<211> LENGTH: 1413
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 235

```
gacatcgagc tgacacagag ccctgccagc ctgtctgtgg ccaccggcga gaaagtgacc     60

atccggtgca tgaccagcac cgacatcgac gacgacatga actggtatca gcagaagccc    120

ggcgagcccc ccaagttcct gatcagcgag ggcaacacac tgcggcctgg cgtgccaagc    180

agattcagca gctctggcac cggcaccgac ttcgtgttca ccatcgagaa caccctgagc    240

gaggacgtgg gcgactacta ctgcctgcag agctggaacg tgcccctgac ctttggcgac    300

ggcaccaagc tggaaatcaa gggcggaggc ggatctggcg gcggaggatc tgggggaggc    360

ggctctcaag tgaagctgca gcagtctggc ggaggcctcg tgaaacctgg cgcctctctg    420

aagctgagct gcgtgaccag cggcttcacc ttcagaaagt tcggcatgag ctgggtgcgc    480

cagaccagcg acaagcggct ggaatgggtg gccagcatca gcaccggcgg ctacaacacc    540

tactacagcg acaacgtgaa gggcagattc accatcagca gagagaacgc caagaatacc    600

ctgtacctgc agatgagcag cctgaagtcc gaggacaccg ccctgtacta ctgcaccaga    660

ggctacagcc cctacagcta cgccatggac tattggggcc agggcaccac cgtgaccgtg    720

tctagtaagc ccaccaccac ccctgcccct agacctccaa ccccagcccc tacaatcgcc    780

agccagcccc tgagcctgag gcccgaagcc tgtagacctg ccgctggcgg agccgtgcac    840

accagaggcc tggatttcgc ctgcgacatc tacatctggg cccctctggc cggcacctgt    900

ggcgtgctgc tgctgagcct ggtcatcacc ctgtactgca accaccggaa taagagaggc    960
```

```
cggaagaaac tgctgtacat cttcaagcag cccttcatgc ggcccgtgca gaccacccag   1020

gaagaggacg gctgcagctg ccggttcccc gaggaagagg aaggcggctg cgaactgcgg   1080

gtgaagttca gccggagcgc cgacgcccct gcctaccagc agggccagaa ccagctgtac   1140

aacgagctga acctgggccg gagggaggag tacgacgtgc tggacaagcg gagaggccgg   1200

gaccctgaga tgggcggcaa gccccggaga aagaaccctc aggagggcct gtataacgaa   1260

ctgcagaaag acaagatggc cgaggcctac agcgagatcg gcatgaaggg cgagcggcgg   1320

aggggcaagg gccacgacgg cctgtaccag ggcctgagca ccgccaccaa ggatacctac   1380

gacgccctgc acatgcaggc cctgcccccc aga                                1413
```

<210> SEQ ID NO 236
<211> LENGTH: 471
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 236

```
Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220

Tyr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
```

```
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 237
<211> LENGTH: 1413
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 237

```
gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480

cagacccccg acaagagact ggaatgggtg gccagcatca gcaccggcgg ctacaatacc    540

tactacagcg acaacgtgaa gggccggttc accatctccc gggacaacgc caagaacacc    600

ctgtacctgc agatgagcag cctgaagtcc gaggacaccg ccatgtacta ctgtgccaga    660

ggctacagcc cctacagcta cgccatggat tactggggcc agggcacaat ggtcaccgtg    720

tcctctaagc ccaccaccac ccctgcccct agacctccaa ccccagcccc tacaatcgcc    780

agccagcccc tgagcctgag gcccgaagcc tgtagacctg ccgctggcgg agccgtgcac    840

accagaggcc tggatttcgc ctgcgacatc tacatctggg cccctctggc cggcacctgt    900
```

```
ggcgtgctgc tgctgagcct ggtcatcacc ctgtactgca accaccggaa taagagaggc    960

cggaagaaac tgctgtacat cttcaagcag cccttcatgc ggcccgtgca gaccacccag   1020

gaagaggacg gctgcagctg ccggttcccc gaggaagagg aaggcggctg cgaactgcgg   1080

gtgaagttca gccggagcgc cgacgcccct gcctaccagc agggccagaa ccagctgtac   1140

aacgagctga acctgggccg gagggaggag tacgacgtgc tggacaagcg gagaggccgg   1200

gaccctgaga tgggcggcaa gccccggaga aagaaccctc aggagggcct gtataacgaa   1260

ctgcagaaag acaagatggc cgaggcctac agcgagatcg gcatgaaggg cgagcggcgg   1320

aggggcaagg gccacgacgg cctgtaccag ggcctgagca ccgccaccaa ggatacctac   1380

gacgccctgc acatgcaggc cctgcccccc aga                                1413
```

<210> SEQ ID NO 238
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

```
Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Tyr Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270
```

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 239
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180
agattttctg gcagcggctc cggcaccgac ttcatcttca ccatcagctc cctgcagccc 240
gaggatatcg ccacctacta ctgcctgcag agctggaacg tgcccctgac ctttggcgga 300
ggcaccaagg tggaaatcaa gggcggaggc ggatctggcg gcggaggatc tgggggaggc 360
ggctctcagg tgcagctgca ggaatctggc ggagggctcg tgaagcctgg cggaagcctg 420
aagctgagct gtgccgccag cggcttcacc ttcagcaagt tcggcatgag ctgggtgcgc 480
cagacccccg acaagagact ggaatgggtg gccagcatca gcaccggcgg ctacaacacc 540
ttctacagcg acaacgtgaa gggccggttc accatctccc gggacaacgc caagaacacc 600
ctgtacctgc agatgagcag cctgaagtcc gaggacaccg ccatgtacta ctgtgccaga 660
ggctacagcc cctacagctt cgccatggat tactggggcc agggcacaat ggtcaccgtg 720
tcctctaagc ccaccaccac ccctgcccct agacctccaa ccccagcccc tacaatcgcc 780
agccagcccc tgagcctgag gcccgaagcc tgtagacctg ccgctggcgg agccgtgcac 840

```
accagaggcc tggatttcgc ctgcgacatc tacatctggg cccctctggc cggcacctgt    900

ggcgtgctgc tgctgagcct ggtcatcacc ctgtactgca accaccggaa taagagaggc    960

cggaagaaac tgctgtacat cttcaagcag cccttcatgc ggcccgtgca gaccacccag   1020

gaagaggacg gctgcagctg ccggttcccc gaggaagagg aaggcggctg cgaactgcgg   1080

gtgaagttca gccggagcgc cgacgcccct gcctaccagc agggccagaa ccagctgtac   1140

aacgagctga acctgggccg gagggaggag tacgacgtgc tggacaagcg gagaggccgg   1200

gaccctgaga tgggcggcaa gccccggaga aagaaccctc aggagggcct gtataacgaa   1260

ctgcagaaag acaagatggc cgaggcctac agcgagatcg gcatgaaggg cgagcggcgg   1320

aggggcaagg gccacgacgg cctgtaccag ggcctgagca ccgccaccaa ggatacctac   1380

gacgccctgc acatgcaggc cctgcccccc aga                                1413


<210> SEQ ID NO 240
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Phe Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Phe Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255
```

```
Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 241
<211> LENGTH: 1554
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 241

```
gacatcgagc tgacacagag ccctgccagc ctgtctgtgg ccaccggcga gaaagtgacc     60

atccggtgca tgaccagcac cgacatcgac gacgacatga actggtatca gcagaagccc    120

ggcgagcccc ccaagttcct gatcagcgag ggcaacacac tgcggcctgg cgtgccaagc    180

agattcagca gctctggcac cggcaccgac ttcgtgttca ccatcgagaa caccctgagc    240

gaggacgtgg gcgactacta ctgcctgcag agctggaacg tgcccctgac ctttggcgac    300

ggcaccaagc tggaaatcaa gggcggaggc ggatctggcg gcggaggatc tgggggaggc    360

ggctctcaag tgaagctgca gcagtctggc ggaggcctcg tgaaacctgg cgcctctctg    420

aagctgagct gcgtgaccag cggcttcacc ttcagaaagt tcggcatgag ctgggtgcgc    480

cagaccagcg acaagcggct ggaatgggtg gccagcatca gcaccggcgg ctacaacacc    540

tactacagcg acaacgtgaa gggcagattc accatcagca gagagaacgc caagaatacc    600

ctgtacctgc agatgagcag cctgaagtcc gaggacaccg ccctgtacta ctgcaccaga    660

ggctacagcc cctacagcta cgccatggac tattggggcc agggcaccac cgtgaccgtg    720

tctagtaaac ctactacaac tcctgccccc cggcctccta caccagctcc tactatcgcc    780
```

tcccagccac tcagtctcag acccgaggct tctaggccag cggccggagg cgcggtccac 840
acccgcgggc tggactttgc atccgataag cccaccacca cccctgcccc tagacctcca 900
accccagccc ctacaatcgc cagccagccc ctgagcctga ggcccgaagc ctgtagacct 960
gccgctggcg gagccgtgca caccagaggc ctggatttcg cctgcgacat ctacatctgg 1020
gcccctctgg ccggcacctg tggcgtgctg ctgctgagcc tggtcatcac cctgtactgc 1080
aaccaccgga ataagagagg ccggaagaaa ctgctgtaca tcttcaagca gcccttcatg 1140
cggcccgtgc agaccaccca ggaagaggac ggctgcagct gccggttccc cgaggaagag 1200
gaaggcggct gcgaactgcg ggtgaagttc agccggagcg ccgacgcccc tgcctaccag 1260
cagggccaga accagctgta caacgagctg aacctgggcc ggagggagga gtacgacgtg 1320
ctggacaagc ggagaggccg ggaccctgag atgggcggca agccccggag aaagaaccct 1380
caggagggcc tgtataacga actgcagaaa gacaagatgg ccgaggccta cagcgagatc 1440
ggcatgaagg gcgagcggcg gaggggcaag ggccacgacg gcctgtacca gggcctgagc 1500
accgccacca aggataccta cgacgccctg cacatgcagg ccctgccccc caga 1554

<210> SEQ ID NO 242
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220
```

Tyr Ser Tyr Ala Met Asp Tyr Trp Gly Gln Gly Thr Thr Val Thr Val
225 230 235 240

Ser Ser Lys Pro Thr Thr Thr Pro Ala Pro Arg Pro Pro Thr Pro Ala
245 250 255

Pro Thr Ile Ala Ser Gln Pro Leu Ser Leu Arg Pro Glu Ala Ser Arg
260 265 270

Pro Ala Ala Gly Gly Ala Val His Thr Arg Gly Leu Asp Phe Ala Ser
275 280 285

Asp Lys Pro Thr Thr Thr Pro Ala Pro Arg Pro Pro Thr Pro Ala Pro
290 295 300

Thr Ile Ala Ser Gln Pro Leu Ser Leu Arg Pro Glu Ala Cys Arg Pro
305 310 315 320

Ala Ala Gly Gly Ala Val His Thr Arg Gly Leu Asp Phe Ala Cys Asp
325 330 335

Ile Tyr Ile Trp Ala Pro Leu Ala Gly Thr Cys Gly Val Leu Leu Leu
340 345 350

Ser Leu Val Ile Thr Leu Tyr Cys Asn His Arg Asn Lys Arg Gly Arg
355 360 365

Lys Lys Leu Leu Tyr Ile Phe Lys Gln Pro Phe Met Arg Pro Val Gln
370 375 380

Thr Thr Gln Glu Glu Asp Gly Cys Ser Cys Arg Phe Pro Glu Glu Glu
385 390 395 400

Glu Gly Gly Cys Glu Leu Arg Val Lys Phe Ser Arg Ser Ala Asp Ala
405 410 415

Pro Ala Tyr Gln Gln Gly Gln Asn Gln Leu Tyr Asn Glu Leu Asn Leu
420 425 430

Gly Arg Arg Glu Glu Tyr Asp Val Leu Asp Lys Arg Arg Gly Arg Asp
435 440 445

Pro Glu Met Gly Gly Lys Pro Arg Arg Lys Asn Pro Gln Glu Gly Leu
450 455 460

Tyr Asn Glu Leu Gln Lys Asp Lys Met Ala Glu Ala Tyr Ser Glu Ile
465 470 475 480

Gly Met Lys Gly Glu Arg Arg Arg Gly Lys Gly His Asp Gly Leu Tyr
485 490 495

Gln Gly Leu Ser Thr Ala Thr Lys Asp Thr Tyr Asp Ala Leu His Met
500 505 510

Gln Ala Leu Pro Pro Arg
515

<210> SEQ ID NO 243
<211> LENGTH: 1695
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 243
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agctggaacg tgcccctgac ctttggcgac 300
ggcaccaagc tggaaatcaa gggcggaggc ggatctggcg gcggaggatc tgggggaggc 360
ggctctcaag tgaagctgca gcagtctggc ggaggcctcg tgaaacctgg cgcctctctg 420
aagctgagct gcgtgaccag cggcttcacc ttcagaaagt tcggcatgag ctgggtgcgc 480
cagaccagcg acaagcggct ggaatgggtg gccagcatca gcaccggcgg ctacaacacc 540
tactacagcg acaacgtgaa gggcagattc accatcagca gagagaacgc caagaatacc 600
ctgtacctgc agatgagcag cctgaagtcc gaggacaccg ccctgtacta ctgcaccaga 660
ggctacagcc cctacagcta cgccatggac tattggggcc agggcaccac cgtgaccgtg 720
tctagtaagc ctaccaccac ccccgcacct cgtcctccaa cccctgcacc tacgattgcc 780
agtcagcctc tttcactgcg gcctgaggcc agcagaccag ctgccggcgg tgccgtccat 840
acaagaggac tggacttcgc gtccgataaa cctactacca ctccagcccc aaggccccca 900
accccagcac cgactatcgc atcacagcct ttgtcactgc gtcctgaagc cagccggcca 960
gctgcagggg gggccgtcca cacaagggga ctcgactttg cgagtgataa gcccaccacc 1020
acccctgccc ctagacctcc aaccccagcc cctacaatcg ccagccagcc cctgagcctg 1080
aggcccgaag cctgtagacc tgccgctggc ggagccgtgc acaccagagg cctggatttc 1140
gcctgcgaca tctacatctg ggcccctctg gccggcacct gtggcgtgct gctgctgagc 1200
ctggtcatca ccctgtactg caaccaccgg aataagagag gccggaagaa actgctgtac 1260
atcttcaagc agcccttcat gcggcccgtg cagaccaccc aggaagagga cggctgcagc 1320
tgccggttcc ccgaggaaga ggaaggcggc tgcgaactgc gggtgaagtt cagccggagc 1380
gccgacgccc ctgcctacca gcagggccag aaccagctgt acaacgagct gaacctgggc 1440
cggagggagg agtacgacgt gctggacaag cggagaggcc gggaccctga gatgggcggc 1500
aagccccgga gaaagaaccc tcaggagggc ctgtataacg aactgcagaa agacaagatg 1560
gccgaggcct acagcgagat cggcatgaag ggcgagcggc ggaggggcaa gggccacgac 1620
ggcctgtacc agggcctgag caccgccacc aaggatacct acgacgccct gcacatgcag 1680
gccctgcccc ccaga 1695

<210> SEQ ID NO 244
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 244

Asp Ile Glu Leu Thr Gln Ser Pro Ala Ser Leu Ser Val Ala Thr Gly
1 5 10 15

Glu Lys Val Thr Ile Arg Cys Met Thr Ser Thr Asp Ile Asp Asp Asp
20 25 30

Met Asn Trp Tyr Gln Gln Lys Pro Gly Glu Pro Pro Lys Phe Leu Ile
35 40 45

Ser Glu Gly Asn Thr Leu Arg Pro Gly Val Pro Ser Arg Phe Ser Ser
50 55 60

Ser Gly Thr Gly Thr Asp Phe Val Phe Thr Ile Glu Asn Thr Leu Ser
65 70 75 80

Glu Asp Val Gly Asp Tyr Tyr Cys Leu Gln Ser Trp Asn Val Pro Leu
85 90 95

Thr Phe Gly Asp Gly Thr Lys Leu Glu Ile Lys Gly Gly Gly Gly Ser
100 105 110

-continued

```
Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220

Tyr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Cys Arg Pro Ala
        355                 360                 365

Ala Gly Gly Ala Val His Thr Arg Gly Leu Asp Phe Ala Cys Asp Ile
    370                 375                 380

Tyr Ile Trp Ala Pro Leu Ala Gly Thr Cys Gly Val Leu Leu Leu Ser
385                 390                 395                 400

Leu Val Ile Thr Leu Tyr Cys Asn His Arg Asn Lys Arg Gly Arg Lys
                405                 410                 415

Lys Leu Leu Tyr Ile Phe Lys Gln Pro Phe Met Arg Pro Val Gln Thr
            420                 425                 430

Thr Gln Glu Glu Asp Gly Cys Ser Cys Arg Phe Pro Glu Glu Glu Glu
        435                 440                 445

Gly Gly Cys Glu Leu Arg Val Lys Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Arg Arg Lys Asn Pro Gln Glu Gly Leu Tyr
            500                 505                 510

Asn Glu Leu Gln Lys Asp Lys Met Ala Glu Ala Tyr Ser Glu Ile Gly
        515                 520                 525

Met Lys Gly Glu Arg Arg Arg Gly Lys Gly His Asp Gly Leu Tyr Gln
```

-continued 530 535 540

Gly Leu Ser Thr Ala Thr Lys Asp Thr Tyr Asp Ala Leu His Met Gln
545 550 555 560

Ala Leu Pro Pro Arg
565

<210> SEQ ID NO 245
<211> LENGTH: 1836
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 245
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agctggaacg tgcccctgac ctttggcgac 300
ggcaccaagc tggaaatcaa gggcggaggc ggatctggcg gcggaggatc tgggggaggc 360
ggctctcaag tgaagctgca gcagtctggc ggaggcctcg tgaaacctgg cgcctctctg 420
aagctgagct gcgtgaccag cggcttcacc ttcagaaagt tcggcatgag ctgggtgcgc 480
cagaccagcg acaagcggct ggaatgggtg gccagcatca gcaccggcgg ctacaacacc 540
tactacagcg acaacgtgaa gggcagattc accatcagca gagagaacgc caagaatacc 600
ctgtacctgc agatgagcag cctgaagtcc gaggacaccg ccctgtacta ctgcaccaga 660
ggctacagcc cctacagcta cgccatggac tattggggcc agggcaccac cgtgaccgtg 720
tctagtaagc ctaccaccac ccccgcacct cgtcctccaa cccctgcacc tacgattgcc 780
agtcagcctc tttcactgcg gcctgaggcc agcagaccag ctgccggcgg tgccgtccat 840
acaagaggac tggacttcgc gtccgataaa cctactacca ctccagcccc aaggccccca 900
accccagcac cgactatcgc atcacagcct ttgtcactgc gtcctgaagc cagccggcca 960
gctgcagggg gggccgtcca cacaagggga ctcgactttg cgagtgataa acctactaca 1020
actcctgccc cccggcctcc tacaccagct cctactatcg cctcccagcc actcagtctc 1080
agacccgagg cttctaggcc agcggccgga ggcgcggtcc acacccgcgg gctggacttt 1140
gcatccgata agcccaccac cacccctgcc cctagacctc caaccccagc ccctacaatc 1200
gccagccagc ccctgagcct gaggcccgaa gcctgtagac ctgccgctgg cggagccgtg 1260
cacaccagag gcctggattt cgcctgcgac atctacatct gggcccctct ggccggcacc 1320
tgtggcgtgc tgctgctgag cctggtcatc accctgtact gcaaccaccg gaataagaga 1380
ggccggaaga aactgctgta catcttcaag cagcccttca tgcggcccgt gcagaccacc 1440
caggaagagg acggctgcag ctgccggttc cccgaggaag aggaaggcgg ctgcgaactg 1500
cgggtgaagt tcagccggag cgccgacgcc cctgcctacc agcagggcca gaaccagctg 1560
tacaacgagc tgaacctggg ccggagggag gagtacgacg tgctggacaa gcggagaggc 1620
cgggaccctg agatgggcgg caagccccgg agaaagaacc ctcaggaggg cctgtataac 1680
gaactgcaga aagacaagat ggccgaggcc tacagcgaga tcggcatgaa gggcgagcgg 1740
cggaggggca agggccacga cggcctgtac cagggcctga gcaccgccac caaggatacc 1800

-continued tacgacgccc tgcacatgca ggccctgccc cccaga 1836

<210> SEQ ID NO 246
<211> LENGTH: 612
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 246

```
Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220

Tyr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350
```

```
Ile Ala Ser Gln Pro Leu Ser Leu Arg Pro Glu Ala Ser Arg Pro Ala
        355                 360                 365

Ala Gly Gly Ala Val His Thr Arg Gly Leu Asp Phe Ala Ser Asp Lys
    370                 375                 380

Pro Thr Thr Thr Pro Ala Pro Arg Pro Pro Thr Pro Ala Pro Thr Ile
385                 390                 395                 400

Ala Ser Gln Pro Leu Ser Leu Arg Pro Glu Ala Cys Arg Pro Ala Ala
                405                 410                 415

Gly Gly Ala Val His Thr Arg Gly Leu Asp Phe Ala Cys Asp Ile Tyr
            420                 425                 430

Ile Trp Ala Pro Leu Ala Gly Thr Cys Gly Val Leu Leu Leu Ser Leu
        435                 440                 445

Val Ile Thr Leu Tyr Cys Asn His Arg Asn Lys Arg Gly Arg Lys Lys
    450                 455                 460

Leu Leu Tyr Ile Phe Lys Gln Pro Phe Met Arg Pro Val Gln Thr Thr
465                 470                 475                 480

Gln Glu Glu Asp Gly Cys Ser Cys Arg Phe Pro Glu Glu Glu Glu Gly
                485                 490                 495

Gly Cys Glu Leu Arg Val Lys Phe Ser Arg Ser Ala Asp Ala Pro Ala
            500                 505                 510

Tyr Gln Gln Gly Gln Asn Gln Leu Tyr Asn Glu Leu Asn Leu Gly Arg
        515                 520                 525

Arg Glu Glu Tyr Asp Val Leu Asp Lys Arg Arg Gly Arg Asp Pro Glu
    530                 535                 540

Met Gly Gly Lys Pro Arg Arg Lys Asn Pro Gln Glu Gly Leu Tyr Asn
545                 550                 555                 560

Glu Leu Gln Lys Asp Lys Met Ala Glu Ala Tyr Ser Glu Ile Gly Met
                565                 570                 575

Lys Gly Glu Arg Arg Arg Gly Lys Gly His Asp Gly Leu Tyr Gln Gly
            580                 585                 590

Leu Ser Thr Ala Thr Lys Asp Thr Tyr Asp Ala Leu His Met Gln Ala
        595                 600                 605

Leu Pro Pro Arg
    610
```

<210> SEQ ID NO 247
<211> LENGTH: 1695
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 247

```
gacatccaga tgacccagag ccccagcagc ctgtctgcca gcgtgggcga cagagtgacc      60

atcacctgta tgaccagcac cgacatcgac gacgacatga actggtatca gcagaagccc     120

ggcaagaccc ccaagctgct gatctacgag ggcaacaccc tgaggcctgg cgtgcccagc     180

agattttctg gcagcggctc cggcaccgac ttcatcttca ccatcagctc cctgcagccc     240

gaggatatcg ccacctacta ctgcctgcag agctggaacg tgcccctgac ctttggcgga     300

ggcaccaagg tggaaatcaa gggcggaggc ggatctggcg gcggaggatc tgggggaggc     360

ggctctcagg tgcagctgca ggaatctggc ggagggctcg tgaagcctgg cggaagcctg     420

aagctgagct gtgccgccag cggcttcacc ttcagcaagt tcggcatgag ctgggtgcgc     480

cagacccccg acaagagact ggaatgggtg gccagcatca gcaccggcgg ctacaatacc     540
```

```
tactacagcg acaacgtgaa gggccggttc accatctccc gggacaacgc caagaacacc    600
ctgtacctgc agatgagcag cctgaagtcc gaggacaccg ccatgtacta ctgtgccaga    660
ggctacagcc cctacagcta cgccatggat tactggggcc agggcacaat ggtcaccgtg    720
tcctctaagc ctaccaccac ccccgcacct cgtcctccaa cccctgcacc tacgattgcc    780
agtcagcctc tttcactgcg gcctgaggcc agcagaccag ctgccggcgg tgccgtccat    840
acaagaggac tggacttcgc gtccgataaa cctactacca ctccagcccc aaggccccca    900
accccagcac cgactatcgc atcacagcct ttgtcactgc gtcctgaagc cagccggcca    960
gctgcagggg gggccgtcca cacaagggga ctcgactttg cgagtgataa gcccaccacc   1020
acccctgccc ctagacctcc aaccccagcc cctacaatcg ccagccagcc cctgagcctg   1080
aggcccgaag cctgtagacc tgccgctggc ggagccgtgc acaccagagg cctggatttc   1140
gcctgcgaca tctacatctg ggcccctctg gccggcacct gtggcgtgct gctgctgagc   1200
ctggtcatca ccctgtactg caaccaccgg aataagagag gccggaagaa actgctgtac   1260
atcttcaagc agcccttcat gcggcccgtg cagaccaccc aggaagagga cggctgcagc   1320
tgccggttcc ccgaggaaga ggaaggcggc tgcgaactgc gggtgaagtt cagccggagc   1380
gccgacgccc ctgcctacca gcagggccag aaccagctgt acaacgagct gaacctgggc   1440
cggagggagg agtacgacgt gctggacaag cggagaggcc gggaccctga gatgggcggc   1500
aagccccgga gaaagaaccc tcaggagggc ctgtataacg aactgcagaa agacaagatg   1560
gccgaggcct acagcgagat cggcatgaag ggcgagcggc ggaggggcaa gggccacgac   1620
ggcctgtacc agggcctgag caccgccacc aaggatacct acgacgccct gcacatgcag   1680
gccctgcccc ccaga                                                    1695
```

```
<210> SEQ ID NO 248
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140
```

```
Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Tyr Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Cys Arg Pro Ala
        355                 360                 365

Ala Gly Gly Ala Val His Thr Arg Gly Leu Asp Phe Ala Cys Asp Ile
    370                 375                 380

Tyr Ile Trp Ala Pro Leu Ala Gly Thr Cys Gly Val Leu Leu Leu Ser
385                 390                 395                 400

Leu Val Ile Thr Leu Tyr Cys Asn His Arg Asn Lys Arg Gly Arg Lys
                405                 410                 415

Lys Leu Leu Tyr Ile Phe Lys Gln Pro Phe Met Arg Pro Val Gln Thr
            420                 425                 430

Thr Gln Glu Glu Asp Gly Cys Ser Cys Arg Phe Pro Glu Glu Glu Glu
        435                 440                 445

Gly Gly Cys Glu Leu Arg Val Lys Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Arg Arg Lys Asn Pro Gln Glu Gly Leu Tyr
            500                 505                 510

Asn Glu Leu Gln Lys Asp Lys Met Ala Glu Ala Tyr Ser Glu Ile Gly
        515                 520                 525

Met Lys Gly Glu Arg Arg Arg Gly Lys Gly His Asp Gly Leu Tyr Gln
    530                 535                 540

Gly Leu Ser Thr Ala Thr Lys Asp Thr Tyr Asp Ala Leu His Met Gln
545                 550                 555                 560

Ala Leu Pro Pro Arg
```

565

<210> SEQ ID NO 249
<211> LENGTH: 1836
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 249
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180
agattttctg gcagcggctc cggcaccgac ttcatcttca ccatcagctc cctgcagccc 240
gaggatatcg ccacctacta ctgcctgcag agctggaacg tgcccctgac ctttggcgga 300
ggcaccaagg tggaaatcaa gggcggaggc ggatctggcg gcggaggatc tgggggaggc 360
ggctctcagg tgcagctgca ggaatctggc ggagggctcg tgaagcctgg cggaagcctg 420
aagctgagct gtgccgccag cggcttcacc ttcagcaagt tcggcatgag ctgggtgcgc 480
cagacccccg acaagagact ggaatgggtg gccagcatca gcaccggcgg ctacaatacc 540
tactacagcg acaacgtgaa gggccggttc accatctccc gggacaacgc caagaacacc 600
ctgtacctgc agatgagcag cctgaagtcc gaggacaccg ccatgtacta ctgtgccaga 660
ggctacagcc cctacagcta cgccatggat tactggggcc agggcacaat ggtcaccgtg 720
tcctctaagc ctaccaccac ccccgcacct cgtcctccaa cccctgcacc tacgattgcc 780
agtcagcctc tttcactgcg gcctgaggcc agcagaccag ctgccggcgg tgccgtccat 840
acaagaggac tggacttcgc gtccgataaa cctactacca ctccagcccc aaggccccca 900
accccagcac cgactatcgc atcacagcct ttgtcactgc gtcctgaagc cagccggcca 960
gctgcagggg gggccgtcca cacaagggga ctcgactttg cgagtgataa acctactaca 1020
actcctgccc cccggcctcc tacaccagct cctactatcg cctcccagcc actcagtctc 1080
agacccgagg cttctaggcc agcggccgga ggcgcggtcc acacccgcgg gctggacttt 1140
gcatccgata agcccaccac cacccctgcc cctagacctc caaccccagc ccctacaatc 1200
gccagccagc ccctgagcct gaggcccgaa gcctgtagac ctgccgctgg cggagccgtg 1260
cacaccagag gcctggattt cgcctgcgac atctacatct gggcccctct ggccggcacc 1320
tgtggcgtgc tgctgctgag cctggtcatc accctgtact gcaaccaccg gaataagaga 1380
ggccggaaga aactgctgta catcttcaag cagcccttca tgcggcccgt gcagaccacc 1440
caggaagagg acggctgcag ctgccggttc cccgaggaag aggaaggcgg ctgcgaactg 1500
cgggtgaagt tcagccggag cgccgacgcc cctgcctacc agcagggcca gaaccagctg 1560
tacaacgagc tgaacctggg ccggagggag gagtacgacg tgctggacaa gcggagaggc 1620
cgggaccctg agatgggcgg caagccccgg agaaagaacc ctcaggaggg cctgtataac 1680
gaactgcaga aagacaagat ggccgaggcc tacagcgaga tcggcatgaa gggcgagcgg 1740
cggaggggca agggccacga cggcctgtac cagggcctga gcaccgccac caaggatacc 1800
tacgacgccc tgcacatgca ggccctgccc cccaga 1836

<210> SEQ ID NO 250
<211> LENGTH: 612
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Tyr Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Ser Arg Pro Ala
        355                 360                 365

Ala Gly Gly Ala Val His Thr Arg Gly Leu Asp Phe Ala Ser Asp Lys
    370                 375                 380

```
Pro Thr Thr Thr Pro Ala Pro Arg Pro Pro Thr Pro Ala Pro Thr Ile
385                 390                 395                 400

Ala Ser Gln Pro Leu Ser Leu Arg Pro Glu Ala Cys Arg Pro Ala Ala
                405                 410                 415

Gly Gly Ala Val His Thr Arg Gly Leu Asp Phe Ala Cys Asp Ile Tyr
            420                 425                 430

Ile Trp Ala Pro Leu Ala Gly Thr Cys Gly Val Leu Leu Leu Ser Leu
        435                 440                 445

Val Ile Thr Leu Tyr Cys Asn His Arg Asn Lys Arg Gly Arg Lys Lys
    450                 455                 460

Leu Leu Tyr Ile Phe Lys Gln Pro Phe Met Arg Pro Val Gln Thr Thr
465                 470                 475                 480

Gln Glu Glu Asp Gly Cys Ser Cys Arg Phe Pro Glu Glu Glu Glu Gly
                485                 490                 495

Gly Cys Glu Leu Arg Val Lys Phe Ser Arg Ser Ala Asp Ala Pro Ala
            500                 505                 510

Tyr Gln Gln Gly Gln Asn Gln Leu Tyr Asn Glu Leu Asn Leu Gly Arg
        515                 520                 525

Arg Glu Glu Tyr Asp Val Leu Asp Lys Arg Arg Gly Arg Asp Pro Glu
    530                 535                 540

Met Gly Gly Lys Pro Arg Arg Lys Asn Pro Gln Glu Gly Leu Tyr Asn
545                 550                 555                 560

Glu Leu Gln Lys Asp Lys Met Ala Glu Ala Tyr Ser Glu Ile Gly Met
                565                 570                 575

Lys Gly Glu Arg Arg Arg Gly Lys Gly His Asp Gly Leu Tyr Gln Gly
            580                 585                 590

Leu Ser Thr Ala Thr Lys Asp Thr Tyr Asp Ala Leu His Met Gln Ala
        595                 600                 605

Leu Pro Pro Arg
    610
```

<210> SEQ ID NO 251
<211> LENGTH: 1695
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 251

```
gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480

cagacccccg acaagagact ggaatgggtg gccagcatca gcaccggcgg ctacaacacc    540

ttctacagcg acaacgtgaa gggccggttc accatctccc gggacaacgc caagaacacc    600

ctgtacctgc agatgagcag cctgaagtcc gaggacaccg ccatgtacta ctgtgccaga    660

ggctacagcc cctacagctt cgccatggat tactggggcc agggcacaat ggtcaccgtg    720
```

```
tcctctaagc ctaccaccac ccccgcacct cgtcctccaa cccctgcacc tacgattgcc    780

agtcagcctc tttcactgcg gcctgaggcc agcagaccag ctgccggcgg tgccgtccat    840

acaagaggac tggacttcgc gtccgataaa cctactacca ctccagcccc aaggcccccca   900

accccagcac cgactatcgc atcacagcct ttgtcactgc gtcctgaagc cagccggcca    960

gctgcagggg gggccgtcca cacaagggga ctcgactttg cgagtgataa gcccaccacc   1020

acccctgccc ctagacctcc aaccccagcc cctacaatcg ccagccagcc cctgagcctg   1080

aggcccgaag cctgtagacc tgccgctggc ggagccgtgc acaccagagg cctggatttc   1140

gcctgcgaca tctacatctg ggcccctctg gccggcacct gtggcgtgct gctgctgagc   1200

ctggtcatca ccctgtactg caaccaccgg aataagagag gccggaagaa actgctgtac   1260

atcttcaagc agcccttcat gcggcccgtg cagaccaccc aggaagagga cggctgcagc   1320

tgccggttcc ccgaggaaga ggaaggcggc tgcgaactgc gggtgaagtt cagccggagc   1380

gccgacgccc ctgcctacca gcagggccag aaccagctgt acaacgagct gaacctgggc   1440

cggagggagg agtacgacgt gctggacaag cggagaggcc gggaccctga gatgggcggc   1500

aagccccgga gaaagaaccc tcaggagggc ctgtataacg aactgcagaa agacaagatg   1560

gccgaggcct acagcgagat cggcatgaag ggcgagcggc ggaggggcaa gggccacgac   1620

ggcctgtacc agggcctgag caccgccacc aaggatacct acgacgccct gcacatgcag   1680

gccctgcccc ccaga                                                    1695
```

<210> SEQ ID NO 252
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 252

```
Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175
```

```
Gly Tyr Asn Thr Phe Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Phe Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Cys Arg Pro Ala
        355                 360                 365

Ala Gly Gly Ala Val His Thr Arg Gly Leu Asp Phe Ala Cys Asp Ile
    370                 375                 380

Tyr Ile Trp Ala Pro Leu Ala Gly Thr Cys Gly Val Leu Leu Leu Ser
385                 390                 395                 400

Leu Val Ile Thr Leu Tyr Cys Asn His Arg Asn Lys Arg Gly Arg Lys
                405                 410                 415

Lys Leu Leu Tyr Ile Phe Lys Gln Pro Phe Met Arg Pro Val Gln Thr
            420                 425                 430

Thr Gln Glu Glu Asp Gly Cys Ser Cys Arg Phe Pro Glu Glu Glu Glu
        435                 440                 445

Gly Gly Cys Glu Leu Arg Val Lys Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Arg Arg Lys Asn Pro Gln Glu Gly Leu Tyr
            500                 505                 510

Asn Glu Leu Gln Lys Asp Lys Met Ala Glu Ala Tyr Ser Glu Ile Gly
        515                 520                 525

Met Lys Gly Glu Arg Arg Arg Gly Lys Gly His Asp Gly Leu Tyr Gln
    530                 535                 540

Gly Leu Ser Thr Ala Thr Lys Asp Thr Tyr Asp Ala Leu His Met Gln
545                 550                 555                 560

Ala Leu Pro Pro Arg
                565
```

<210> SEQ ID NO 253
<211> LENGTH: 1836
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 253
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180
agattttctg gcagcggctc cggcaccgac ttcatcttca ccatcagctc cctgcagccc 240
gaggatatcg ccacctacta ctgcctgcag agctggaacg tgcccctgac ctttggcgga 300
ggcaccaagg tggaaatcaa gggcggaggc ggatctggcg gcggaggatc tgggggaggc 360
ggctctcagg tgcagctgca ggaatctggc ggagggctcg tgaagcctgg cggaagcctg 420
aagctgagct gtgccgccag cggcttcacc ttcagcaagt tcggcatgag ctgggtgcgc 480
cagacccccg acaagagact ggaatgggtg gccagcatca gcaccggcgg ctacaacacc 540
ttctacagcg acaacgtgaa gggccggttc accatctccc gggacaacgc caagaacacc 600
ctgtacctgc agatgagcag cctgaagtcc gaggacaccg ccatgtacta ctgtgccaga 660
ggctacagcc cctacagctt cgccatggat tactggggcc agggcacaat ggtcaccgtg 720
tcctctaagc ctaccaccac ccccgcacct cgtcctccaa cccctgcacc tacgattgcc 780
agtcagcctc tttcactgcg gcctgaggcc agcagaccag ctgccggcgg tgccgtccat 840
acaagaggac tggacttcgc gtccgataaa cctactacca ctccagcccc aaggccccca 900
accccagcac cgactatcgc atcacagcct ttgtcactgc gtcctgaagc cagccggcca 960
gctgcagggg gggccgtcca cacaagggga ctcgactttg cgagtgataa acctactaca 1020
actcctgccc cccggcctcc tacaccagct cctactatcg cctcccagcc actcagtctc 1080
agacccgagg cttctaggcc agcggccgga ggcgcggtcc acacccgcgg gctggacttt 1140
gcatccgata agcccaccac cacccctgcc cctagacctc caaccccagc ccctacaatc 1200
gccagccagc ccctgagcct gaggcccgaa gcctgtagac ctgccgctgg cggagccgtg 1260
cacaccagag gcctggattt cgcctgcgac atctacatct gggcccctct ggccggcacc 1320
tgtggcgtgc tgctgctgag cctggtcatc accctgtact gcaaccaccg gaataagaga 1380
ggccggaaga aactgctgta catcttcaag cagcccttca tgcggcccgt gcagaccacc 1440
caggaagagg acggctgcag ctgccggttc cccgaggaag aggaaggcgg ctgcgaactg 1500
cgggtgaagt tcagccggag cgccgacgcc cctgcctacc agcagggcca gaaccagctg 1560
tacaacgagc tgaacctggg ccggagggag gagtacgacg tgctggacaa gcggagaggc 1620
cgggaccctg agatgggcgg caagccccgg agaaagaacc ctcaggaggg cctgtataac 1680
gaactgcaga aagacaagat ggccgaggcc tacagcgaga tcggcatgaa gggcgagcgg 1740
cggaggggca agggccacga cggcctgtac cagggcctga gcaccgccac caaggatacc 1800
tacgacgccc tgcacatgca ggccctgccc cccaga 1836

<210> SEQ ID NO 254
<211> LENGTH: 612
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 254

-continued

```
Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Phe Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Phe Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Ser Arg Pro Ala
        355                 360                 365

Ala Gly Gly Ala Val His Thr Arg Gly Leu Asp Phe Ala Ser Asp Lys
    370                 375                 380

Pro Thr Thr Thr Pro Ala Pro Arg Pro Pro Thr Pro Ala Pro Thr Ile
385                 390                 395                 400

Ala Ser Gln Pro Leu Ser Leu Arg Pro Glu Ala Cys Arg Pro Ala Ala
                405                 410                 415
```

-continued

Gly Gly Ala Val His Thr Arg Gly Leu Asp Phe Ala Cys Asp Ile Tyr
420 425 430

Ile Trp Ala Pro Leu Ala Gly Thr Cys Gly Val Leu Leu Leu Ser Leu
435 440 445

Val Ile Thr Leu Tyr Cys Asn His Arg Asn Lys Arg Gly Arg Lys Lys
450 455 460

Leu Leu Tyr Ile Phe Lys Gln Pro Phe Met Arg Pro Val Gln Thr Thr
465 470 475 480

Gln Glu Glu Asp Gly Cys Ser Cys Arg Phe Pro Glu Glu Glu Glu Gly
485 490 495

Gly Cys Glu Leu Arg Val Lys Phe Ser Arg Ser Ala Asp Ala Pro Ala
500 505 510

Tyr Gln Gln Gly Gln Asn Gln Leu Tyr Asn Glu Leu Asn Leu Gly Arg
515 520 525

Arg Glu Glu Tyr Asp Val Leu Asp Lys Arg Arg Gly Arg Asp Pro Glu
530 535 540

Met Gly Gly Lys Pro Arg Arg Lys Asn Pro Gln Glu Gly Leu Tyr Asn
545 550 555 560

Glu Leu Gln Lys Asp Lys Met Ala Glu Ala Tyr Ser Glu Ile Gly Met
565 570 575

Lys Gly Glu Arg Arg Arg Gly Lys Gly His Asp Gly Leu Tyr Gln Gly
580 585 590

Leu Ser Thr Ala Thr Lys Asp Thr Tyr Asp Ala Leu His Met Gln Ala
595 600 605

Leu Pro Pro Arg
610

<210> SEQ ID NO 255
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Gly Gly Gly Gly Ser Gly Gly Gly Gly Ser Gly Gly Gly Gly Ser Gly
1 5 10 15

Gly Gly Gly Ser
20

<210> SEQ ID NO 256
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Gly Gly Gly Gly Ser
1 5

<210> SEQ ID NO 257
<211> LENGTH: 25
<212> TYPE: PRT
<213> ORGANISM: Artificial Sequence
<220> FEATURE:
<223> OTHER INFORMATION: Description of Artificial Sequence: Synthetic
peptide
<220> FEATURE:

-continued

```
<221> NAME/KEY: MISC_FEATURE
<222> LOCATION: (1)..(25)
<223> OTHER INFORMATION: This sequence may encompass 1-5 "Gly Gly Gly
      Gly Ser" repeating units or may be absent in its entirety

<400> SEQUENCE: 257

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

POLYPEPTIDE COMPOSITIONS COMPRISING SPACERS

CROSS-REFERENCE TO RELATED APPLICATION

The present application claims the benefit of U.S. provisional Patent Application No. 62/574,061; filed Oct. 18, 2017, which is hereby incorporated by reference in its entirety.

REFERENCE TO SEQUENCE LISTING

The present application contains a Sequence Listing which has been filed electronically in ASCII format and is hereby incorporated by reference in its entirety. Said ASCII copy, created on Oct. 11, 2018, is named 50471-704_201_SL.txt and is 344,022 bytes in size.

BACKGROUND OF THE DISCLOSURE

Recombinant polypeptides such as chimeric polypeptides have been a valuable for research, diagnostic, manufacturing and therapeutic applications. Indeed, adaptive T cell immunotherapy using chimeric antigen receptors (CAR) and T-cell receptors (TCR) has been shown to successfully direct killing of tumor cells. Modified effector cells expressing antigen binding polypeptides such as CARs are useful in the treatment of diseases and disorders such as autoimmune disorders and cancers. In order to further develop this innovative technology it is valuable to devise ways of increasing CAR expression on a cell surface and/or increasing antigen-binding efficiency.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided herein is a chimeric polypeptide comprising (i) an antigen-binding region, (ii) a transmembrane region, and (iii) a spacer region connecting said trans-membrane region with said antigen binding region, wherein said spacer region comprises a stalk region(s) comprising at least one dimerization site, and a stalk extension region (s'-n), said stalk extension region comprising fewer dimerization sites as compared to said stalk region.

Provided herein is a chimeric polypeptide comprising (i) an antigen-binding region, (ii) a transmembrane region, and (iii) a spacer region connecting said trans-membrane region with said antigen binding region, wherein said spacer region comprises a stalk region which is from about 20 to about 60 amino acids in length and comprises at least one dimerization site, and a stalk extension region comprising from about 1 to about 5 times the length of the stalk region as measured by number of amino acids.

Provided herein is a chimeric polypeptide comprising (i) an antigen-binding region, (ii) a transmembrane region, and (iii) a spacer region connecting said trans-membrane region with the antigen binding region, wherein the spacer region comprises a stalk region designated as "s" and at least one stalk extension region, designated as "s'-n," wherein n represents the number of units of s' in the space region, and wherein n can be 1, 2, 3, 4, 5, 6, 7, 8, 9, 10, 11, 12, 13, 14, 15, 16, 17, 18, 19, or 20.

In some embodiments, at least one stalk extension region in the chimeric polypeptide has a sequence homologous to the stalk region except for the dimerization sites of the stalk region. In some embodiments, the spacer region in the chimeric polypeptide is proximal to the membrane region. In some embodiments, the spacer region in the chimeric polypeptide is distal to the membrane region. In some embodiments, the chimeric polypeptide further comprises an intracellular signaling domain. In some embodiments, the chimeric polypeptide does not comprise an intracellular signaling domain.

In some embodiments, the stalk extension region of the chimeric polypeptide contains at least one fewer dimerization site as compared to the stalk region. In one embodiment, the chimeric polypeptide has improved functional activity compared to an otherwise identical antigen-binding polypeptide lacking the stalk extension region. In other embodiments, the chimeric polypeptide has increased expression on a cell surface compared to an otherwise identical polypeptide lacking the stalk extension region. In another embodiment, the stalk extension region lacks a dimerization site. In yet another embodiment, each of the stalk extension regions is from about 20 to about 60 amino acids in length, wherein n is 1, 2, 3 or 4. In yet another embodiment, the stalk extension region has a sequence which has at least about 80% identity to the stalk region. In some cases, at least one stalk extension region in the chimeric polypeptide has a sequence comprising at least one less dimerization site as compared to the stalk region. In some cases, each of the stalk extension regions has a sequence which has at least about 80% identity to the stalk region, wherein n is 2. In another case, each of the stalk extension regions has a sequence which has at least about 80% identity to the stalk region, wherein n is 3. In yet another case, each of the stalk extension region has a sequence which has at least about 80% identity to the stalk region, wherein n is 4. In yet another case, each of the stalk extension region has a sequence which has at least about 80% identity to the stalk region, wherein n is at least 5.

In some cases, the stalk region of the chimeric polypeptide provided herein comprises a sequence with at least about 70%, 75%, 80%. 85%, 90%, 95% or 99% identity to at least one of a CD8alpha hinge domain, a CD28 hinge domain and a CTLA-4 hinge domain. In one embodiment, the stalk region is a CD8 alpha hinge domain having a sequence as shown in SEQ ID NO: 1. In other embodiments, the stalk region is a CD28 hinge domain having a sequence as shown in SEQ ID NO: 7. In another embodiment, the stalk region is a CTLA-4 hinge domain having a sequence as shown in SEQ ID NO: 12.

In some embodiments, interchain dimerization of the chimeric polypeptide provided herein is mediated by at least one disulfide bond between cysteine residues. In some embodiments, the antigen binding region of the chimeric polypeptide binds an epitope on CD19. In some embodiments, the antigen binding region of the chimeric polypeptide binds an epitope on CD33. In some embodiments, the antigen binding region of the chimeric polypeptide binds an epitope on at least one of CD19, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, Folate receptor α, Mucins, MUC-1, MUC-16, MAGE-A1, h5T4, PSMA, TAG-72, EGFR, CD20, EGFRvIII, CD123 VEGF-R2, NY-ESO-1, Titin, MART-1, HPV, HBV, MAGE-A4, MAGE-A10, MAGE A3/A6, gp100, MAGE-A1, or PRAME.

In some embodiments, the chimeric polypeptide comprises a chimeric antigen receptor (CAR). In some embodiments, the CAR further comprises at least one costimulatory signaling domain. In some embodiments, the at least one costimulatory signaling domain comprises a signaling domain from CD27, CD28, 4-1BB, ICOS, OX40, DAP10, DAP12, CD134, CD3-zeta or fragment or combination thereof. In some embodiments, the at least one costimulatory signaling domain comprises a signaling domain from 4-1BB, CD28 or a combination thereof. In some embodiments, the CAR further comprises a CD28 costimulatory signaling domain and CD3-zeta. In some embodiments, the CAR further comprises a CD28 costimulatory signaling domain. In some embodiments, the intracellular cell signaling domain interacts with a T cell, a Natural Killer (NK) cell, a cytotoxic T lymphocyte (CTL), or a regulatory T cell.

In some embodiments, the chimeric polypeptide comprises an engineered T-cell receptor (TCR). In some embodiments, the engineered TCR is an αβ TCR. In some embodiments, the engineered TCR is a γδ TCR. In some embodiments, the antigen binding region of the engineered TCR binds an epitope on at least one of CD19, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, Folate receptor α, Mucins, MUC-1, MUC-16, MAGE-A1, h5T4, PSMA, TAG-72, EGFR, CD20, EGFRvIII, CD123, VEGF-R2, NY-ESO-1, Titin, MART-1, HPV, HBV, MAGE-A4, MAGE-A10, MAGE A3/A6, gp100, MAGE-A1, or PRAME. In some embodiments, the antigen binding region of the engineered TCR binds an epitope on at least one of NY-ESO-1, Titin, MART-1, HPV, HBV, MAGE-A4, MAGE-A10, MAGE A3/A6, gp100, MAGE-A1, or PRAME.

Also provided is a polynucleotide encoding the chimeric polypeptide as described herein. Provided herein is an expression vector comprising the polynucleotide. In some embodiments, the vector is a lentivirus vector, a retroviral vector or a non-viral vector. In some embodiments, the vector is a non-viral vector which is a sleeping beauty vector.

Further provided is an engineered cell comprising the expression vector comprising the polypeptide encoding the chimeric polypeptide as described herein. In some cases, the engineered cell further comprises a Sleeping Beauty transposase. In some cases, the Sleeping Beauty transposase is SB11, SB100X or SB110. In some cases, the engineered cell is an animal cell. In some cases, the animal cell is a human cell. In some cases, the human cell is a T cell or NK cell. In some cases, the engineered cell as described herein further expresses a polypeptide comprising an intracellular signaling domain.

Provided herein is a chimeric antigen receptor (CAR) comprising an antigen binding region, a transmembrane region a stalk region and a stalk extension region, wherein the stalk extension region is homologous to the stalk region and comprises at least one amino acid substitution relative to the stalk region. In some embodiments, the stalk region is capable of dimerizing with a homologous stalk region of a second CAR. In some embodiments, the stalk extension region is not capable of dimerizing. In some embodiments, the stalk region is connected to the transmembrane region. In some embodiments, the antigen binding region comprises a scFv. In some embodiments, the scFv binds an epitope on CD19, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, EGFR, Folate receptor α, Mucins, MUC-1, MUC-16, MAGE-A1, h5T4, PSMA, TAG-72, EGFR, CD20, EGFRvIII, CD123 or VEGF-R2.

In some embodiments, the stalk extension region of the CAR is designated as s'-n, wherein n comprises two or more, thereby comprising a first stalk extension region and a second stalk extension region. In some embodiments, the first stalk extension region is homologous to the second stalk extension region. In some embodiments, the first stalk extension region comprises at least one amino acid residue substitution compared to the stalk region. In some embodiments, the first stalk extension region is not capable of dimerizing to a stalk region of a CAR. In some embodiments, the second stalk extension region comprises at least one amino acid residue substitution compared to the stalk region. In some embodiments, the second stalk extension region is not capable of dimerizing to another stalk extension region. In some embodiments, the CAR further comprises a third stalk extension region. In some embodiments, the CAR further comprises a fourth stalk extension region. In some embodiments, the CAR comprises five or more stalk extension region. In some embodiments, at least one stalk extension region in the CAR is not capable of forming a disulfide bond. In some embodiments, the stalk region comprises a sequence with at least about 70%, 75%, 80%. 85%, 90%, 95% or 99% identity to at least one of a CD8alpha hinge domain, a CD28 hinge domain and a CTLA-4 hinge domain. In some embodiments, the stalk region is a CD8alpha hinge domain, a CD28 hinge domain or a CTLA-4 hinge domain.

In some cases, a T cell or NK cell expresses the CAR as described herein. In some cases, the CAR comprises the sequence shown as SEQ ID No. 53-68, or a variant thereof which has at least 80% sequence identity but retains antigen binding capacity.

Provided herein is a nucleic acid sequence encoding the CAR as presently described. In some cases, the nucleic acid sequence comprises the sequence shown as SEQ ID No 147-162 or a variant thereof having at least 70%, 75%, 80%, 85%, 90%, 95% or 99% sequence identity.

Provided herein is a vector comprising the nucleic acid sequence encoding the CAR as presently described. In some embodiments, the vector is a lentivirus vector, a retroviral vector, a Sleeping Beauty transposon or a non-viral vector.

Provided herein is a method for making a T cell or NK cell, wherein the method comprises the step of introducing the nucleic acid sequence encoding the CAR as presently described into the T cell or NK cell. In some embodiments, the T cell is modified at a point-of-care site and administered to a subject in need thereof, without undergoing propagation and activation. In some embodiments, the T cell is stimulated for at least 0, 1, 2, 4, 6, 8, 10, 12, 14, 16, 18, 20, 22, 24, 26, 28, 30 or more days. In some embodiments, the T cell is stimulated for at least 5, 10, 15, 20, 25, 30, 35, 40, 45, 50, 55, 60 or more days. In some embodiments, the T cell is stimulated for at least 7, 14, 21, 28, 35, 42, 49, 56, 63 or more days.

Provided herein is a pharmaceutical composition which comprises at least one of: a vector comprising the nucleic acid sequence encoding the CAR as presently described; and a T cell or a NK cell expressing the CAR as presently described; and a pharmaceutically acceptable carrier, diluent or excipient.

Provided herein is a population of cells comprising the CAR as presently described.

Provided herein is a method for stimulating a T cell-mediated immune response in a subject, comprising contacting the subject with an effective amount of a cell genetically modified to express the CAR as presently described.

Provided herein is a method of increasing expression of a chimeric antigen receptor (CAR) on a cell surface comprising engineering a nucleic acid encoding the CAR to comprise a stalk extension domain, thereby generating an engineered CAR.

Provided herein is a method of increasing expansion of an engineered T cell expressing a chimeric polypeptide comprising engineering a nucleic acid encoding the chimeric polypeptide to comprise a stalk extension domain, thereby generating an engineered T cell.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 3A shows that Sleeping Beauty modified CD19-CAR-T cells were proliferated ex vivo in presence of Activating and Propagating Cells (AaPC) expressing CD19 antigen on the surface. CAR-T cells expressing CARs with spacers incorporating one, two or three stalk extension regions (CD8-2×, CD8-3× and CD8-4×) showed similar proliferative potential compared to CAR with a spacer incorporating a CD8 stalk. T cells expressing CARs with spacers incorporating stalk extension regions CD8-3×v2 containing amino acid substitutions in stalk extension region compared to CD8-3× failed to expand ex vivo. FIG. 3B demonstrates higher expression (MFI) of CD19 CAR with spacers incorporating two stalk extension regions (CD8-3×) as compared to CD19 CAR with spacers incorporating a CD8α hinge stalk (CD8-1×).

FIG. 5A shows cytotoxic activity of T cells expressing CD19-CAR with varying spacer lengths against a K562 cell line engineered to express CD19 (K562/CD19) antigen at different effector to target cell (E:T) ratios. T cells expressing CARs with spacers incorporating one, two or three stalk extension regions (CD8-2×, CD8-3× and CD8-4×) exerted similar cytotoxicity at 10:1 E:T ratio and improved cytotoxicity at lower E:T ratios of K562/CD19 cell line compared to T cells expressing CARs incorporating a spacer with just a CD8a hinge stalk (CD8-1×). FIG. 5B shows cytotoxic response of T cells expressing CD19-CAR with varying spacer lengths at E:T ratio of 10:1 towards CD19 negative K562 or EL4 cell lines as well as CD19 positive K562/CD19 cell line. T cells expressing CD19-CARs with spacers incorporating one, two or three stalk extension regions (CD8-2×, CD8-3× and CD8-4×) exerted similar cytotoxicity effects against the K562/CD19 cell line compared to T cells expressing CAR with a CD8a hinge stalk (CD8-1×). However, T cells expressing CARs with extended stalk length regions (CD8-2×, CD8-3× and CD8-4×) showed lower non-specific cytotoxicity of CD19 negative K562 and EL4 cell lines.

FIG. 6A demonstrates that T cells expressing CD19-specific CARs with spacers incorporating one, two or three stalk extension regions (CD8-2×, CD8-3× and CD8-4×) demonstrated an enhanced release of IFNγ cytokine compared to T cells expressing CARs with CD8a hinge stalk (CD8-1×) when cultured with CD19 positive K562/CD19 cell line at 10:1 E:T ratio. FIG. 6B demonstrates that T cells expressing CD19-specific CARs with spacers incorporating one, two or three stalk extension regions (CD8-2×, CD8-3× and CD8-4×) demonstrated an enhanced release of TNF cytokine compared to T cells expressing CARs with CD8a hinge stalk and no stalk extension regions (CD8-1×) when cultured with CD19 positive K562/CD19 cell line at 10:1 E:T ratio. FIG. 6C demonstrates that T cells expressing CD19-specific CARs with spacers incorporating one, two or three stalk extension regions (CD8-2×, CD8-3× and CD8-4×) demonstrated an enhanced release of Granzyme B cytokine compared to T cells expressing CARs with CD8α hinge stalk (CD8-1×) when cultured with CD19 positive K562/CD19 cell line at 10:1 E:T ratio.

DETAILED DESCRIPTION OF THE DISCLOSURE

Figure 1A:
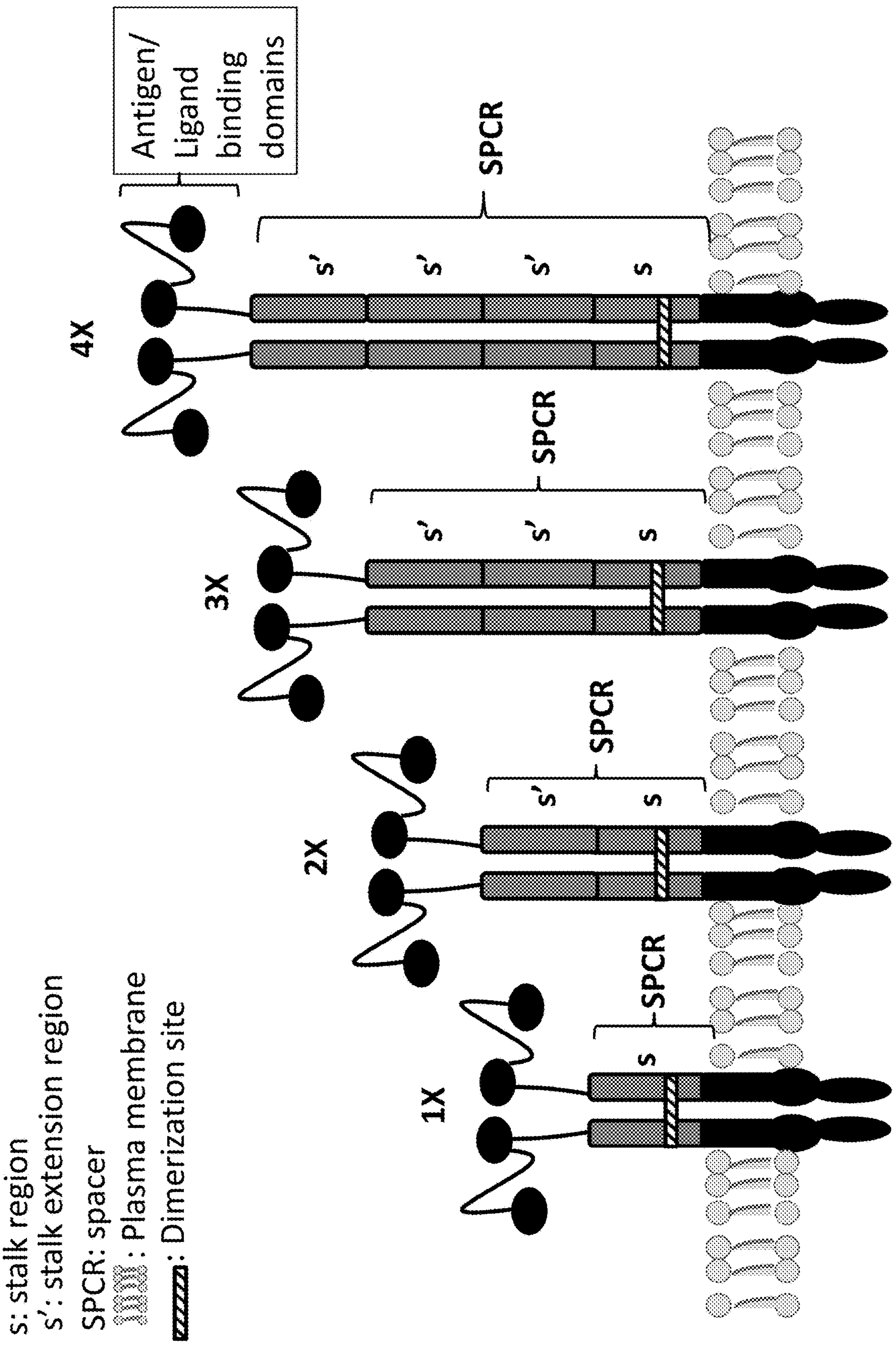
FIG. 1A depicts diagrams of polypeptides with spacers that incorporate a stalk and varying numbers of stalk extension regions (s'-1, s'-2, s'-3).

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Although various features may be described in the context of a single embodiment, the features may also be provided separately or in any suitable combination. Conversely, although the present disclosure may be described herein in the context of separate embodiments for clarity, it may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments described herein.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition described herein, and vice versa. Furthermore, compositions described herein can be used to achieve methods described herein.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

By "isolated" or its grammatical equivalent is meant the removal of a nucleic acid from its natural environment. By "purified" or its grammatical equivalent is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins may be formulated with diluents or adjuvants and still for practical purposes be isolated. For example, nucleic acids typically are mixed with an acceptable carrier or diluent when used for introduction into cells.

"Polynucleotide" or "oligonucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

"Polypeptide" is used interchangeably with the terms "polypeptides," "peptide(s)," and "protein(s)", and refers to a polymer of amino acid residues. A "mature protein" is a protein which is full-length and which, optionally, includes glycosylation or other modifications typical for the protein in a given cellular environment.

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology.

The terms "identical" or "sequence identity" in the context of two nucleic acid sequences or amino acid sequences of polypeptides refers to the residues in the two sequences which are the same when aligned for maximum correspondence over a specified comparison window.

In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

Proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first they are transcribed from DNA to RNA, and the RNA produced is then reverse transcribed to DNA. This copied DNA is then inserted at a new position into the genome. The reverse transcription step is catalyzed by a reverse transcriptase, which may be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons may be identified by short direct repeats which may be created by the staggered cut in the target DNA and filling in by DNA polymerase, followed by a series of inverted repeats important for the TE excision by transposase. Cut-and-paste TEs may be duplicated if their transposition takes place during S phase of the cell cycle when a donor site has already been replicated, but a target site has not yet been replicated. Transposition can be classified as either "autonomous" or "non-autonomous" in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism. In some embodiments, the transposase's catalytic activity can be utilized to move gene(s) from a vector to the genome.

In some instances, polynucleotides encoding gene-switch polypeptides for expressing CARs and/or TCRs described herein can also be introduced into T cells using non-viral based delivery systems, such as the "Sleeping Beauty (SB) Transposon System," which refers a synthetic DNA transposon system for introducing DNA sequences into the chromosomes of vertebrates. Some exemplary embodiments of the system are described, for example, in U.S. Pat. Nos. 6,489,458; 8,227,432; 9,228,180 and WO/2016/145146. The Sleeping Beauty transposon system is composed of a Sleeping Beauty (SB) transposase and a SB transposon. In embodiments, the Sleeping Beauty transposon system can include the SB11 transposon system, the SB100× transposon system, or the SB110 transposon system.

The nucleic acid sequences and vectors disclosed or contemplated herein can be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)). Phage or viral vectors can be introduced into host cells, after growth of infectious particles in suitable packaging cells, many of which are commercially available.

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter.

The term "promoter activity" refers to the extent of expression of nucleotide sequence that is operably linked to the promoter whose activity is being measured. Promoter activity may be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch.

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors may contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences.

Vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77: 3567 (1980); O'Hare et al., Proc. Natl. Acad. Sci. USA, 78: 1527 (1981); Mulligan & Berg, Proc. Natl. Acad. Sci. USA, 78: 2072 (1981); Colberre-Garapin et al., J. Mol. Biol., 150:1 (1981); Santerre et al., Gene, 30: 147 (1984); Kent et al., Science, 237: 901-903 (1987); Wigler et al., Cell, 11: 223 (1977); Szybalska & Szybalski, Proc. Natl. Acad. Sci. USA, 48: 2026 (1962); Lowy et al., Cell, 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

"Antibody" as used herein refers to monoclonal or polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

The terms "fragment of an antibody," "antibody fragment," "functional fragment of an antibody," and "antigen-binding portion" are used interchangeably herein to mean one or more fragments or portions of an antibody that retain the ability to specifically bind to an antigen (see, generally, Holliger et al., Nat. Biotech., 23(9):1126-1129 (2005)). The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., Science, 242: 423-426 (1988); Huston et al., Proc. Natl.

Acad. Sci. USA, 85: 5879-5883 (1988); and Osbourn et al., Nat. Biotechnol., 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Patent Application Publication 2009/0093024 A1.

The term "functional portion," when used in reference to a CAR, refers to any part or fragment of the CAR described herein, which part or fragment retains the biological activity of the CAR of which it is a part (the parent CAR). In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

The term "functional variant," as used herein, refers to a polypeptide, or a protein having substantial or significant sequence identity or similarity to the reference polypeptide, and retains the biological activity of the reference polypeptide of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

"Proliferative disease" as referred to herein means a unifying concept that excessive proliferation of cells and turnover of cellular matrix contribute significantly to the pathogenesis of several diseases, including cancer is presented.

"Administering" is referred to herein as providing the compositions described herein to a patient. By way of example and not limitation, composition administration, e.g., injection, may be performed by intravenous (i.v.) injection, sub-cutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route. Additionally, administration may also be by surgical deposition of a bolus or pellet of cells, or positioning of a medical device.

Modified or engineered cell compositions described herein may comprises host cells expressing one or more nucleic acid sequences described herein, or a vector comprising one or more nucleic acid sequences described herein, in an amount that is effective to treat or prevent proliferative disorders. As used herein, the terms "treatment," "treating," and the like refer to obtaining a desired pharmacologic and/or physiologic effect. In embodiments, the effect is therapeutic, i.e., the effect partially or completely cures a disease and/or adverse symptom attributable to the disease. To this end, the inventive method comprises administering an "amount" of the composition comprising the host cells expressing the inventive nucleic acid sequence, or a vector comprising the inventive nucleic acid sequences.

An "amount" or "dose" refers to an amount effective, at dosages and for periods of time necessary, to achieve a desired therapeutic result. The amount can vary according to factors such as the disease state, age, sex, and weight of the individual, and the ability of the inventive nucleic acid sequences to elicit a desired response in the individual.

Alternatively, the pharmacologic and/or physiologic effect can be "prophylactic," i.e., the effect completely or partially prevents a disease or symptom thereof.

A "prophylactically effective amount" refers to an amount effective, at dosages and for periods of time necessary, to achieve a desired prophylactic result (e.g., prevention of disease onset).

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

Spacers

Described herein are spacers that connect two regions of a polypeptide construct described herein. For instance, spacers described herein can connect a transmembrane region of a polypeptide to an antigen or ligand binding region of a polypeptide. In some cases, the polypeptide can be a chimeric polypeptide. A chimeric polypeptide or chimeric protein as described herein includes polypeptides or proteins created by joining of two or more genes or portions or derivatives thereof, that originally coded for separate proteins. Exemplary depictions of various spacers can be found at FIGS. 1 and 2. In some embodiments, the spacer extends the distance between different domains of a chimeric polypeptide resulting in improved expression or functional activity of the polypeptide compared to an otherwise identical polypeptide lacking the spacer. In some instances, a spacer comprises any polypeptide that functions to link the transmembrane region to, either the extracellular region or, the cytoplasmic region in the chimeric polypeptide. In some embodiments, the spacer is flexible enough to allow the antigen or ligand-binding region to align in different orientations to facilitate antigen or ligand receptor recognition. In other embodiments, the spacer extends the distance between different domains of a chimeric polypeptide resulting in improved expansion or propagation of the cell(s) that expresses the chimeric polypeptide compared to cell(s) expressing an otherwise identical polypeptide lacking the spacer.

The spacer can comprise a stalk region and stalk extension region(s). In one embodiment, a spacer can include a single stalk region. In another embodiment, a spacer can comprise a stalk region (designated as "s") and stalk extension region(s), which is herein designated as "s'-n." For example, a spacer can comprise one (1) stalk region and s'-n, wherein n can be 0, 1, 2, 3, 4, 5, 6, 7, 8, 9, 10, 11, 12, 13, 14, 15, 16, 17, 18, 19, or 20. In further embodiments, the stalk region can be linked to stalk extension region s'-n via a linker. A linker as described herein can include for instance, a GSG linker (SEQ ID NO: 9 and SEQ ID NO: 115), SGSG linker (SEQ ID NO: 10 and SEQ ID NO: 116), (G4S)3 linker (SEQ ID NO: 11 and SEQ ID NO: 117), (G4S)4 linker (SEQ ID NO: 255) and/or a Whitlow linker (SEQ ID NO: 8 and SEQ ID NO: 114). In certain cases, a peptide linker of any length or size to link a stalk region and stalk extension region(s). For example, in some embodiments, a peptide linker is sized to maintain a desired or optimal distance between the stalk region and stalk extension region. In some embodiments are different size G4S linkers (SEQ ID NO: 256) (G4S)n, wherein n=0, 1, 2, 3, 4, 5 (SEQ ID NO: 257).

In some embodiments, the stalk region can be from about 20 to about 300 amino acids in length and comprises at least one dimerization site, and a stalk extension region can comprise from about 1 to about 10 times the length of the stalk region as measured by number of amino acids.

In some cases, a stalk region can be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or greater amino acids in length. In other cases, the stalk region can be about: 100, 125, 150, 175, 200, 225, 250, 275 or 300 amino acids in length. In some cases, a stalk region can be less than 20 amino acids in length.

In some cases, a stalk extension region can comprise from about 1 to about 10 times the length of the stalk region as measured by number of amino acids. For example, a stalk extension region can comprise about 1, 2, 3, 4, 5, 6, 7, 8, 9, or 10 times the length of the stalk region as measured by number of amino acids. In some cases, a stalk extension region can comprise greater than 10 times the length of the stalk region as measured by number of amino acids. In some examples, a stalk extension region can comprise up to 2 times the length of the stalk region as measured by number of amino acids but comprise fewer dimerization sites than the stalk region.

A stalk extension region of a subject antigen-binding polypeptide can contain at least one fewer dimerization site as compared to a stalk region. For example, if a stalk region comprises two dimerization sites, a stalk extension region can comprise one or zero dimerization sites. As another example, if a stalk region comprises one dimerization site, a stalk extension region can comprise zero dimerization sites. In some examples, a stalk extension region lacks a dimerization site. In some examples, a stalk extension region can comprise up to 2 times the length of the stalk region as measured by number of amino acids but comprise no dimerization sites. In some examples, a stalk extension region can comprise up to 3 times the length of the stalk region as measured by number of amino acids but comprise no dimerization sites. In some examples, a stalk extension region can comprise up to 4 times the length of the stalk region as measured by number of amino acids but comprise zero dimerization sites. In some cases, one or more dimerization site(s) can be membrane proximal. In other cases, one or more dimerization site(s) can be membrane distal.

Each of the stalk extension regions can, in some examples, be from about 20 to about 60 amino acids in length. In other examples, stalk extension regions can be about 10, 15, 20, 25, 30, 35, 40, 45, 50, 55, 60, 65, greater amino acids in length, or any integer within or outside of that range. In some cases, each stalk extension region has a sequence which has at least about 60% identity to the stalk region. In some examples, each stalk extension region has a sequence which has at least about 65%, 70%, 75%, 80%, 85%, 90%, 95%, 96%, 97%, 98%, 99% or greater identity to the stalk region.

Figure 1B:
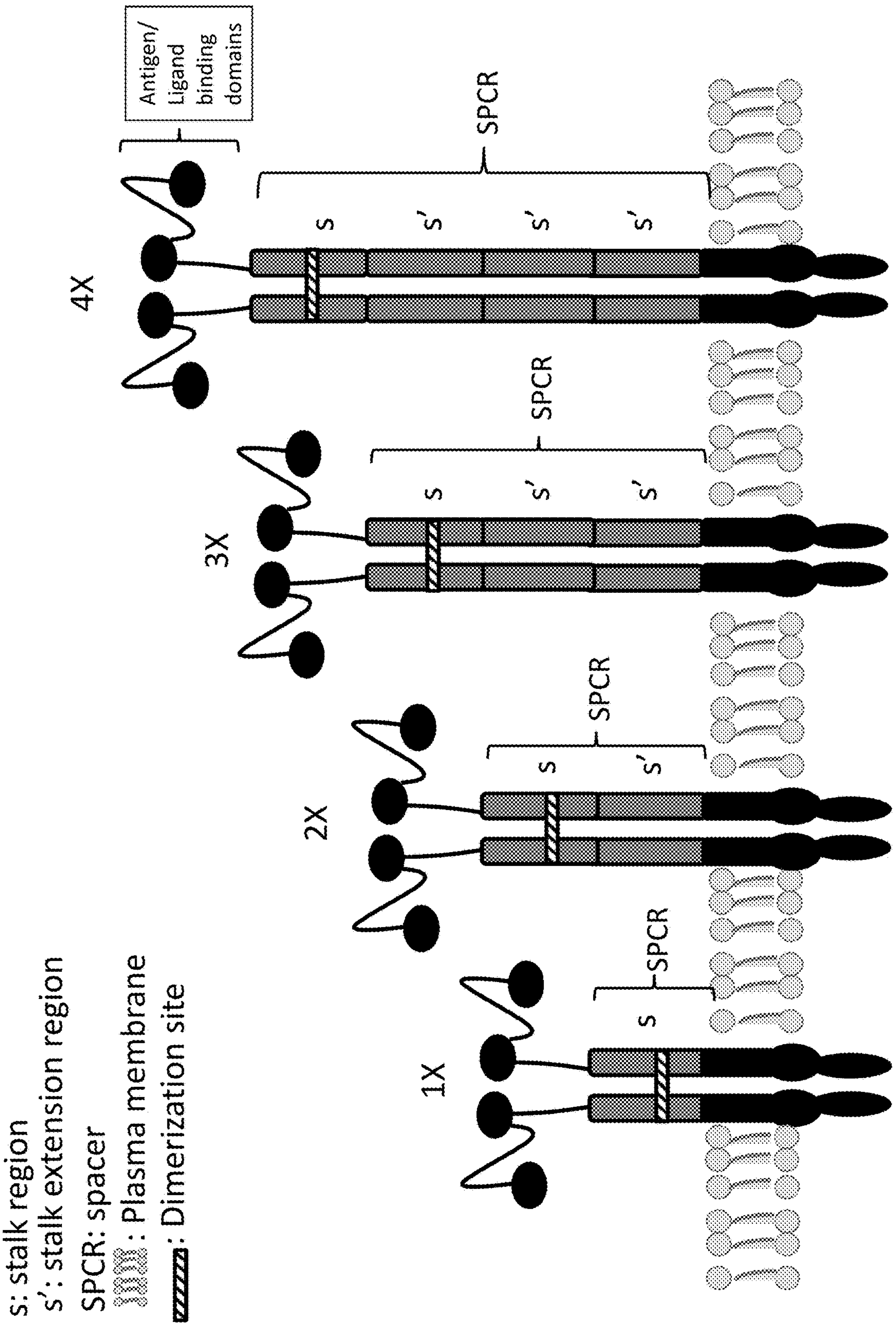
FIG. 1B depicts diagrams of polypeptides with spacers that incorporate a stalk and varying numbers of stalk extension regions (s'-1, s'-2, s'-3). The diagrams also depict exemplary dimerization sites.
Figure 2A:
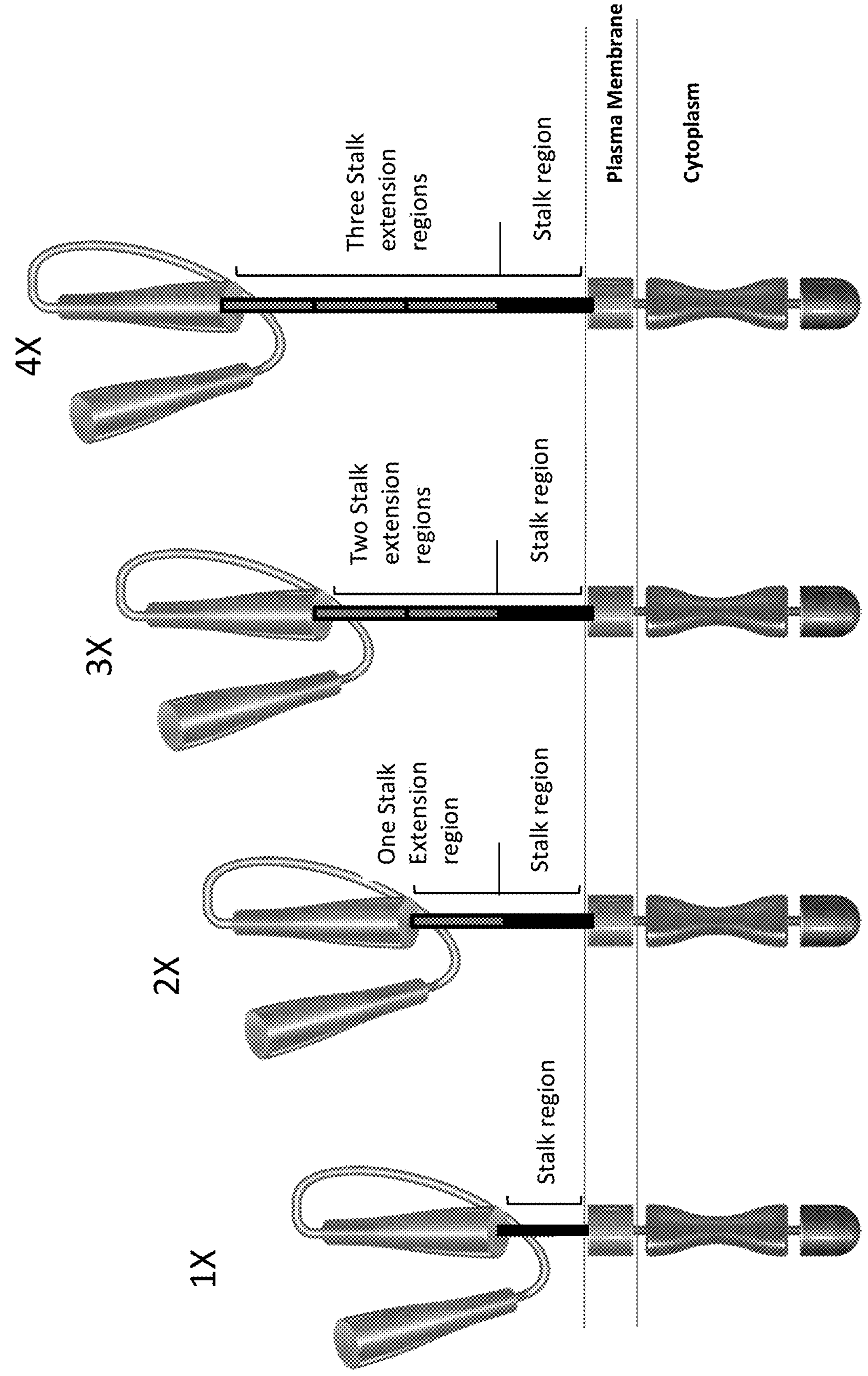
FIG. 2A depicts diagrams of exemplary polypeptides such as chimeric antigen receptors, with various spacer lengths.
Figure 2B:
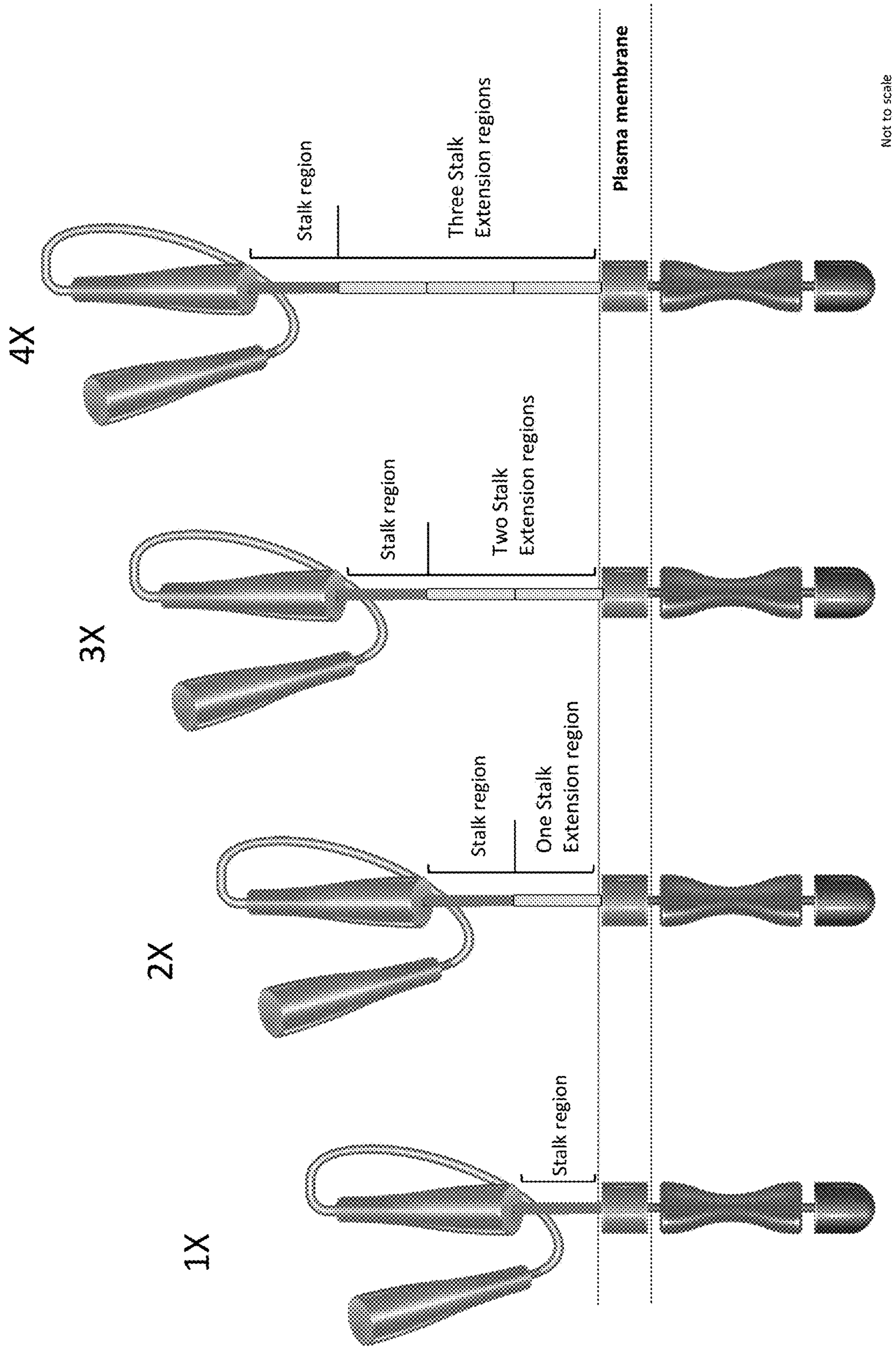
FIG. 2B depicts diagrams of exemplary polypeptides such as chimeric antigen receptors, with various spacer lengths. The illustration shows chimeric antigen receptors with spacers that incorporate a stalk and one, two or three stalk extension regions.

In one embodiment, the stalk region is proximal to the membrane region as depicted in FIG. 1A. In another embodiment, the stalk region is distal to the membrane region as depicted in FIG. 1B.

In one embodiment, the stalk region and stalk extension region(s) can be derived or designed from a polypeptide of natural or of synthetic origin. The stalk region and/or stalk extension region(s) can comprise hinge domain(s) derived from a cell surface protein or derivatives or variants thereof. In some embodiments, the stalk region and/or stalk extension region(s) can comprise a hinge domain derived from CD28 or CD8alpha (CD8α). In some embodiments, each of the stalk region and stalk extension region(s) can be derived from at least one of a CD8alpha hinge domain, a CD28 hinge domain, a CTLA-4 hinge domain, a LNGFR extracellular domain, IgG1 hinge, IgG4 hinge and CH2-CH3 domain. The stalk and stalk extension region(s) can be separately derived from any combination of CD8alpha hinge domain, CD28 hinge domain, CTLA-4 hinge domain, LNGFR extracellular domain, IgG1 hinge, IgG4 hinge or CH2-CH3 domain. As an example, the stalk region can be derived from CD8alpha hinge domain and at least one stalk extension region can be derived from CD28 hinge domain thus creating a hybrid spacer. As another example, the stalk region can be derived from an IgG1 hinge or IgG4 hinge and at least one stalk extension region can be derived from a CH2-CH3 domain of IgG.

In certain embodiments, the stalk region may comprise one or more dimerization sites to form homo or hetero dimerized chimeric polypeptides. In other embodiments, the stalk region or one or more stalk extension regions may contain mutations that eliminate dimerization sites altogether. In some embodiments, a stalk extension region(s) can contain at least one fewer dimerization site as compared to a stalk region. For example, if a stalk region comprises two dimerization sites, a stalk extension region can comprise one or zero dimerization sites. As another example, if a stalk region comprises one dimerization site, a stalk extension region can comprise zero dimerization sites. In some examples, the stalk extension region(s) lacks a dimerization site.

Polypeptides

Disclosed herein are polypeptides that can be used with spacers described herein. In one embodiment, such polypeptides that comprise s pacers described herein are polypeptides that do not express on the cell membrane surface or polypeptides that are unable to bind their target due to lack of proximity or steric hindrance. Examples of polypeptides include, but are not limited to, ligands, ligand binding receptors, peptides, antibodies or antigen binding fragments thereof, such as Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain, a chimeric antigen receptor (CAR). Antigen binding regions can also include ligand regions, for example a proliferation-inducing ligand (APRIL), a B cell-activating factor (BAFF), transmembrane activator and calcium-modulator and cyclophilin ligand interactor (TACT), or a synthetically derived peptide.

In some embodiments, the polypeptide is a chimeric polypeptide. In certain instances, a chimeric polypeptide described herein is an antigen binding polypeptide. In some embodiments the polypeptide is a chimeric antigen receptor (CAR). A polypeptide such as a CAR, as described herein, comprises an antigen-binding region, a transmembrane region, and a spacer connecting said trans-membrane region with said antigen binding region. In one embodiment, the spacer comprises a stalk region comprising at least one dimerization site, and a stalk extension region. In other embodiments, said stalk extension region can comprise fewer dimerization sites as compared to said stalk region. In certain cases, a chimeric polypeptide described herein, also comprises an intracellular signaling domain. In some cases, the chimeric polypeptide does not comprise an intracellular signaling domain. In certain cases, an intracellular signaling domain is expressed on as a separate polypeptide in an engineered cell expressing a chimeric polypeptide described herein.

Additionally disclosed herein are antigen-binding polypeptides comprising an antigen-binding region, a transmembrane region, and a spacer region connecting said transmembrane region with said antigen binding region, wherein said spacer region can comprise a stalk region (designated as "s") and stalk extension region(s), which is herein designated as "s-n" as discussed herein.

Antigen binding polypeptides comprising a spacer are disclosed, wherein the spacer comprises a stalk region and one stalk extension region, i.e. s'-n, wherein n=1. In some cases, the stalk extension region has a sequence which has at least 60% identity to the stalk region. In other examples, the stalk extension regions has a sequence which has at least 65%, 70%, 75%, 80%, 85%, 90%, 95%, 99% or greater identity to the stalk region.

Antigen binding polypeptides comprising a spacer are disclosed, wherein the spacer comprises a stalk region and two stalk extension region, i.e. s'-n, wherein n=2. In some cases, each of the stalk extension regions has a sequence which has at least 60% identity to the stalk region. In other examples, each of the stalk extension regions has a sequence which has at least 65%, 70%, 75%, 80%, 85%, 90%, 95%, 99% or greater identity to the stalk region.

Antigen binding polypeptides comprising a spacer are disclosed, wherein the spacer comprises a stalk region and three stalk extension region, i.e. s'-n, wherein n=3. In some cases, each of the stalk extension regions has a sequence which has at least 60% identity to the stalk region. In other examples, each of the stalk extension regions has a sequence which has at least 65%, 70%, 75%, 80%, 85%, 90%, 95%, 99% or greater identity to the stalk region.

Antigen binding polypeptides comprising a spacer are disclosed, wherein the spacer comprises a stalk region and four stalk extension region, i.e. s'-n, wherein n=4. In some cases, each of the stalk extension regions has a sequence which has at least 60% identity to the stalk region. In other examples, each of the stalk extension regions has a sequence which has at least 65%, 70%, 75%, 80%, 85%, 90%, 95%, 99% or greater identity to the stalk region.

Antigen binding polypeptides comprising a spacer are disclosed, wherein the spacer comprises a stalk region and five stalk extension region, i.e. s'-n, wherein n=5. In some cases, each of the stalk extension regions has a sequence which has at least 60% identity to the stalk region. In other examples, each of the stalk extension regions has a sequence which has at least 65%, 70%, 75%, 80%, 85%, 90%, 95%, 99% or greater identity to the stalk region.

Antigen binding polypeptides comprising a spacer are disclosed, wherein the spacer comprises a stalk region and a stalk extension region, wherein the stalk extension region comprises more than 5 stalk extension regions, i.e. s'-n, wherein n>5. In such cases, the stalk extension region can comprise n=6, 7, 8, 9, 10, 11, 12, 13, 14, 15, 16, 17, 18, 19, 20, or more stalk extension regions. In some cases, each of said stalk extension regions has a sequence which has at least 60% identity to the stalk region. In other examples, each of said stalk extension regions has a sequence which has at least 65%, 70%, 75%, 80%, 85%, 90%, 95%, 99% or greater identity to the stalk region. In some cases, the spacer comprises a peptide sequence with at least about 10%, 11%, 12%, 13%, 14%, 15%, 16%, 17%, 18%, 19%, 20%, 21%, 22%, 23%, 24%, 25%, 26%, 25%, 26%, 27%, 28%, 29%, 30%, 40%, 50%, 60%, 65%, 70%, 75%, 80%, 85%, 90%, 95%, 99% or greater identity to the CD8a sequence shown in SEQ ID NO: 1. In some cases, the spacer comprises a peptide sequence encoded by a nucleotide sequence with at least about 10%, 11%, 12%, 13%, 14%, 15%, 16%, 17%, 18%, 19%, 20%, 21%, 22%, 23%, 24%, 25%, 26%, 25%, 26%, 27%, 28%, 29%, 30%, 40%, 50%, 60%, 65%, 70%, 75%, 80%, 85%, 90%, 95%, 99% or greater identity to the CD8a nucleotide sequence shown in SEQ ID NO: 107.

In some aspects of the embodiments disclosed herein, a stalk region of a subject antigen binding polypeptide comprises a sequence with at least about 65%, 70%, 75%, 80%, 85%, 90%, 95%, 99% or greater identity to a CD8alpha hinge domain. A CD8a hinge domain can comprise a peptide sequence with at least 65%, 70%, 75%, 80%, 85%, 90%, 95%, 99% or greater identity to the sequence shown in SEQ ID NO: 3 or a peptide sequence encoded by a nucleotide sequence with at least 65%, 70%, 75%, 80%, 85%, 90%, 95%, 99% or greater identity to the sequence shown in SEQ ID NO: 109. In some cases, a stalk extension region comprises a peptide sequence with at least 65%, 70%, 75%, 80%, 85%, 90%, 95%, or greater identity to the sequence shown in SEQ ID NO: 2 or a peptide sequence encoded by a nucleotide sequence with at least 65%, 70%, 75%, 80%, 85%, 90%, 95%, or greater identity to the sequence shown in SEQ ID NO: 108. In some examples, a stalk region and stalk extension region can together comprise a peptide sequence with at least 65%, 70%, 75%, 80%, 85%, 90%, 95% or greater identity to the sequence shown in SEQ ID NO: 4, 5, 6 or 7, or a peptide sequence encoded by a nucleotide sequence with at least 65%, 70%, 75%, 80%, 85%, 90%, 95% or greater identity to the sequence shown in SEQ ID NO: 110, 111, 112 or 113.

In some embodiment, the stalk region and the stalk extension region(s) can be connected via a linker, such as whitlow linker (SEQ ID NO: 8 and SEQ ID NO: 114), GSG linker (SEQ ID NO: 9 and SEQ ID NO: 115), SGSG linker (SEQ ID NO: 10) or (G4S)3 linker (SEQ ID NO: 11 and SEQ ID NO: 117). In one embodiment, the CD8a hinge domain connected to (G4S)3 linker (SEQ ID NO: 11) can comprise a peptide sequence shown in SEQ ID NO: 12 or a peptide sequence encoded by a nucleotide sequence shown in SEQ ID NO: 118. In another embodiment, the CD8α hinge domain connected to whitlow linker can comprise a peptide sequence shown in SEQ ID NO: 13 or a peptide sequence encoded by a nucleotide sequence shown in SEQ ID NO: 119. In yet another embodiment, the CD8α hinge domain connected to whitlow linker (2×) can comprise a peptide sequence shown in SEQ ID NO: 14 or a peptide sequence encoded by a nucleotide sequence shown in SEQ ID NO: 120. In another embodiment, the CD8α hinge domain connected to whitlow linker (2×) can comprise a peptide sequence shown in SEQ ID NO: 15 or a peptide sequence encoded by a nucleotide sequence shown in SEQ ID NO: 121.

In some cases, the spacer comprises a peptide sequence with at least about 10%, 11%, 12%, 13%, 14%, 15%, 16%, 17%, 18%, 19%, 20%, 21%, 22%, 23%, 24%, 25%, 26%, 25%, 26%, 27%, 28%, 29%, 30%, 40%, 50%, 60%, 65%, 70%, 75%, 80%, 85%, 90%, 95%, 99% or greater identity to the CD28 sequence shown in SEQ ID NO: 31. In some cases, the spacer comprises a peptide sequence encoded by a nucleotide sequence with at least about 10%, 11%, 12%, 13%, 14%, 15%, 16%, 17%, 18%, 19%, 20%, 21%, 22%, 23%, 24%, 25%, 26%, 25%, 26%, 27%, 28%, 29%, 30%, 40%, 50%, 60%, 65%, 70%, 75%, 80%, 85%, 90%, 95%, 99% or greater identity to the CD28 nucleotide sequence shown in SEQ ID NO: 137. In some aspects of at least one embodiment disclosed herein, a stalk region of a polypeptide described herein comprises a sequence with at least about 65%, 70%, 75%, 80%, 85%, 90%, 95%, or greater identity to a CD28 hinge domain. A CD28 hinge domain can comprise a peptide sequence with at least 65%, 70%, 75%, 80%, 85%, 90%, 95%, or greater identity to the sequence shown in SEQ ID NO: 32 or a peptide sequence encoded by a nucleotide sequence with at least 65%, 70%, 75%, 80%, 85%, 90%, 95%, 99% or greater identity to the sequence shown in SEQ ID NO: 138. In some examples, a stalk region and stalk extension region can together comprise a peptide sequence with at least 65%, 70%, 75%, 80%, 85%, 90%, 95% or greater identity to the sequence shown in SEQ ID NO: 33, 34 or 35, or a peptide sequence encoded by a nucleotide sequence with at least 65%, 70%, 75%, 80%, 85%, 90%, 95%, 99% or greater identity to the sequence shown in SEQ ID NO: 139, SEQ ID NO: 140 or SEQ ID NO: 141.

In some aspects of the embodiments disclosed herein, a stalk region of a polypeptide described herein comprises a sequence with at least about 65%, 70%, 75%, 80%, 85%, 90%, 95%, or greater identity to a CTLA-4 extracellular domain. In some aspects, the CTLA-4 extracellular domain may comprise a partial sequence. In some cases, the CTLA-4 partial sequence comprises a peptide sequence with at least about 10%, 11%, 12%, 13%, 14%, 15%, 16%, 17%, 18%, 19%, 20%, 21%, 22%, 23%, 24%, 25%, 26%, 25%, 26%, 27%, 28%, 29%, 30%, 40%, 50%, 60%, 65%, 70%, 75%, 80%, 85%, 90%, 95%, 99% or greater identity to the CTLA-4 sequence shown in SEQ ID NO: 36. In some cases, the spacer comprises a peptide sequence encoded by a nucleotide sequence with at least about 10%, 11%, 12%, 13%, 14%, 15%, 16%, 17%, 18%, 19%, 20%, 21%, 22%, 23%, 24%, 25%, 26%, 25%, 26%, 27%, 28%, 29%, 30%, 40%, 50%, 60%, 65%, 70%, 75%, 80%, 85%, 90%, 95%, 99% or greater identity to the CTLA-4 nucleotide sequence shown in SEQ ID NO: 142. A CTLA-4 extracellular domain can comprise a sequence with at least 65%, 70%, 75%, 80%, 85%, 90%, 95%, or greater identity to the sequence shown in SEQ ID NO: 37. In some cases, a stalk extension region comprises a sequence with at least 65%, 70%, 75%, 80%, 85%, 90%, 95%, or greater identity to the sequence shown in SEQ ID NO: 37. In some examples, a stalk region and stalk extension region can together comprise a sequence with at least 65%, 70%, 75%, 80%, 85%, 90%, 95%, or greater identity to the sequence shown in SEQ ID NO: 38, SEQ ID NO: 39 or SEQ ID NO: 40.

In some aspects of the embodiments disclosed herein, a stalk region or a stalk extension region of a polypeptide described herein comprises a sequence with at least about 65%, 70%, 75%, 80%, 85%, 90%, 95%, or greater identity to a full length LNGFR extracellular domain (ECD). In some cases, the LNGFR ECD is incapable of dimerization. A LNGFR ECD can comprise a peptide sequence with at least 65%, 70%, 75%, 80%, 85%, 90%, 95%, or greater identity to the sequence shown in SEQ ID NO: 16 or a peptide sequence encoded by a nucleotide sequence with at least 65%, 70%, 75%, 80%, 85%, 90%, 95%, 99% or greater identity to the sequence shown in SEQ ID NO: 122. In some cases, a stalk extension region comprises a peptide sequence with at least 65%, 70%, 75%, 80%, 85%, 90%, 95%, or greater identity to the sequence shown in SEQ ID NO: 16 or a peptide sequence encoded by a nucleotide sequence with at least 65%, 70%, 75%, 80%, 85%, 90%, 95%, 99% or greater identity to the sequence shown in SEQ ID NO: 122. In some examples, a stalk region and stalk extension region can together comprise a peptide sequence with at least 65%, 70%, 75%, 80%, 85%, 90%, 95%, 99% or greater identity to the sequence shown in SEQ ID NO: 17, SEQ ID NO: 18, SEQ ID NO: 19, SEQ ID NO: 20, SEQ ID NO: 21, SEQ ID NO: 22 or SEQ ID NO: 23, or a peptide sequence encoded by a nucleotide sequence with at least 65%, 70%, 75%, 80%, 85%, 90%, 95%, 99% or greater identity to the sequence shown in SEQ ID NO: 123, SEQ ID NO: 124, SEQ ID NO: 125, SEQ ID NO: 126, SEQ ID NO: 127, SEQ ID NO: 128 or SEQ ID NO: 129.

In some cases, a stalk extension region comprises a sequence with at least 65%, 70%, 75%, 80%, 85%, 90%, 95%, or greater identity to the sequence shown in SEQ ID NO: 72 or SEQ ID NO: 73 or a peptide sequence encoded by a nucleotide sequence with at least 65%, 70%, 75%, 80%, 85%, 90%, 95%, 99% or greater identity to the sequence shown in SEQ ID NO: 166 or SEQ ID NO: 167. In some examples, a stalk region and stalk extension region can together comprise a peptide sequence with at least 65%, 70%, 75%, 80%, 85%, 90%, 95% or greater identity to the sequence shown in SEQ ID NO: 77, SEQ ID NO: 78 or SEQ ID NO: 79, or a peptide sequence encoded by a nucleotide sequence with at least 65%, 70%, 75%, 80%, 85%, 90%, 95%, 99% or greater identity to the sequence shown in SEQ ID NO: 171, SEQ ID NO: 172 or SEQ ID NO: 173. In some examples, a stalk region and stalk extension region can together comprise a peptide sequence with at least 65%, 70%, 75%, 80%, 85%, 90%, 95% or greater identity to the sequence shown in SEQ ID NO: 80, SEQ ID NO: 81 or SEQ ID NO: 82, or a peptide sequence encoded by a nucleotide sequence with at least 65%, 70%, 75%, 80%, 85%, 90%, 95%, 99% or greater identity to the sequence shown in SEQ ID NO: 174, SEQ ID NO: 175 or SEQ ID NO: 176.

In some embodiment, the stalk region and the stalk extension region(s) can be connected via a linker, such as whitlow linker (SEQ ID NO: 8 and SEQ ID NO: 114), GSG linker (SEQ ID NO: 9 and SEQ ID NO: 115), SGSG linker (SEQ ID NO: 10) or (G4S)3 linker (SEQ ID NO: 11 and SEQ ID NO: 117). In one embodiment, the TCRα hinge domain connected to (G4S)3 linker (SEQ ID NO: 11) can comprise a peptide sequence shown in SEQ ID NO: 74 or a peptide sequence encoded by a nucleotide sequence shown in SEQ ID NO: 168. In one embodiment, the TCRβ hinge domain connected to (G4S)3 linker (SEQ ID NO: 11) can comprise a peptide sequence shown in SEQ ID NO: 75 or a peptide sequence encoded by a nucleotide sequence shown in SEQ ID NO: 169. In yet another embodiment, the TCRβ hinge domain connected to whitlow linker can comprise a peptide sequence shown in SEQ ID NO: 76 or a peptide sequence encoded by a nucleotide sequence shown in SEQ ID NO: 170.

In some cases, a stalk extension region comprises a sequence with at least 65%, 70%, 75%, 80%, 85%, 90%, 95%, or greater identity to the sequence shown in SEQ ID NO: 86 or SEQ ID NO: 87 or a peptide sequence encoded by a nucleotide sequence with at least 65%, 70%, 75%, 80%, 85%, 90%, 95%, 99% or greater identity to the sequence shown in SEQ ID NO: 180 or SEQ ID NO: 181. In some examples, a stalk region and stalk extension region can together comprise a peptide sequence with at least 65%, 70%, 75%, 80%, 85%, 90%, 95% or greater identity to the sequence shown in SEQ ID NO: 91, SEQ ID NO: 92 or SEQ ID NO: 93, or a peptide sequence encoded by a nucleotide sequence with at least 65%, 70%, 75%, 80%, 85%, 90%, 95%, 99% or greater identity to the sequence shown in SEQ ID NO: 185, SEQ ID NO: 186 or SEQ ID NO: 187. In some examples, a stalk region and stalk extension region can together comprise a peptide sequence with at least 65%, 70%, 75%, 80%, 85%, 90%, 95% or greater identity to the sequence shown in SEQ ID NO: 94, SEQ ID NO: 95 or SEQ ID NO: 96, or a peptide sequence encoded by a nucleotide sequence with at least 65%, 70%, 75%, 80%, 85%, 90%, 95%, 99% or greater identity to the sequence shown in SEQ ID NO: 188, SEQ ID NO: 189 or SEQ ID NO: 190.

In some embodiment, the stalk region and the stalk extension region(s) can be connected via a linker, such as whitlow linker (SEQ ID NO: 8 and SEQ ID NO: 114), GSG linker (SEQ ID NO: 9 and SEQ ID NO: 115), SGSG linker (SEQ ID NO: 10) or (G4S)3 linker (SEQ ID NO: 11 and SEQ ID NO: 117). In one embodiment, the TCRβ hinge domain connected to (G4S)3 linker (SEQ ID NO: 11) can comprise a peptide sequence shown in SEQ ID NO: 88 or a peptide sequence encoded by a nucleotide sequence shown in SEQ ID NO: 182. In one embodiment, the TCRβ hinge domain connected to (G4S)3 linker (SEQ ID NO: 11) can comprise a peptide sequence shown in SEQ ID NO: 89 or a peptide sequence encoded by a nucleotide sequence shown in SEQ ID NO: 183. In yet another embodiment, the TCRβ hinge domain connected to whitlow linker can comprise a peptide sequence shown in SEQ ID NO: 90 or a peptide sequence encoded by a nucleotide sequence shown in SEQ ID NO: 184.

In some aspects of the embodiments disclosed herein, a dimerization site comprises a cysteine. In some cases, a dimerization site in a stalk region described herein comprises two cysteines. In some aspects, the dimerization site can be ligand induced.

Additionally disclosed herein are polynucleotides encoding any of the polypeptides disclosed herein, as well as vectors comprising one or more of said polynucleotides. Vectors can be cloning vectors, delivery vectors, expression vectors, or any combination thereof. Such vectors can be viral vectors or non-viral vectors. For example, a vector can be a lentivirus vector, retroviral vector, adenoviral vector, adeno-associated viral vector, a Sleeping Beauty transposon, AttSite™ Recombinase, PiggyBac™ transposon or other non-viral vector.

In some cases, an antigen-binding polypeptide comprising spacers with stalk extension region(s) as disclosed herein can have increased antigen-binding compared to an otherwise identical antigen-binding polypeptide which lacks the stalk extension region(s). Antigen-binding of the antigen-binding polypeptide comprising the stalk extension region(s) can be increased by at least 5%, 10%, 15%, 20%, 25%, 30%, 35%, 40%, 45%, 50%, 60%, 65%, 70%, 75%, 80%, 85%, 90%, 95%, 100%, 150%, 200% 500%, 1000% or greater as compared to an otherwise identical antigen-binding polypeptide which lacks the stalk extension region.

Antigen-binding can be assessed by flow cytometry or a cell based assay or any other equivalent assay. Cell based assays may utilize a cell type expressing antigen of interest on the surface to assess antigen-binding. An antigen or a fragment thereof expressed as a soluble protein can be utilized to assess antigen-binding using flow cytometry or similar assay. Improvements in antigen-binding may be indirectly assessed by functional measurement of antigen-binding polypeptide or a chimeric receptor. For example, improved antigen-binding of a chimeric receptor or a CAR, as described herein, can be measured by increased specific cytotoxicity against target cells expressing the antigen.

In some cases, a polypeptide as disclosed herein can have increased expression on a cell surface compared to an otherwise identical polypeptide which lacks one or more stalk extension region(s). Cell surface expression of the polypeptide comprising the stalk extension region(s) can be increased by at least 5%, 10%, 15%, 20%, 25%, 30%, 35%, 40%, 45%, 50%, 60%, 65%, 70%, 75%, 80%, 85%, 90%, 95%, 100%, 150%, 200% 500%, 1000% or greater as compared to an otherwise identical polypeptide which lacks the stalk extension region.

Cell surface expression level of a polypeptide of the present disclosure can be assessed, for example, using a flow cytometry based assay. Improved expression of an antigen-binding polypeptide can be measured as percentage of analyzed cells expressing said antigen-binding polypeptide or alternatively as average density of said antigen-binding polypeptide on the surface of a cell. Additional suitable methods that can be used for assessing cell surface expression of the antigen-binding polypeptides described herein include western blotting or any other equivalent assay.

Chimeric Receptors

Polypeptides disclosed herein can be expressed in a modified effector cell. In some embodiments, a modified effector cell comprises a chimeric receptor expressed on the surface of the cell. In some instances, the chimeric receptor comprises an antigen binding region that enables recognition and binding to a tumor antigen, e.g., a tumor-associated antigen or a tumor-specific antigen. In some instances, the antigen binding region comprises an antibody or binding fragment, for example, an Fab, an Fab', an $F(ab')_2$, an $F(ab')_3$, an scFv, an $sc(Fv)_2$, a dsFv, a diabody, a minibody, and a nanobody or binding fragments thereof. In some cases, the antigen binding region comprises an scFv. In some cases, the antigen-binding polypeptide is a chimeric antigen receptor (CAR) that comprises a scFv as an antigen binding domain. In some instances, the chimeric antigen receptor comprises a pattern-recognition receptor. In other cases, the chimeric receptor comprises an engineered T-cell receptor (TCR).

Chimeric Antigen Receptors (CARs)

Polypeptides disclosed herein can comprise a chimeric antigen receptor (CAR). A CAR is an engineered receptor which grafts an exogenous specificity onto an immune effector cell.

In some cases, a CAR disclosed herein comprises a spacer region connecting a transmembrane region with an antigen binding region. In some cases, a spacer region of a CAR disclosed herein comprises 1) a stalk region and 2) stalk extension region(s) adjacent to said stalk region. Illustrative embodiments are described in FIGS. 1 and 2. In some embodiments, a CAR disclosed herein incorporates a spacer that comprises a stalk region and a stalk extension region (s'-n, wherein n=0, 1, 2, 3, 4, 5, 6, 7, 8, 9, 10, 11, 12, 13, 14, 15, 16, 17, 18, 19 or 20).

In some instances, a CAR comprises an extracellular region (ectodomain) that comprises an antigen binding region, a stalk region, a stalk extension region, a transmembrane region and, optionally an intracellular (endodomain) region. In some instances, the intracellular region further comprises one or more intracellular signaling regions or domains. In some instances, a CAR described herein comprises an antigen binding region, a stalk region, a stalk extension region, a transmembrane region, one or more costimulatory regions or domains, and a signaling region for T-cell activation.

An antigen binding region can comprise complementary determining regions of a monoclonal antibody, variable regions of a monoclonal antibody, and/or antigen binding fragments thereof. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor can contain three CDRs (CDR1, CDR2, and CDR3). In some instances, an antigen binding region comprises $F(ab')_2$, Fab', Fab, Fv, or scFv. In some cases, an antigen binding region is an scFv. In some cases, an antigen binding region is a Fab. In some cases, an antigen binding region is a Fab'. In some cases, an antigen binding region is $F(ab')_2$. In some cases, an antigen binding region is an Fv.

In some embodiments, a CAR or a chimeric receptor or antigen binding polypeptide described herein comprises an antigen binding region that binds to an epitope on CD19, BCMA, CD44, α-Folate receptor, CAIX, CD30, ROR1, CEA, EGP-2, EGP-40, HER2, HER3, Folate-binding Protein, GD2, GD3, IL-13Ra2, KDR, EDB-F, mesothelin, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, CD22, EGFR, Folate receptor α, Mucins such as MUC-1 or MUC-16, MAGE-A1, h5T4, PSMA, TAG-72, EGFR, CD20, EGFRvIII, CD123 or VEGF-R2. In some embodiments, a CAR or a chimeric receptor or antigen binding polypeptide described herein comprises an antigen binding region that binds to an epitope on CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, CD22, EGFR, Mucins such as MUC-1 or MUC-16, MAGE-A1 h5T4, PSMA, TAG-72, EGFRvIII, CD123 and VEGF-R2. In some embodiments, a CAR or a chimeric receptor or antigen binding polypeptide described herein comprises an antigen binding region that binds to an epitope on CD19 or CD33. In some instances, a CAR or a chimeric receptor or antigen binding polypeptide described herein comprises an antigen binding region that binds to an epitope on CD19. In some cases, a CAR or a chimeric receptor or antigen binding polypeptide described herein comprises an antigen binding region that binds to an epitope on CD33. In some cases, a CAR or a chimeric receptor or antigen binding polypeptide described herein comprises an antigen binding region that binds to an epitope on ROR-1. In some cases, a CAR or a chimeric receptor or antigen binding polypeptide described herein comprises an antigen binding region that binds to an epitope on EGFRvIII. In further embodiments, a CAR or a chimeric receptor or antigen binding polypeptide described herein comprises an autoantigen or an antigen binding region that binds to an epitope on HLA-A2, myelin oligodendrocyte glycoprotein (MOG), factor VIII (FVIII), MAdCAM1, SDF1, or collagen type II In some embodiments, the polynucleotides, polypeptides and methods described herein can be used for the treatment of a hyperproliferative disease, such as a cancer, an autoimmune disease or for the treatment of an infection, such as a viral, bacterial or parasitic infection. In some aspects, the antigen is an antigen that is elevated in cancer cells, in autoimmune cells or in cells that are infected by a virus, bacteria or parasite. Pathogens that may be targeted include, without limitation, *Plasmodium*, trypanosome, *Aspergillus, Candida*, Hepatitis A, Hepatitis B, Hepatitis C, HSV, HPV, RSV, EBV, CMV, JC virus, BK virus, or Ebola pathogens. Autoimmune diseases can include graft-versus-host disease, rheumatoid arthritis, lupus, celiac disease, Crohn's disease, Sjogren Syndrome, polymyalgia rheumatic, multiple sclerosis, neuromyelitis optica, ankylosing spondylitis, Type 1 diabetes, alopecia areata, vasculitis, temporal arteritis, bullous pemphigoid, psoriasis, pemphigus vulgaris or autoimmune uveitis.

The pathogen recognized by a CAR may be essentially any kind of pathogen, but in some embodiments the pathogen is a fungus, bacteria, or virus. Exemplary viral pathogens include those of the families of Adenoviridae, Epstein-Barr virus (EBV), Cytomegalovirus (CMV), Respiratory Syncytial Virus (RSV), JC virus, BK virus, HPV, HSV, HHV family of viruses, Hepatitis family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia, Spirochetes*, and *Salmonella*. In some embodiments the pathogen receptor Dectin-1 may be used to generate a CAR that recognizes the carbohydrate structure on the cell wall of fungi such as *Aspergillus*. In another embodiment, CARs can be made based on an antibody recognizing viral determinants (e.g., the glycoproteins from CMV and Ebola) to interrupt viral infections and pathology.

In some embodiments, a spacer region as described herein can be used to link the antigen-binding region to the transmembrane region of a CAR. In some instances, a spacer can comprise any oligonucleotide- or polypeptide that functions to link the transmembrane region to, either the extracellular region or, the cytoplasmic region in the polypeptide chain. In some embodiments, the spacer is flexible enough to allow the antigen-binding region to orient in different directions to facilitate antigen recognition.

As described herein, a spacer region can comprise a stalk region and stalk extension region(s). In some instances, the stalk region comprises the hinge region from IgG1, or the stalk region comprises a sequence with at least 80% homology to the hinge region from IgG1. In alternative instances, the stalk region comprises IgG3 hinge region or a sequence with at least 80% homology to the IgG3 hinge region (SEQ ID NO: 41). In alternative instances, the stalk region comprises IgG4 hinge region or a sequence with at least 80% homology to the IgG4 hinge region (SEQ ID NO: 42). In other cases, a stalk region comprises a peptide sequence with at least about 65%, 70%, 75%, 80%, 85%, 90%, 95%, 99% or greater homology to a peptide sequence shown in SEQ ID NO: 43, 44, 45, 46, 47 or 48. In another case, a stalk region comprises a peptide sequence encoded by a nucleotide sequence with at least about 65%, 70%, 75%, 80%, 85%, 90%, 95%, 99% or greater identity to the sequence shown in SEQ ID NO: 144. In some cases, the stalk region comprises a CD8α hinge region, or a sequence with at least 80% homology to the hinge region of CD8α. For example, the stalk region can comprise a sequence with at least 80%, 85%, 90%, 95%, or greater than 95% homology to the hinge region of CD8α. In some cases, the stalk region comprises a CD28 hinge region, or a sequence with at least 80% homology to the hinge region of CD28. For example, the stalk region can comprise a sequence with at least 80%, 85%, 90%, 95%, or greater than 95% homology to the hinge region of CD28. In some cases, the stalk region comprises an IgG4 12 amino acid hinge region (ESKYGPPCPPCP (SEQ ID NO: 43)) or IgG4 hinge regions (SEQ ID NO: 42) as described in WO/2016/073755.

In some embodiments, the stalk region comprises a dimerization site. A dimerization site can comprise a disulfide bond formation site. A dimerization site can comprise cysteine residue(s). A stalk region can be capable of forming a disulfide bond. Such a disulfide bond can be formed at a disulfide bond forming site or a dimerization site. In some examples, the dimerization occurs between the stalk region of a first CAR and a homologous stalk region of a homologous second CAR.

In some embodiments, a stalk extension region is used to link the antigen-binding region to the stalk region. In additional embodiments, a stalk extension region is used to link the stalk region to the transmembrane region of the CAR. For instance, when the stalk region comprises a hinge domain derived from an IgG, a non-Fc CH2 or CH3 domain can be used as a stalk extension region. In another embodiment, the stalk region and the stalk extension region(s) can be connected via a linker. In other embodiments, one stalk extension region can be connected to another stalk extension region via a linker. Examples of such linkers can include a glycine-serine rich linker. In one embodiment, a stalk region or a stalk extension region of a polypeptide described herein comprises a peptide sequence with at least about 60%, 65%, 70%, 75%, 80%, 85%, 90%, 95%, 99% or greater identity to the IgG4 hinge-CH2-CH3 spacer sequence shown in SEQ ID NO: 49. In some cases, a stalk region or a stalk extension region of a polypeptide described herein comprises a peptide sequence encoded by a nucleotide sequence with at least about 60%, 65%, 70%, 75%, 80%, 85%, 90%, 95%, 99% or greater identity to the IgG4 hinge-CH2-CH3 spacer nucleotide sequence shown in SEQ ID NO: 145. In one embodiment, a stalk region or a stalk extension region of a polypeptide described herein comprises a peptide sequence with at least about 60%, 65%, 70%, 75%, 80%, 85%, 90%, 95%, 99% or greater identity to the IgG4 hinge-CH3 spacer sequence shown in SEQ ID NO: 50.

In some instances, the stalk extension domain comprises a sequence that is partially homologous to the stalk region. In some instances, each of the stalk extension region comprises a sequence that is homologous to the stalk region, except that the stalk extension region lacks the dimerization site of the stalk region. In some cases, each of the stalk extension regions comprises a sequence identical to the stalk region. In other cases, each of the stalk extension regions comprises a sequence identical to the stalk region with at least one amino acid residue substitution relative to the stalk region. In some cases, each of the stalk extension region is not capable of forming a disulfide bond or is not capable of dimerization with a homologous stalk extension region.

In embodiments described herein, a polypeptide can comprise a transmembrane region or transmembrane domain that can be derived from either a natural or a synthetic source. Where the source is natural, the region can be derived from any membrane-bound or transmembrane protein. Suitable transmembrane regions can include, but not limited to, the transmembrane region(s) of alpha, beta or zeta chain of the T-cell receptor; or a transmembrane region from CD28, CD3 epsilon, CD3ζ, CD45, CD4, CD5, CD8alpha, CD9, CD16, CD22, CD33, CD37, CD64, CD80, CD86, CD134, CD137, CD152 (CTLA-4) or CD154. Alternatively, the transmembrane region or domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length may form the linkage between the transmembrane domain and the cytoplasmic signaling domain of a CAR. In some embodiments, the linker is a glycine-serine linker.

In some embodiments, the transmembrane region comprises a CD8α transmembrane domain, a CD152 (CTAL-4), TCRγ1, TCRδ or a CD3ζ transmembrane domain. In some embodiments, the transmembrane region comprises a CD8α transmembrane domain (SEQ ID NO: 24 and SEQ ID NO: 130). In other embodiments, the transmembrane region comprises a CD3ζ transmembrane domain. In another embodiment, the transmembrane region comprises a CD152 (CTLA-4) transmembrane domain (SEQ ID NO: 25 and SEQ ID NO: 131). In yet another embodiment, the transmembrane region comprises a TCRα transmembrane domain (SEQ ID NO: 71 and SEQ ID NO: 165), a TCRβ transmembrane domain (SEQ ID NO: 85 and SEQ ID NO: 179), a TCRγ1 transmembrane domain (SEQ ID NO: 101 and SEQ ID NO: 195). In some embodiments, the transmembrane region comprises a TCRδ transmembrane domain (SEQ ID NO: 106 and SEQ ID NO: 200).

The intracellular region or intracellular domain can comprise one or more costimulatory domains. Exemplary costimulatory domains include, but are not limited to, CD3ζ, CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD3ζ, CD8, CD27, CD28, 4-1BB (CD137), ICOS, DAP10, DAP 12, OX40 (CD134) or fragment or combination thereof. In some instances, a CAR described herein comprises one or more, or two or more of costimulatory domains selected from CD3ζ, CD27, CD28, 4-1BB (CD137), ICOS, OX40 (CD134) or fragment or combination thereof. In some instances, a CAR described herein comprises one or more, or two or more of costimulatory domains selected from CD3ζ, CD8, CD28, 4-1BB (CD137), or fragment or combination thereof. In some instances, a CAR described herein comprises one or more, or two or more of costimulatory domains selected from CD3ζ, CD28, 4-1BB (CD137), or fragment or combination thereof. In some instances, a CAR described herein comprises costimulatory domains CD3ζ, CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domain CD28 (SEQ ID NO: 26 and SEQ ID NO: 132) or a fragment thereof. In some instances, a CAR described herein comprises costimulatory domain 4-1BB (CD137) (SEQ ID NO: 27 and SEQ ID NO: 133) or a fragment thereof. In some instances, a CAR described herein comprises costimulatory domain OX40 (CD134) or a fragment thereof. In some instances, a CAR described herein comprises costimulatory domain CD8 or a fragment thereof. In some instances, a CAR described herein comprises costimulatory domain CD3ζ (SEQ ID NO: 28 and SEQ ID NO: 134) or a fragment thereof.

In some embodiments, the intracellular region or intracellular domain further comprises a signaling domain for T-cell activation. In some instances, the signaling domain for T-cell activation comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ.

CD19-Specific CARS

CD19 is a cell surface glycoprotein of the immunoglobulin superfamily and is found predominately in malignant B-lineage cells. In some instances, CD19 has also been detected in solid tumors such as pancreatic cancer, liver cancer, and prostate cancer.

In some embodiments, described herein include a CD19-specific CAR, in which the antigen binding region comprises a $F(ab')_2$, Fab' Fab, Fv, or scFv. In some instances, the antigen binding region recognizes an epitope on CD19.

In some embodiments, an antigen binding region encompassed by a polypeptide described herein recognizes an epitope on CD19 that is also recognized by JCAR014, JCAR015, JCAR017, or 19-28z CAR (Juno Therapeutics). In some embodiments, CD19 comprises a peptide sequence at least 80% homology to the CD19 sequence shown in SEQ ID NO: 51. In some embodiments, described herein include a CD19-specific CAR expressed on an effector cell such as a T cell, in which the antigen binding region recognizes an epitope on CD19 that is also recognized by JCAR014, JCAR015, JCAR017, or 19-28z CAR (Juno Therapeutics). In some instances, the CD19-specific CAR is encompassed by a polypeptide which further comprises a transmembrane region or transmembrane domain selected from a CD8alpha transmembrane domain (SEQ ID NO: 24 and SEQ ID NO: 130) or a CD3ζ transmembrane domain; one or more costimulatory domains selected from CD27, CD28, 4-1BB (CD137), ICOS, DAP10, DAP12, OX40 (CD134) or fragment or combination thereof; and a signaling region or signaling domain from CD3ζ. In some instances, the CD19-specific CAR is expressed as part of a polypeptide which further comprises a stalk region and a stalk extension region as disclosed herein. For example, the CD19-specific CAR comprising polypeptide can further comprise a stalk region comprising a CD8α hinge region, and a stalk extension region (s'-n), wherein n=0, 1, 2, 3, 4, 5, 6, 7, 8, 9, 10, 11, 12, 13, 14, 15, 16, 17, 18, 19, or 20, wherein each stalk extension region being homologous to a CD8α hinge region except for lacking a dimerization site.

In some embodiments, a CD19-specific CAR encompassed by a polypeptide described herein comprises an scFv antigen binding region, and the antigen binding region recognizes an epitope on CD19 that is also recognized by JCAR014, JCAR015, JCAR017, or 19-28z CAR (Juno Therapeutics). In some instances, the CD19-specific CAR is encompassed by a polypeptide that further comprises a transmembrane domain selected from a CD8alpha transmembrane domain (SEQ ID NO: 24 and SEQ ID NO: 130) or a CD3ζ transmembrane domain; one or more costimulatory domains selected from CD27, CD28, 4-1BB (CD137), ICOS, DAP10, DAP 12, OX40 (CD134) or fragment or combination thereof; and a signaling domain from CD3ζ. In some cases, the CD19-specific CAR is encompassed by a polypeptide that further comprises a transmembrane domain selected from a CD152 (CTLA-4) transmembrane domain (SEQ ID NO: 25 and SEQ ID NO: 131), a TCRα transmembrane domain (SEQ ID NO: 71 and SEQ ID NO: 165), a TCRβ transmembrane domain (SEQ ID NO: 85 and SEQ ID NO: 179), a TCRγ1 transmembrane domain (SEQ ID NO: 101 and SEQ ID NO: 195) or a TCRδ transmembrane domain (SEQ ID NO: 106 and SEQ ID NO: 200). In some instances, the polypeptide comprising a CD19-specific CAR cell further comprises a stalk region and a stalk extension region as disclosed herein. For example, the polypeptide can further comprise a stalk region comprising a CD8α hinge region, and a stalk extension region (s'-n), wherein n=0, 1, 2, 3, 4, 5, 6, 7, 8, 9, 10, 11, 12, 13, 14, 15, 16, 17, 18, 19, or 20, wherein each stalk extension region being homologous to a CD8α hinge region except for lacking a dimerization site.

In some embodiments, a CD19-specific CAR expressed on an effector cell such as a T cell described herein comprises an anti-CD19 antibody described in US20160152723.

In some embodiments, an antigen binding region encompassed by a polypeptide described herein recognizes an epitope on CD19 that is also recognized by KTE-C19 (Kite Pharma, Inc.). In some embodiments, described herein include a CD19-specific CAR-T cell, in which the antigen binding region recognizes an epitope on CD19 that is also recognized by KTE-C19. In some instances, the CD19-specific CAR further comprises a transmembrane domain selected from a CD8alpha transmembrane domain (SEQ ID NO: 24 and SEQ ID NO: 130) or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ. In some cases, the CD19-specific CAR is encompassed by a polypeptide that further comprises a transmembrane domain selected from a CD152 (CTLA-4) transmembrane domain (SEQ ID NO: 25 and SEQ ID NO: 131), a TCRα transmembrane domain (SEQ ID NO: 71 and SEQ ID NO: 165), a TCRβ transmembrane domain (SEQ ID NO: 85 and SEQ ID NO: 179), a TCRγ1 transmembrane domain (SEQ ID NO: 101 and SEQ ID NO: 195) or a TCR transmembrane domain (SEQ ID NO: 106 and SEQ ID NO: 200).

Some embodiments, described herein include a CD19-specific CAR comprising an scFv antigen binding region, and the antigen binding region recognizes an epitope on CD19 that is also recognized by RTE-C19. In some instances, the CD19-specific CAR-T cell further comprises a transmembrane domain selected from a CD8alpha transmembrane domain (SEQ ID NO: 24 and SEQ ID NO: 130) or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, a CD19-specific CAR described herein comprises an anti-CD19 antibody described in WO2015187528 or fragment or derivative thereof.

In some embodiments, the antigen binding region recognizes an epitope on CD19 that is also recognized by CTL019 (Novartis). In some embodiments, the antigen binding region recognizes an epitope on CD19 that is also recognized by UCART19 (Cellectis). In some embodiments, the antigen binding region recognizes an epitope on CD1.9 that is also recognized by BPX-401 (Bellicum). In some cases, the antigen binding region recognizes an epitope on CD19 that is also recognized by blinatumomab (Amgen), coltuximabravtansine (ImmunoGen Inc./Sanoli-aventis), MOR208 (Morphosys AG/Xencor Inc.), MEDI-551 (Medimmune), denintuzumabmafodotin (Seattle Genetics), B4 (or DI-B4) (Merck Serono), taplitumornabpaptox (National Cancer Institute), XmAb 5871 (Amgen/Xencor, Inc.), MDX-1342 (Medarex) or AFM11 (Affimed). In some embodiments, described herein include a CD19-specific CAR expressed on an effector cell such as a T cell, in which the antigen binding region recognizes an epitope on CD19 that is also recognized by CTL019. In some instances, the CD19-specific CAR further comprises a transmembrane domain selected from a CD8alpha transmembrane domain (SEQ ID NO: 24 and SEQ ID NO: 130) or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ. In some cases, the CD19-specific CAR is encompassed by a polypeptide that further comprises a transmembrane domain selected from a CD152 (CTLA-4) transmembrane domain (SEQ ID NO: 25 and SEQ ID NO: 131), a TCRα transmembrane domain (SEQ ID NO: 71 and SEQ ID NO: 165), a TCRβ transmembrane domain (SEQ ID NO: 85 and SEQ ID NO: 179), a TCRγ1 transmembrane domain (SEQ ID NO: 101 and SEQ ID NO: 195) or a TCR transmembrane domain (SEQ ID NO: 106 and SEQ ID NO: 200). In some instances, the CD19-specific CAR is encoded as part of a polypeptide that further comprises a stalk region and a stalk extension region as disclosed herein. For example, the CD19-specific CAR can be encompassed by a polypeptide that further comprise a stalk region comprising a CD8α hinge region, and a stalk extension region (s'-n), wherein n=0, 1, 2, 3, 4, 5, 6, 7, 8, 9, 10, 11, 12, 13, 14, 15, 16, 17, 18, 19, or 20, wherein each stalk extension region being homologous to a CD8α hinge region except for lacking a dimerization site.

Some embodiments, described herein include a CD19-specific CAR expressed on an effector cell such as a T cell comprising an scFv antigen binding region, and the antigen binding region recognizes an epitope on CD19 that is also recognized by at least one of CTL019, BPX-401, blinatumomab (Amgen), coltuximabravtansine (ImmunoGen Inc./Sanofi-aventis), MOR208 (Morphosys AG/Xencor Inc), MEDI-551 (Medimmune), denintuzumabmafodotin (Seattle Genetics), B4 (or DI-B4) (Merck Serono), taplitumomabpaptox (National Cancer institute), XmAb 5871 (Amgen/Xencor, Inc.)), MDX-1342 (Medarex) and AFM11 (Affimed). In some instances, the CD19-specific CAR is encompassed by a polypeptide which further comprises a transmembrane domain selected from a CD8alpha transmembrane domain (SEQ ID NO: 24 and SEQ ID NO: 130) or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ. In some cases, the CD19-specific CAR is encompassed by a polypeptide that further comprises a transmembrane domain selected from a CD152 (CTLA-4) transmembrane domain (SEQ ID NO: 25 and SEQ ID NO: 131), a TCRα transmembrane domain (SEQ ID NO: 71 and SEQ ID NO: 165), a TCRβ transmembrane domain (SEQ ID NO: 85 and SEQ ID NO: 179), a TCRγ1 transmembrane domain (SEQ ID NO: 101 and SEQ ID NO: 195) or a TCR transmembrane domain (SEQ ID NO: 106 and SEQ ID NO: 200). In some cases, the CD19-specific CAR is encompassed by a polypeptide that further comprises a signaling domain selected from a DAP10 signaling domain (SEQ ID NO: 29 and SEQ ID NO: 135), or a DAP12 signaling domain (SEQ ID NO: 30 and SEQ ID NO: 136). In some instances, a polypeptide comprising the CD19-specific CAR further comprises a stalk region and a stalk extension region as disclosed herein. For example, the polypeptide can further comprise a stalk region comprising a CD8α hinge region, and a stalk extension region (s'-n), wherein n=0, 1, 2, 3, 4, 5, 6, 7, 8, 9, 10, 11, 12, 13, 14, 15, 16, 17, 18, 19, or 20, wherein each stalk extension region being homologous to a CD8α hinge region except for lacking a dimerization site.

In some embodiments, the CD19-specific CAR described herein comprises an anti-CD19 monoclonal antibody variable light chain comprising a peptide sequence with at least 80% homology to the sequence shown in SEQ ID NO: 53 or a peptide sequence encoded by a nucleotide sequence with at least 80% homology to the sequence shown in SEQ ID NO: 147. In some embodiments, the CD19-specific CAR described herein comprises an anti-CD19 monoclonal antibody variable heavy chain comprising a peptide sequence with at least 80% homology to the sequence shown in SEQ ID NO: 54 or a peptide sequence encoded by a nucleotide sequence with at least 80% homology to the sequence shown in SEQ ID NO: 148. In some embodiments, the CD19-specific CAR described herein comprises an anti-CD19 scFv with Whitlow linker comprising a peptide sequence with at least 80% homology to the sequence shown in SEQ ID NO: 55 or a peptide sequence encoded by a nucleotide sequence with at least 80% homology to the sequence shown in SEQ ID NO: 149. In some embodiments, the CD19-specific CAR described herein comprises CD19 specific chimeric antigen receptor with CD8-1× spacer (CD19-CD8α-CD28-CD3ζ) comprising a peptide sequence with at least 80% homology to the sequence shown in SEQ ID NO: 56 or a peptide sequence encoded by a nucleotide sequence with at least 80% homology to the sequence shown in SEQ ID NO: 150. In some embodiments, the CD19-specific CAR described herein comprises CD19 specific chimeric antigen receptor with CD8-2× spacer comprising a peptide sequence with at least 80% homology to the sequence shown in SEQ ID NO: 57 or a peptide sequence encoded by a nucleotide sequence with at least 80% homology to the sequence shown in SEQ ID NO: 151. In some embodiments, the CD19-specific CAR described herein comprises CD19 specific chimeric antigen receptor with CD8-3× spacer comprising a peptide sequence with at least 80% homology to the sequence shown in SEQ ID NO: 58 or a peptide sequence encoded by a nucleotide sequence with at least 80% homology to the sequence shown in SEQ ID NO: 152. In some embodiments, the CD19-specific CAR described herein comprises CD19 specific chimeric antigen receptor with CD8-3× v2 spacer comprising a peptide sequence with at least 80% homology to the sequence shown in SEQ ID NO: 59 or a peptide sequence encoded by a nucleotide sequence with at least 80% homology to the sequence shown in SEQ ID NO: 153. In some embodiments, the CD19-specific CAR described herein comprises CD19 specific chimeric antigen receptor with CD8-4× spacer comprising a peptide sequence with at least 80% homology to the sequence shown in SEQ ID NO: 60 or a peptide sequence encoded by a nucleotide sequence with at least 80% homology to the sequence shown in SEQ ID NO: 154.

CD33-Specific CARS

CD33/Siglec-3 is a restricted leukocyte antigen expressed specifically in myeloid lineage cells. In some instances, CD33 has also been detected in lymphoid cells.

In some embodiments, the disclosure herein includes a CD33-specific CAR, in which the antigen binding region comprises a F(ab')2, Fab', Fab, Fv, or scFv that binds CD33.

In some embodiments, the antigen binding region recognizes an epitope on CD33 that is also recognized by Lintuzumab (Seattle Genetics), BI 836858 (Boehringer Ingelheim). In some instances, a polypeptide described herein comprises the CD33-specific CAR and further comprises a transmembrane region or transmembrane domain selected from a CD8alpha transmembrane domain (SEQ ID NO: 24 and SEQ ID NO: 130) or a CD3ζ transmembrane domain; one or more costimulatory domains selected from CD27, CD28, 4-1BB (CD137), ICOS, DAP10, DAP12, OX40 (CD134), CD3-zeta or fragment or combination thereof; and a signaling region or signaling domain from CD3ζ. In some cases, the CD33-specific CAR is encompassed by a polypeptide that further comprises a transmembrane domain selected from a CD152 (CTLA-4) transmembrane domain (SEQ ID NO: 25 and SEQ ID NO: 131), a TCRα transmembrane domain (SEQ ID NO: 71 and SEQ ID NO: 165), a TCRβ transmembrane domain (SEQ ID NO: 85 and SEQ ID NO: 179), a TCRγ1 transmembrane domain (SEQ ID NO: 101 and SEQ ID NO: 195) or a TCR transmembrane domain (SEQ ID NO: 106 and SEQ ID NO: 200). In some cases, the CD33-specific CAR is encompassed by a polypeptide that further comprises a signaling domain selected from a DAP10 signaling domain (SEQ ID NO: 29 and SEQ ID NO: 135), or a DAP12 signaling domain (SEQ ID NO: 30 and SEQ ID NO: 136). In some cases, the CD33-specific CAR is encompassed by a polypeptide that further comprises a signaling domain selected from a DAP10 signaling domain (SEQ ID NO: 29 and SEQ ID NO: 135), or a DAP12 signaling domain (SEQ ID NO: 30 and SEQ ID NO: 136). In some instances, the CD33-specific CAR further comprises a stalk region and a stalk extension region as disclosed herein. For example, the CD33-specific CAR can further comprise a spacer wherein the spacer comprises a stalk region comprising a CD8α hinge region, and stalk extension region(s), s'-n, wherein n=0, 1, 2, 3 or 4.

In some embodiments, the CD33-specific CAR described herein comprises an anti-CD33 monoclonal antibody variable light chain comprising a peptide sequence with at least 80% homology to the sequence shown in SEQ ID NO: 61 or a peptide sequence encoded by a nucleotide sequence with at least 80% homology to the sequence shown in SEQ ID NO: 155. In some embodiments, the CD33-specific CAR described herein comprises an anti-CD33 monoclonal antibody variable heavy chain comprising a peptide sequence with at least 80% homology to the sequence shown in SEQ ID NO: 62 or a peptide sequence encoded by a nucleotide sequence with at least 80% homology to the sequence shown in SEQ ID NO: 156. In some embodiments, the CD33-specific CAR described herein comprises an anti-CD33 monoclonal antibody scFv comprising a peptide sequence with at least 80% homology to the sequence shown in SEQ ID NO: 63 or a peptide sequence encoded by a nucleotide sequence with at least 80% homology to the sequence shown in SEQ ID NO: 157. In some embodiments, the CD33-specific CAR described herein comprises CD33 specific chimeric antigen receptor with CD8 1× spacer comprising a peptide sequence with at least 80% homology to the sequence shown in SEQ ID NO: 64 or a peptide sequence encoded by a nucleotide sequence with at least 80% homology to the sequence shown in SEQ ID NO: 158. In some embodiments, the CD33-specific CAR described herein comprises CD33 specific chimeric antigen receptor with CD8 2× spacer comprising a peptide sequence with at least 80% homology to the sequence shown in SEQ ID NO: 65 or a peptide sequence encoded by a nucleotide sequence with at least 80% homology to the sequence shown in SEQ ID NO: 159. In some embodiments, the CD33-specific CAR described herein comprises CD33 specific chimeric antigen receptor with CD8 3× spacer comprising a peptide sequence with at least 80% homology to the sequence shown in SEQ ID NO: 66 or a peptide sequence encoded by a nucleotide sequence with at least 80% homology to the sequence shown in SEQ ID NO: 160. In some embodiments, the CD33-specific CAR described herein comprises CD33 specific chimeric antigen receptor with CD8 3× v2 spacer comprising a peptide sequence with at least 80% homology to the sequence shown in SEQ ID NO: 67 or a peptide sequence encoded by a nucleotide sequence with at least 80% homology to the sequence shown in SEQ ID NO: 161. In some embodiments, the CD33-specific CAR described herein comprises CD33 specific chimeric antigen receptor with CD8 4× spacer comprising a peptide sequence with at least 80% homology to the sequence shown in SEQ ID NO: 68 or a peptide sequence encoded by a nucleotide sequence with at least 80% homology to the sequence shown in SEQ ID NO: 162.

EGFRvIII-Specific CARs

In another embodiment, a CAR described herein is a EGFRvIII specific CAR. "EGFRvIII", "EGFR variant III", "EGFR type III mutant", "EGFR.D2-7" or "de2-7EGFR" is a mutated form of epidermal growth factor receptor (EGFR; ErbB-1; HER1), a transmembrane protein that is a receptor for members of the epidermal growth factor (EGF) family of extracellular protein ligands in human and non-human subjects. EGFRvIII is characterized by a deletion of exons 2-7 of the wild type EGFR gene, which results in an in-frame deletion of 267 amino acids in the extracellular domain of the full length wild type EGFR protein. EGFRvIII also contains a novel glycine residue inserted at the fusion junction compared to wild type EGFR. The truncated receptor EGFRvIII is unable to bind any known EGFR ligand; however, it shows constitutive tyrosine kinase activity. This constitutive activation is important to its pro-oncogenic effect. A kinase-deficient EGFRvIII is unable to confer a similar oncogenic advantage. EGFRvIII is highly expressed in glioblastoma (GBM) and can be detected in some other solid tumor types but not in normal tissues.

In some embodiments, the antigen binding moiety of a CAR described herein is specific to EGFRvIII (EGFRvIII CAR). The EGFRvIII-specific CAR, when expressed on the cell surface, redirects the specificity of T cells to human EGFRvIII. In embodiments, the antigen binding domain comprises a single chain antibody fragment (scFv) comprising a variable domain light chain (VL) and variable domain heavy chain (VH) of a target antigen specific monoclonal anti-EGFRvIII antibody joined by a flexible linker, such as a glycine-serine linker or a Whitlow linker. In embodiments, the scFv is clone 139 (SEQ ID NO: 221 and 222). In some embodiments, the scFv is anti-EGFRvIII scFv clone MR1 (SEQ ID NO 223; SEQ ID NO 224), anti-EGFRvIII scFv clone MR1-1 (SEQ ID NO 225; SEQ ID NO 226), anti-EGFRvIII scFv clone huMR1-1 (SEQ ID NO 227; SEQ ID NO 228), anti-EGFRvIII scFv clone huMR1-2 (SEQ ID NO 229; SEQ ID NO 230). In some embodiments, the antigen binding moiety may comprise VH and VL that are directionally linked, for example, from N to C terminus, VH-linker-VL or VL-linker-VH.

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 204 (anti-EGFRvIII clone 139 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 202 (anti-EGFRvIII clone 139 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 208 (anti-EGFRvIII clone MR1 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 206 (anti-EGFRvIII clone MR1 VH). In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 212 (anti-EGFRvIII clone MR1-1 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 210 (anti-EGFRvIII clone MR1-1 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 216 (anti-EGFRvIII clone humMR1-1 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 214 (anti-EGFRvIII clone humMR1-1 VH). In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 220 (anti-EGFRvIII clone humMR1-2 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 218 (anti-EGFRvIII clone humMR1-2 VH).

In some embodiments, the EGFRvIII-specific CAR described herein comprises an anti-EGFRvIII monoclonal antibody scFv (clone 139) comprising a peptide sequence with at least 80% homology to the sequence shown in SEQ ID NO: 222 or a peptide sequence encoded by a nucleotide sequence with at least 80% homology to the sequence shown in SEQ ID NO: 221. In some embodiments, the EGFRvIII-specific CAR described herein comprises an anti-EGFRvIII monoclonal antibody scFv (MR1) comprising a peptide sequence with at least 80% homology to the sequence shown in SEQ ID NO: 224 or a peptide sequence encoded by a nucleotide sequence with at least 80% homology to the sequence shown in SEQ ID NO: 223. In some embodiments, the EGFRvIII-specific CAR described herein comprises an anti-EGFRvIII monoclonal antibody scFv (MR1-1) comprising a peptide sequence with at least 80% homology to the sequence shown in SEQ ID NO: 226 or a peptide sequence encoded by a nucleotide sequence with at least 80% homology to the sequence shown in SEQ ID NO: 225. In some embodiments, the EGFRvIII-specific CAR described herein comprises an anti-EGFRvIII monoclonal antibody scFv (huMR1-1) comprising a peptide sequence with at least 80% homology to the sequence shown in SEQ ID NO: 228 or a peptide sequence encoded by a nucleotide sequence with at least 80% homology to the sequence shown in SEQ ID NO: 227. In some embodiments, the EGFRvIII-specific CAR described herein comprises an anti-EGFRvIII monoclonal antibody scFv (huMR1-2) comprising a peptide sequence with at least 80% homology to the sequence shown in SEQ ID NO: 230 or a peptide sequence encoded by a nucleotide sequence with at least 80% homology to the sequence shown in SEQ ID NO: 229.

In some instances, a polypeptide described herein comprises the EGFRvIII-specific CAR and further comprises a transmembrane region or transmembrane domain selected from a CD8alpha transmembrane domain (SEQ ID NO: 24 and SEQ ID NO: 130) or a CD3ζ transmembrane domain; one or more costimulatory domains selected from CD27, CD28, 4-1BB (CD137), ICOS, DAP10, DAP12, OX40 (CD134), CD3ζ or fragment or combination thereof; and a signaling region or signaling domain from CD3ζ. In some cases, the EGFRvII-specific CAR is encompassed by a polypeptide that further comprises a transmembrane domain selected from a CD152 (CTLA-4) transmembrane domain (SEQ ID NO: 25 and SEQ ID NO: 131), a TCRα transmembrane domain (SEQ ID NO: 71 and SEQ ID NO: 165), a TCRβ transmembrane domain (SEQ ID NO: 85 and SEQ ID NO: 179), a TCRγ1 transmembrane domain (SEQ ID NO: 101 and SEQ ID NO: 195) or a TCR transmembrane domain (SEQ ID NO: 106 and SEQ ID NO: 200). In some cases, the EGFRvIII-specific CAR is encompassed by a polypeptide that further comprises a signaling domain selected from a DAP10 signaling domain (SEQ ID NO: 29 and SEQ ID NO: 135), or a DAP12 signaling domain (SEQ ID NO: 30 and SEQ ID NO: 136). In some cases, the EGFRvIII-specific CAR is encompassed by a polypeptide that further comprises a signaling domain selected from a DAP10 signaling domain (SEQ ID NO: 29 and SEQ ID NO: 135), or a DAP12 signaling domain (SEQ ID NO: 30 and SEQ ID NO: 136). In some instances, the EGFRvIII-specific CAR further comprises a stalk region and a stalk extension region as disclosed herein. For example, the EGFRvIII-specific CAR can further comprise a spacer wherein the spacer comprises a stalk region comprising a CD8α hinge region, and stalk extension region(s), s'-n, wherein n=0, 1, 2, 3, 4, 5, 6, 7, 8, 9, 10, 11, 12, 13, 14, 15, 16, 17, 18, 19, or 20, wherein each stalk extension region being homologous to a CD8α hinge region except for lacking a dimerization site.

In some embodiments, the EGFRvIII-specific CAR described herein comprises EGFRvIII-specific chimeric antigen receptor with CD8-1× spacer (clone 139scFv-CD8α-4-1BB-CD3ζ) comprising a peptide sequence with at least 80% homology to the sequence shown in SEQ ID NO: 232 or a peptide sequence encoded by a nucleotide sequence with at least 80% homology to the sequence shown in SEQ ID NO: 231. In some embodiments, the EGFRvIII-specific CAR described herein comprises EGFRvIII-specific chimeric antigen receptor with CD8-1× spacer (clone MR1scFv-CD8α-4-1BB-CD3ζ) comprising a peptide sequence with at least 80% homology to the sequence shown in SEQ ID NO: 234 or a peptide sequence encoded by a nucleotide sequence with at least 80% homology to the sequence shown in SEQ ID NO: 233.

In some embodiments, the EGFRvIII-specific CAR described herein comprises EGFRvIII-specific chimeric antigen receptor with CD8-1× spacer (clone MR1-1scFv-CD8α-4-1BB-CD3ζ) comprising a peptide sequence with at least 80% homology to the sequence shown in SEQ ID NO: 236 or a peptide sequence encoded by a nucleotide sequence with at least 80% homology to the sequence shown in SEQ ID NO: 235. In some embodiments, the EGFRvIII-specific CAR described herein comprises EGFRvIII specific chimeric antigen receptor with CD8-2× spacer comprising a peptide sequence with at least 80% homology to the sequence shown in SEQ ID NO: 242 or a peptide sequence encoded by a nucleotide sequence with at least 80% homology to the sequence shown in SEQ ID NO: 241. In some embodiments, the EGFRvIII-specific CAR described herein comprises EGFRvIII specific chimeric antigen receptor with CD8-3× spacer comprising a peptide sequence with at least 80% homology to the sequence shown in SEQ ID NO: 244 or a peptide sequence encoded by a nucleotide sequence with at least 80% homology to the sequence shown in SEQ ID NO: 243. In some embodiments, the EGFRvIII-specific CAR described herein comprises EGFRvIII specific chimeric antigen receptor with CD8-4× spacer comprising a peptide sequence with at least 80% homology to the sequence shown in SEQ ID NO: 246 or a peptide sequence encoded by a nucleotide sequence with at least 80% homology to the sequence shown in SEQ ID NO: 245.

In some embodiments, the EGFRvIII-specific CAR described herein comprises EGFRvIII-specific chimeric antigen receptor with CD8-1× spacer (huMR1-1-CD8α-4-1BB-CD3) comprising a peptide sequence with at least 80% homology to the sequence shown in SEQ ID NO: 238 or a peptide sequence encoded by a nucleotide sequence with at least 80% homology to the sequence shown in SEQ ID NO: 237. In some embodiments, the EGFRvIII-specific CAR described herein comprises EGFRvIII-specific chimeric antigen receptor with CD8-3× spacer comprising a peptide sequence with at least 80% homology to the sequence shown in SEQ ID NO: 248 or a peptide sequence encoded by a nucleotide sequence with at least 80% homology to the sequence shown in SEQ ID NO: 247. In some embodiments, the EGFRvIII-specific CAR described herein comprises EGFRvIII-specific chimeric antigen receptor with CD8-4× spacer comprising a peptide sequence with at least 80% homology to the sequence shown in SEQ ID NO: 250 or a peptide sequence encoded by a nucleotide sequence with at least 80% homology to the sequence shown in SEQ ID NO: 249.

In some embodiments, the EGFRvIII-specific CAR described herein comprises EGFRvIII-specific chimeric antigen receptor with CD8-1× spacer (huMR1-2-CD8α-4-1BB-CD3ζ) comprising a peptide sequence with at least 80% homology to the sequence shown in SEQ ID NO: 240 or a peptide sequence encoded by a nucleotide sequence with at least 80% homology to the sequence shown in SEQ ID NO: 239. In some embodiments, the EGFRvIII-specific CAR described herein comprises EGFRvIII-specific chimeric antigen receptor with CD8-3× spacer comprising a peptide sequence with at least 80% homology to the sequence shown in SEQ ID NO: 252 or a peptide sequence encoded by a nucleotide sequence with at least 80% homology to the sequence shown in SEQ ID NO: 251. In some embodiments, the EGFRvIII-specific CAR described herein comprises EGFRvIII-specific chimeric antigen receptor with CD8-4× spacer comprising a peptide sequence with at least 80% homology to the sequence shown in SEQ ID NO: 254 or a peptide sequence encoded by a nucleotide sequence with at least 80% homology to the sequence shown in SEQ ID NO: 253.

Modified Effector Cells

In some embodiments, modified effector cells expressing polypeptides are described herein, including antigen binding polypeptides such as CARs described herein. In some embodiments, the modified effector cells are modified immune cells that comprise T cells and/or natural killer cells. T cells or T lymphocytes are a subtype of white blood cells that are involved in cell-mediated immunity. Exemplary T cells include T helper cells, cytotoxic T cells, TH17 cells, stem memory T cells ($T_{SCM}$), naïve T cells, memory T cells, effector T cells, regulatory T cells, or natural killer T cells.

T helper cells (TH cells) assist other white blood cells in immunologic processes, including maturation of B cells into plasma cells and memory B cells, and activation of cytotoxic T cells and macrophages. In some instances, TH cells are known as CD4+ T cells due to expression of the CD4 glycoprotein on the cell surfaces. Helper T cells become activated when they are presented with peptide antigens by MEW class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate different types of immune responses. Signaling from the APC directs T cells into particular subtypes.

Cytotoxic T cells (TC cells or CTLs) destroy virus-infected cells and tumor cells, and are also implicated in transplant rejection. These cells are also known as CD8+ T cells since they express the CD8 glycoprotein at their surfaces. These cells recognize their targets by binding to antigen associated with MEW class I molecules, which are present on the surface of all nucleated cells. Through IL-10, adenosine, and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise subtypes: stem memory T cells ($T_{SCM}$), central memory T cells ($T_{CM}$ cells) and two types of effector memory T cells ($T_{EM}$ cells and $T_{EMRA}$ cells). Memory cells may be either CD4+ or CD8+. Memory T cells may express the cell surface proteins CD45RO, CD45RA and/or CCR7.

Regulatory T cells (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

Natural killer T cells (NKT cells) bridge the adaptive immune system with the innate immune system. Unlike conventional T cells that recognize peptide antigens presented by major histocompatibility complex (MEW) molecules, NKT cells recognize glycolipid antigen presented by a molecule called CD1d. Once activated, these cells can perform functions ascribed to both Th and Tc cells (i.e., cytokine production and release of cytolytic/cell killing molecules). They are also able to recognize and eliminate some tumor cells and cells infected with herpes viruses.

Natural killer (NK) cells are a type of cytotoxic lymphocyte of the innate immune system. In some instances, NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

Engineered T-Cell Receptor (TCR)

In some embodiments, a polypeptide described herein comprises an engineered T-cell receptor. The T cell receptor (TCR) is composed of two chains (αβ or γδ) that pair on the surface of the T cell to form a heterodimeric receptor. In some instances, the αβ TCR is expressed on most T cells in the body and is known to be involved in the recognition of specific MHC-restricted antigens. Each α and β chain are composed of two domains: a constant domain (C) which anchors the protein to the cell membrane and is associated with invariant subunits of the CD3 signaling apparatus; and a variable domain (V) that confers antigen recognition through six loops, referred to as complementarity determining regions (CDRs). In some instances, each of the V domains comprises three CDRs; e.g., CDR1, CDR2 and CDR3 with CDR3 as the hypervariable region. These CDRs interact with a complex formed between an antigenic peptide bound to a protein encoded by the major histocompatibility complex (pepMHC) (e.g., HLA-A, HLA-B, HLA-C, HLA-DPA1, HLA-DPB1, HLA-DQA1, HLA-DQB1, HLA-DRA, or HLA-DRB1 complex). In some instances, the constant domain further comprises a joining region that connects the constant domain to the variable domain. In some cases, the beta chain further comprises a short diversity region which makes up part of the joining region.

In some cases, such TCR are reactive to specific tumor antigen, e.g. NY-ESO, Titin, MART-1, HPV, HBV, MAGE-A4, MAGE-A10, MAGE A3/A6, gp100, MAGE-A1 or PRAME In other cases, such TCR are reactive to specific neoantigens expressed within a patient's tumor (i.e. patient-specific, somatic, non-synonymous mutations expressed by tumors). In some cases, engineered TCRs can be affinity-enhanced.

In some embodiments, a TCR is described using the International Immunogenetics (IMGT) TCR nomenclature, and links to the IMGT public database of TCR sequences. For example, there can be several types of alpha chain variable (Vα) regions and several types of beta chain variable (Vβ) regions distinguished by their framework, CDR1, CDR2, and CDR3 sequences. As such, a Vα type can be referred to in IMGT nomenclature by a unique TRAV number. For example, "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. Similarly, "TRBV5-1" defines a TCR Vβ region having unique framework and CDR1 and CDR2 sequences, but with only a partly defined CDR3 sequence.

In some cases, the beta chain diversity region is referred to in IMGT nomenclature by the abbreviation TRBD.

In some instances, the unique sequences defined by the IMGT nomenclature are widely known and accessible to those working in the TCR field. For example, they can be found in the IMGT public database and in "T cell Receptor Factsbook," (2001) LeFranc and LeFranc, Academic Press, ISBN 0-12-441352-8.

In some embodiments, an αβ heterodimeric TCR is, for example, transfected as full length chains having both cytoplasmic and transmembrane domains. In some cases, the TCRs contain an introduced disulfide bond between residues of the respective constant domains, as described, for example, in WO 2006/000830.

In some instances, TCRs described herein are in single chain format, for example see WO 2004/033685. Single chain formats include αβ TCR polypeptides of the Vα-L-Vβ, Vβ-L-Vα, Vα-Cα-L-Vβ, Vα-L-Vβ-Cβ, Vα-Cα-L-Vβ-Cβ types, wherein Vα and Vβ are TCR α and β variable regions respectively, Cα and Cβ are TCR α and β constant regions respectively, and L is a linker sequence. In certain embodiments single chain TCRs of the invention may have an introduced disulfide bond between residues of the respective constant domains, as described in WO 2004/033685.

The TCR described herein may be associated with a detectable label, a therapeutic agent or a PK modifying moiety.

Exemplary detectable labels for diagnostic purposes include, but are not limited to, fluorescent labels, radiolabels, enzymes, nucleic acid probes and contrast reagents.

In some cases, each chain of TCR disclosed herein, for example αβ or γδ, comprises a modified spacer region connecting constant region of a TCR chain to transmembrane region.

In some cases, a spacer region of each chain of TCR disclosed herein comprises 1) a stalk region and 2) stalk extension region(s) (s'-n, wherein n=0, 1, 2, 3 or more) adjacent to said stalk region. Illustrative embodiments are described in FIG. 1A and FIG. 1B. In some embodiments, each chain of TCR disclosed herein incorporates a spacer that comprises a stalk region (s) and a stalk extension region (s'-n, wherein n=0, 1, 2, 3, 4, 5, 6, 7, 8, 9, 10, 11, 12, 13, 14, 15, 16, 17, 18, 19 or 20).

As described herein, a spacer region can comprise a stalk region and stalk extension region(s). In some instances, the stalk region comprises the extracellular hinge region from TCRα or TCRβ chain or the stalk region comprises a sequence with at least 80% homology to the extracellular hinge region from TCRα or TCRβ chain. For example, the stalk region can comprise a sequence with at least 80%, 85%, 90%, 95%, or greater than 95% homology to the hinge region of the extracellular region of TCRα or TCRβ chain. In alternative instances, the stalk region comprises any portion of extracellular region of TCRα or TCRβ constant region with at least 80% homology to the extracellular region of TCRα or TCRβ constant region respectively. For example, the stalk region can comprise a sequence with at least 80%, 85%, 90%, 95%, or greater than 95% homology to the any portion of extracellular region of TCRα or TCRβ constant region.

TCR chain heterodimers are formed by inter-chain disulfide bonds in extracellular hinge region of α and β chains. In some embodiments, the stalk region comprises a dimerization site. A dimerization site can comprise a disulfide bond formation site. A dimerization site can comprise cysteine residue(s). A stalk region can be capable of forming a disulfide bond. Such a disulfide bond can be formed at a disulfide bond forming site or a dimerization site. In some examples, the dimerization occurs between α and β chains of TCR.

In some embodiments, a stalk extension region is used. In some embodiments, a stalk extension region is used to link the stalk region to the transmembrane region TCR α and β chains. In additional embodiments, a stalk extension region is used to link the stalk region to constant region of TCR α and β chains. In another embodiment, the stalk region and the stalk extension region(s) can be connected via a linker.

In some instances, the stalk extension domain comprises a sequence that is partially homologous to the stalk region. In some instances, each of the stalk extension region comprises a sequence that is homologous to the stalk region, except that the stalk extension region lacks the dimerization site of the stalk region. In some cases, each of the stalk extension region comprises a sequence identical to the stalk region. In other cases, each of the stalk extension regions comprise a sequence identical to the stalk region with at least one amino acid residue substitution relative to the stalk region. In some cases, each of the stalk extension region is not capable of forming a disulfide bond or is not capable of dimerization with a homologous stalk extension region.

In other embodiments, one stalk extension region can be connected to another stalk extension region via a linker. Examples of such linkers can include glycine-serine rich linkers.

In some embodiments, addition of stalk extension region(s) prevents mispairing of transgenic TCR α and β chains with native TCR α and β chains expressed by T cells that are genetically modified.

In some embodiments, the TCR described herein comprises TCRα chain constant region comprising a peptide sequence with at least 80% homology to the sequence shown in SEQ ID NO: 69 or a peptide sequence encoded by a nucleotide sequence with at least 80% homology to the sequence shown in SEQ ID NO: 163. In some embodiments, the TCR described herein comprises TCRβ1 chain constant region comprising a peptide sequence with at least 80% homology to the sequence shown in SEQ ID NO: 83 or a peptide sequence encoded by a nucleotide sequence with at least 80% homology to the sequence shown in SEQ ID NO: 177. In some embodiments, the TCR described herein comprises TCRβ2 chain constant region comprising a peptide sequence with at least 80% homology to the sequence shown in SEQ ID NO: 97 or a peptide sequence encoded by a nucleotide sequence with at least 80% homology to the sequence shown in SEQ ID NO: 191. In some embodiments, the TCR described herein comprises TCRγ1 chain constant region comprising a peptide sequence with at least 80% homology to the sequence shown in SEQ ID NO: 99 or a peptide sequence encoded by a nucleotide sequence with at least 80% homology to the sequence shown in SEQ ID NO: 193. In some embodiments, the TCR described herein comprises TCRγ2 chain constant region comprising a peptide sequence with at least 80% homology to the sequence shown in SEQ ID NO: 102 or a peptide sequence encoded by a nucleotide sequence with at least 80% homology to the sequence shown in SEQ ID NO: 196. In some embodiments, the TCR described herein comprises TCR chain constant region comprising a peptide sequence with at least 80% homology to the sequence shown in SEQ ID NO: 104 or a peptide sequence encoded by a nucleotide sequence with at least 80% homology to the sequence shown in SEQ ID NO: 198.

In some aspects of the embodiments disclosed herein, a stalk region or a stalk extension region of a polypeptide described herein comprises a peptide sequence with at least about 10%, 11%, 12%, 13%, 14%, 15%, 16%, 17%, 18%, 19%, 20%, 21%, 22%, 23%, 24%, 25%, 26%, 25%, 26%, 27%, 28%, 29%, 30%, 40%, 50%, 60%, 65%, 70%, 75%, 80%, 85%, 90%, 95%, 99% or greater identity to the extracellular region of human TCRα chain constant region sequence shown in SEQ ID NO: 70. In some cases, a stalk region or a stalk extension region of a polypeptide described herein comprises a peptide sequence encoded by a nucleotide sequence with at least about 10%, 11%, 12%, 13%, 14%, 15%, 16%, 17%, 18%, 19%, 20%, 21%, 22%, 23%, 24%, 25%, 26%, 25%, 26%, 27%, 28%, 29%, 30%, 40%, 50%, 60%, 65%, 70%, 75%, 80%, 85%, 90%, 95%, 99% or greater identity to the human TCRα chain constant region nucleotide sequence shown in SEQ ID NO: 164. In some cases, a stalk extension region comprises a sequence with at least 65%, 70%, 75%, 80%, 85%, 90%, 95%, or greater identity to the sequence shown in SEQ ID NO: 72 or SEQ ID NO: 73 or a peptide sequence encoded by a nucleotide sequence with at least 65%, 70%, 75%, 80%, 85%, 90%, 95%, 99% or greater identity to the sequence shown in SEQ ID NO: 166 or SEQ ID NO: 167. In some examples, a stalk region and stalk extension region can together comprise a peptide sequence with at least 65%, 70%, 75%, 80%, 85%, 90%, 95% or greater identity to the sequence shown in SEQ ID NO: 77, SEQ ID NO: 78 or SEQ ID NO: 79, or a peptide sequence encoded by a nucleotide sequence with at least 65%, 70%, 75%, 80%, 85%, 90%, 95%, 99% or greater identity to the sequence shown in SEQ ID NO: 171, SEQ ID NO: 172 or SEQ ID NO: 173. In some examples, a stalk region and stalk extension region can together comprise a peptide sequence with at least 65%, 70%, 75%, 80%, 85%, 90%, 95% or greater identity to the sequence shown in SEQ ID NO: 80, SEQ ID NO: 81 or SEQ ID NO: 82, or a peptide sequence encoded by a nucleotide sequence with at least 65%, 70%, 75%, 80%, 85%, 90%, 95%, 99% or greater identity to the sequence shown in SEQ ID NO: 174, SEQ ID NO: 175 or SEQ ID NO: 176.

In some embodiment, the stalk region and the stalk extension region(s) can be connected via a linker, such as whitlow linker (SEQ ID NO: 8 and SEQ ID NO: 114), GSG linker (SEQ ID NO: 9 and SEQ ID NO: 115), SGSG linker (SEQ ID NO: 10) or (G4S)3 linker (SEQ ID NO: 11 and SEQ ID NO: 117). In one embodiment, the TCRα hinge domain connected to (G4S)3 linker (SEQ ID NO: 11) can comprise a peptide sequence shown in SEQ ID NO: 74 or a peptide sequence encoded by a nucleotide sequence shown in SEQ ID NO: 168. In one embodiment, the TCRβ hinge domain connected to (G4S)3 linker (SEQ ID NO: 11) can comprise a peptide sequence shown in SEQ ID NO: 75 or a peptide sequence encoded by a nucleotide sequence shown in SEQ ID NO: 169. In yet another embodiment, the TCRβ hinge domain connected to whitlow linker can comprise a peptide sequence shown in SEQ ID NO: 76 or a peptide sequence encoded by a nucleotide sequence shown in SEQ ID NO: 170.

In some aspects of the embodiments disclosed herein, the extracellular region of human TCRα chain constant region described herein comprises a peptide sequence with at least 80% or greater identity to a peptide sequence shown in SEQ ID NO: 70. In some cases, the extracellular region of human TCRβ1 chain constant region described herein comprises a peptide sequence encoded by a nucleotide sequence with at least about 80% or greater identity to the human TCRβ1 chain constant region nucleotide sequence shown in SEQ ID NO: 164. In some aspects of the embodiments disclosed herein, the extracellular region of human TCRβ1 chain constant region described herein comprises a peptide sequence with at least 80% or greater identity to a peptide sequence shown in SEQ ID NO: 84. In some cases, the extracellular region of human TCRβ1 chain constant region described herein comprises a peptide sequence encoded by a nucleotide sequence with at least about 80% or greater identity to the human TCRβ1 chain constant region nucleotide sequence shown in SEQ ID NO: 178. In some aspects of the embodiments disclosed herein, the extracellular region of human TCRβ2 chain constant region described herein comprises a peptide sequence with at least 80% or greater identity to a peptide sequence shown in SEQ ID NO: 98. In some cases, the extracellular region of human TCRβ2 chain constant region described herein comprises a peptide sequence encoded by a nucleotide sequence with at least about 80% or greater identity to the human TCRβ1 chain constant region nucleotide sequence shown in SEQ ID NO: 192. In some aspects of the embodiments disclosed herein, the extracellular region of human TCRγ1 chain constant region described herein comprises a peptide sequence with at least 80% or greater identity to a peptide sequence shown in SEQ ID NO: 100. In some cases, the extracellular region of human TCR γ1 chain constant region described herein comprises a peptide sequence encoded by a nucleotide sequence with at least about 80% or greater identity to the human TCRβ1 chain constant region nucleotide sequence shown in SEQ ID NO: 194. In some aspects of the embodiments disclosed herein, the extracellular region of human TCRγ2 chain constant region described herein comprises a peptide sequence with at least 80% or greater identity to a peptide sequence shown in SEQ ID NO: 103. In some cases, the extracellular region of human TCR γ2 chain constant region described herein comprises a peptide sequence encoded by a nucleotide sequence with at least about 80% or greater identity to the human TCRβ1 chain constant region nucleotide sequence shown in SEQ ID NO: 197. In some aspects of the embodiments disclosed herein, the extracellular region of human TCRδ chain constant region described herein comprises a peptide sequence with at least 80% or greater identity to a peptide sequence shown in SEQ ID NO: 105. In some cases, the extracellular region of human TCRδ chain constant region described herein comprises a peptide sequence encoded by a nucleotide sequence with at least about 80% or greater identity to the human TCRβ1 chain constant region nucleotide sequence shown in SEQ ID NO: 199.

Modified Effector Cell Doses

In some embodiments, an amount of modified effector cells is administered to a subject in need thereof and the amount is determined based on the efficacy and the potential of inducing a cytokine-associated toxicity. In some cases, an amount of modified immune effector cells comprises about $10^2$ to about $10^9$ modified immune effector cells/kg. In some cases, an amount of modified immune effector cells comprises about $10^3$ to about $10^9$ modified immune effector cells/kg. In some cases, an amount of modified effector cells comprises about $10^4$ to about $10^9$ modified effector cells/kg. In some cases, an amount of modified effector cells comprises about $10^5$ to about $10^9$ modified effector cells/kg. In some cases, an amount of modified effector cells comprises about $10^5$ to about $10^8$ modified effector cells/kg. In some cases, an amount of modified effector cells comprises about $10^5$ to about $10^7$ modified effector cells/kg. In some cases, an amount of modified effector cells comprises about $10^6$ to about $10^9$ modified effector cells/kg. In some cases, an amount of modified effector cells comprises about $10^6$ to about $10^8$ modified effector cells/kg. In some cases, an amount of modified effector cells comprises about $10^7$ to about $10^9$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises about $10^7$ to about $10^8$ modified effector cells/kg. In some cases, an amount of modified effector cells comprises about $10^8$ to about $10^9$ modified effector cells/kg. In some instances, an amount of modified effector cells comprises about $10^9$ modified effector cells/kg. In some instances, an amount of modified effector cells comprises about $10^8$ modified effector cells/kg. In some instances, an amount of modified effector cells comprises about $10^7$ modified effector cells/kg. In some instances, an amount of modified effector cells comprises about $10^6$ modified effector cells/kg. In some instances, an amount of modified effector cells comprises about $10^5$ modified effector cells/kg. In some instances, an amount of modified effector cells comprises about $10^4$ modified effector cells/kg.

In some embodiments, the modified effector cells expressing a polypeptide described herein, are modified T cells. In some instances, the modified T cells are CAR-T cells. In some cases, an amount of CAR-T cells comprises about $10^2$ to about $10^9$ CAR-T cells/kg. In some cases, an amount of CAR-T cells comprises about $10^3$ to about $10^9$ CAR-T cells/kg. In some cases, an amount of CAR-T cells comprises about $10^4$ to about $10^9$ CAR-T cells/kg. In some cases, an amount of CAR-T cells comprises about $10^5$ to about $10^8$ CAR-T cells/kg. In some cases, an amount of CAR-T cells comprises about $10^5$ to about $10^7$ CAR-T cells/kg. In some cases, an amount of CAR-T cells comprises about $10^6$ to about $10^9$ CAR-T cells/kg. In some cases, an amount of CAR-T cells comprises about $10^6$ to about $10^8$ CAR-T cells/kg. In some cases, an amount of CAR-T cells comprises about $10^7$ to about $10^9$ CAR-T cells/kg. In some cases, an amount of CAR-T cells comprises about $10^5$ to about $10^6$ CAR-T cells/kg. In some cases, an amount of CAR-T cells comprises about $10^6$ to about $10^7$ CAR-T cells/kg. In some cases, an amount of CAR-T cells comprises about $10^7$ to about $10^8$ CAR-T cells/kg. In some cases, an amount of CAR-T cells comprises about $10^8$ to about $10^9$ CAR-T cells/kg. In some instances, an amount of CAR-T cells comprises about $10^9$ CAR-T cells/kg. In some instances, an amount of CAR-T cells comprises about $10^8$ CAR-T cells/kg. In some instances, an amount of CAR-T cells comprises about $10^7$ CAR-T cells/kg. In some instances, an amount of CAR-T cells comprises about $10^6$ CAR-T cells/kg. In some instances, an amount of CAR-T cells comprises about $10^5$ CAR-T cells/kg. In some instances, an amount of CAR-T cells comprises about $10^4$ CAR-T cells/kg. In some instances, an amount of CAR-T cells comprises about $10^3$ CAR-T cells/kg. In some instances, an amount of CAR-T cells comprises about $10^2$ CAR-T cells/kg.

In some embodiments, the CAR-T cells are CD19-specific CAR-T cells. In some cases, an amount of CD19-specific CAR-T cells comprises about $10^2$ to about $10^9$ CAR-T cells/kg. In some cases, an amount of CD19-specific CAR-T cells comprises about $10^3$ to about $10^9$ CAR-T cells/kg. In some cases, an amount of CD19-specific CAR-T cells comprises about $10^4$ to about $10^9$ CAR-T cells/kg. In some cases, an amount of CD19-specific CAR-T cells comprises about $10^5$ to about $10^8$ CAR-T cells/kg. In some cases, an amount of CD19-specific CAR-T cells comprises about $10^5$ to about $10^7$ CAR-T cells/kg. In some cases, an amount of CD19-specific CAR-T cells comprises about $10^6$ to about $10^9$ CAR-T cells/kg. In some cases, an amount of CD19-specific CAR-T cells comprises about $10^6$ to about $10^8$ CAR-T cells/kg. In some cases, an amount of CD19-specific CAR-T cells comprises about $10^7$ to about $10^9$ CAR-T cells/kg. In some cases, an amount of CD19-specific CAR-T cells comprises about $10^5$ to about $10^6$ CAR-T cells/kg. In some cases, an amount of CD19-specific CAR-T cells comprises about $10^6$ to about $10^7$ CAR-T cells/kg. In some cases, an amount of CD19-specific CAR-T cells comprises about $10^7$ to about $10^8$ CAR-T cells/kg. In some cases, an amount of CD19-specific CAR-T cells comprises about $10^8$ to about $10^9$ CAR-T cells/kg. In some instances, an amount of CD19-specific CAR-T cells comprises about $10^9$ CAR-T cells/kg. In some instances, an amount of CD19-specific CAR-T cells comprises about $10^8$ CAR-T cells/kg. In some instances, an amount of CD19-specific CAR-T cells comprises about $10^7$ CAR-T cells/kg. In some instances, an amount of CD19-specific CAR-T cells comprises about $10^6$ CAR-T cells/kg. In some instances, an amount of CD19-specific CAR-T cells comprises about $10^5$ CAR-T cells/kg. In some instances, an amount of CD19-specific CAR-T cells comprises about $10^4$ CAR-T cells/kg. In some instances, an amount of CD19-specific CAR-T cells comprises about $10^3$ CAR-T cells/kg. In some instances, an amount of CD19-specific CAR-T cells comprises about $10^2$ CAR-T cells/kg.

In some embodiments, a polypeptide described herein is expressed in modified T cells which are engineered TCR T-cells. In some cases, an amount of engineered TCR T-cells comprises about $10^2$ to about $10^9$ TCR cells/kg. In some cases, an amount of engineered TCR T-cells comprises about $10^3$ to about $10^9$ TCR cells/kg. In some cases, an amount of engineered TCR T-cells comprises about $10^4$ to about $10^9$ TCR cells/kg. In some cases, an amount of engineered TCR T-cells comprises about $10^5$ to about $10^9$ TCR cells/kg. In some cases, an amount of engineered TCR cells comprises about $10^5$ to about $10^8$ TCR cells/kg. In some cases, an amount of engineered TCR cells comprises about $10^5$ to about $10^7$ TCR cells/kg. In some cases, an amount of engineered TCR cells comprises about $10^6$ to about $10^9$ TCR cells/kg. In some cases, an amount of engineered TCR cells comprises about $10^6$ to about $10^8$ TCR cells/kg. In some cases, an amount of engineered TCR cells comprises about $10^7$ to about $10^9$ TCR cells/kg. In some cases, an amount of engineered TCR cells comprises about $10^5$ to about $10^6$ TCR cells/kg. In some cases, an amount of engineered TCR cells comprises about $10^6$ to about $10^7$ TCR cells/kg. In some cases, an amount of engineered TCR cells comprises about $10^7$ to about $10^8$ TCR cells/kg. In some cases, an amount of engineered TCR cells comprises about $10^8$ to about $10^9$ TCR cells/kg. In some instances, an amount of engineered TCR cells comprises about $10^9$ TCR cells/kg. In some instances, an amount of engineered TCR cells comprises about $10^8$ TCR cells/kg. In some instances, an amount of engineered TCR cells comprises about $10^7$ TCR cells/kg. In some instances, an amount of engineered TCR cells comprises about $10^6$ TCR cells/kg. In some instances, an amount of engineered TCR cells comprises about $10^5$ TCR cells/kg. In some instances, an amount of engineered TCR cells comprises about $10^4$ TCR cells/kg. In some instances, an amount of engineered TCR cells comprises about $10^3$ TCR cells/kg. In some instances, an amount of engineered TCR cells comprises about $10^2$ TCR cells/kg.

Indications

In some embodiments, disclosed herein are methods of administering a modified effector cell comprising a polypeptide described herein to a subject having a disorder, for instance a cancer. In some cases, the cancer is a cancer associated with an expression of CD19, CD20, CD33, CD44, BCMA, CD123, EGFRvIII, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, CD22, EGFR, Folate receptor α, Mucins such as MUC-1 or MUC-16, MAGE-A1, h5T4, PSMA, CSPG4, TAG-72 or VEGF-R2.

In some embodiments, disclosed herein are methods of administering a polynucleotide, polypeptide or a modified effector cell encoding a polynucleotide described herein, to a subject having a cancer associated with an overexpression of CD19. In some embodiments, disclosed herein are methods of administering a modified effector cell to a subject having a cancer associated with an overexpression of CD33. In some embodiments, disclosed herein are methods of administering a modified effector cell to a subject having a cancer associated with an overexpression of CD44, CD19, BCMA, CD123, EGFRvIII, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, CD22, EGFR, Mucins such as MUC-1 or MUC-16, MAGE-A1, h5T4, PSMA, TAG-72 or VEGF-R2. In some cases, the cancer is a metastatic cancer. In other cases, the cancer is a relapsed or refractory cancer.

In some cases, a cancer is a solid tumor or a hematologic malignancy. In some instances, the cancer is a solid tumor. In other instances, the cancer is a hematologic malignancy. In some cases, the cancer is a metastatic cancer. In some cases, the cancer is a relapsed or refractory cancer.

In some instances, the cancer is a solid tumor. Exemplary solid tumors include, but are not limited to, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer.

In some instances, the cancer is a hematologic malignancy. In some cases, a hematologic malignancy comprises a lymphoma, a leukemia, a myeloma, or a B-cell malignancy. In some cases, a hematologic malignancy comprises a lymphoma, a leukemia or a myeloma. In some instances, exemplary hematologic malignancies include chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the hematologic malignancy comprises a myeloid leukemia. In some embodiments, the hematologic malignancy comprises acute myeloid leukemia (AML) or chronic myeloid leukemia (CML).

In some instances, disclosed herein are methods of administering to a subject having a hematologic malignancy selected from chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis a modified effector cell described herein. In some instances, disclosed herein are methods of administering to a subject having a hematologic malignancy selected from AML or CML a modified effector cell to the subject.

Viral Based Delivery Systems

Certain embodiments disclosed herein also provide delivery systems, such as viral-based systems, in which a nucleic acid encoding a polypeptide described herein is inserted. Representative viral expression vectors include, but are not limited to, adeno-associated viral vectors, adenovirus-based vectors (e.g., the adenovirus-based Per.C6 system available from Crucell, Inc. (Leiden, The Netherlands)), lentivirus-based vectors (e.g., the lentiviral-based pLPI from Life Technologies (Carlsbad, Calif.)), retroviral vectors (e.g., the pFB-ERV plus pCFB-EGSH), and herpes virus-based vectors. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In an additional embodiment, the viral vector is an adeno-associated viral vector. In a further embodiment, the viral vector is a retroviral vector. In general, and in embodiments, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

Another example of a suitable promoter is human elongation growth factor 1 alpha 1 (hEF1a1). In embodiments, the vector construct comprising the CARs and/or TCRs described herein comprises hEF1a1 functional variants.

However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Cell type specific, for example T cell specific, promoters can also be used. Further, the disclosed embodiments should not be limited to the use of constitutive promoters. Inducible promoters are also contemplated as part of one or more embodiments disclosed herein. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In order to assess the expression of a CAR or TCR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neomycin resistance gene (neo) and ampicillin resistance gene and the like. In some embodiments, a truncated epidermal growth factor receptor (HERR) tag may be used as a selectable marker gene.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and may be prepared using known techniques or obtained commercially. In general, the construct with the minimal 5' flanking region showing the highest level of expression of reporter gene is identified as the promoter.

Such promoter regions may be linked to a reporter gene and used to evaluate agents for the ability to modulate promoter-driven transcription.

In some embodiments, the vectors comprise a hEF1a1 promoter to drive expression of transgenes, a bovine growth hormone polyA sequence to enhance transcription, a woodchuck hepatitis virus posttranscriptional regulatory element (WPRE), as well as LTR sequences derived from the pFUGW plasmid.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing a polynucleotide encoding a polypeptide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In certain embodiments, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5: 505-10 (1991)). However, compositions that have different structures in solution than the normal vesicular structure are also encompassed. For example, the lipids may assume a micellar structure or merely exist as non-uniform aggregates of lipid molecules. Also contemplated are lipofectamine-nucleic acid complexes.

Non-Viral Based Delivery Systems

In some instances, polypeptides described herein can also be introduced into effector cells such as T cells using non-viral based delivery systems, such as the "Sleeping Beauty (SB) Transposon System," which refers a synthetic DNA transposon system to introduce DNA sequences into the chromosomes of vertebrates. The system is described, for example, in U.S. Pat. Nos. 6,489,458 and 8,227,432.

The Sleeping Beauty transposon system is composed of a Sleeping Beauty (SB) transposase and a SB transposon. DNA transposons translocate from one DNA site to another in a simple, cut-and-paste manner. Transposition is a precise process in which a defined DNA segment is excised from one DNA molecule and moved to another site in the same or different DNA molecule or genome. As do other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy.

Briefly, the Sleeping Beauty (SB) system (Hackett et al., Mol Ther 18:674-83, (2010)) was adapted to genetically modify the T cells (Cooper et al., Blood 105:1622-31, (2005)). This involved two steps: (i) the electro-transfer of DNA plasmids expressing a SB transposon [i.e., chimeric antigen receptor (CAR) to redirect T-cell specificity (Jin et al., Gene Ther 18:849-56, (2011); Kebriaei et al., Hum Gene Ther 23:444-50, (2012)) and SB transposase and (ii) the propagation and expansion of T cells stably expressing integrants on designer artificial antigen-presenting cells (AaPC) derived from the K562 cell line (also known as AaPCs (Activating and Propagating Cells). In one embodiment, the SB transposon system includes coding sequence encoding mbIL-15, a cell tag and/or a chimeric antigen receptor. In one embodiment, the SB transposon system includes coding sequence encoding mbIL-15, a cell tag and/or a T-cell receptor (TCR). In another, embodiment, the second step (ii) is eliminated and the genetically modified T cells are cryopreserved or immediately infused into a patient. In certain embodiments, the genetically modified T cells are not cryopreserved before infusion into a patient.

Such systems are described for example in Hudecek et al., Critical Reviews in Biochemistry and Molecular Biology, 52:4, 355-380 (2017), Singh et al., Cancer Res (8):68 (2008). Apr. 15, 2008 and Maiti et al., J Immunother. 36(2): 112-123 (2013), incorporated herein by reference in their entireties.

In some embodiments, a modified effector cell (e.g., a CAR effector cell or a TCR effector cell) expressing a polypeptide described herein and a cytokine such as IL-2, IL-22 or IL-15 for instance membrane-bound IL-15 (mbIL-15) is encoded in a transposon DNA plasmid vector, and the SB transposase is encoded in a separate vector. In specific embodiments, a CAR is encoded in a transposon DNA plasmid vector, mbIL-15 is encoded in a second transposon DNA plasmid vector, and the SB transposase is encoded in a third DNA plasmid vector. In some embodiments, the mbIL-15 is encoded with a truncated epidermal growth factor receptor tag.

Regardless of the method used to introduce exogenous nucleic acids into a host cell or otherwise expose a cell to the polypeptides described herein, in order to confirm the presence of the recombinant DNA sequence in the host cell, a variety of assays may be performed. Such assays include, for example, molecular assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the instant disclosure.

In embodiments, a modified effector cell comprising a polynucleotide encoding a polypeptide described herein and other genetic elements are delivered to a cell using the SB11 transposon system, the SB100X transposon system, the SB110 transposon system, the piggyBac transposon system (see, e.g., U.S. Pat. No. 9,228,180, Wilson et al, "PiggyBac Transposon-mediated Gene Transfer in Human Cells," Molecular Therapy 15:139-145 (2007), incorporated herein by reference in its entirety) and/or the piggyBat transposon system (see, e.g., Mitra et al., "Functional characterization of piggyBat from the bat *Myotis lucifugus* unveils an active mammalian DNA transposon," Proc. Natl. Acad. Sci USA 110:234-239 (2013). Additional transposases and transposon systems are provided in U.S. Pat. Nos. 7,148,203; 8,227,432; U.S. Patent Publn. No. 2011/0117072; Mates et al., Nat Genet, 41(6):753-61 (2009). doi: 10.1038/ng.343. Epub 2009 May 3, Gene Ther., 18(9):849-56 (2011). doi: 10.1038/gt.2011.40. Epub 2011 Mar. 31 and in Ivies et al., Cell. 91(4):501-10, (1997), each of which is incorporated herein by reference in their entirety.

In other embodiments, a polypeptide described herein and other genetic elements such as cytokines, for example, mbIL-15 and/or a tag, can be integrated into the immune effector cell's DNA through a recombinase and integrating expression vectors. Such vectors can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein can be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

The recombinases can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

A recombinase can be from the Integrase or Resolvase families. The Integrase family of recombinases has over one hundred members and includes, for example, FLP, Cre, and lambda integrase. The Integrase family, also referred to as the tyrosine family or the lambda integrase family, uses the catalytic tyrosine's hydroxyl group for a nucleophilic attack on the phosphodiester bond of the DNA. Typically, members of the tyrosine family initially nick the DNA, which later forms a double strand break. Examples of tyrosine family integrases include Cre, FLP, SSV1, and lambda ($\lambda$) integrase. In the resolvase family, also known as the serine recombinase family, a conserved serine residue forms a covalent link to the DNA target site (Grindley, et al., (2006) Ann Rev Biochem 16:16).

In one embodiment, the recombinase is an isolated polynucleotide sequence comprising a nucleic acid sequence that encodes a recombinase selecting from the group consisting of a SPβc2 recombinase, a SF370.1 recombinase, a Bxb1 recombinase, an A118 recombinase and a ϕRv1 recombinase. Examples of serine recombinases are described in detail in U.S. Pat. No. 9,034,652, hereby incorporated by reference in its entirety.

Recombinases for use in the practice of the present invention can be produced recombinantly or purified. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.)

In one embodiment, the recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide.

In one embodiment, a method for site-specific recombination comprises providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase can be *Listeria monocytogenes* phage recombinase, a *Streptococcus pyogenes* phage recombinase, a *Bacillus subtilis* phage recombinase, a *Mycobacterium tuberculosis* phage recombinase or a *Mycobacterium smegmatis* phage recombinase, provided that when the first recombination attachment site is attB, the second recombination attachment site is attP, and when the first recombination attachment site is attP, the second recombination attachment site is attB Further embodiments provide for the introduction of a site-specific recombinase into a cell whose genome is to be modified. One embodiment relates to a method for obtaining site-specific recombination in an eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In an embodiment the recombinase is selected from the group consisting of an A118 recombinase, a SF370.1 recombinase, a SPβc2 recombinase, a ϕRv1 recombinase, and a Bxb1 recombinase. In one embodiment the recombination results in integration.

Regardless of the method used to introduce exogenous nucleic acids into a host cell, in order to confirm the presence of the recombinant DNA sequence in the host cell, a variety of assays can be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify peptides or proteins or nucleic acids falling within the scope of the invention Immune Effector Cell Sources In certain aspects, the embodiments described herein include methods of making and/or expanding antigen-specific redirected immune effector cells (e.g., T-cells, NK-cell or NK T-cells) expressing polypeptides described herein, the methods comprising transfecting the cells with an expression vector containing a DNA (or RNA) construct encoding the polypeptide, then, optionally, stimulating the cells with feeder cells, recombinant antigen, or an antibody to the receptor to cause the cells to proliferate. In certain aspects, the cell (or cell population) engineered to express a CAR or TCR is a stem cell, iPS cell, immune effector cell or a precursor of these cells.

Sources of immune effector cells can include both allogeneic and autologous sources. In some cases, immune effector cells may be differentiated from stem cells or induced pluripotent stem cells (iPSCs). Thus, cell for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells such as T cells derived from human peripheral blood mononuclear cells (PBMC). PBMCs can be collected from the peripheral blood or after stimulation with G-CSF (Granulocyte colony stimulating factor) from the bone marrow, or umbilical cord blood. In some embodiments, G-CSF comprises a peptide sequence at least 80% homology to the sequence shown in SEQ ID NO: 52 or a peptide sequence encoded by a nucleotide sequence at least 80% homology to the sequence shown in SEQ ID NO: 146.

Following transfection or transduction (e.g., with a CAR expression construct), the cells may be immediately infused or may be cryo-preserved. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells.

The recombinant T cells may be expanded by stimulation with IL-2, or other cytokines that bind the common gamma-chain (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be further selected with the use of magnetic bead based isolation methods and/or fluorescence activated cell sorting technology and further cultured with the AaPCs. In a further aspect, the genetically modified cells may be cryopreserved.

T cells can also be obtained from a number of sources, including peripheral blood, bone marrow, lymph node tissue, cord blood, thymus tissue, tissue from a site of infection, ascites, pleural effusion, spleen tissue, and tumor (tumor-infiltrating lymphocytes). In certain embodiments described herein, any number of T cell lines available in the art, may be used. In certain embodiments, T cells can be obtained from a unit of blood collected from a subject using any number of techniques known to the skilled artisan, such as Ficoll® separation. In embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL® gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used herein. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods described herein.

Also contemplated is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., *Cell* 66:807-815, (1991); Henderson et al., *Immun* 73:316-321, (1991); Bierer et al., *Curr. Opin. Immun* 5:763-773, (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of Effector Cells

Whether prior to or after genetic modification of effector cells, for instance T cells to express a desirable polypeptide described herein, the cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the effector cells described herein are expanded by contact with a surface having attached thereto an agent that stimulates a CD3/TCR complex associated signal and a ligand that stimulates a co-stimulatory molecule on the surface of the cells. In particular, effector cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the cells, a ligand that binds the accessory molecule is used. For example, a population of effector cells, for instance T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, (1998); Haanen et al., *J. Exp. Med.* 190(9):13191328, (1999); Garland et al., *J. Immunol Meth.* 227(1-2):53-63, (1999)).

In certain embodiments, the primary stimulatory signal and the co-stimulatory signal for the effector cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects described herein, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect described herein, more anti-CD28 antibody is bound to the particles than anti-CD3 antibody, i.e., the ratio of CD3:CD28 is less than one. In certain embodiments described herein, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In embodiments, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate effector cells such as T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate effector cells. The ratio of anti-CD3- and anti-CD28-coupled particles to T cells that result in T cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one ratio being at least 1:1 particles per T cell. In one embodiment, a ratio of particles to cells of 1:1 or less is used. In one particular embodiment, the particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use herein. In particular, ratios will vary depending on particle size and on cell size and type.

In further embodiments described herein, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1, or MACS® MicroBeads from Miltenyi Biotec) are combined in a buffer, for example, PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context described herein. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment described herein, the mixture may be cultured for several hours (about 3 hours) to about 14 days or any hourly integer value in between. In another embodiment, the mixture may be cultured for 21 days. In one embodiment described herein the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-.gamma., IL-4, IL-7, GM-CSF, IL-10, IL-12, IL-15, TGFbeta, and TNF-alpha or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, alpha-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

Effector cells, for instance T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some cases, immune effector cells of the embodiments (e.g., T-cells) are co-cultured with activating and propagating cells (AaPCs), to aid in cell expansion. AaPCs can also be referred to as artificial Antigen Presenting cells (aAPCs). For example, antigen presenting cells (APCs) are useful in preparing therapeutic compositions and cell therapy products of the embodiments. In one aspect, the AaPCs may be transgenic K562 cells. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009, each of which is incorporated by reference. In yet a further aspect of the embodiments, culturing the transgenic CAR cells comprises culturing the transgenic CAR cells in the presence of dendritic cells or activating and propagating cells (AaPCs) that stimulate expansion of the CAR-expressing immune effector cells. In still further aspects, the AaPCs comprise a CAR-binding antibody or fragment thereof expressed on the surface of the AaPCs. The AaPCs may comprise additional molecules that activate or co-stimulate T-cells in some cases. The additional molecules may, in some cases, comprise membrane-bound Cy cytokines. In yet still further aspects, the AaPCs are inactivated or irradiated, or have been tested for and confirmed to be free of infectious material. In still further aspects, culturing the transgenic CAR cells in the presence of AaPCs comprises culturing the transgenic CAR cells in a medium comprising soluble cytokines, such as IL-15, IL-21 and/or IL-2. The cells may be cultured at a ratio of about 10:1 to about 1:10; about 3:1 to about 1:5; about 1:1 to about 1:3 (immune effector cells to AaPCs); or any range derivable therein. For example, the co-culture of T cells and AaPCs can be at a ratio of about 1:1, about 1:2 or about 1:3.

In one aspect, the AaPCs may express CD137L. In other aspects, the AaPCs may further express CD19, CD64, CD86, or mIL15 (or mbIL-15). In certain aspects, the AaPCs may express at least one anti-CD3 antibody clone or its fragment, such as, for example, OKT3 and/or UCHT1. In one aspect, the AaPCs may be inactivated (e.g., irradiated or mitomycin C treated). In one aspect, the AaPCs may have been tested for and confirmed to be free of infectious material. Methods for producing such AaPCs are known in the art. In one aspect, culturing the CAR-modified T cell population with AaPCs may comprise culturing the cells at a ratio of about 10:1 to about 1:10; about 3:1 to about 1:5; about 1:1 to about 1:3 (T cells to AaPCs); or any range derivable therein. For example, the co-culture of T cells and AaPCs can be at a ratio of about 1:1, about 1:2 or about 1:3. In one aspect, the culturing step may further comprise culturing with an aminobisphosphonate (e.g., zoledronic acid).

In a further aspect, the population of CAR expressing effector cells is cultured and/or stimulated for no more than 7, 14, 21, 28, 35 42 days, 49, 56, 63 or 70 days. In some embodiments, the population of CAR-T cells is cultured and/or stimulated for at least 0, 2, 4, 6, 8, 10, 12, 14, 16, 18, 20, 22, 24, 26, 28, 30 or more days. In some embodiments, the population of CAR-T cells is cultured and/or stimulated for at least 5, 10, 15, 20, 25, 30, 35, 40, 45, 50, 55, 60 or more days. In some embodiments, the population of CAR expressing effector cells is cultured and/or stimulated for at least 7, 14, 21, 28, 35, 42, 49, 56, 63 or more days. In other embodiments, a stimulation includes the co-culture of the CAR expressing effector cells with AaPCs to promote the growth of CAR positive cells. In another aspect, the population of transgenic CAR cells is stimulated for not more than: 1× stimulation, 2× stimulation, 3× stimulation, 4× stimulation, 5× stimulation, 5× stimulation, 6× stimulation, 7× stimulation, 8× stimulation, 9× stimulation or 10× stimulation. In some instances, the transgenic cells are not cultured ex vivo in the presence of AaPCs. In some specific instances, the method of the embodiment further comprises enriching the cell population for CAR-expressing immune effector cells (e.g., T-cells) after the transfection and/or culturing step. The enriching may comprise fluorescence-activated cell sorting (FACS) and sorting for CAR-expressing cells. In a further aspect, the sorting for CAR-expressing cells comprises use of a CAR-binding antibody. The enriching may also comprise depletion of CD56+ cells. In yet still a further aspect of the embodiment, the method further comprises cryopreserving a sample of the population of transgenic CAR cells.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in WO/2014/190273, which is incorporated herein by reference. In addition to peptide-MHC molecules or antigens of interest, the AaPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

Cells selected to become AaPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs may be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs may be frozen and stored for an extended period of time prior to thawing. Frozen AaPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, may be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000, which is incorporated herein by reference.

In certain embodiments there are further provided an engineered antigen presenting cell (APC). Such cells may be used, for example, as described above, to propagate immune effector cells ex vivo. In further aspects, engineered APCs may, themselves be administered to a patient and thereby stimulate expansion of immune effector cells in vivo. Engineered APCs of the embodiments may, themselves, be used as a therapeutic agent. In other embodiments, the engineered APCs can used as a therapeutic agent that can stimulate activation of endogenous immune effector cells specific for a target antigen and/or to increase the activity or persistence of adoptively transferred immune effector cells specific to a target antigen.

As used herein the term “engineered APC” refers to cell(s) that comprises at least a first transgene, wherein the first transgene encodes a HLA. Such engineered APCs may further comprise a second transgene for expression of an antigen, such that the antigen is presented at the surface on the APC in complex with the HLA. In some aspects, the engineered APC can be a cell type that presented antigens (e.g., a dendritic cell). In further aspects, engineered APC can be produced from a cell type that does not normally present antigens, such a T-cell or T-cell progenitor (referred to as “T-APC”). Thus, in some aspects, an engineered APC of the embodiments comprises a first transgene encoding a target antigen and a second transgene encoding a human leukocyte antigen (HLA), such that the HLA is expressed on the surface of the engineered APC in complex with an epitope of the target antigen. In certain specific aspects, the HLA expressed in the engineered APC is HLA-A2.

In some aspects, an engineered APC of the embodiments may further comprise at least a third transgene encoding co-stimulatory molecule. The co-stimulatory molecule may be a co-stimulatory cytokine that may be a membrane-bound Cy cytokine. In certain aspects, the co-stimulatory cytokine is IL-15, such as membrane-bound IL-15. In some further aspects, an engineered APC may comprise an edited (or deleted) gene. For example, an inhibitory gene, such as PD-1, LIM-3, CTLA-4 or a TCR, can be edited to reduce or eliminate expression of the gene. An engineered APC of the embodiments may further comprise a transgene encoding any target antigen of interest. For example, the target antigen can be an infectious disease antigen or a tumor-associated antigen (TAA).

Point-of-Care

In one embodiment of the present disclosure, the immune effector cells described herein are modified at a point-of-care site. In one embodiment of the present disclosure, the immune effector cells described herein are modified at or near a point-of-care site. In some cases, modified immune effector cells are also referred to as engineered T cells. In some cases, the point-of-care site is at a hospital or at a facility (e.g., a medical facility) near a subject in need of treatment. The subject undergoes apheresis and peripheral blood mononuclear cells (PBMCs) or a sub population of PBMC can be enriched for example, by elutriation, bead selection or Ficoll gradient separation. Enriched PBMC or a subpopulation of PBMC can be cryopreserved in any appropriate cryopreservation solution prior to further processing. In one instance, the elutriation process is performed using a buffer solution containing human serum albumin. Immune effector cells, such as T cells can be isolated by selection methods described herein. In one instance, the selection method for T cells includes beads specific for CD3 or beads specific for CD4 and CD8 on T cells. In one case, the beads can be paramagnetic beads. The harvested immune effector cells can be cryopreserved in any appropriate cryopreservation solution prior to modification. The immune effector cells can be thawed up to 24 hours, 36 hours, 48 hours, 72 hours or 96 hours ahead of infusion. The thawed cells can be placed in cell culture, for example in cell culture (e.g. RPMI) supplemented with fetal bovine serum (FBS) or human serum AB or placed in a buffer that includes cytokines such as IL-2 and IL-21, prior to modification. In another aspect, the harvested immune effector cells can be modified without the need for cryopreservation.

In some cases, the immune effector cells are modified by engineering/introducing a chimeric receptor, one or more cell tag(s), and/or cytokine(s) into the immune effector cells and then rapidly infused into a subject. In some cases, the sources of immune effector cells can include both allogeneic and autologous sources. In one case, the immune effector cells can be T cells or NK cells. In another case, the cytokine can be mbIL-15 or IL-12 or variants thereof. In further cases, the cytokine can be modulated by ligand inducible gene-switch expression systems described herein. For example, a ligand such as veledimex can be delivered to the subject to modulate the expression of mbIL-15 or IL-12.

In another aspect, veledimex is provided at 5 mg, 10 mg, 15 mg, 20 mg, 30 mg, 40 mg, 50 mg, 60 mg, 70 mg, 80 mg, 90 mg or 100 mg. In a further aspect, lower doses of veledimex are provided, for example, 0.5 mg, 1 mg, 5 mg, 10 mg, 15 mg or 20 mg. In one embodiment, veledimex is administered to the subject 0, 1, 2, 3, 4, 5, 6, 7, 8, 9, 10, 11, 12, 13, 14, 15, 16, 17, 18, 19, 20, or 21 days prior to infusion of the modified immune effector cells. In a further embodiment, veledimex is administered about once every 12 hours, about once every 24 hours, about once every 36 hours or about once every 48 hours, for an effective period of time to a subject post infusion of the modified immune effector cells. In one embodiment, an effective period of time for veledimex administration is about: 7, 8, 9, 10, 11, 12, 13, 14, 15, 16, 17, 18, 19, 20, 21, 22, 23, 24, 25, 26, 27, 28, 29, 30 days e.g., post immune effector cell administration. In other embodiments, veledimex can be re-administered after a rest period, after a drug holiday or when the subject experiences a relapse.

In certain cases, where an adverse effect on a subject is observed or when treatment is not needed, the cell tag can be activated, for example via cetuximab, for conditional in vivo ablation of modified immune effector cells comprising cell tags such as truncated epidermal growth factor receptor tags as described herein.

In some embodiments, such immune effectors cells are modified by the constructs as described herein through electroporation. In one instance, electroporation is performed with electroporators such as Lonza's Nucleofector™ devices. In other embodiments, the vector comprising the above-mentioned constructs is a non-viral or viral vector. In one case, the non-viral vector includes a Sleeping Beauty transposon-transposase system. In one instance, the immune effector cells are electroporated using a specific sequence. For example, the immune effector cells can be electroporated with one transposon followed by the DNA encoding a Sleeping Beauty transposase followed by a second transposon. In another instance, the immune effector cells can be electroporated with all transposons and transposase at the same time. In another instance, the immune effector cells can be electroporated with a transposase followed by both transposons or one transposon at a time. While undergoing sequential electroporation, the immune effector cells can be rested for a period of time prior to the next electroporation step.

In some cases, the modified immune effector cells do not undergo a propagation and activation step. In some cases, the modified immune effector cells do not undergo an incubation or culturing step (e.g. ex vivo propagation). In certain cases, the modified immune effector cells are placed in a buffer that includes IL-2 and IL-21 prior to infusion. In other instances, the modified immune effector cells are placed or rested in cell culture buffer, for example in cell culture buffer (e.g. RPMI) supplemented with fetal bovine serum (FBS) prior to infusion. Prior to infusion, the modified immune effector cells can be harvested, washed and formulated in a saline buffer in preparation for infusion into the subject.

In one instance, the subject has undergone lymphodepletion prior to infusion. Exemplary lymphodepletion regimens can include the administration of a fludarabine or cyclophosphamide or combination thereof.

In other instances, lymphodepletion is not required and the modified immune effector cells are rapidly infused into the subject.

In a further instance, the subject undergoes minimal lymphodepletion. Minimal lymphodepletion herein refers to a reduced lymphodepletion protocol such that the subject can be infused within 1 day, 2 days or 3 days following the lymphodepletion regimen. In one instance, a reduced lymphodepletion protocol can include lower doses of fludarabine and/or cyclophosphamide. In another instance, a reduced lymphodepletion protocol can include a shortened period of lymphodepletion, for example 1 day or 2 days.

In one embodiment, the immune effector cells are modified by engineering/introducing a chimeric receptor and a cytokine into said immune effector cells and then rapidly infused into a subject. In other cases, the immune effector cells are modified by engineering/introducing a chimeric receptor and a cytokine into said cells and then infused within at least: 0, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 hours into a subject. In other cases, immune effector cells are modified by engineering/introducing a chimeric receptor and a cytokine into the immune effector cells and then infused in 0 days, <1 day, <2 days, <3 days, <4 days, <5 days, <6 days or <7 days into a subject.

In some embodiments, an amount of modified effector cells is administered to a subject in need thereof and the amount is determined based on the efficacy and the potential of inducing a cytokine-associated toxicity. In another embodiment, the modified effector cells are $CAR^+$ and $CD3^+$ cells. In some cases, an amount of modified effector cells comprises about $10^4$ to about $10^9$ modified effector cells/kg. In some cases, an amount of modified effector cells comprises about $10^4$ to about $10^5$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises $>10^4$ but $\leq 10^5$ modified effector cells/kg. In some cases, an amount of modified effector cells comprises $>10^5$ but $\leq 10^6$ modified effector cells/kg. In some cases, an amount of modified effector cells comprises $>10^6$ but $\leq 10^7$ modified effector cells/kg.

In one embodiment, the modified immune effector cells are targeted to the cancer via regional delivery directly to the tumor tissue. For example, in ovarian cancer, the modified immune effector cells can be delivered intraperitoneally (IP) to the abdomen or peritoneal cavity. Such IP delivery can be performed via a port or pre-existing port placed for delivery of chemotherapy drugs. Other methods of regional delivery of modified immune effector cells can include catheter infusion into resection cavity, ultrasound guided intratumoral injection, hepatic artery infusion or intrapleural delivery.

In one embodiment, a subject in need thereof, can begin therapy with a first dose of modified immune effector cells delivered via IP followed by a second dose of modified immune effector cells delivered via IV. In a further embodiment, the second dose of modified immune effector cells can be followed by subsequent doses which can be delivered via IV or IP. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In another embodiment, the duration between the first and second or further subsequent dose can be about: 0, 1, 2, 3, 4, 5, 6, 7, 8, 9 or 10 years.

In another embodiment, a catheter can be placed at the tumor or metastasis site for further administration of 1, 2, 3, 4, 5, 6, 7, 8, 9, 10 doses of modified immune effector cells.

In some cases, doses of modified effector cells can comprise about $10^2$ to about $10^9$ modified effector cells/kg. In cases where toxicity is observed, doses of modified effector cells can comprise about $10^2$ to about $10^5$ modified effector cells/kg. In some cases, doses of modified effector cells can start at about $10^2$ modified effector cells/kg and subsequent doses can be increased to about: $10^4$, $10^5$, $10^6$, $10^7$, $10^8$ or $10^9$ modified effector cells/kg.

In other embodiments, a method of stimulating the proliferation and/or survival of engineered cells comprises obtaining a sample of cells from a subject, and transfecting cells of the sample of cells with one or more polynucleotides that comprise one or more transposons. In one embodiment, the transposon(s) encode a chimeric antigen receptor (CAR) as described herein, a cytokine, one or more cell tags, and a transposase effective to integrate said one or more polynucleotides into the genome of said cells, to provide a population of engineered cells. In an embodiment, the transposon(s) encode a chimeric antigen receptor (CAR) as described herein, a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In one instance, a method of in vivo expansion or propagation of engineered cells comprises obtaining a sample of cells from a subject, and transfecting cells of the sample of cells with one or more polynucleotides that comprise one or more transposons comprising the chimeric polypeptides described herein. In one embodiment, the transposon(s) encode a chimeric antigen receptor (CAR) as described herein, a cytokine, one or more cell tags, and a transposase effective to integrate said one or more polynucleotides into the genome of said cells, to provide a population of engineered cells. In an embodiment, the transposon(s) encode a chimeric antigen receptor (CAR) as described herein, a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In another embodiment, a method of enhancing in vivo persistence of engineered cells in a subject in need thereof comprises obtaining a sample of cells from a subject, and transfecting cells of the sample of cells with one or more polynucleotides that comprise one or more transposons comprising the chimeric polypeptides described herein. In some cases, one or more transposons encode a chimeric antigen receptor (CAR), a cytokine, one or more cell tags, and a transposase effective to integrate the DNA into the genome of said cells, to provide a population of engineered cells. In some cases, one or more transposons encode a chimeric antigen receptor (CAR), a cytokine, one or more cell tags, gene switch polypeptides for ligand-inducible control of the cytokine and a transposase effective to integrate the DNA into the genome of said cells, to provide a population of engineered cells. In some cases, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and the second gene switch polypeptide are connected by a linker. In one instance, lymphodepletion is not required prior to administration of the engineered cells to a subject.

In another embodiment, a method of treating a subject with a tumor comprises obtaining a sample of cells from a subject, transfecting cells of the sample with one or more polynucleotides that comprise one or more transposons comprising the chimeric polypeptides described herein, and administering the population of engineered cells to the subject. In one instance, lymphodepletion is not required prior to administration of the engineered cells to a subject. In some cases, the one or more transposons encode a chimeric antigen receptor (CAR), a cytokine, one or more cell tags, and a transposase effective to integrate the DNA into the genome of the cells. In some cases, the one or more transposons encode a chimeric antigen receptor (CAR), a cytokine, one or more cell tags, gene switch polypeptides for ligand-inducible control of the cytokine and a transposase effective to integrate the DNA into the genome of the cells. In some cases, the gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and second gene switch polypeptide are connected by a linker. In some cases, the cells are transfected via electroporation. In some cases, the polynucleotides encoding the gene switch polypeptides are modulated by a promoter. In some cases, the promoter is a tissue-specific promoter or an EF1A promoter or functional variant thereof. In some cases, the tissue-specific promoter comprises a T cell specific response element or an NFAT response element. In some cases, the cytokine comprises at least one of IL-1, IL-2, IL-15, IL-12, IL-21, a fusion of IL-15, IL-15Ralpha or an IL-15 variant. In some cases, the cytokine is in secreted form. In some cases, the cytokine is in membrane-bound form. In some cases, the cells are NK cells, NKT cells, T-cells or T-cell progenitor cells. In some cases, the cells are administered to a subject (e.g. by infusing the subject with the engineered cells). In some cases, the method further comprises administering an effective amount of a ligand (e.g. veledimex) to induce expression of the cytokine. In some cases, the CAR is capable of binding at least ROR1. In some cases, the transposase is salmonid-type Tc1-like transposase. In some cases, the transposase is SB11 or SB100x transposase. In other cases, the transposase is PiggyBac. In some cases, the cell tag comprises at least one of a HER1 truncated variant or a CD20 truncated variant.

Therapeutic Applications

In embodiments described herein, is an immune effector cell (e.g., T cell) transduced with Sleeping Beauty transposon(s) and Sleeping Beauty transposase. For example, the Sleeping Beauty transposon or transposons can include a CAR that combines an antigen recognition domain with a spacer of CD8 alpha hinge wherein the spacer region comprises a stalk region designated as "s" and at least one stalk extension region, designated as "s'-n," wherein n represents the number of units of s' in the space region, and wherein n can be 1, 2, 3, 4, 5, 6, 7, 8, 9, 10, 11, 12, 13, 14, 15, 16, 17, 18, 19, or 20, an intracellular domain of CD3-zeta, CD28, 4-1BB, or any combinations thereof and the intracellular domain CD3-zeta, one or more cell tags, one or more cytokines and optionally, components of the gene switch system as described herein. Therefore, in some instances, the transduced T cell can elicit a CAR-mediated T-cell response.

In embodiments described herein, the use of a CAR is provided to redirect the specificity of a primary T cell to a surface antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with an antigen, a spacer, a zeta chain portion comprising for example the intracellular domain of human CD3-zeta, and a costimulatory signaling region.

In one embodiment, the present disclosure includes a cellular therapy where T cells are genetically modified to express the antigen-specific CARs of the invention and the CAR T cell is infused to a recipient in need thereof. The infused cell is able to kill cells overexpressing an antigen in the recipient. Unlike antibody therapies, CAR T cells as described herein are able to replicate in vivo resulting in long-term persistence that can lead to sustained effect on tumor cells.

The invention additionally provides a method for detecting a disease that comprises overexpression of an antigen in a subject, comprising a) providing i) a sample from a subject, and ii) any one or more of the antibodies, or antigen-binding fragments thereof, that are described herein, b) contacting the sample with the antibody under conditions for specific binding of the antibody with its antigen, and c) detecting an increased level of binding of the antibody to the sample compared to a control sample lacking the disease, thereby detecting the disease in the subject. In one embodiment, the disease is cancer. In a preferred embodiment, the cancer is selected from the group of ovarian cancer and breast cancer. While not intending to limit the method of detection, in one embodiment, detecting binding of the antibody to the sample is immunohistochemical, enzyme-linked immunosorbent assay (ELISA), fluorescence-activated cell sorting (FACS), Western blot, immunoprecipitation, and/or radiographic imaging.

Also provided herein is a method for treating a disease that comprises overexpression of an antigen, comprising administering to a subject having the disease a therapeutically effective amount of any one or more of the polypeptides that are described herein.

The modified T cells described herein can also serve as a type of vaccine for ex vivo immunization and/or in vivo therapy in a mammal. In embodiments, the mammal is a human. With respect to ex vivo immunization, at least one of the following occurs in vitro prior to administering the immune effector cell into a mammal: i) expansion of the cells, ii) introducing a nucleic acid encoding a CAR to the cells, and/or iii) cryopreservation of the cells.

Ex vivo procedures are well known and are discussed more fully below. Briefly, cells are isolated from a mammal (for example, a human) and genetically modified (i.e., transduced or transfected in vitro) with a vector expressing a CAR disclosed herein. The CAR-modified cell can be administered to a mammalian recipient to provide a therapeutic benefit. The mammalian recipient can be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein can be utilized in the treatment and prevention of diseases that arise in individuals who are immunocompromised. In particular, the modified T cells of the invention are used in the treatment of malignancies. In certain embodiments, the cells of the invention are used in the treatment of patients at risk for developing malignancies. Thus, the methods for the treatment or prevention of malignancies comprising administering to a subject in need thereof, a therapeutically effective amount of the modified T cells of the invention. In embodiments, the cells activated and expanded as described herein can be utilized in the treatment of malignancies Briefly, pharmaceutical compositions described herein can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In embodiments, compositions of the present invention are formulated for intravenous administration.

Pharmaceutical compositions described herein can be administered in a manner appropriate to the disease to be treated (or prevented). The quantity and frequency of administration will be determined by such factors as the condition of the patient, and the type and severity of the patient's disease, although appropriate dosages can be determined by clinical trials.

When "an immunologically effective amount", or "therapeutic amount" is indicated, the precise amount of the compositions described herein to be administered can be determined by a physician with consideration of individual differences in age, weight, and condition of the patient (subject). It can generally be stated that a pharmaceutical composition comprising the T cells described herein can be administered at a dosage of $10^4$ to $10^9$ cells/kg body weight, $10^5$ to $10^6$ cells/kg body weight, including all integer values within those ranges. T cell compositions can also be administered multiple times at these dosages. The cells can be administered by using infusion techniques that are commonly known in immunotherapy (see, e.g., Rosenberg et al., New Eng. J. of Med. 319:1676, (1988)). The optimal dosage and treatment regime for a particular patient can readily be determined by one skilled in the art of medicine by monitoring the patient for signs of disease and adjusting the treatment accordingly.

In certain embodiments, it can be desired to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol can serve to select out certain populations of T cells. In another embodiment, it can be desired to administer activated T cells of the subject composition following lymphodepletion of the patient, either via radiation or chemotherapy.

The administration of compositions described herein can be carried out in any convenient manner, including by aerosol inhalation, injection, ingestion, transfusion, implantation or transplantation. The compositions described herein can be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the CAR-T cell compositions of the present invention are administered by i.v. injection. The compositions of T cells can be injected directly into a lymph node, or site of primary tumor or metastasis.

The dosage of the above treatments to be administered to a patient will vary with the precise nature of the condition being treated and the recipient of the treatment. The scaling of dosages for human administration can be performed according to art-accepted practices. For example, the dose of the above treatment can be in the range of $1\times10^4$ CAR+ cells/kg to $5\times10^6$ CAR+ cells/kg. Exemplary doses can be $1\times10^2$ CAR+ cells/kg, $1\times10^3$ CAR+ cells/kg, $1\times10^4$ CAR+ cells/kg, $1\times10^5$ CAR+ cells/kg, $3\times10^5$ CAR+ cells/kg, $1\times10^6$ CAR+ cells/kg, $5\times10^6$ CAR+ cells/kg, $1\times10^7$ CAR+ cells/kg, $1\times10^8$ CAR+ cells/kg or $1\times10^9$ CAR+ cells/kg. The appropriate dose can be adjusted accordingly for an adult or a pediatric patient.

Alternatively, a typical amount of immune effector cells administered to a mammal (e.g., a human) can be, for example, in the range of one hundred, one thousand, ten thousand, one million to 100 billion cells; however, amounts below or above this exemplary range are within the scope of the invention. For example, the dose of inventive host cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens can be useful and are within the scope of the invention. The desired dosage can be delivered by a single bolus administration of the composition, by multiple bolus administrations of the composition, or by continuous infusion administration of the composition.

The composition comprising the immune effector cells expressing the disclosed nucleic acid sequences, or a vector comprising the those nucleic acid sequences, can be administered with one or more additional therapeutic agents, which can be co-administered to the mammal. By "co-administering" is meant administering one or more additional therapeutic agents and the composition comprising the inventive host cells or the inventive vector sufficiently close in time to enhance the effect of one or more additional therapeutic agents, or vice versa. In this regard, the composition comprising the immune effector cells described herein or a vector described herein can be administered simultaneously with one or more additional therapeutic agents, or first, and the one or more additional therapeutic agents can be administered second, or vice versa. Alternatively, the composition comprising the disclosed immune effector cells or the vectors described herein and the one or more additional therapeutic agents can be administered simultaneously.

An example of a therapeutic agents that can be included in or co-administered with the composition (or included in kits) comprising the inventive host cells and/or the inventive vectors are interleukins, cytokines, interferons, adjuvants and chemotherapeutic agents. In embodiments, the additional therapeutic agents are IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, and TLR10.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof cellulose derivatives such as carboxymethylcellulose, methylcellulose (e.g., Methocel®), hydroxypropylmethylcellulose, hydroxyethyl cellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and an anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as) Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil)(Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethyl cellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethyl cellulose, hydroxyethyl cellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include CAR-T cells (e.g., CD19 CAR-T cells) described herein, and optionally in addition with cytokines and/or chemotherapeutic agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Sequences

Provided below is a representative list of certain sequences included in embodiments provided herein.

| | Nucleotide Sequences SEQ ID NO | Amino Acid Sequences SEQ ID NO |
|---|---|---|
| CD8α (*Homo sapiens*) | 107 | 1 |
| CD8α (C164S, C181S) hinge | 108 | 2 |
| CD8α hinge (CD8α 1X spacer) | 109 | 3 |
| CD8α 2X spacer | 110 | 4 |
| CD8α 3X spacer | 111 | 5 |
| CD8α 3X V2 spacer | 112 | 6 |
| CD8α 4X spacer | 113 | 7 |
| Whitlow Linker | 114 | 8 |
| GSG linker | 115 | 9 |
| SGSG linker | 116 | 10 |
| (G4S)3 Linker | 117 | 11 |
| (G4S)3 · CD8α Hinge spacer | 118 | 12 |
| Whitlow linker · CD8α Hinge spacer | 119 | 13 |
| Whitlow linker(2x) · CD8α Hinge spacer | 120 | 14 |
| Whitlow linker · CD8α Hinge(2x) spacer | 121 | 15 |
| LNGFR extracellular domain (LNGFR 1X spacer) | 122 | 16 |
| LNGFR 2X spacer | 123 | 17 |
| LNGFR Cys 2, 3, 4 spacer | 124 | 18 |
| LNGFR Cys 2, 3, 4 2X spacer | 125 | 19 |
| LNGFR Cys 3, 4 spacer | 126 | 20 |
| LNGFR Cys 3, 4 2X spacer | 127 | 21 |
| LNGFR Cys 3, 4 3X spacer | 128 | 22 |
| LNGFR Cys 3, 4 4X spacer | 129 | 23 |
| CD8α transmembrane domain | 130 | 24 |
| Cytotoxic T-lymphocyte protein 4 transmembrane domain | 131 | 25 |
| CD28 co-stimulatory endodomain | 132 | 26 |
| 4-1BB (CD137) co-stimulatory endodomain | 133 | 27 |
| CD3 zeta stimulatory endodomain | 134 | 28 |
| DNAX-activation protein 10 (DAP 10) Signaling Domain | 135 | 29 |
| DNAX-activation protein 12 (DAP12) Signaling Domain | 136 | 30 |
| *Homo sapiens* CD28 | 137 | 31 |
| CD28 hinge (CD28 1X spacer) | 138 | 32 |
| CD28 2X spacer | 139 | 33 |
| CD28 3X spacer | 140 | 34 |
| CD28 4X spacer | 141 | 35 |
| *Homo sapiens* Cytotoxic T-lymphocyte protein 4 (CTLA-4) | 142 | 36 |
| CTLA-4 1X spacer | | 37 |
| CTLA-4 2X spacer | | 38 |
| CTLA-4 3X spacer | | 39 |
| CTLA-4 4X spacer | | 40 |
| *Homo sapiens* IgG3 hinge | | 41 |
| *Homo sapiens* IgG4 hinge | | 42 |
| *Homo sapiens* IgG4 hinge (S108P) (IgG4 1X spacer) | 144 | 43 |
| IgG4 2X spacer | | 44 |
| IgG4 3X spacer | | 45 |
| IgG4 4X spacer | | 46 |
| IgG4 5X spacer | | 47 |
| IgG4 6X spacer | | 48 |
| *Homo sapiens* IgG4 hinge (S108P)-CH2-CH3 spacer | 145 | 49 |
| *Homo sapiens* IgG4 hinge (S108P)-CH3 spacer | | 50 |
| *Homo sapiens* B-lymphocyte antigen CD19 | | 51 |
| Granulocyte macrophage colony-stimulating factor receptor alpha Signal Peptide | 146 | 52 |
| Anti-CD19 monoclonal antibody clone FMC63 variable light chain | 147 | 53 |
| Anti-CD19 monoclonal antibody clone FMC63 variable heavy chain | 148 | 54 |
| Anti-CD19 clone FMC63 single chain fragment variable (scFv) with Whitlow linker | 149 | 55 |
| CD19-specific chimeric antigen receptor with CD8-1X spacer (CD19-CD8a-CD28-CD3z) | 150 | 56 |
| CD19-specific chimeric antigen receptor with CD8-2X spacer | 151 | 57 |
| CD19-specific chimeric antigen receptor with CD8-3X spacer | 152 | 58 |
| CD19-specific chimeric antigen receptor with CD8-3X v2 spacer | 153 | 59 |
| CD19-specific chimeric antigen receptor with CD8-4X spacer | 154 | 60 |
| Anti-CD33 monoclonal antibody clone hM195 variable light chain | 155 | 61 |
| Anti-CD33 monoclonal antibody clone hM195 variable heavy chain | 156 | 62 |
| Anti-CD33 monoclonal antibody clone hM195 scFv | 157 | 63 |
| CD33-specific chimeric antigen receptor with CD8α hinge (CD8 1X) spacer | 158 | 64 |
| CD33-specific chimeric antigen receptor with CD8 2X spacer | 159 | 65 |
| CD33-specific chimeric antigen receptor with CD8 3X spacer | 160 | 66 |
| CD33-specific chimeric antigen receptor with CD8 3X V2 spacer | 161 | 67 |
| CD33-specific chimeric antigen receptor with CD8 4X spacer | 162 | 68 |
| HUMAN T-cell receptor alpha (TCRα) chain constant (C) region | 163 | 69 |

-continued

| | Nucleotide Sequences SEQ ID NO | Amino Acid Sequences SEQ ID NO |
|---|---|---|
| Extracellular region of HUMAN T-cell receptor alpha (TCRα) chain constant (C) region | 164 | 70 |
| TCRα TM domain | 165 | 71 |
| TCRα hinge (1X spacer) | 166 | 72 |
| TCRα (C96S) hinge | 167 | 73 |
| TCRα hinge · (G4S)3 Spacer | 168 | 74 |
| (G4S)3 · TCRα hinge Spacer | 169 | 75 |
| Whitlow linker · TCRα hinge Spacer | 170 | 76 |
| TCRα 2X spacer | 171 | 77 |
| TCRα 3X spacer | 172 | 78 |
| TCRα 4X spacer | 173 | 79 |
| TCRα 2X V2 spacer | 174 | 80 |
| TCRα 3X V2 spacer | 175 | 81 |
| TCRα 4X V2 spacer | 176 | 82 |
| HUMAN T-cell receptor beta-1 (TCRβ or TCRβ1) chain constant (C) region | 177 | 83 |
| Extracellular region of HUMAN T-cell receptor beta-1 (TCRβ1) chain constant (C) region | 178 | 84 |
| TCRβ TM domain | 179 | 85 |
| TCRβ hinge (1X spacer) | 180 | 86 |
| TCRβ (C131S) hinge | 181 | 87 |
| TCRβ hinge · (G4S)3 Spacer | 182 | 88 |
| (G4S)3 · TCRβ hinge Spacer | 183 | 89 |
| Whitlow linker · TCRβ hinge Spacer | 184 | 90 |
| TCRβ 2X spacer | 185 | 91 |
| TCRβ 3X spacer | 186 | 92 |
| TCRβ 4X spacer | 187 | 93 |
| TCRβ 2X V2 spacer | 188 | 94 |
| TCRβ 3X V2 spacer | 189 | 95 |
| TCRβ 4X V2 spacer | 190 | 96 |
| HUMAN T-cell receptor beta-2 (TCRβ2) chain constant (C) region | 191 | 97 |
| Extracellular region of HUMAN T-cell receptor beta-2 (TCRβ2) chain constant (C) region | 192 | 98 |
| HUMAN T-cell receptor gamma-1 (TCRγ1) chain constant (C) region 1 | 193 | 99 |
| Extracellular region of HUMAN T-cell receptor gamma-1 (TCRγ1) chain constant (C) region 1 | 194 | 100 |
| TCRγ1 transmembrane domain | 195 | 101 |
| HUMAN T-cell receptor gamma-2 (TCRγ2) chain constant (C) region | 196 | 102 |
| Extracellular region of HUMAN T-cell receptor gamma-2 (TCRγ2) chain constant (C) region | 197 | 103 |
| HUMAN T-cell receptor delta (TCRδ) chain C region | 198 | 104 |
| Extracellular region of HUMAN T-cell receptor delta (TCRδ) chain C region | 199 | 105 |
| TCRδ transmembrane domain | 200 | 106 |
| Anti-EGFRvIII Clone 139 VH | 201 | 202 |
| Anti-EGFRvIII Clone 139 VL | 203 | 204 |
| Anti-EGFRvIII Clone MR1 VH | 205 | 206 |
| Anti-EGFRvIII Clone MR1 VL | 207 | 208 |
| Anti-EGFRvIII Clone MR1-1 VH | 209 | 210 |
| Anti-EGFRvIII Clone MR1-1 VL | 211 | 212 |
| Anti-EGFRvIII Clone humMR1-1 VH | 213 | 214 |
| Anti-EGFRvIII Clone humMR1-1 VL | 215 | 216 |
| Anti-EGFRvIII Clone humMR1-2 VH | 217 | 218 |
| Anti-EGFRvIII Clone humMR1-2 VL | 219 | 220 |
| Anti-EGFRvIII scFv Clone 139 | 221 | 222 |
| Anti-EGFRvIII scFv clone MR1 | 223 | 224 |
| Anti EGFRvIII scFv clone MR1-1 | 225 | 226 |
| Anti-EGFRvIII scFv clone huMR1-1 | 227 | 228 |
| Anti-EGFRvIII scFv clone huMR1-2 | 229 | 230 |
| EGFRvIII CAR (clone 139 scFv · CD8alpha hinge&TM · 4-1BB · CD3ς) | 231 | 232 |
| EGFRvIII CAR (MR1 scFv · CD8alpha hinge&TM · 4-1BB · CD3ς) | 233 | 234 |
| EGFRvIII CAR (MR1-1 scFv · CD8alpha hinge&TM · 4-1BB · CD3ς) | 235 | 236 |

-continued

| | Nucleotide Sequences SEQ ID NO | Amino Acid Sequences SEQ ID NO |
|---|---|---|
| EGFRvIII CAR (humMR1-1 scFv · CD8alpha hinge&TM · 4-1BB · CD3ς) | 237 | 238 |
| EGFRvIII CAR (humMR1-2 scFv · CD8alpha hinge&TM · 4-1BB · CD3ς) | 239 | 240 |
| EGFRvIII CAR (MR1-1 scFv · CD8alpha 2x hinge&TM · 4-1BB · CD3ς) | 241 | 242 |
| EGFRvIII CAR (MR1-1 scFv · CD8alpha 3x hinge&TM · 4-1BB · CD3ς) | 243 | 244 |
| EGFRvIII CAR (MR1-1 scFv · CD8alpha 4x hinge&TM · 4-1BB · CD3ς) | 245 | 246 |
| EGFRvIII CAR (huMR1-1 scFv · CD8alpha 3x hinge & TM · 4-1BB · CD3ς) | 247 | 248 |
| EGFRvIII CAR (huMR1-1 scFv · CD8alpha 4x hinge & TM · 4-1BB · CD3ς) | 249 | 250 |
| EGFRvIII CAR (huMR1-2 scFv · CD8alpha 3x hinge & TM · 4-1BB · CD3ς) | 251 | 252 |
| EGFRvIII CAR (huMR1-2 scFv · CD8alpha 4x hinge & TM · 4-1BB · CD3ς) | 253 | 254 |

EXAMPLES

These examples are provided for illustrative purposes only and not to limit the scope of the claims provided herein.

Example 1 Chimeric Antigen Receptors with CD8α-Derived Spacers of Varying Lengths Chimeric antigen receptors incorporating a spacer comprising a stalk region and a stalk extension region(s) were generated. The stalk region comprised the sequence of the CD8α hinge region (SEQ ID NO: 3), and the stalk extension region(s) comprised 1, 2, or 3 regions. Each stalk extension region comprised an altered CD8α hinge region sequence (SEQ ID NO: 2) in which the disulfide-bond forming cysteine residues (bold residues in Table 1) were converted to serines (underlined residues in Table 1). In the 2×, 3×, and 4× versions depicted in FIG. 2, the stalk region comprising CD8α hinge sequence retained the disulfide bond forming cysteines. This stalk region was downstream of the altered regions lacking the cysteines. A second version of the 3× stalk (3×v2) was generated in which the stalk extension region retaining the disulfide bond-forming cysteines was upstream of the stalk region and the stalk extension region, both regions lacking cysteines. The amino acid sequences of generated 1×, 2×, 3×, 4×, and 3×v2 stalks are listed in Table 1.

TABLE 1

| CD8α spacer terminology | CD8α spacer description | Amino Acid Sequence SEQ ID NO: |
|---|---|---|
| 1X | Stalk only | 3 |
| 2X | Stalk and 1 stalk extension regions; s'-1 | 4 |
| 3X | Stalk and two stalk extension-regions; s'-2 | 5 |
| 4X | Stalk and three stalk extension regions; s'-3 | 7 |
| 3X v2 | Stalk and two stalk extension-regions; s'-2 | 6 |

Example 2. Nucleofection of PBMC with SB System to Generate CD19-CAR-T Cells with CD8α-Derived Spacers of Varying Lengths DNA plasmids to express CD19-specific CARs with varying spacer lengths were cloned in SB transposon vectors. SB transposons were transfected into peripheral blood mononuclear cells (PBMC) via nucleofection to redirect T cell specificity.

On day 0, 20 million PBMCs were resuspended in 100 μL of Amaxa Human T cell Nucleofector solution (Lonza, Basel, Switzerland) mixed with a total of 15 μg of transposons and 5 of transposase (SB11) and electroporated.

The following day (day 1) cells were counted, and CAR expression was measured by flow cytometry. CAR-T Cells were stimulated with either γ-irradiated (100 Gy) or mitomycin C treated AaPCs at a 1:1 ratio. The AaPC cells used were K562-AaPC expressing CD19 antigen. Cultures were supplemented with IL-21 (30 ng/ml) only for the first round of stimulation and subsequently with recombinant human IL-2 (50 IU/ml) and IL-21 (30 ng/ml) (Pepro Tech) for remaining stimulations. CAR-T cell cultures were phenotyped at the end of each stimulation cycle, which typically lasted 7 days. The cultures were phenotyped for CAR expression by multi-parameter flow cytometry utilizing either Protein L or anti-idiotype antibody that recognizes CD19-specific CAR. Cultures were also closely monitored for the outgrowth of NK cells (defined as $CD3^{neg}CD56+$ population) and were removed from the CAR T cell cultures when the percentage exceeded 10% of total cell populations using magnetic beads for specific for CD56 (Stem Cell Technologies and/or Miltenyi Biotec), according to the manufacturer's instructions.

Example 3. Expression of CD19-Specific CARs with CD8α-Derived Spacers of Varying Lengths T cells expressing CARs with CD19-specific antigen binding region and CD8α-derived spacers listed in Table 1 were generated.

Figure 3A:
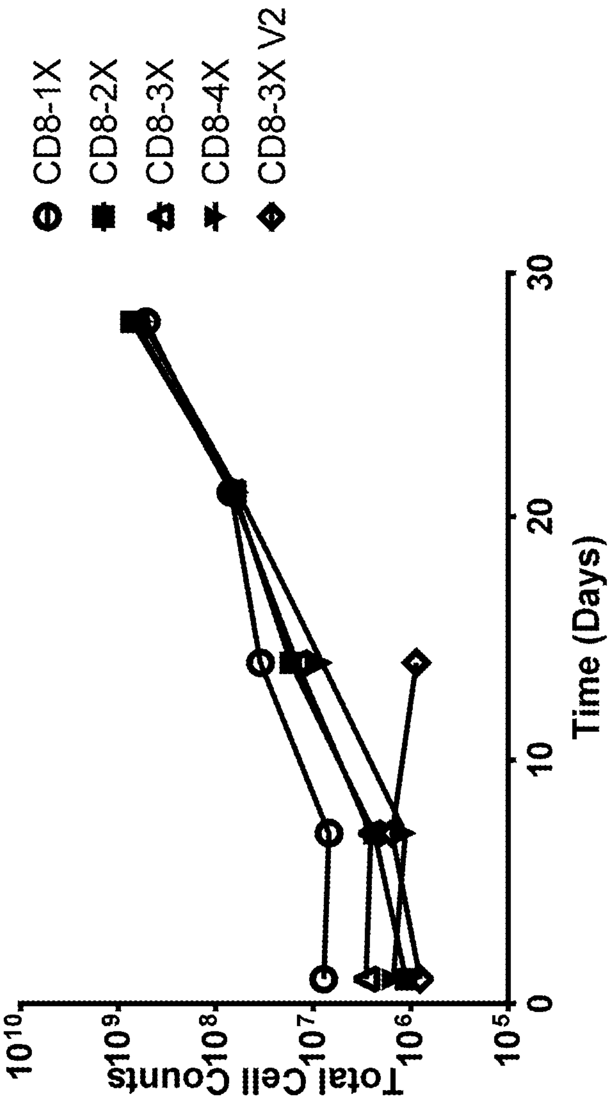
FIGS. 3A-3B depict exemplary data showing expansion of CD19-CAR-T cells expressing CARs of varying spacer lengths in ex vivo culture.

The expression level of the CD19-specific CARs with varying spacer lengths was determined after successive rounds of stimulation by co-culture with AaPC as described in Example 2. CAR expression level was determined by flow cytometry. For flow cytometry experiments, cells were gently resuspended and cell number and viability were measured using Trypan blue exclusion method with the Countess instrument. $5\times10^5$ cells for each of the samples were harvested at 330×g for 4 min. Harvested cells were incubated on ice for at least 15 min with 10% human AB serum in HBSS. Antibody cocktails containing fluorescently conjugated antibodies included one or more of antibodies specific to CD4 (Clone RPA-T4), CD8 (Clone SK1), CD3 (Clone UCHT1), CD56, and CD19-specific CAR (anti-idiotype antibody), in HBSS+0.1% BSA+2 mM EDTA. The prepared antibody cocktails and associated fluorescence minus one/isotype control were added to stain the cell samples, and then the samples were incubated on ice for 30 min. The samples were then washed then with FACS buffer (HBSS+0.5% BSA+2 mM EDTA) and stained with Fixable Viability Dye (eBiosciences) for 30 min on ice. Cells were washed with FACS buffer and then fixed with a 4% paraformaldehyde solution (BD Cytofix; BD Biosciences). All samples were run on a LSR II flow cytometer, a Fortessa X-20 flow cytometer (BD Biosciences) or iQue Screener Plus (Intellicyt) and data was analyzed using FlowJo V10 (TreeStar, Ashland, Oreg.) or iQue Screener software. The data from two example experiments is summarized in Table 2. T-cell counts from ex vivo expansion were also tracked and the corresponding data is depicted in FIG. 3.

As shown in Table 2, improved CD19-specific CAR expression was observed as measured by % of T cells expressing CAR as well as Molecules of Equivalent Soluble Fluorochrome (MESF) when spacers included stalk extension regions (CD8-2×, CD8-3× and CD8-4×) compared to when spacer only included stalk region (CD8-1×). Similar level of expansion of CD19-CAR-T cells with spacer of varying lengths was observed as shown in FIG. 3. CD19-CAR-T cells with CD8-3×v2 spacer failed to express CAR on the cell surface and failed to expand ex vivo upon co-culture with AaPC. Difference between CD8-3× and CD8-3×v2 spacer is the position of amino acid substitutions to disrupt inter-chain disulfide bonds. This data suggests that positioning of amino acid substitutions for dimerization sites is critical for expression of proteins when using spacers of varying lengths.

Figure 3B:
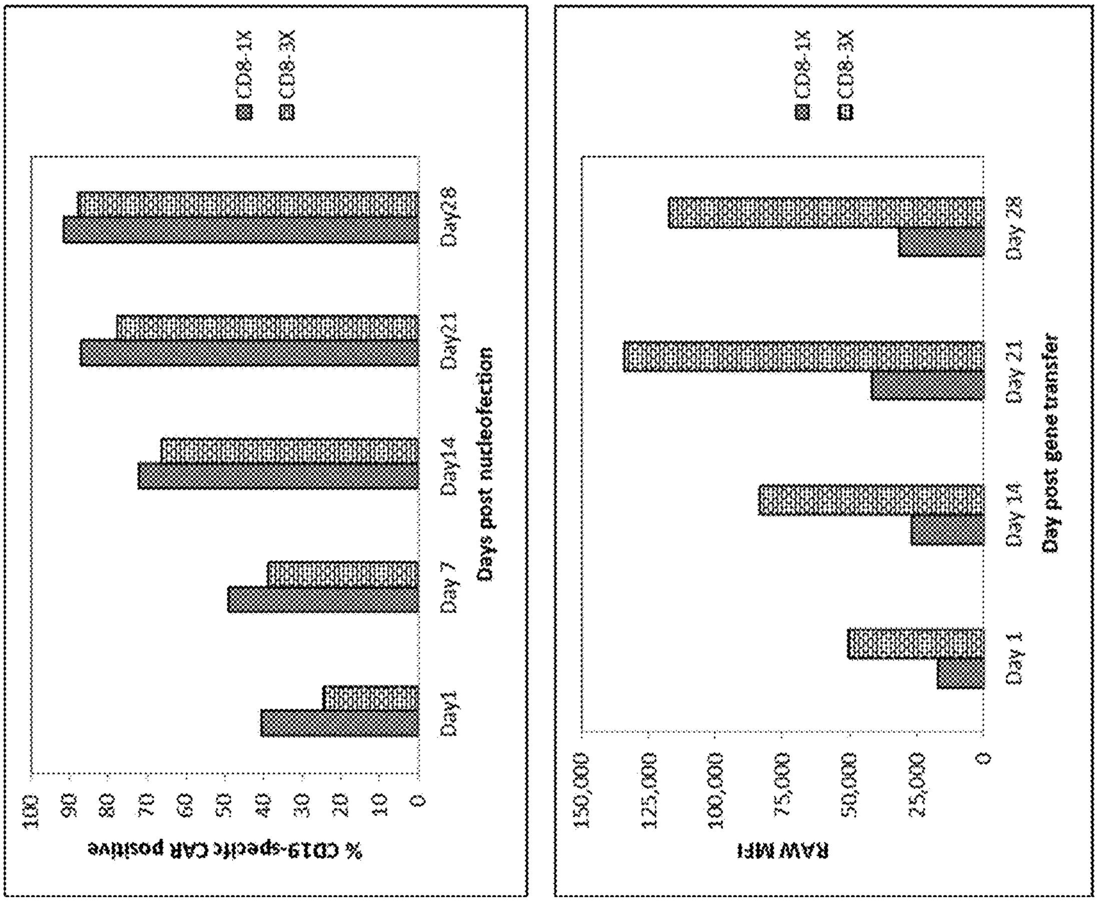

Expression of CD19-specific CAR with (CD8-3×) or without (CD8-1×) stalk extension regions was compared in human T cells derived from PBMC of another healthy donor. CD19-specific CARs were introduced using SB system and CD19-CAR-T cells were propagated by co-culture with AaPC ex vivo for 28 days as described in Example 2. T cells were analyzed by flow cytometry on day 1, 14, 21 and 28 post nucleofection to measure expression of CD19-specific CAR. FIG. 3B captures % of T cells in culture that were positive for CD19-specific CAR and FIG. 3B captures raw mean fluorescence intensity (MFI) of CD19-specific CAR. Data presented in FIG. 3B shows that similar percentage of T cells showed CD19-specific CAR expression through the ex vivo expansion phase of CAR-T cells for this donor. However, MFI was significantly higher when CD19-specific CAR with stalk extension region (CD8-3×) compared to without (CD8-1×) stalk extension region meaning improved expression levels of CAR when stalk extension region was utilized.

Figure 4:
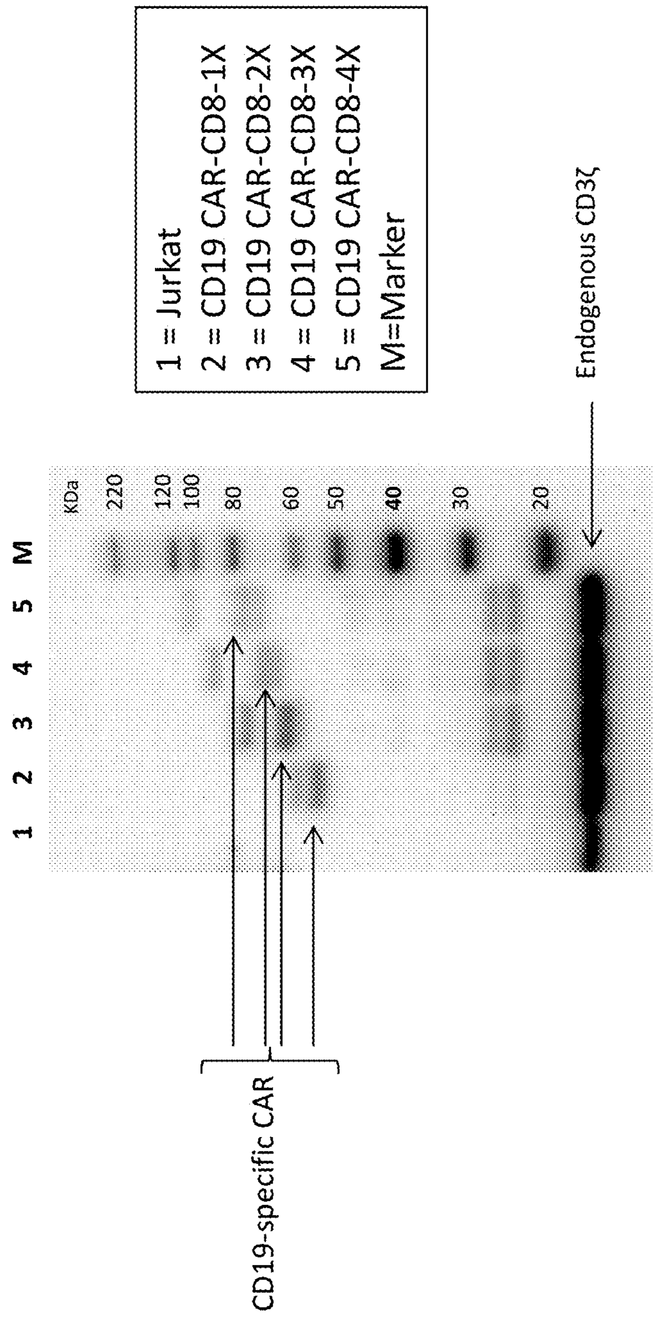
FIG. 4 shows expression of CD19-specific CARs of varying spacer lengths in T cells as measured by western blot analysis.

Expression of CD19-specific CAR with spacers of varying lengths was also confirmed via Western Blot analysis (FIG. 4).

PBMC were nucleofected with plasmids of Sleeping Beauty system to express CD19-specific CAR of varying spacer lengths. Nucleofected cells were cultured in presence of AaPC as described in Example 2.

After four rounds of stimulations, cell lysates were prepared for western blot analysis. Approximately 10 μg lysate/lane of NuPAGE 10% Bis-Tris gel was loaded. Proteins were transferred from gel to a polyvinylidene fluoride (PVDF) membranes using the iBlot® (Life Technologies) semi-dry transfer apparatus. Membrane was blocked using a 5% (w/v) powdered milk solution in a PBS+Tween-20 (PBST; 1×PBS+0.05% Tween-20) solution stained with goat anti-human CD3ζ primary antibody and rabbit anti-goat IgG HRP (KPL Laboratories) secondary antibody. SuperSignal™ West Pico Chemiluminescent Substrate (Thermo Fisher Scientific) for enhanced chemiluminescence (ECL) detection was utilized.

Image of the western blot was captured on the FluorChem™ E Imager (ProteinSimple, San Jose, Calif.) system using the Digital Darkroom software and AlphaView® software (ProteinSimple). FIG. 4 shows image of western blot. As shown by arrows in FIG. 4, increasingly higher molecular weight bands were detected by anti-CD3ζ antibody corresponding to increased spacer lengths from stalk extension regions. Native CD3ζ bands at expected molecular weight were also detected.

TABLE 2

| | Day 1 | | Day 7 | | Day 14 | | Day 21 | | Day 28 | |
|---|---|---|---|---|---|---|---|---|---|---|
| CD19 CAR | % CAR | MESF | % CAR | MESF | % CAR | MESF | % CAR | MESF | % CAR | MESF |
| CD8-1X | 42.00 | 28845 | 39.90 | 34068 | 51.30 | 20984 | 77.80 | 21118 | 86.00 | 33611 |
| CD8-2X | 6.63 | 14595 | 76.90 | 178206 | 90.10 | 69583 | 93.90 | 69875 | 97.50 | 94415 |
| CD8-3X | 12.50 | 10846 | 60.60 | 145928 | 86.30 | 44231 | 91.30 | 54830 | 97.20 | 87394 |
| CD8-4X | 6.98 | 7319 | 63.50 | 158301 | 87.00 | 31716 | 91.00 | 45239 | 97.20 | 57106 |
| CD8-3X V2 | 0.17 | 123 | 0.41 | 236 | 1.16 | 460 | | | | |

Example 4. Cytotoxicity of CD19-CAR-T Cells with CD8α-Derived Spacers of Varying Lengths Cytotoxicity of CD19-CAR-T cells with CD8α derived spacers of varying lengths towards K562 cell line modified to express CD19 antigen (K562/CD19) was measured in a 2 hr Europium release assay. K562/CD19 target cell line was labeled using the DELFIA BATDA reagent (DELFIA EuTDA Cytotoxicity assay; Perkin Elmer). CD19-CAR-T effector (E) cells were co-cultured with labeled K562/CD19 target (T) cells at (E:T) ratios of 10:1, 5:1 2:2 or 1:1. After 2 hr, supernatant from the co-cultures were harvested and developed with addition of the DELFIA Europium assay and read on a time-resolved fluorescence instrument to measure cytotoxicity of target cells. The results from example experiments are depicted in FIG. 5A.

Figure 5A:
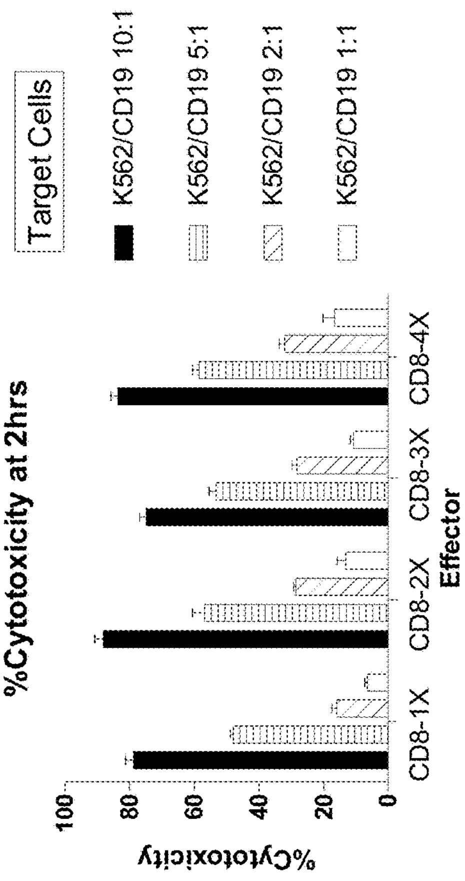
FIGS. 5A-5B show that T cells expressing CD19-CARs with varying spacer lengths are capable of exerting specific cytotoxicity effects against target cells expressing CD19.

As shown in FIG. 5A, CD19-CAR-T cells with varying lengths of spacers showed dose dependent cytotoxicity of K562/CD19 target cells. CD19-CAR-T cells with CD8α derived spacers with stalk extension region(s) (CD8-2×, CD8-3× and CD8-4×) showed similar or improved cytotoxicity of K562/CD19 cells compared to CD19-CAR-T cells lacking extended stalk region (CD8-1×). Cytotoxicity exerted by CD19-CAR-T cells with longer CD8α derived spacers (CD8-2×, CD8-3× and CD8-4×) was improved especially at lower E:T ratios (2:1 and 1:1) suggesting increased potency of these CAR-T cells compared to CAR-T cells lacking stalk extension region (CD8-1×).

Furthermore, specificity of CD19-CAR-T cells with spacers of varying lengths was demonstrated by co-culture assay with K562/CD19 cell line as well as parental K562 ($CD19^{neg}$) as well as $CD19^{neg}$EL4 cell line. All target cell lines were labeled using the DELFIA BATDA reagent (DELFIA EuTDA Cytotoxicity assay; Perkin Elmer). CD19-CAR-T effector (E) cells were co-cultured with $CD19^+$ or $CD19^{neg}$ labeled target (T) cells at (E:T) ratio of 10:1. After 2 hr, supernatant from co-cultures were harvested and developed with addition of the DELFIA Europium assay and read on a time-resolved fluorescence instrument to measure cytotoxicity of target cells. Results from assay are shown in FIG. 5B.

Figure 5B:
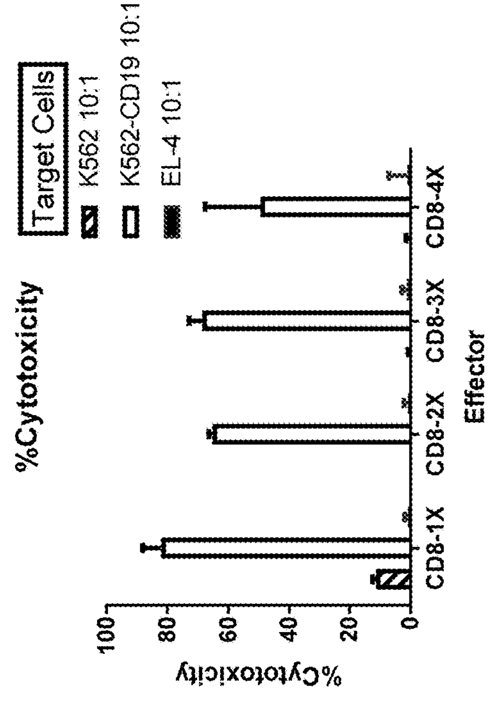

As shown in FIG. 5B, compared to CD19-CAR-T cells with CD8-1× spacer, similar (CD8-2× and CD8-3×) or somewhat lower (CD8-4×) cytotoxicity of K562/CD19 cell line was observed by CD19-CAR-T cells with extended spacers. However, CD19-CAR-T cells with CD8-1× spacer showed non-specific cytotoxicity of $CD19^{neg}$ parental K562 cell line in this assay. Whereas, CD19-CAR-T cells with stalk extension regions did not show non-specific cytotoxicity of $CD19^{neg}$ parental K562 cell line. This may explain slightly lower cytotoxicity of K562/CD19 cells observed with CD19-CAR-T cells with extended spacers. Importantly, CD19-CAR-T cells with extended spacers exhibited higher CD19 target specificity.

In summary, FIG. 5 shows that CD19-CAR-T cells with stalk extension regions displayed superior functionality compared to CD19-CAR-T cells lacking stalk extension region as shown by improved cytotoxicity of $CD19^+$ target cell lines especially at lower E:T ratios as well as improved specificity towards CD19 antigen.

Figure 6A:
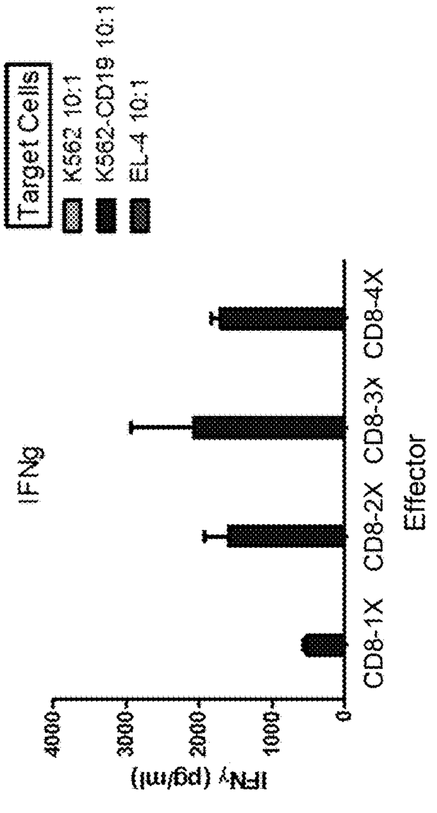
FIGS. 6A-6C show the ability of T cells expressing CD19-CARs with varying spacer lengths to produce cytokines in response to CD19 antigen expressing cells. Levels of cytokines released in response to CD19 negative cell lines (K562 and EL4) were undetectable or very low demonstrating specificity of CD19 CAR-T cells towards CD19 antigen.
Figure 6B:
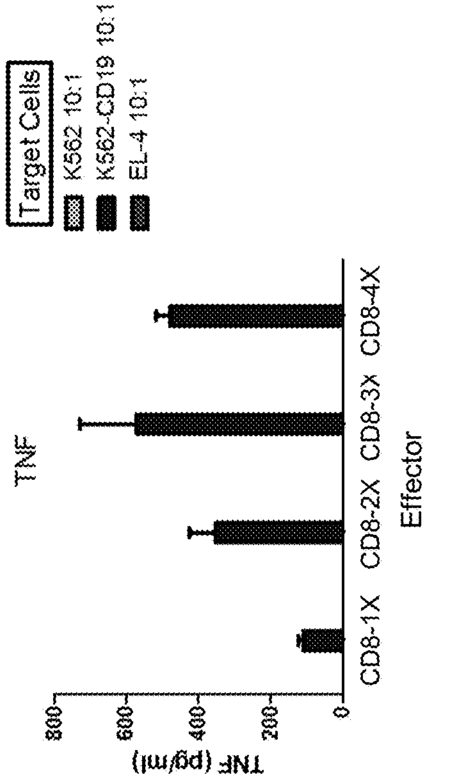
Figure 6C:
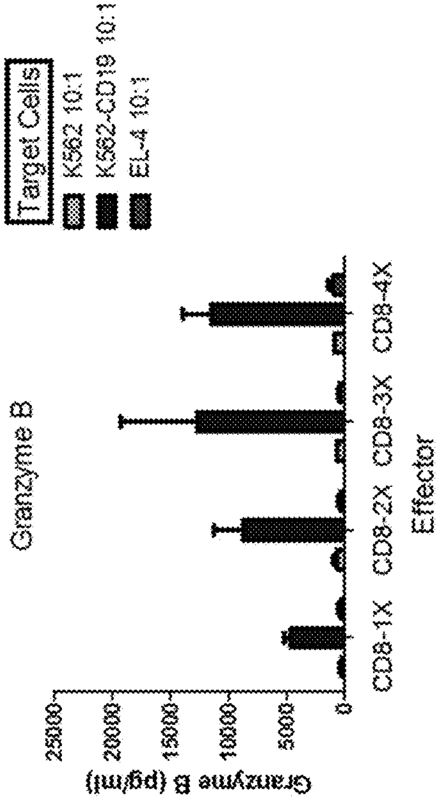

Example 5. Specific Cytokine Production by CD19-CAR-T Cells in Response to CD19 Antigen Expressing Cells Cytokine production was measured after co-culture of the CD19 CAR-T cells with varying CD8α-derived spacer lengths to $CD19^+$ or $CD19^{neg}$ tumor cells. Briefly, CD19-CAR-T cells with varying CD8α-derived spacers were co-cultured overnight with K562/CD19 ($CD19^+$) or K562 ($CD19^{neg}$) or EL4 ($CD19^{neg}$) cell lines at an E:T ratio of 10:1. Culture supernatants were harvested for multiplex cytokine analysis using the QBeads® (Intellicyt). The multiplex analysis was performed for expression of human IFNγ, IL-2 and TNF present in harvested culture media. Data from an example experiment is depicted in FIGS. 6A-6C.

Significantly higher levels of IFNγ, IL-2 and TNF cytokines were detected following co-cultures with K562/CD19 cell line when CD19-specific CAR included CD8α-derived stalk extension region compared to CD19-specific CAR that only included CD8α hinge stalk region. Elevated cytokine response of all tested CD19-CAR-T cells was in specific response to CD19 antigen present on surface of K562/CD19 cell line as $CD19^{neg}$ cell lines failed to induce a cytokine response. Values plotted represent mean±SD of samples tested in duplicates.

In summary, FIG. 6 shows that CD19-CAR-T cells with stalk extension regions displayed superior cytokine secretion compared to CD19-CAR-T cells lacking stalk extension region in response to CD19 expressing tumor cells.

Example 6. Characterization of CD33-CAR-T Cells with CD8α-Derived Spacers of Varying Lengths T cells expressing CARs with CD33-specific antigen binding region and CD8α-derived spacers listed in Table 1 were generated by SB system.

Briefly, CD33-specific CAR vectors were introduced into PBMC via electroporation, using a Sleeping Beauty-based transposon system to mediate genomic integration of the transposons. On day 0, 20 million PBMC were suspended in 100 μL of Amaxa human T cell Nucleofector solution (Cat. no. VPA-1002; Lonza, Basel, Switzerland) mixed with 15 μg of CAR transposon and 5 μg of SB transposase and electroporated. The following day (day 1) cells count and viability were measured followed by flow cytometry to quantify CAR expression. CAR-T cells were stimulated with either γ-irradiated (100 Gy) or mitomycin C treated AaPCs at a 1:1 ratio. The AaPC cells used were K562 cell line expressing CD33 antigen. CD33-CAR-T cells were expanded ex vivo by once weekly stimulation with the AaPCs at a 1:1 ratio. Cultures were maintained in IL-2 (50 IU/ml) and/or IL-21 (30 ng/ml). CD33-specific CAR expression was measured using recombinant CD33/Fc protein staining as detected by multi-parameter flow cytometry.

Figure 9:
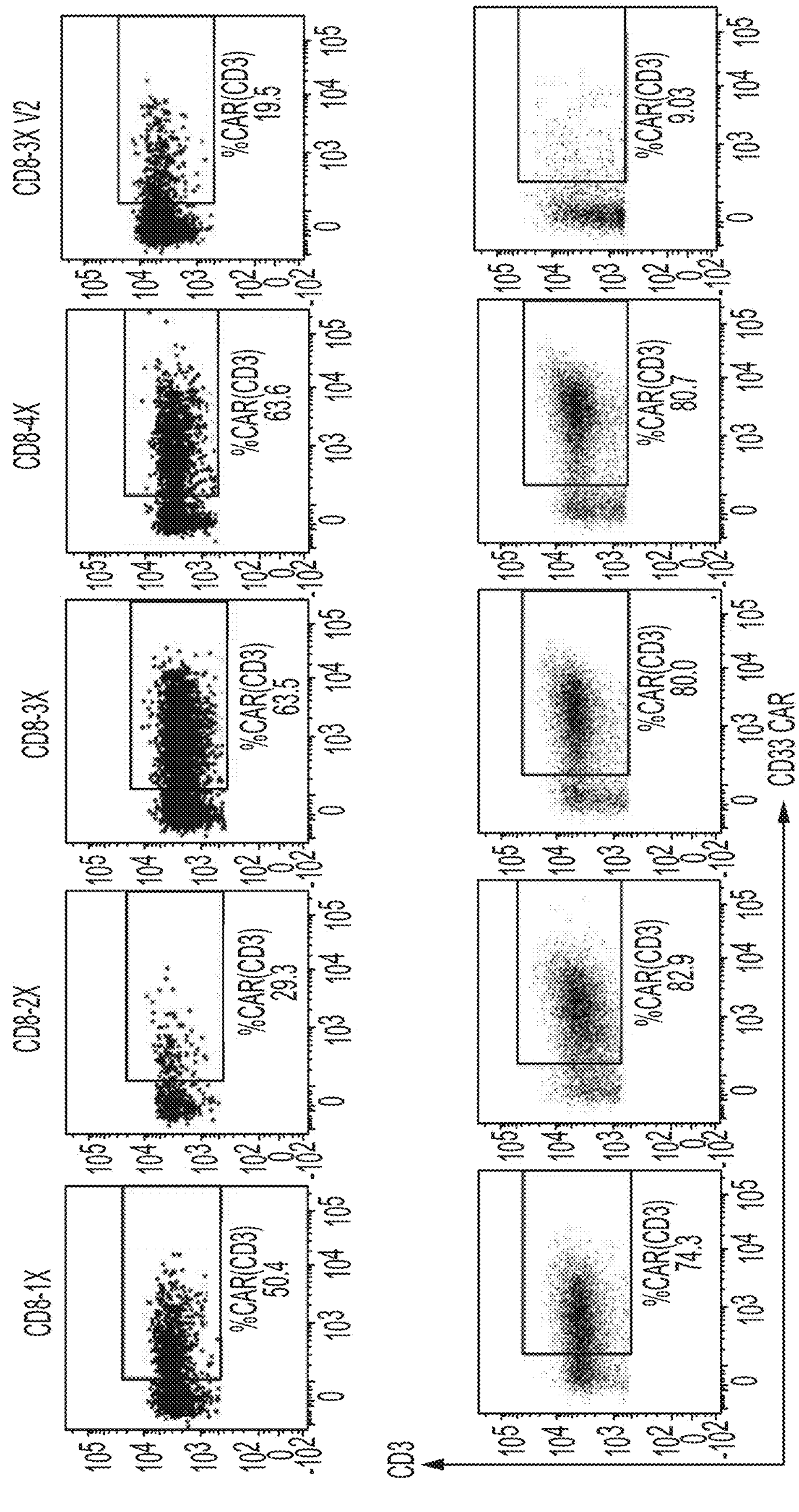
FIG. 9 shows expression of CD33-specific CAR with varying spacer lengths on surface of T cells. Human PBMCs were electroporated with Sleeping Beauty transposons encoding for CD33-specific CAR with spacers incorporating one, two or three stalk extension regions (CD8-2×, CD8-3× and CD8-4×) and co-cultured with AaPC expressing CD33 antigen for ex vivo proliferation of CAR-T cells. Expression of CD33-specific CAR was measured by flow cytometry using CD33-Fc protein. CD33-specific CARs with spacers incorporating two or three stalk extension regions (CD8-3× and CD8-4×) exhibited improved expression and CAR-T cell growth at Day 7 when compared with CD33-specific CAR with CD8a hinge stalk (CD8-1×).
Figure 10A:
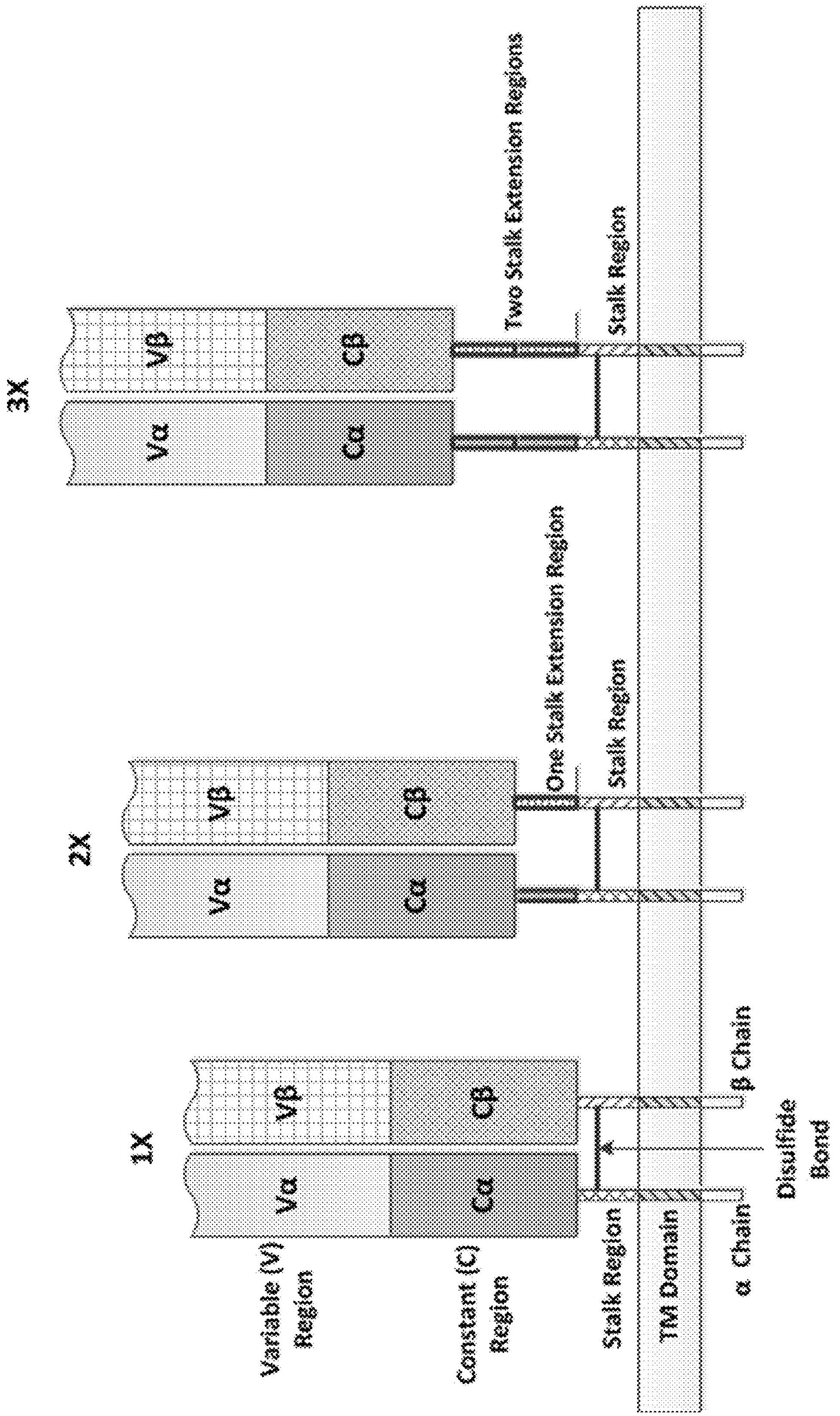
FIG. 10A depicts diagrams of engineered T cell receptors (TCR) with spacers that incorporate a stalk (s) and varying numbers of stalk extension regions (s'-1, s'-2).
Figure 10B:
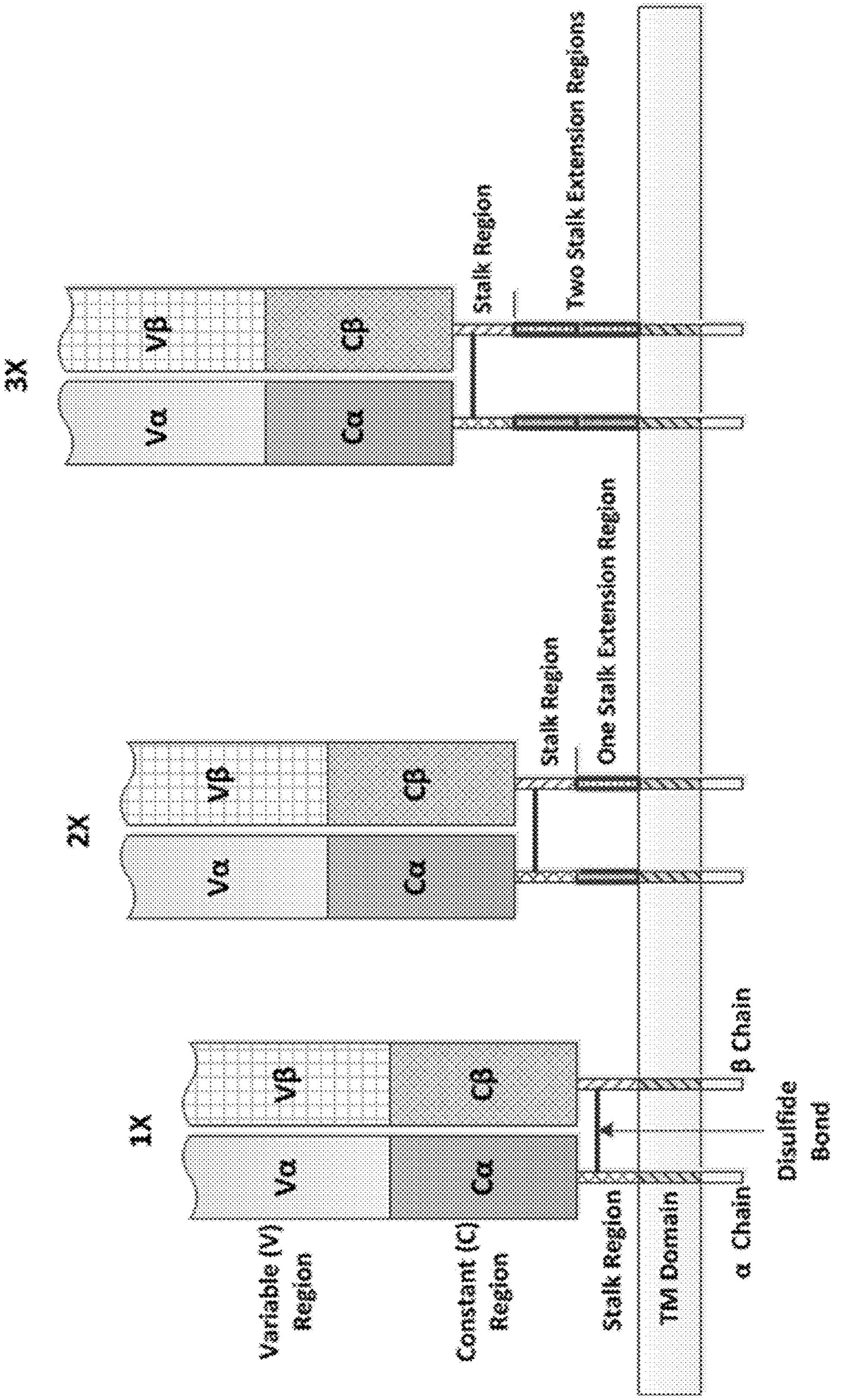
FIG. 10B depicts diagrams of engineered T cell receptors (TCR) with spacers that incorporate a stalk (s) and varying numbers of stalk extension regions (s'-1, s'-2). The diagrams also depict exemplary disulfide bond mediated dimerization sites.

The expression level of CD33-specific CARs with varying spacer lengths from in T cells from two healthy donors is summarized in Table 3 and FIG. 9.

As shown in Table 3, improved CD33-specific CAR expression was observed post gene transfer as measured by % of T cells expressing CAR when spacer included CD8α-derived stalk extension region (CD8-3×) compared to when spacer only included CD8α stalk region (CD8-1×). As observed with CD19 CAR-T cells, CD33-CAR-T cells with CD8-3×v2 spacer failed to show significant CAR expression on T cell surface as well as failed to expand upon co-culture with AaPC. Difference between CD8-3× and CD8-3×v2 spacer is the position of amino acid substitutions to disrupt inter-chain disulfide bonds. This data suggests that positioning of amino acid substitutions is critical for expression of proteins using spacers of varying lengths.

TABLE 3

| CD33 CAR Spacer Length | Donor # 1 % $CD3^+$ $CAR^+$ | Donor # 2 % $CD3^+$ $CAR^+$ |
|---|---|---|
| CD8-1X | 50.4 | 74.3 |
| CD8-2X | 29.3 | 82.9 |
| CD8-3X | 63.5 | 80.0 |
| CD8-4X | 63.6 | 80.7 |
| CD8-3X V2 | 19.5 | 9.03 |

Example 7. Characterization of ROR-1 CAR T Cells with Spacers of Varying Lengths As T cells expressing CARs with ROR-1-specific antigen binding region and CD8α-derived spacers listed in Table 1, as well as LNGFR ECD spacer (Table 4) were generated using SB system using method explained in Example 2.

Figure 7A:
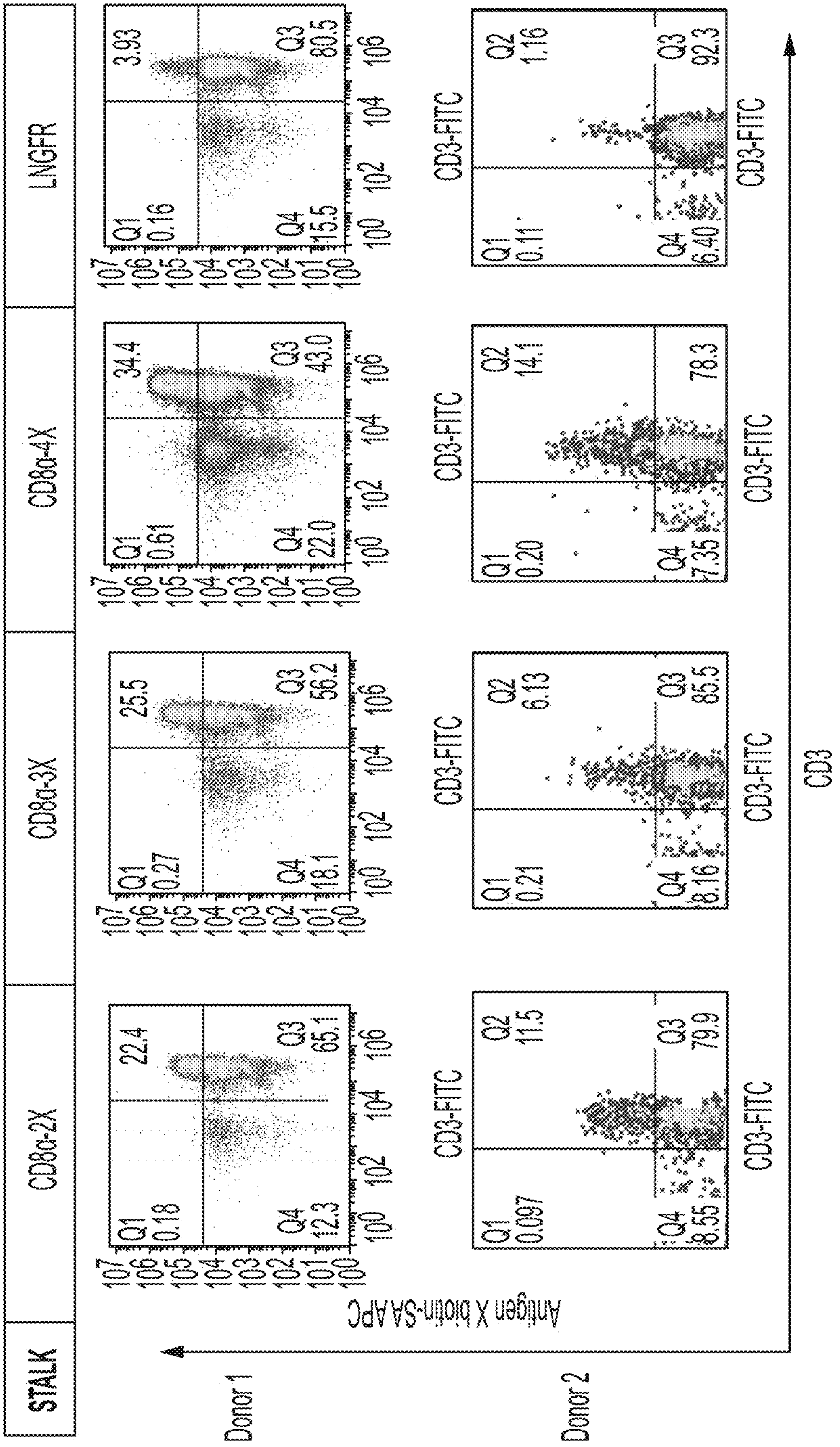
FIG. 7A depicts expression data for ROR-1 CARs with varying spacer lengths after successive rounds of stimulation on aAPC.
Figure 7B:
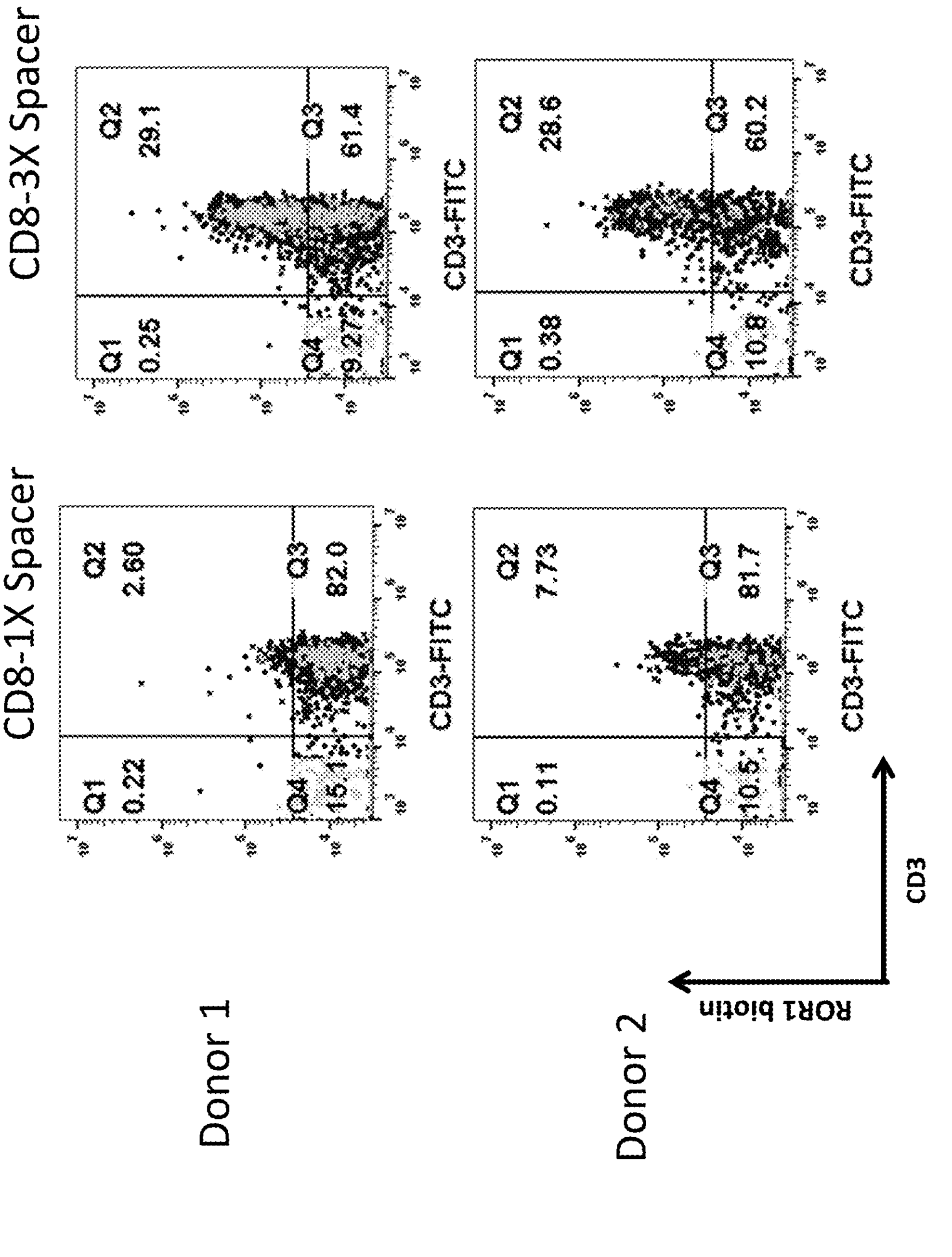
FIG. 7B depicts expression data for ROR-1 CARs with varying spacer lengths after successive rounds of stimulation on aAPC. As seen from the data, the incorporation of stalk extension regions resulted in improved expression.

The expression level of ROR-1 CARs with varying stalk lengths was determined using flow cytometry by staining with ROR-1-Fc fusion protein using method similar to explained in Example 6. Data from two different healthy donor cells is depicted in FIGS. 7A-B. As shown in FIGS. 7A and 7B, ROR-1 CAR without stalk extension region (CD8-1×) failed to express on surface of T cells. ROR-1 CAR without stalk extension region (CD8-1×) also failed to expand in ex vivo culture (data not shown). ROR-1 CAR with stalk extension regions (CD8-2×, CD8-3× and CD8-4×) showed high levels of CAR expression on cell surface. In summary, ROR-1 CAR requires stalk extension region(s) to allow for expression of CAR on T cell surface.

T cells expressing CARs with ROR-1-specific antigen binding region were generated with CD8α-derived stalks listed in Table land CD28-CD3zeta costimulatory domain using SB system using method explained in Example 2. These CAR-T cells were assessed for their functional activity against ROR-1 expressing tumor cells.

Figure 8A:
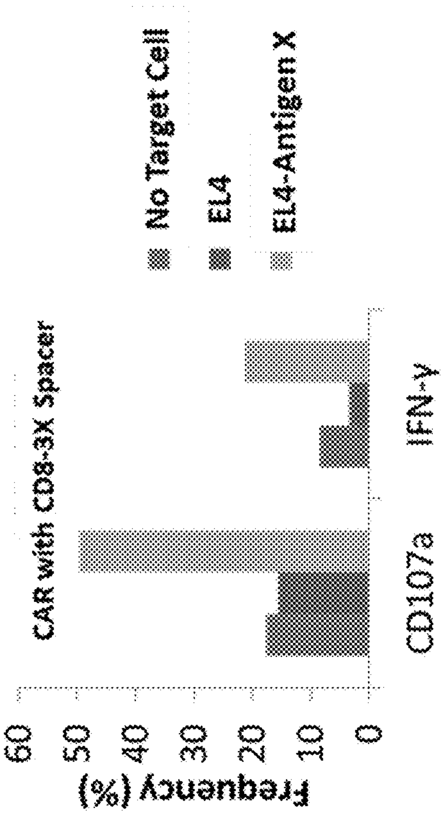
FIG. 8A depicts exemplary data from functional activity assays to measure degranulation of T cells expressing ROR-1 CAR with varying spacer lengths, as measured by CD107a expression and IFNγ release.
Figure 8B:
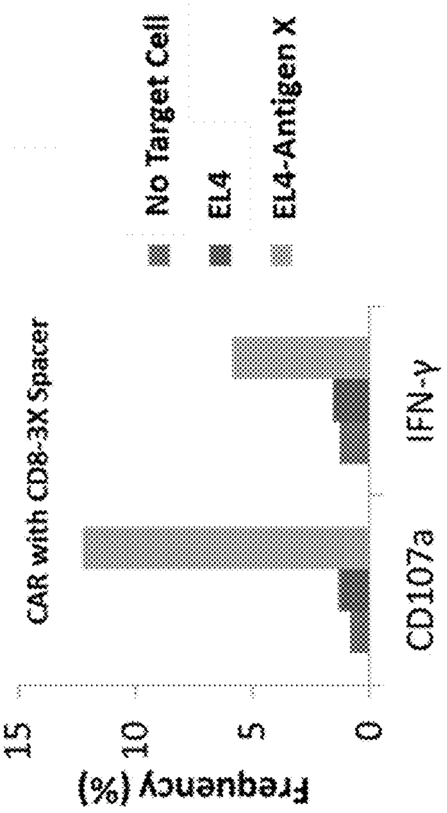
FIG. 8B depicts exemplary data from functional activity assays to measure degranulation of T cells expressing CAR with varying spacer lengths, as measured by CD107a expression and IFNγ release.

CD107a, also known as lysosomal-associate membrane protein-1 (LAMP-1), is constitutively expressed in the late endosomes-lysosomes of cells but transiently expressed on the cell surface on degranulating cells. The degranulation assay was established to assess the capability of the ROR-1 CAR-T cells with CD8-3× spacer to recognize target cells with or without ROR-1 expression with concurrent intracellular IFNγ detection on a per cell basis. ROR-1 CAR-T cells were co-cultured with target cells at a 10:1 E:T ratio. Target cell included EL4 (ROR-$1^{neg}$), EL4-ROR-1 (ROR-$1^+$). At the start of the co-culture, the fluorescently conjugated CD107a or isotype antibody was added along with the Transport Inhibitor Cocktail (containing monensin and brefeldin, 1×; eBioscience) and incubated at 37° C. for 4 hrs. At the end of the incubation period, cells were pelleted in the plate and cell surface antigens were stained for detection of CAR expression and T cell markers. Following cell surface staining, cells were also stained with the Fixable Cell viability dye (eBioscience) according to the manufacturer's instructions then washed followed by fixation with Fix/Perm Solution (BD Biosciences). After fixing the samples, cells were washed in a Perm/Wash solution (BD Biosciences) then intracellularly stained with the fluorescently conjugated anti-human IFNγ antibody. Samples were washed then resuspended in appropriate staining buffer with data acquired on a LSR II flow cytometer (BD Biosciences). Data from an example experiment is depicted in FIGS. 8A-8B. ROR-1 CAR-T cells with CD8-3× spacer showed antigen specific degranulation and IFNγ expression.

Example 8. Chimeric Antigen Receptors with LNGFR-Derived Spacers of Varying Lengths Chimeric antigen receptors comprising a stalk region and a stalk extension region were generated. The spacer region comprised the sequence of the LNGFR ECD (SEQ ID NO: 17), LNGFR Cys 2, 3, 4 (SEQ ID NO: 18) or Cys 3, 4 (SEQ ID NO: 19) as shown in Table 4.

TABLE 4

| LNGFR spacer | Amino Acid Sequence SEQ ID NO: |
|---|---|
| ECD | 16 |
| Cys 2, 3, 4 | 18 |
| Cys 3, 4 | 20 |

Example 9. Chimeric Antigen Receptors with CD28-Derived Spacers of Varying Lengths Chimeric antigen receptors comprising a stalk region and a stalk extension region were generated. The stalk region comprised the sequence of the CD28 hinge region (SEQ ID NO: 32), and the stalk extension region (s'-n), wherein n=1, 2, or 3, wherein each stalk extension region of an altered CD28 hinge region in which the disulfide-bond forming cysteine residues (bold residues in Table 5) were converted to serines (underlined residues in Table 5). In the 2× (SEQ ID NO: 33), 3× (SEQ ID NO: 34), and 4× (SEQ ID NO: 35) versions, the CD28 hinge region retaining the disulfide bond forming cysteines was downstream of the altered regions lacking the cysteines. The generated CD28-derived 1×, 2×, 3×, and 4× stalks comprising (s'-n), wherein n=0, 1, 2, and 3 respectively are listed in Table 5.

TABLE 5

| CD28 spacer | Amino Acid Sequence SEQ ID NO: |
|---|---|
| 1X | 32 |
| 2X | 33 |

TABLE 5-continued

| CD28 spacer | Amino Acid Sequence SEQ ID NO: |
|---|---|
| 3X | 34 |
| 4X | 35 |

Example 10. Chimeric Antigen Receptors with CTLA-4-Derived Spacers of Varying Lengths Chimeric antigen receptors comprising a stalk region and a stalk extension region were generated. The stalk region comprised the sequence of the CTLA-4 hinge region (SEQ ID NO: 37), and the stalk extension region (s'-n), n=1, 2, or 3, and each stalk extension region an altered CLTA-4 hinge region in which the disulfide-bond forming cysteine residues (bold residues in Table 6) were converted to serines (underlined residues in Table 6). In the 2× (SEQ ID NO: 38), 3× (SEQ ID NO: 39), and 4× (SEQ ID NO: 40) versions, the CTLA-4 hinge region retaining the disulfide bond forming cysteines was downstream of the altered regions lacking the cysteines. The generated CTLA-4-derived 1×, 2×, 3×, and 4× stalks comprising (s'-n), n=0, 1, 2, and 3 respectively are listed in Table 6.

TABLE 6

| CTLA-4 spacer | Amino Acid Sequence SEQ ID NO: |
|---|---|
| 1X | 37 |
| 2X | 38 |
| 3X | 39 |
| 4X | 40 |

Example 10. T Cell Receptor (TCR) with TCRα and TCRβ Hinge Domain Derived Spacers of Varying Lengths T cell receptor (TCR) α and β chains comprising a stalk region and a stalk extension region were generated. The stalk region for TCRα chain comprised the sequence of the TCRα hinge region (SEQ ID NO: 72), and the stalk extension region (s'-n), n=1, 2, or 3, and each stalk extension region of an altered TCRα hinge region in which the disulfide-bond forming cysteine residues (bold residues in Table 7) were converted to serine (underlined residues in Table 7). In the 2× (SEQ ID NO: 77), 3× (SEQ ID NO: 78), and 4× (SEQ ID NO: 79) versions shown in Table 7, the TCRα hinge region retaining the disulfide bond forming cysteine was downstream (C-terminal) of the altered regions lacking the cysteines. The generated TCRα hinge region derived 1×, 2×, 3×, and 4× stalks comprising (s'-n), n=0, 1, 2, and 3, respectively, are listed in Table 7.

TABLE 7

| TCRα spacer | Amino Acid Sequence SEQ ID NO: |
|---|---|
| 1X | 72 |
| 2X | 77 |
| 3X | 78 |
| 4X | 79 |

The stalk region for TCRβ chain comprised the sequence of the TCRβ hinge region (SEQ ID NO: 86), and the stalk extension region (s'-n), n=1, 2, or 3, and each stalk extension region of an altered TCRβ hinge region in which the disulfide-bond forming cysteine residues (bold residues in Table 8) were converted to serine (underlined residues in Table 8) (SEQ ID NO: 87). In the 2× ((SEQ ID NO: 91), 3× (SEQ ID NO: 92), and 4× (SEQ ID NO: 93) versions shown in Table 8, the TCRβ hinge region retaining the disulfide bond forming cysteine was downstream (C-terminal) of the altered regions lacking the cysteines. The generated TCRβ hinge region derived 1×, 2×, 3×, and 4× stalks comprising (s'-n), n=0, 1, 2, and 3 respectively, are listed in Table 8.

TABLE 8

| TCRβ spacer | Amino Acid Sequence SEQ ID NO: |
|---|---|
| 1X | 86 |
| 2X | 91 |
| 3X | 92 |
| 4X | 93 |

Example 11. Expression of EGFRvIII Specific CARs with CD8α-Derived Spacers of Varying Lengths T cells expressing CARs with EGFRvIII-specific antigen binding region (MR1-1 and huMR1-1) and CD8α-derived spacers listed in Table 1 were generated by SB system.

Briefly, EGFRvIII-specific CAR vectors were introduced into via electroporation, using a Sleeping Beauty-based transposon system to mediate genomic integration of the transposons. On day 0, PBMC were mixed with CAR transposon and SB transposase and electroporated. The following day (day1) cells count and viability were measured followed by flow cytometry to quantify CAR expression. CAR-T cells were stimulated by co-culture with either γ-irradiated) or mitomycin C treated AaPCs. The AaPC cells used were K562 cell line expressing EGFRvIII antigen. EGFRvIII-CAR-T cells were expanded ex vivo by once weekly stimulation with the AaPCs. Cultures were maintained in media supplemented with IL-2 (and/or IL-21. EGFRvIII-specific CAR expression was measured using recombinant EGFRvIII/Fc protein staining as detected by multi-parameter flow cytometry.

Figure 11A:
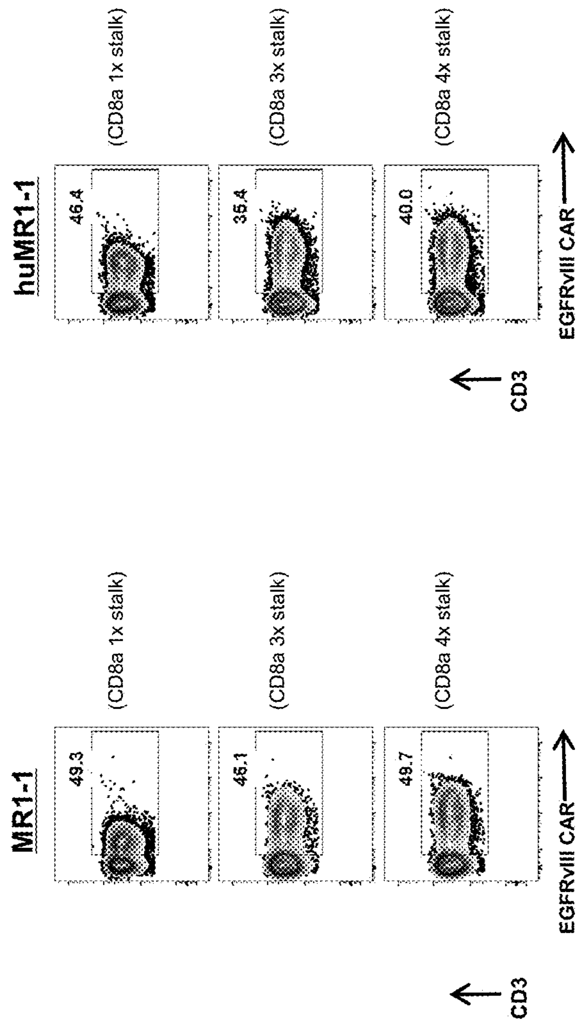
FIG. 11A depicts expression data for MR1-1 and huMR1-1 CARs specific for EGFRvIII with varying spacer lengths after a round of stimulation on aAPC.
Figure 11B:
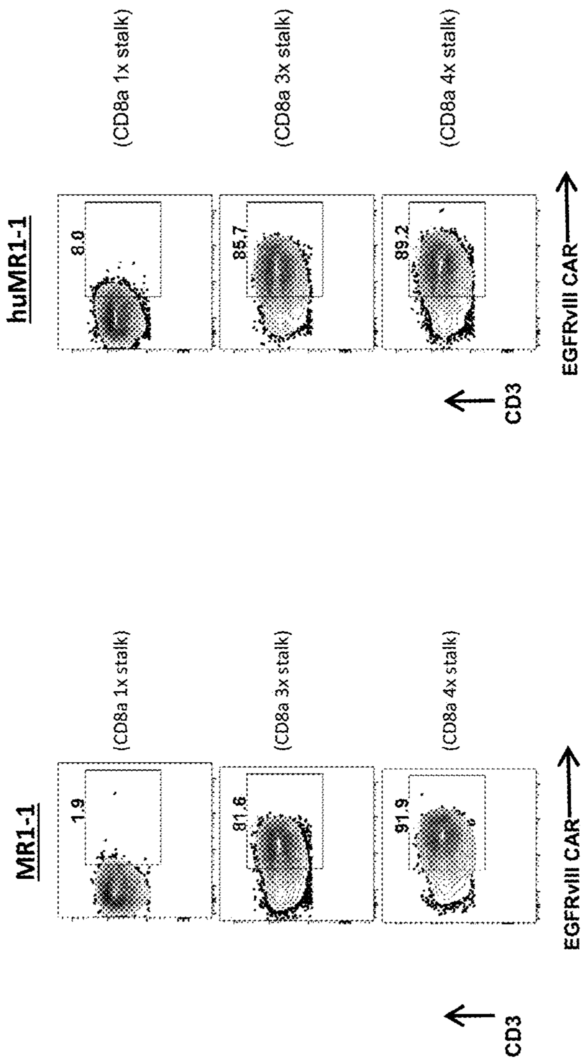
FIG. 11B depicts expression data for MR1-1 and huMR1-1 CARs specific for EGFRvIII with varying spacer lengths after three rounds of stimulation on aAPC. As seen from the data, the incorporation of stalk extension regions resulted in improved expression.

The expression level of EGFRvIII-specific CARs with varying spacer lengths from in T cells from two healthy donors is summarized in FIG. 11A-B. One day after nucleofection, similar levels of EGFRvIII-specific CAR of different CD8α spacer lengths was observed using either MR1-1 or huMR1-1 based CARs (FIG. 11A). However, only CAR-T cells expressing EGFRvIII-specific CARs with longer CD8α spacer lengths (3× and 4×) could be enriched via EGFRvIII antigen specific stimulation using AaPC co-culture (FIG. 11B) showing importance of longer spacers for interaction with EGFRvIII antigen on surface of AaPC.

Example 12. Expansion of EGFRvIII Specific CARs with CD8α-Derived Spacers of Varying Lengths CAR-T cells undergo in vivo expansion after infusion upon recognition of tumor cells expressing antigen that CAR recognizes. In vivo expansion of CAR-T cells is very important for their anti-tumor activity. Ex vivo expansion via co-culture with antigen specific cell line, e.g. AaPC, simulates expansion of CAR-T cells in absence of tumor cells. Ex vivo expansion of CAR-T cells is often performed during manufacturing to obtain sufficient $CAR^+$ T cells for patient treatment.

Figure 11C:
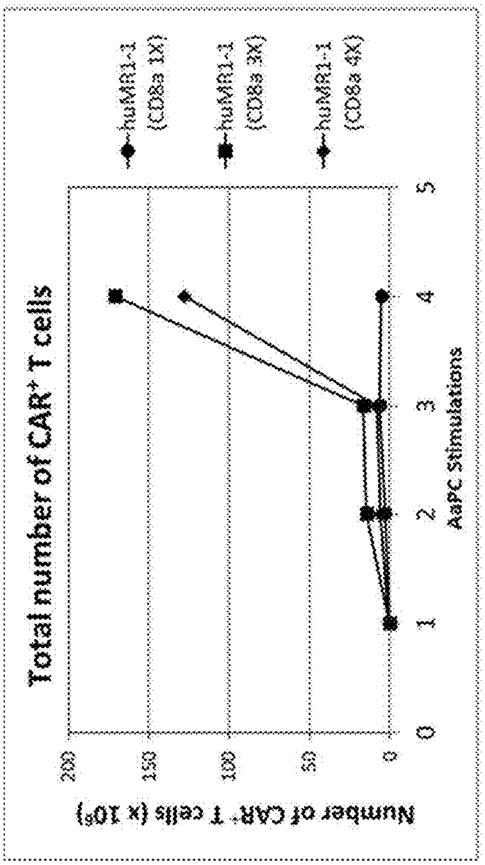
FIG. 11C-D depicts total number of $CAR^+$ T cells and fold expansion of huMR1-1 $CAR^+$ T cells with varying spacer lengths after consecutive rounds of AaPC stimulations.
Figure 11D:
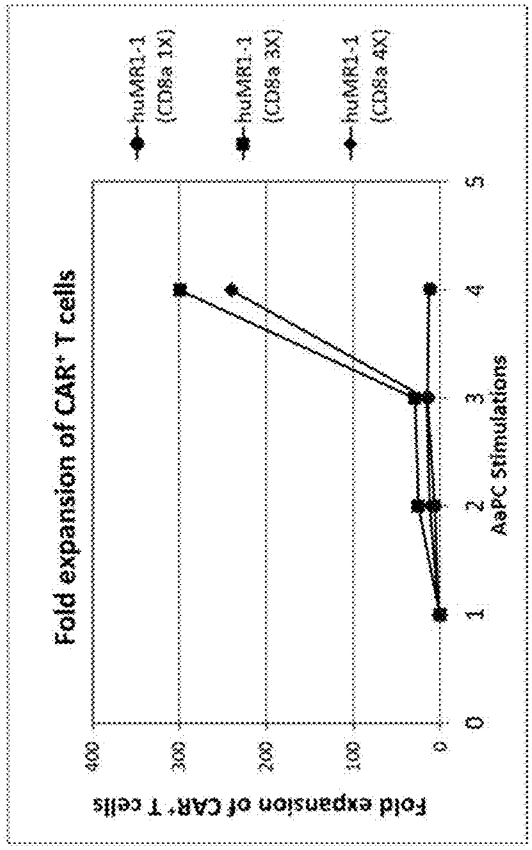

EGFRvIII-specific CAR-T cells were expanded in vitro by recurring stimulations using co-culture with an AaPC cell line expressing EGFRvIII antigen following gene transfer with SB derived transposon/transposase as described in Example 11. Total numbers of EGFRvIII-specific $CAR^+$ T cells and their fold expansion in ex vivo culture following each AaPC stimulation were measured. As shown in FIG. 11C, CAR-T cells expressing EGFRvIII-specific CARs with longer CD8α spacer lengths (3× and 4×) showed robust expansion after four AaPC stimulations. However CAR-T cells expressing EGFRvIII-specific CARs with 1× CD8α spacer failed to expand. Robust expansion of CAR-T cells with longer CD8α spacer lengths (3× and 4×) is further evident with >200 fold expansion upon four AaPC stimulations (FIG. 11D).

Example 13. Cytotoxicity of EGFRvIII CAR T Cells with Spacers of Varying Lengths Cytotoxicity of huMR1-1 EGFRvIII-specific CAR-T cells with CD8α derived spacers of varying lengths towards a K562 cell line modified to express EGFRvIII antigen (K562-EGFRvIII) was measured in a 2 hr Europium release assay. K562 parental cell line which does not express EGFRvIII was used as control. K562 and K562-EGFRvIII target cell lines were labeled using the DELFIA BATDA reagent. EGFRvIII-specific CAR-T effector (E) cells were co-cultured with labeled K562-EGFRvIII target (T) cells at (E:T) ratios of 10:1, 5:1 or 1:1. After 2 hr, supernatant from the co-cultures were harvested and developed with addition of the DELFIA Europium assay and read on a time-resolved fluorescence instrument to measure cytotoxicity of target cells. The results from example experiments are depicted in FIG. 11E.

Figure 11E:
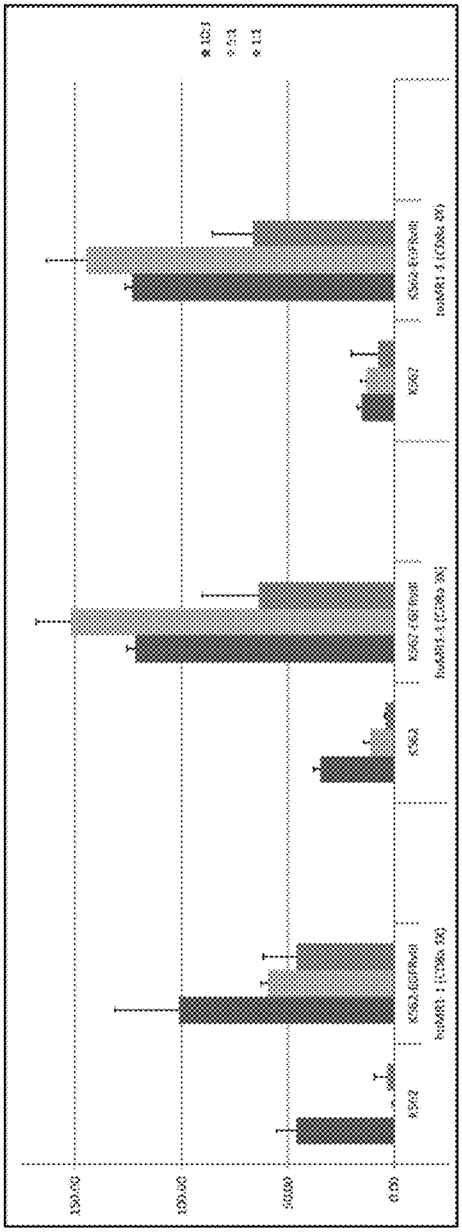
FIG. 11E depicts the depicts exemplary data measuring cytotoxicity activity of T cells expressing huMR1-1 $CAR^+$ T cells with varying spacer lengths, as measured by Europium release assay.

As shown in FIG. 11E, EGFRvIII-specific CAR-T cells with varying lengths of spacers showed dose dependent cytotoxicity of K562-EGFRvIII target cells. Very low background cytotoxicity of K562 cells which do not express EGFRvIII was observed except for at highest E:T ratio of 10:1 which may be due to high concentrations of effector cells present. EGFRvIII-specific CAR-T cells with CD8α derived spacers with stalk extension region(s) (CD8-3× and CD8-4×) showed improved cytotoxicity of K562-EGFRvIII cells compared to EGFRvIII-specific CAR-T cells lacking extended stalk region (CD8-1×). Cytotoxicity exerted by EGFRvIII-specific CAR-T cells with longer CD8α derived spacers (CD8-3× and CD8-4×) was improved especially at lower E:T ratios (5:1 and 1:1) suggesting increased potency of these CAR-T cells compared to CAR-T cells lacking stalk extension region (CD8-1×).

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein may be employed in practicing the present disclosure. It is intended that the following claims define the scope of the present disclosure and that methods and structures within the scope of these claims and their equivalents be covered thereby.

What is claimed is:

1. A chimeric polypeptide comprising:

(a) an antigen-binding region;

(b) a transmembrane region; and (c) a spacer region connecting the trans-membrane region with the antigen binding region, wherein the spacer region comprises: (i) a stalk region comprising about 20 to about 60 amino acids and at least one dimerization site; and (ii) one to five stalk extension regions, wherein each stalk extension region comprises fewer dimerization sites than the stalk region.

2. The chimeric polypeptide of claim 1, wherein at least one stalk extension region comprises an amino acid sequence having at least 80% sequence identity with the amino acid sequence of the stalk region.

3. The chimeric polypeptide of claim 1, wherein the stalk region is proximal to the transmembrane region.

4. The chimeric polypeptide of claim 1, wherein the stalk region is distal to the transmembrane region.

5. The chimeric polypeptide of claim 1, wherein the chimeric polypeptide exhibits increased expression on a cell surface compared to an otherwise identical polypeptide that lacks the stalk extension region.

6. The chimeric polypeptide of claim 1, wherein at least one stalk extension region lacks a dimerization site.

7. The chimeric polypeptide of claim 1, wherein each stalk extension region comprises about 20 to about 60 amino acids.

8. The chimeric polypeptide of claim 7, wherein each stalk extension region comprises an amino acid sequence that has at least about 80% sequence identity to the amino acid sequence of the stalk region.

9. The chimeric polypeptide of claim 1, wherein the stalk region comprises a sequence with at least about 80% identity to a CD8alpha hinge domain, a CD28 hinge domain, and/or a CTLA-4 hinge domain.

10. The chimeric polypeptide of claim 1, wherein the antigen binding region binds an epitope on CD19, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, Folate receptor α, Mucins, MUC-1, MUC-16, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, MAGE-A1, h5T4, PSMA, TAG-72, EGFR, CD20, EGFRvIII, CD123, and/or VEGF-R2.

11. The chimeric polypeptide of claim 1, wherein the chimeric polypeptide comprises a chimeric antigen receptor (CAR).

12. The chimeric polypeptide of claim 1, wherein the chimeric polypeptide comprises an engineered T-cell receptor (TCR).

13. The chimeric polypeptide of claim 12, wherein the engineered TCR is an αβ TCR.

14. The chimeric polypeptide of claim 12, wherein the engineered TCR is a γδ TCR.

15. The chimeric polypeptide of claim 12, wherein the antigen binding region binds an epitope on at least one of NY-ESO-1, Titin, MART-1, HPV, HBV, MAGE-A4, MAGE-A10, MAGE A3/A6, gp100, MAGE-A1, or PRAME.

16. The chimeric polypeptide of claim 11, wherein at least one stalk extension region comprises: (a) an amino acid sequence that has at least 80% sequence identity with the amino acid sequence of the stalk region; and (b) at least one amino acid substitution relative to the stalk region.

17. The chimeric polypeptide of claim 16, wherein the stalk region is capable of dimerizing with a second stalk region present in a second CAR and comprises at least 80% sequence identity with the amino acid sequence of the second stalk region.

18. A method of increasing expansion of an engineered T cell expressing a chimeric polypeptide comprising engineering a nucleic acid encoding the chimeric polypeptide to comprise a stalk extension domain, thereby generating an engineered T cell.

19. The chimeric polypeptide of claim 1, wherein the antigen binding region binds an epitope on CD33, MUC-16, and/or ROR1.

20. The chimeric polypeptide of claim 1, wherein the antigen binding region binds an epitope on ROR1.

21. The chimeric polypeptide of claim 1, wherein the stalk region comprises an amino acid sequence that has at least 80% sequence identity with SEQ ID NO: 3.

22. The chimeric polypeptide of claim 1, wherein the spacer region comprises an amino acid sequence that has at least 80% sequence identity with SEQ ID NO: 5.

23. A modified immune effector cell that expresses the chimeric polypeptide of claim 1.

24. A modified immune effector cell that expresses the chimeric polypeptide of claim 20.

25. The modified immune effector cell of claim 24, wherein the cell is a CAR-T cell.

26. The modified immune effector cell of claim 23, wherein the cell expresses a cytokine.

27. The modified immune effector cell of claim 26, wherein the cytokine is a membrane-bound IL15.

28. The modified immune effector cell of claim 23, wherein the cell expresses a cell tag.

29. The modified immune effector cell of claim 28, wherein the cell tag comprises a truncated epidermal growth factor receptor.

30. The modified cell of claim 23, wherein the cell expresses a membrane-bound IL15 and a cell tag comprising a truncated epidermal growth factor receptor.

31. The modified cell of claim 24, wherein the cell expresses a membrane-bound IL15 and a cell tag comprising a truncated epidermal growth factor receptor.

32. The modified cell of claim 23, wherein the cell has improved cytotoxicity as compared to a cell expressing an otherwise identical antigen-binding polypeptide that lacks the stalk extension region.

33. A method for making the modified immune effector cell of claim 23, the method comprising transfecting an immune effector cell with an expression vector encoding the chimeric polypeptide.

34. The method of claim 33, wherein the vector is a Sleeping Beauty transposon.

* * * * *